US009823254B2

(12) United States Patent
Burkart et al.

(10) Patent No.: US 9,823,254 B2
(45) Date of Patent: Nov. 21, 2017

(54) REVERSIBLE CHEMOENZYMATIC LABELING OF NATIVE AND FUSION CARRIER PROTEIN MOTIFS

(71) Applicant: The Regents of the University of California, Oakland, CA (US)

(72) Inventors: Michael D. Burkart, San Diego, CA (US); Nicolas M. Kosa, La Jolla, CA (US); Robert W. Haushalter, Emeryville, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/657,221

(22) Filed: Mar. 13, 2015

(65) Prior Publication Data

US 2015/0253335 A1 Sep. 10, 2015

Related U.S. Application Data

(63) Continuation of application No. PCT/US2013/059792, filed on Sep. 13, 2013.

(60) Provisional application No. 61/701,166, filed on Sep. 14, 2012.

(51) Int. Cl.
*G01N 33/68* (2006.01)
*C07K 19/00* (2006.01)
*C12P 21/06* (2006.01)
*C07F 9/6561* (2006.01)
*C07K 14/195* (2006.01)
*C07K 14/37* (2006.01)

(52) U.S. Cl.
CPC ......... *G01N 33/68* (2013.01); *C07F 9/65616* (2013.01); *C07K 14/195* (2013.01); *C07K 14/37* (2013.01); *C07K 19/00* (2013.01); *C12P 21/06* (2013.01); *C07K 2319/00* (2013.01); *C07K 2319/21* (2013.01); *C07K 2319/24* (2013.01); *C07K 2319/60* (2013.01); *G01N 2333/245* (2013.01)

(58) Field of Classification Search
None
See application file for complete search history.

(56) References Cited

U.S. PATENT DOCUMENTS

| 5,087,563 A * | 2/1992 | Beremand | C07K 14/31 435/320.1 |
| 6,951,729 B1 | 10/2005 | Dewolf et al. | |
| 7,666,612 B2 | 2/2010 | Johnsson et al. | |

FOREIGN PATENT DOCUMENTS

EP 0861321 B1 5/2006

OTHER PUBLICATIONS

Thomas et al. ("The Enigmatic Acyl Carrier Protein Phosphodiesterase of *Escherichia coli*"; The Journal of Biological Chemistry: vol. 280, No. 41; p. 34675-34683, 2005).*
Worthington et al. ("Mechanism based protein cross-linking probes to investigate carrier protein-mediated biosynthesis"; ACS Chemical Biology, vol. 1, No. 11 (2006)).*
Murugan et al. ("Expression, purification and characterization of the acyl carrier protein phosphodiesterase from Pseudomonas Aeruginosa"; Protein Expression and Purification, vol. 71, Issue 2, Jun. 2010, p. 132-138).*
Yin et al. ("Genetically encoded short protein tag for versatile protein labeling by sfp phophopantetheinyl transferase" :PNAS, Nov. 2005, vol. 102 (44) p. 15815-15820).*
Blatti, J.L. et al. (2012, e-published Sep. 13, 2012). "Manipulating fatty acid biosynthesis in microalgae for biofuel through protein-protein interactions," *PLoS One* 7(9):e42949.
Chan, D.I. et al. (Aug. 15, 2010). "Current understanding of fatty acid biosynthesis and the acyl carrier protein," *Biochem J* 430(1):1-19.
Clarke, K.M. et al. (Aug. 17, 2005). "In vivo reporter labeling of proteins via metabolic delivery of coenzyme A analogues," *J Am Chem Soc* 127(32):11234-11235.
Foley, T.L. et al. (Nov. 1, 2009, e-published Jun. 30, 2009). "A homogeneous resonance energy transfer assay for phosphopantetheinyl transferase," *Anal Biochem* 394(1)39-47.
Foley, T.L. et al. (Oct. 21, 2010, e-published Aug. 20, 2010). "Preparation of FRET reporters to support chemical probe development," *Org Biomol Chem* 8(20):4601-4606.
George, N. et al. (Jul. 28, 2004). "Specific labeling of cell surface proteins with chemically diverse compounds," *J Am Chem Soc* 126(29):8896-8897.
International Search Report mailed on Dec. 23, 2013, for PCT Application No. PCT/US2013/059792, filed Sep. 13, 2013, 4 pages.
Ishikawa, F. et al. (Jun. 19, 2013, e-published Jun. 4, 2013). "Sulfonyl 3-alkynyl pantetheinamides as mechanism-based cross-linkers of acyl carrier protein dehydratase," *J Am Chem Soc* 135(24):8846-8849.
Kosa, N.M. et al. (Oct. 2012, e-published Sep. 16, 2012). "Reversible labeling of native and fusion-protein motifs," Nat Methods 9(10):981-984.
Lambalot, R.H. et al. (Oct. 20, 1995). "Cloning, overproduction, and characterization of the *Escherichia coli* holo-acyl carrier protein synthase," *J Biol Chem* 270(42):24658-24661.
Lee, J.H. et al. (Febraury 2013, e-published Aug. 17, 2012). "Glutamine (Q)-peptide screening for transglutaminase reaction using mRNA display," *Biotechnol Bioeng* 110(2):353-362.

(Continued)

*Primary Examiner* — James H Alstrum Acevedo
*Assistant Examiner* — Tara Martinez
(74) *Attorney, Agent, or Firm* — Zachary L. Terranova; Mintz, Levin, Cohn, Ferris, Glovsky and Popeo, P.C.

(57) ABSTRACT

Provided herein, inter alia, are methods and compositions for removing a phosphopantethiene analog moiety from an ACP-phosphopantetheine conjugate thereby providing Apo-ACP proteins.

16 Claims, 56 Drawing Sheets

(56) References Cited

OTHER PUBLICATIONS

Mayfield, S.P. et al. (Feb. 2004). "Development of a luciferase reporter gene, luxCt, for Chlamydomonas reinhardtii chloroplast," *Plant J* 37(3):449-458.

McCafferty, D.G. et al. (Aug. 26, 1997). "Mutational analysis of potential zinc-binding residues in the active site of the enterococcal D-Ala-D-Ala dipeptidase VanX," *Biochemistry* 36(34):10498-10505.

Meier, J.L. et al. (Aug. 15, 2010, e-published Jun. 17, 2010). "A mechanism based protein crosslinker for acyl carrier protein dehydratases," *Bioorg Med Chem Lett* 20(16):4936-4939.

Meier, J.L. et al. (Feb. 2011, e-published Nov. 17, 2010). "Proteomic analysis of polyketide and nonribosomal peptide biosynthesis," *Curr Opin Chem Biol* 15(1):48-56.

Mosiewicz, K.A. et al. (May 5, 2010). "Phosphopantetheinyl transferase-catalyzed formation of bioactive hydrogels for tissue engineering," *J Am Chem Soc* 132(17):5972-5974.

Quadri, L.E. et al. (Feb. 10, 1998). "Characterization of Sfp, a Bacillus subtilis phosphopantetheinyl transferase for peptidyl carrier protein domains in peptide synthetases," *Biochemistry* 37(6):1585-1595.

Rashidian, M. et al. (May 23, 2012, e-published May 8, 2012). "Chemoenzymatic reversible immobilization and labeling of proteins without prior purification," *J Am Chem Soc* 134(20):8455-8467.

Takahara, M. et al. (Dec. 2013, e-published Jun. 25, 2013). "Tailing DNA aptamers with a functional protein by two-step enzymatic reaction," *J Biosci Bioeng* 116(6):660-665.

Thomas, J. et al. (Jan. 2007). "Acyl carrier protein phosphodiesterase (AcpH) of *Escherichia coli* is a non-canonical member of the HD phosphatase/phosphodiesterase family," *Biochemistry* 46(1):129-136.

Williamson, D.J. et al. (Sep. 10, 2012, e-published Aug. 13, 2012). "Efficient N-terminal labeling of proteins by use of sortase," *Angew Chem Int Ed Engl* 51(37):9377-9380.

Written Opinion dated Dec. 23, 2013, for PCT Application No. PCT/US2013/059792, filed Sep. 13, 2013, 16 pages.

* cited by examiner

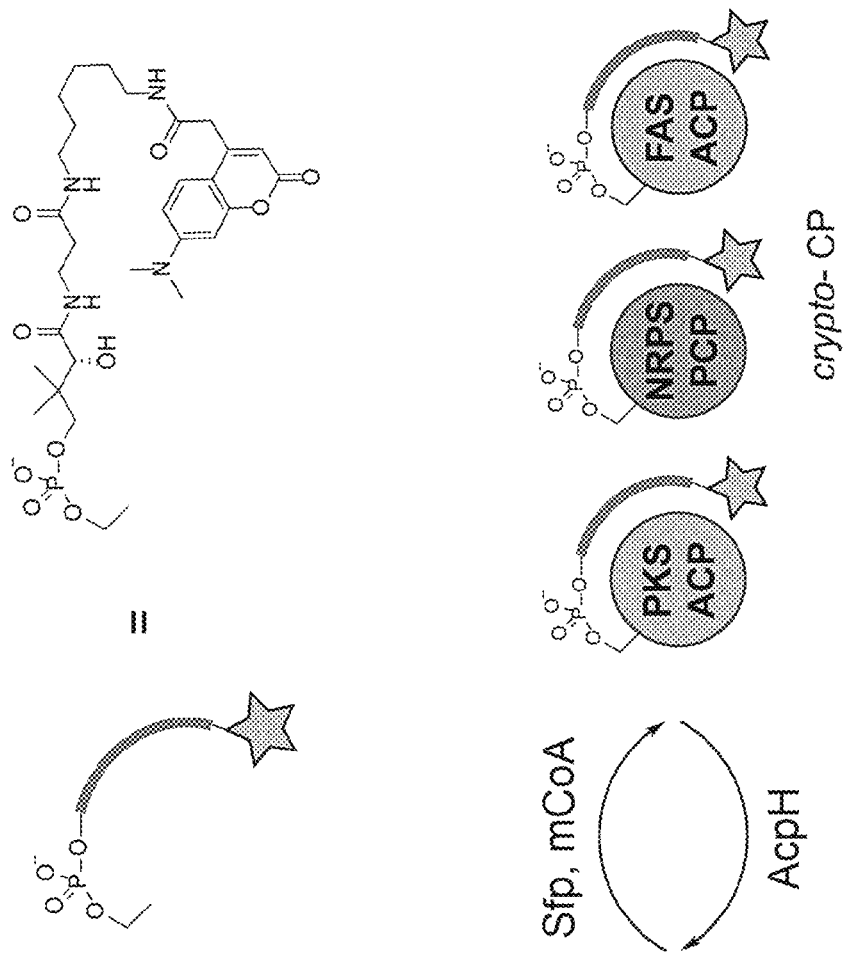
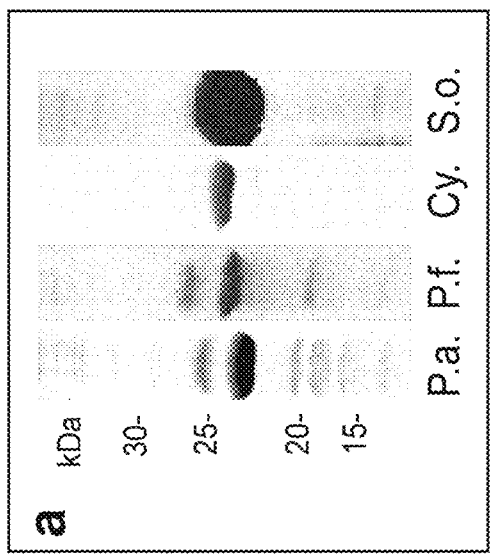
Fig. 2A
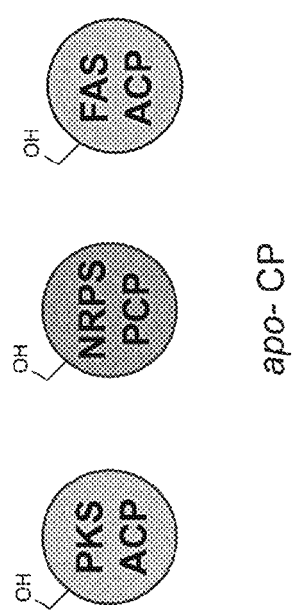
Fig. 2B

Cyanothece
PCC 7822
AcpH

Pseudomonas
aeruginosa
AcpH

P. fluorescens    S. oneidensis

Fig. 19

EcAcpH    MNFLAHLHLAHLAESSLSGNLLADFVRGNPE----ESFPPDVVAGIHMHRIDVLIDNLPE
CyAcpH    MNYLAHLFLADFTPESQIGNLLGDFVKGKIDNLSSIYSPEIIRGVKTHQKIDFFDHHPI
PaAcpH    MNYLAHLHLGGPQAQLLGSLYGDFVKGRLQ----GQWPDEIERAIQLHERIDAFTDRHPL
PfAcpH    MNYLAHLHIGGQLPAQILGSLYGDFVKGRLQ----GQFSPQIEAAIQLHRSIDFFTDSHPL
SoAcpH    MNILTLHLHLAEISKTHLGANLAGNFITAPIEN------APRALRQGLWLNNEIDLQATHEL
            :*.*                         .:  *:  :   :  :   :

EcAcpH    VREAREWFRNETRRVAPITLDVMDHFLSRHWSQLSPDFLQEFTCYAREQVMIL------
CyAcpH    FKTSKQRLNQNHRKFAGVIIDIYYDHFLAKNWLIYS-EQDLDEFVANTYQMLEQHQ---
PaAcpH    VHAAKRRFPLERRFFAGVLLDVFFDHCLARDWNDYA-DEPLPQFVERVYGTLRTA----
PfAcpH    VGEALSRFSQTRRRYAGIVLDVFEDHCLARDWALYA-DQPLERFTSHVYQVLAAE----
SoAcpH    TQELMALFPTQLTSIATDLMFVSFDHYLAFYWEEYH-HLPLPEFSQKAYAELAQYAAKAD
              :  *          *:: .:**:*:  *  :    * :*.:   : :

EcAcpH    PDSPPRFINLNNYLWSERWLVRYRDMDFIQSVLNGMASRRPPLDALRDSWYDLDAHYDAL
CyAcpH    LLLPEKLQKALPCMIQEDWLGSYRYFEGIDQTFSRLSRRIKRTNNIAFALEDLIONYSQL
PaAcpH    SPLPERLARIAPRMAAQDWLGSYREFAVLREVLGGMSRRLSRPHLLDGSWEELAQRYDDL
PfAcpH    PALPGRLAQIAPYMAADDWLGSYREAVMEQVIRGISRRLTQPEELGYAMQELRVLYEPL
SoAcpH    EVHPQPYLNIITDMHPEDWLNNYATPKGIQQALAQRAKGHPQSALFSGADKILAKMQIET
              :    :      ::  *.:                   ::     :

EcAcpH    ETRFWQFYPRMMEQASRKAL-----
CyAcpH    EEDFLQFFQLIDYVNLA--------
PaAcpH    SADFRAFYPQLQAFALSQR------
PfAcpH    SEDFRLFYPELQAFALQF-------
SoAcpH    ETAFRTFYPQLMAYTRIWSRKTPIDYLPE
          .  * :* :::

☐ = Proposed Mn²⁺ binding residues

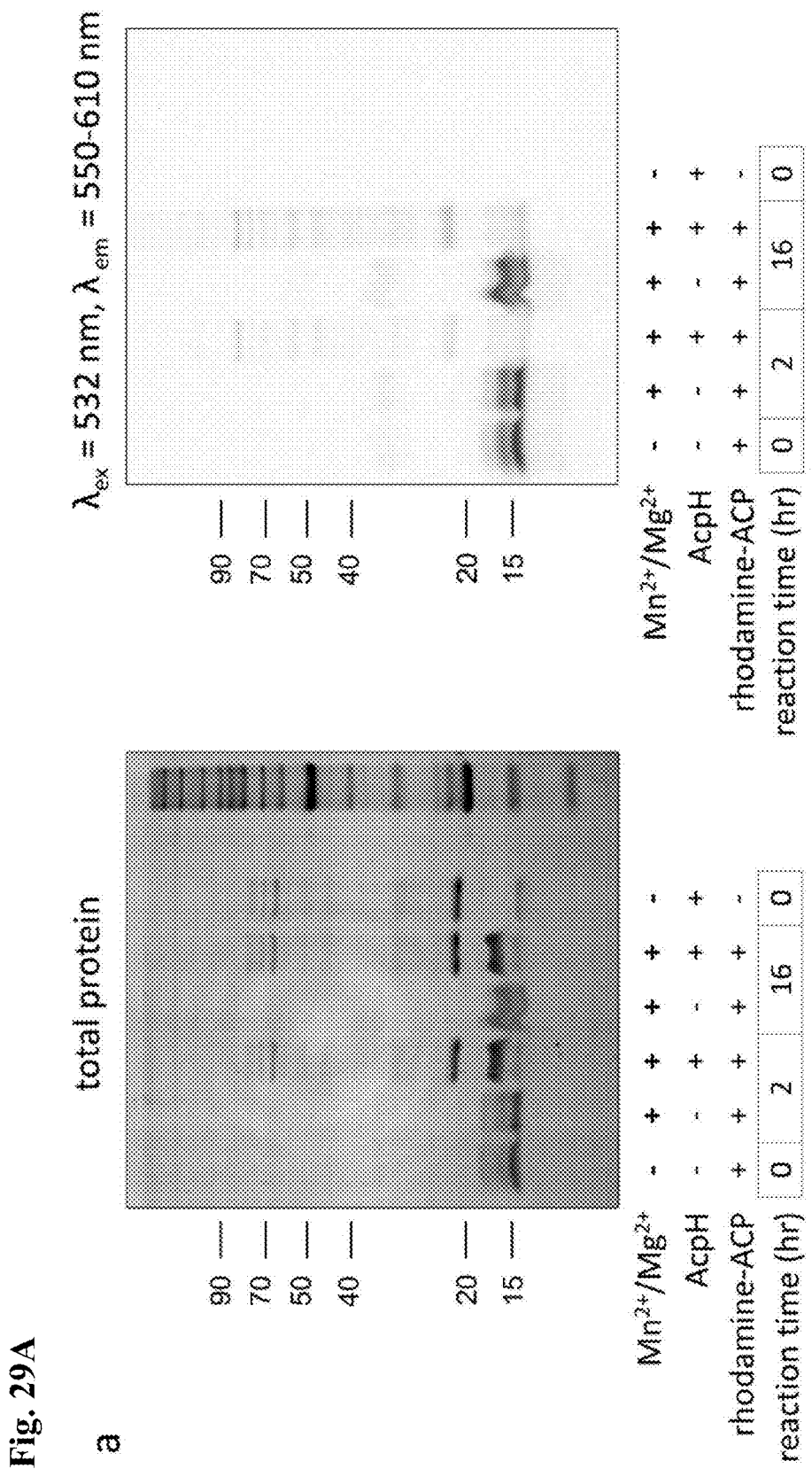

MBP-PaACP

GFP-ACP

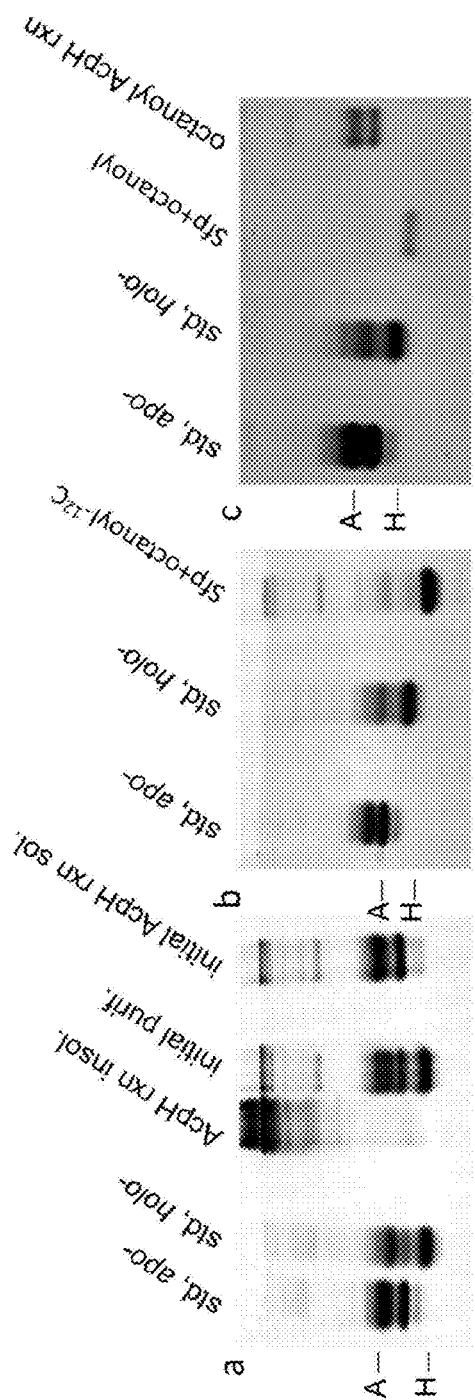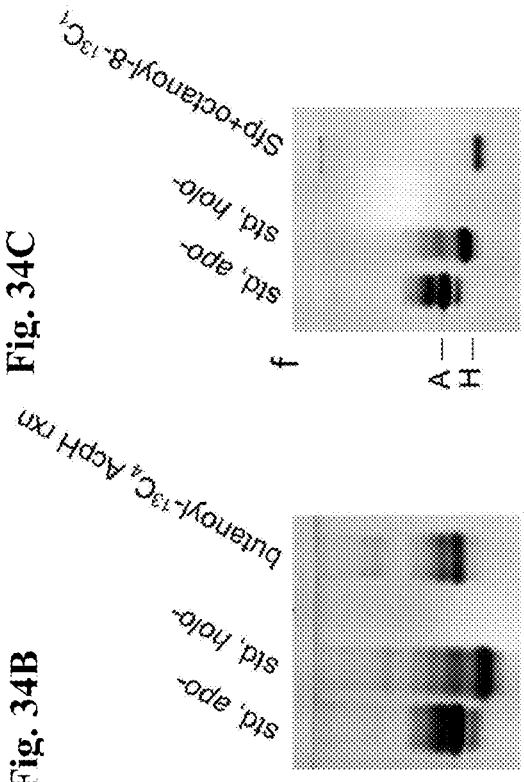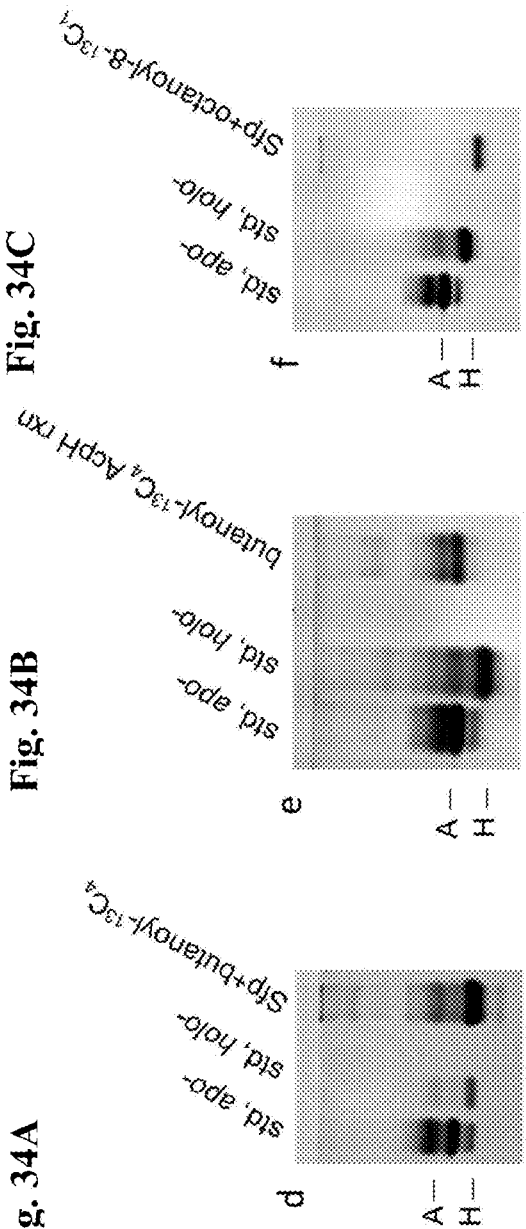
Fig. 34A Fig. 34B Fig. 34C Fig. 34D Fig. 34E Fig. 34F

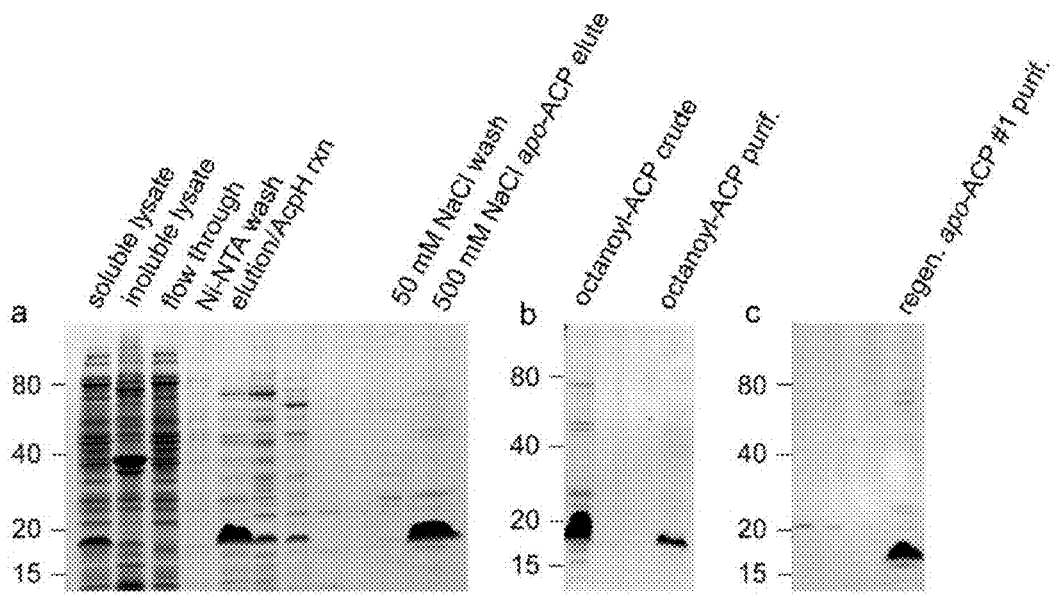
Fig. 35A      Fig. 35B      Fig. 35C
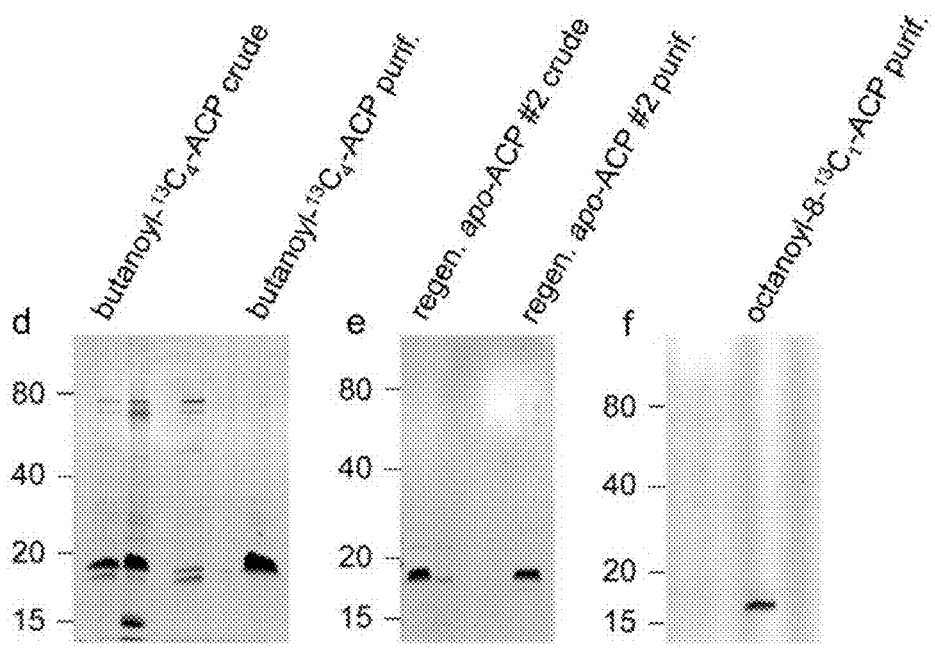
Fig. 35D      Fig. 35E      Fig. 35F

$\lambda_{ex}$ = UV
$\lambda_{em}$ = visible $\lambda_{ex}$ = 532 nm
$\lambda_{em}$ = 550-610 nm total protein

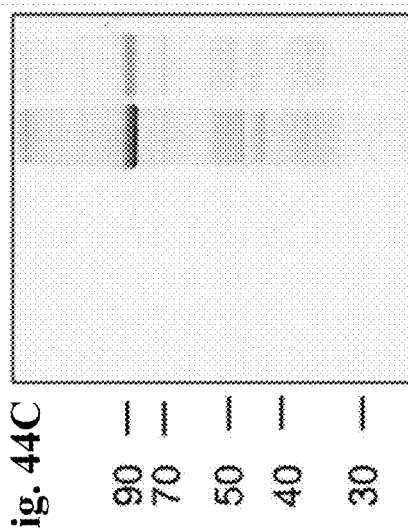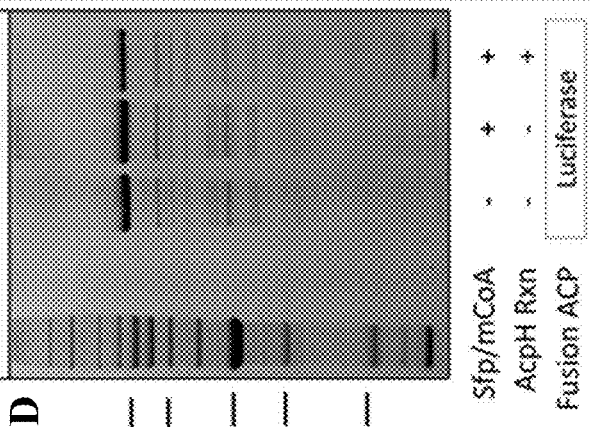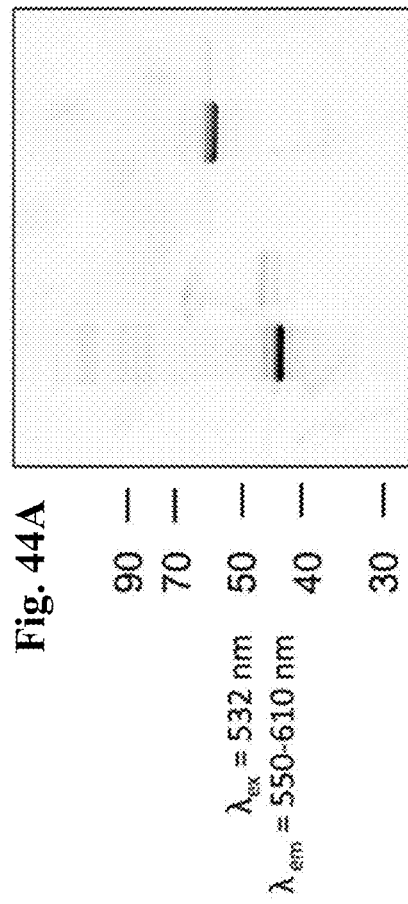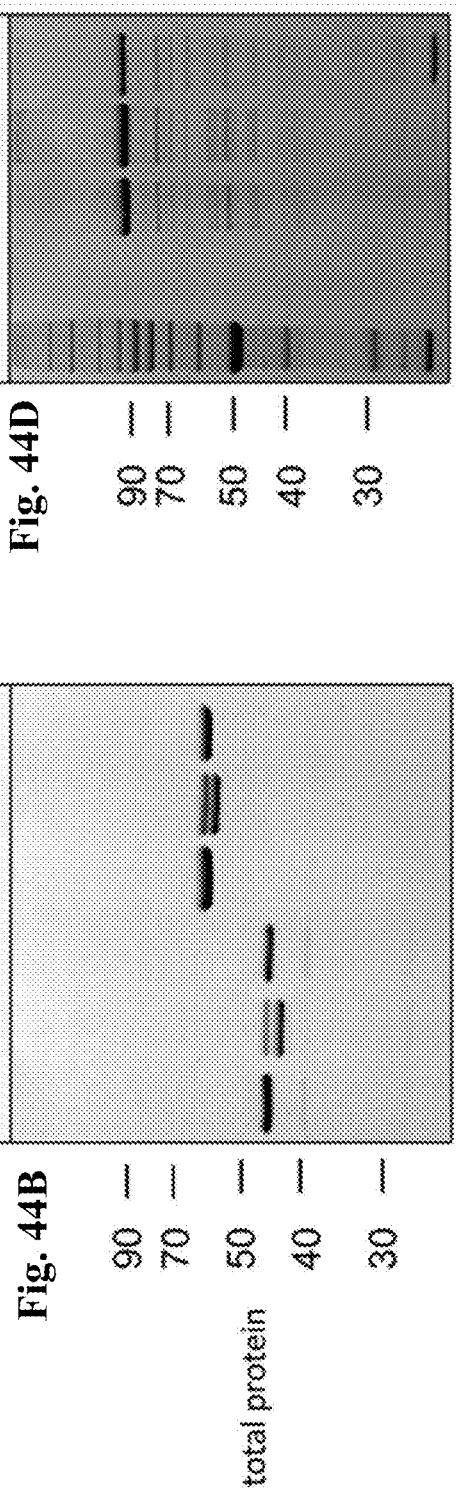
Fig. 44A
Fig. 44B
Fig. 44C
Fig. 44D

REVERSIBLE CHEMOENZYMATIC LABELING OF NATIVE AND FUSION CARRIER PROTEIN MOTIFS

CROSS-REFERENCES TO RELATED APPLICATIONS

This application is a continuation of International Appl. No. PCT/US2013/059792, filed Sep. 13, 2013, which in turn claims priority to U.S. Provisional Application No. 61/701,166, filed Sep. 14, 2012, each of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support under grant number R21AI090213 and R01GM094924 awarded by the National Institutes of Health. The Government may have certain rights in this invention.

REFERENCE TO A "SEQUENCE LISTING," A TABLE, OR A COMPUTER PROGRAM LISTING APPENDIX SUBMITTED ON A COMPACT DISK

The Sequence Listing written in file 48537-526N01US_ST25.TXT, created on Mar. 10, 2015, 81,699 bytes, machine format IBM-PC, MS Windows operating system, is hereby incorporated by reference.

BACKGROUND OF THE INVENTION

Post-translational protein modification plays a pivotal role in selective protein functionalization for therapeutics, protein engineering, affinity design, and enzyme immobilization, among other applications.[1] Within these, acyl carrier protein (ACP) labeling by 4'-phosphopantetheinyltransferase (PPTase) offers a highly versatile tool for site-selective covalent protein modification. Labeling of ACP fusion proteins represents one of the most flexible covalent protein labeling methods, as illustrated by orthogonal tagging with ACP peptides, bio-gel formation, and protein immobilization.[2] This technique has also been successfully leveraged for visualization, isolation, functional, and structural studies of carrier protein-dependent biosynthetic enzymes.[3] However, further advancement of these tools has been hampered by an inability to reverse this post-translational modification. Indeed, naturally occurring ACPs, often isolated in holo-form, may not be further modified selectively. Thus, there is a need in the art for reversibly labeling an ACP with a phosphopantetheine and with functionalized phosphopantetheine analogs. Provided herein are solutions to these and other problems in the art.

BRIEF SUMMARY OF THE INVENTION

Accordingly, herein are provided, inter alia, methods for reversibly labeling acyl carrier proteins (ACP) with pantethiene analogues.

In a first aspect is a method of forming an Apo-ACP from an ACP-phosphopantetheine conjugate. The method includes contacting an ACP-phosphopantetheine conjugate with an ACP hydrolase. The ACP-phosphopantetheine conjugate is composed of a phosphopantetheine analogue moiety covalently bonded to an ACP through a phosphodiester linker. The ACP hydrolase is allowed to cleave the phosphodiester linker thereby forming an Apo-ACP. The ACP-phosphopantetheine conjugate has the formula:

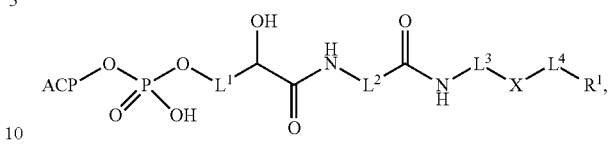

ACP is an ACP protein moiety or an ACP protein fusion moiety. $L^1$, $L^2$ and $L^3$ are independently substituted or unsubstituted alkylene. $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. X is —S—, —NH— or —O—. $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, a detectable moiety or a reactive probe.

In another aspect is provided a compound including an amino acid sequence having the formula:

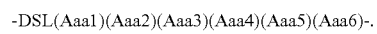

Aaa1 is D, E, or S. Aaa2 is T, F, or W. Aaa3 is V, L, or I. Aaa4 is E, A, or L. Aaa5 is A, S, R, or L. Aaa6 is V, K, or L. The sequence is not -DSLDTVELV-.

In another aspect is a compound having formula:

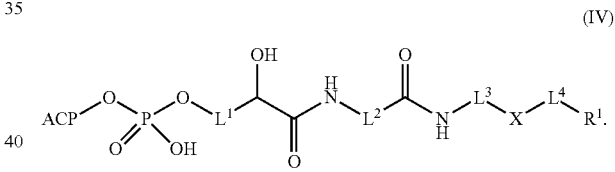

ACP is an ACP protein moiety or an ACP protein fusion moiety. $L^1$, $L^2$ and $L^3$ are independently substituted or unsubstituted alkylene. $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. X is —S—, —NH— or —O—. $R^1$ is substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene, a detectable moiety or a reactive probe.

In another aspect is a kit for reversibly labeling an ACP. The kit includes an ACP hydrolase and a phosphopantetheinyl transferase.

BRIEF DESCRIPTION OF THE DRAWINGS

FIGS. 2A-2B: AcpH homolog activity against crypto-CP. AcpH homologs were cloned and expressed as soluble proteins (FIG. 2A); Crypto-carrier proteins (CP) were generated by labeling apo-CP with Sfp and modified coenzyme A (mCoA) generated in situ with CoaA, CoaD, CoaE, ATP and coumarin-pantetheine (FIG. 2B); the most active substrates were from FAS and PKS-type CP.

FIGS. 3A-3B: AcpH accommodates multiple ybbR modifications. Various ybbR peptide substrate variations were evaluated for AcpH activity (FIG. 3A) qualitatively as well as quantitatively using a FRET quench assay (FIG. 3B). PfAcpH was found to accommodate all ybbR appendages, and generate useful kinetic data.

FIG. 13A: Analysis of AcpH activity with holo-SoAcpP at various time-points: AcpH homologs from P. fluorescens (Pf), P. aeruginosa (Pa), Cyanothece PCC 7822 (Cy) and S. oneidensis (So) are evaluated by Urea-PAGE with holo-CP (+) compared to buffer blanks (−E) after various incubation times at 37° C.; Samples were quenched with EDTA at listed times; FIG. 13B: Blank samples were also prepared without $Mn^{2+}$ (−E-Mn) and without $Mn^{2+}/Mg^{2+}$ in order to evaluate non-enzymatic PPant hydrolysis.

FIG. 19: Sequence alignment of known active AcpH homologs to SoAcpH: Known active AcpH homologs from E. coli (EcAcpH) (SEQ ID NO:73),[1,2] Cyanothece PCC7822 (CyAcpH) (SEQ ID NO:74), P. aeruginosa (PaAcpH) (SEQ ID NO:75),[3,4] and P. fluorescens (PfAcpH) (SEQ ID NO:76) are aligned.

(FIG. 20C) rhodamine-PPant conjugate was synthesized for FRET kinetics evaluation (SEQ ID NO:80)

```
EcAcpP:
                                 (SEQ ID NO: 81)
ASFVEDLGADSLDTVELVMAL

PaAcpP:
                                 (SEQ ID NO: 82)
ASFVEDLGADSLDTVELVMAL

SoAcpP:
                                 (SEQ ID NO: 83)
ASFVDDLGADSLDTVELVMAL

Plas. ACP:
                                 (SEQ ID NO: 84)
SNFTKDLGADSLDLVELIMAL MtbAcpM:
                                 (SEQ ID NO: 85)
KSFVEDLDIDSLSMVEIAVQT PksA:
                                 (SEQ ID NO: 86)
DSNFADMGIDSLSSMVIGSRF Pks4:
                                 (SEQ ID NO: 87)
TTLLADLGVDSLMSLTILGNF JamC:
                                 (SEQ ID NO: 88)
STSFNRYGLDSSASISLTSDF ActACP:
                                 (SEQ ID NO: 89)
DLRFEDIGYDSLALMETAARL Ybbr13
                                 (SEQ ID NO: 1),
```

Figure 1:
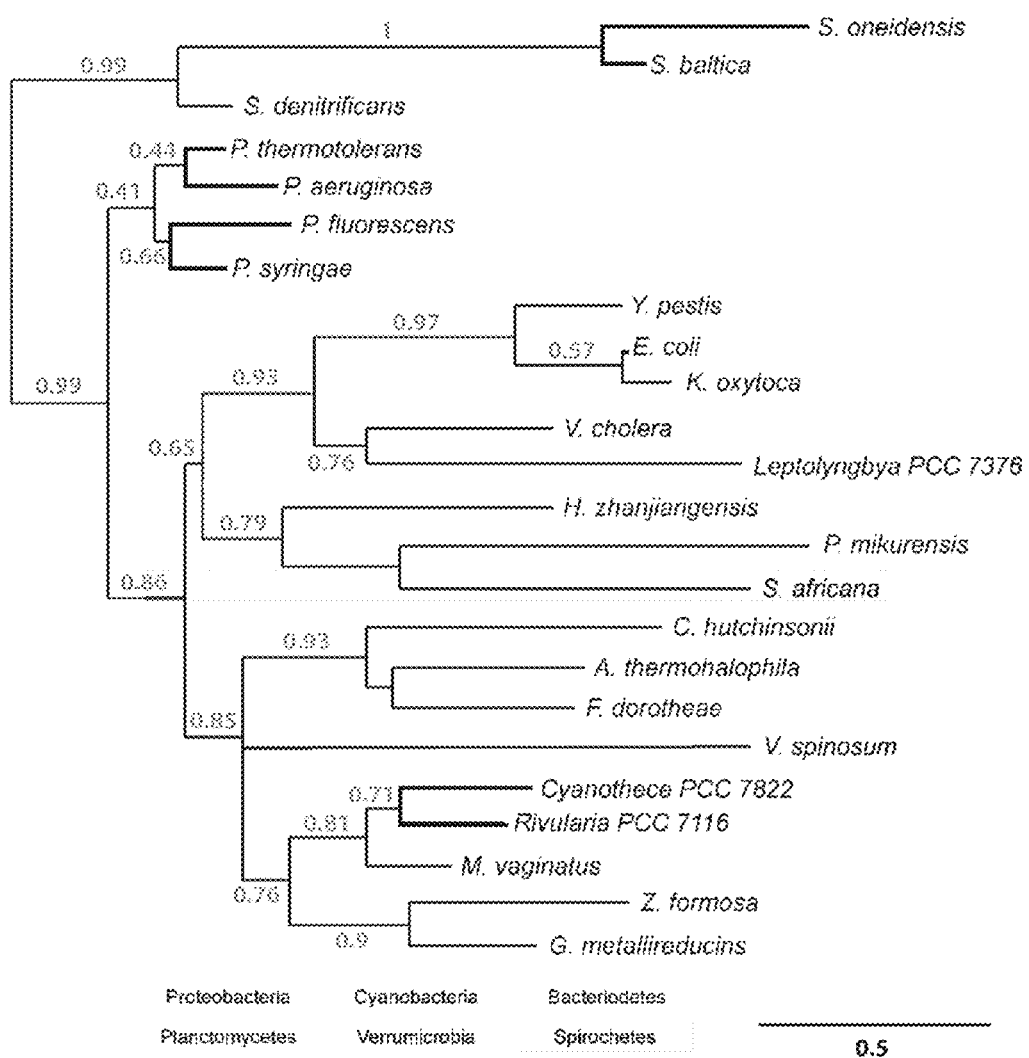
FIG. 1: Phylogenetic analysis of AcpH homologs: Phylogenetic map calculatings are derived from protein sequences using Phylogeny.fr web utility.
Figure 3A:
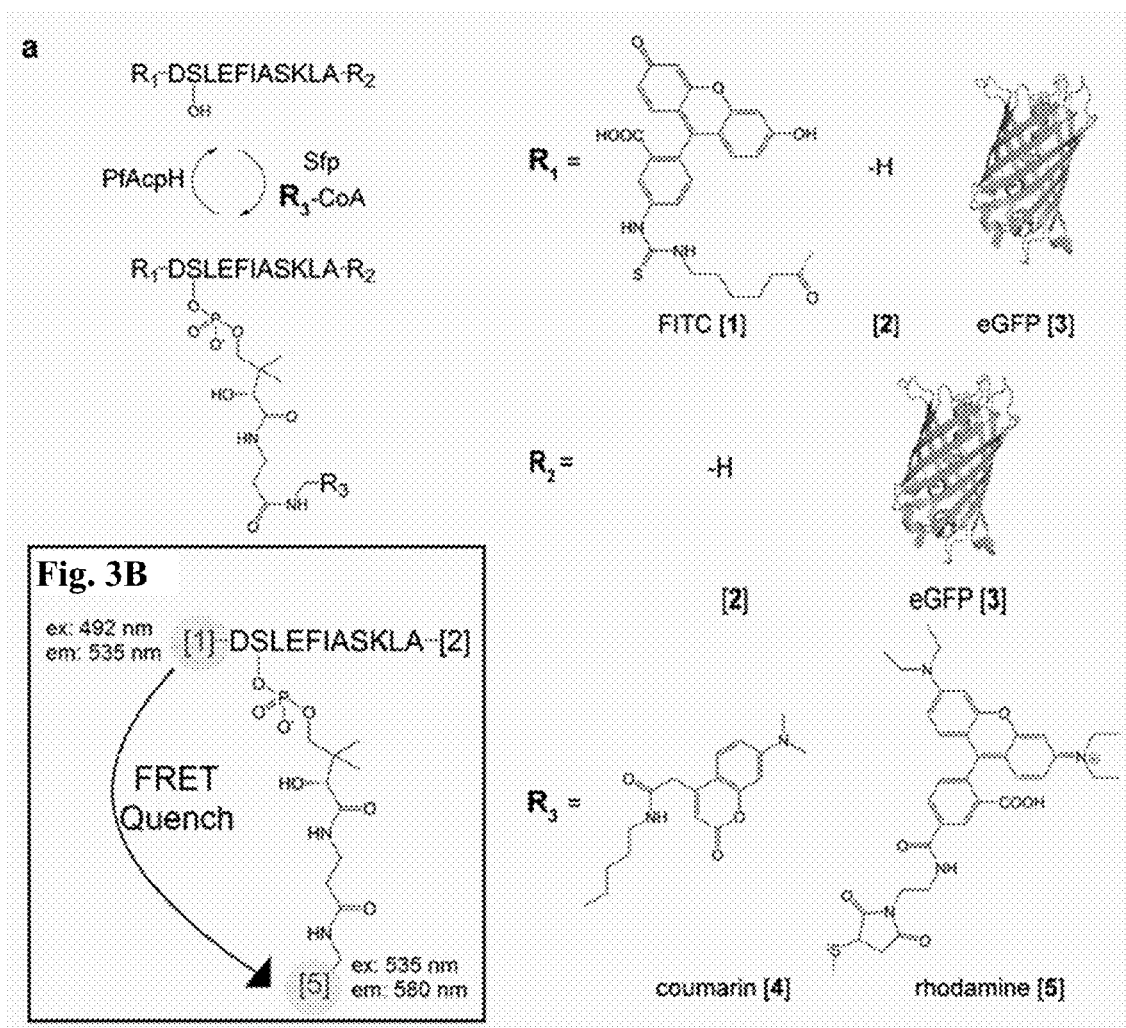
Figure 4A:
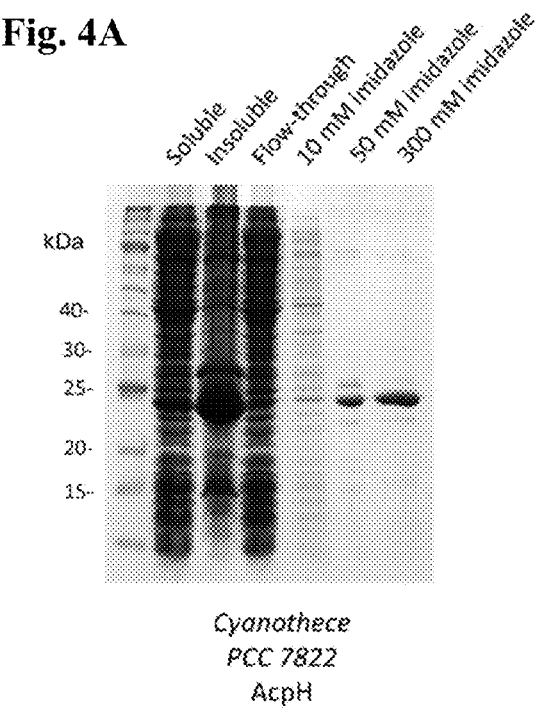
FIGS. 4A-4C: Purification of AcpH protein homologs: AcpH homolog protein from Cyanothece PCC7822 (FIG. 4A), P. aeruginosa (FIG. 4B), P. fluorescens (FIG. 4C), and S. oneidensis (FIG. 4C) was expressed recombinantly and purified using Ni-NTA chromatography.
Figure 4B:
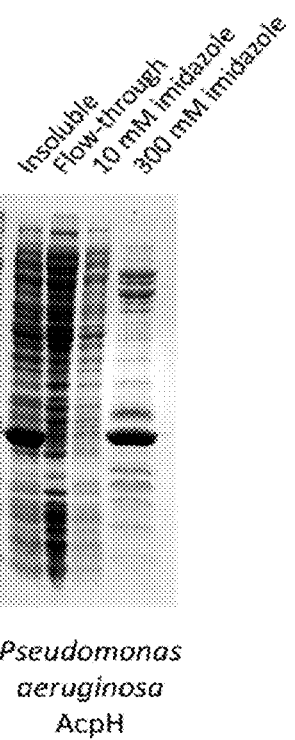
Figure 4C:
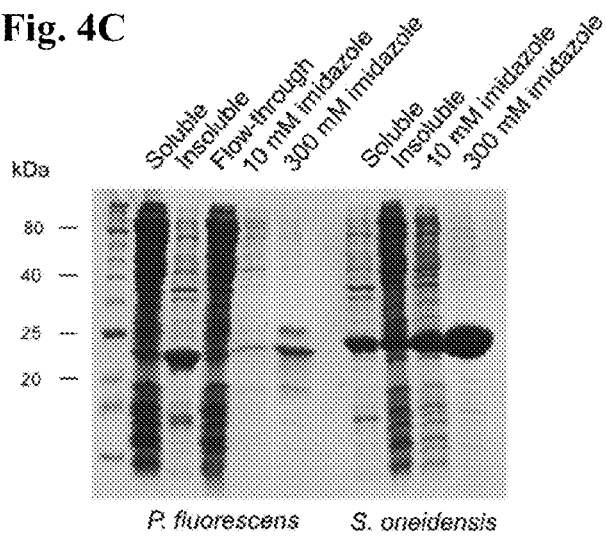
Figure 5:
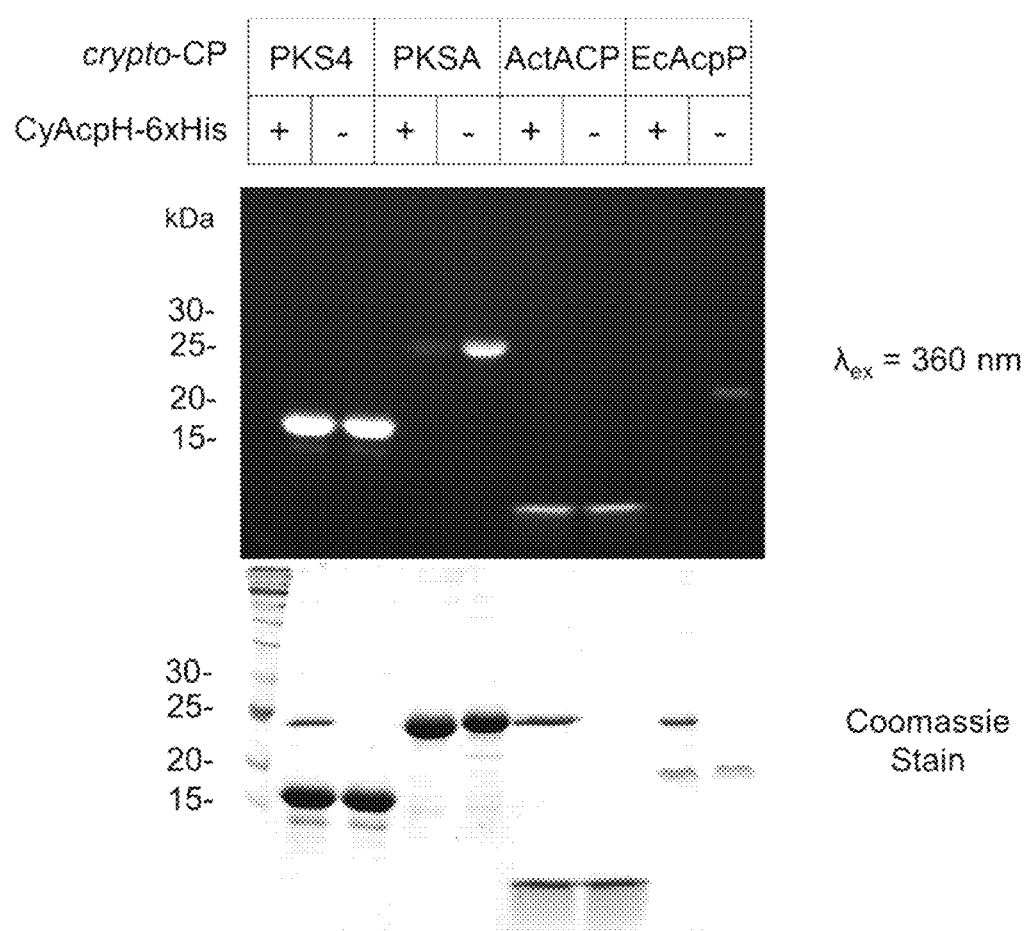
FIG. 5: Analysis of CyAcpH activity with PKS-ACP and E. coli AcpP: CyAcpH is evaluated by SDS-PAGE with various crypto-CP (+) compared to buffer blanks (−) after overnight incubation at 37° C.
Figure 6:
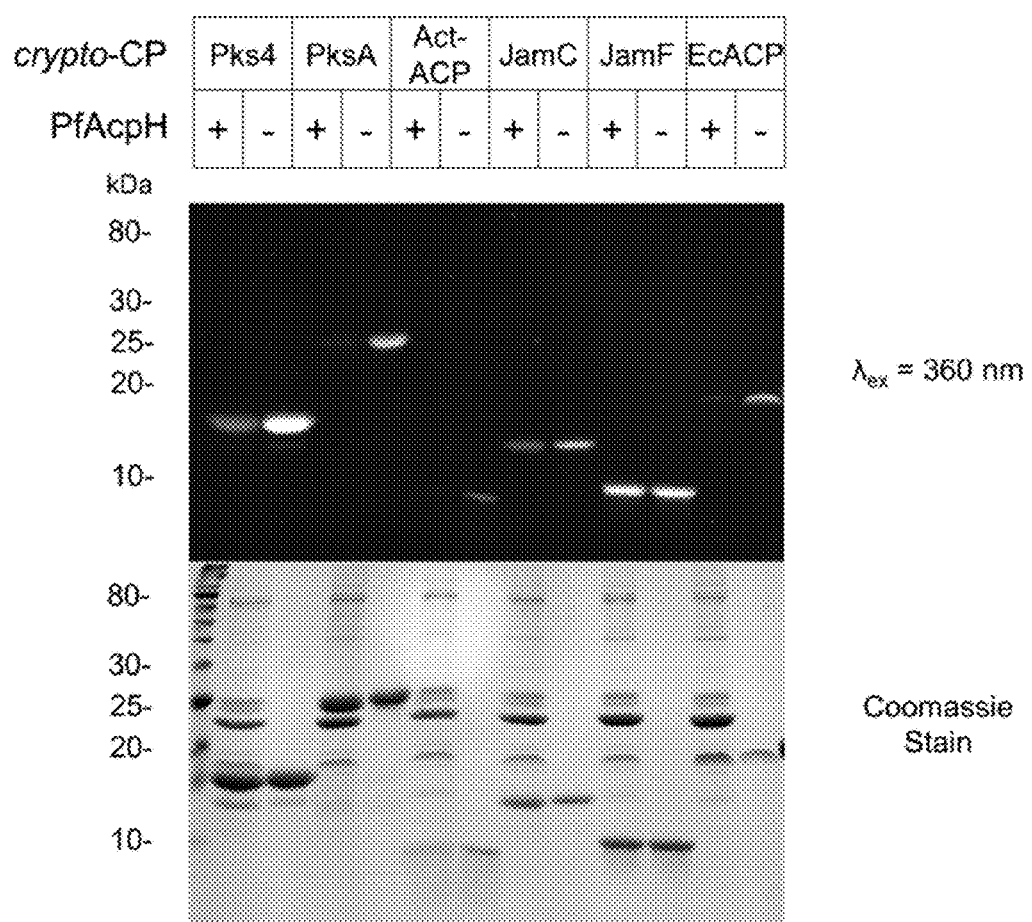
FIG. 6: P. fluorescens AcpH activity vs. various CP: PfAcpH is evaluated by SDS-PAGE with various crypto-CP (+) compared to buffer blanks (−) after overnight incubation at 37° C.
Figure 7:
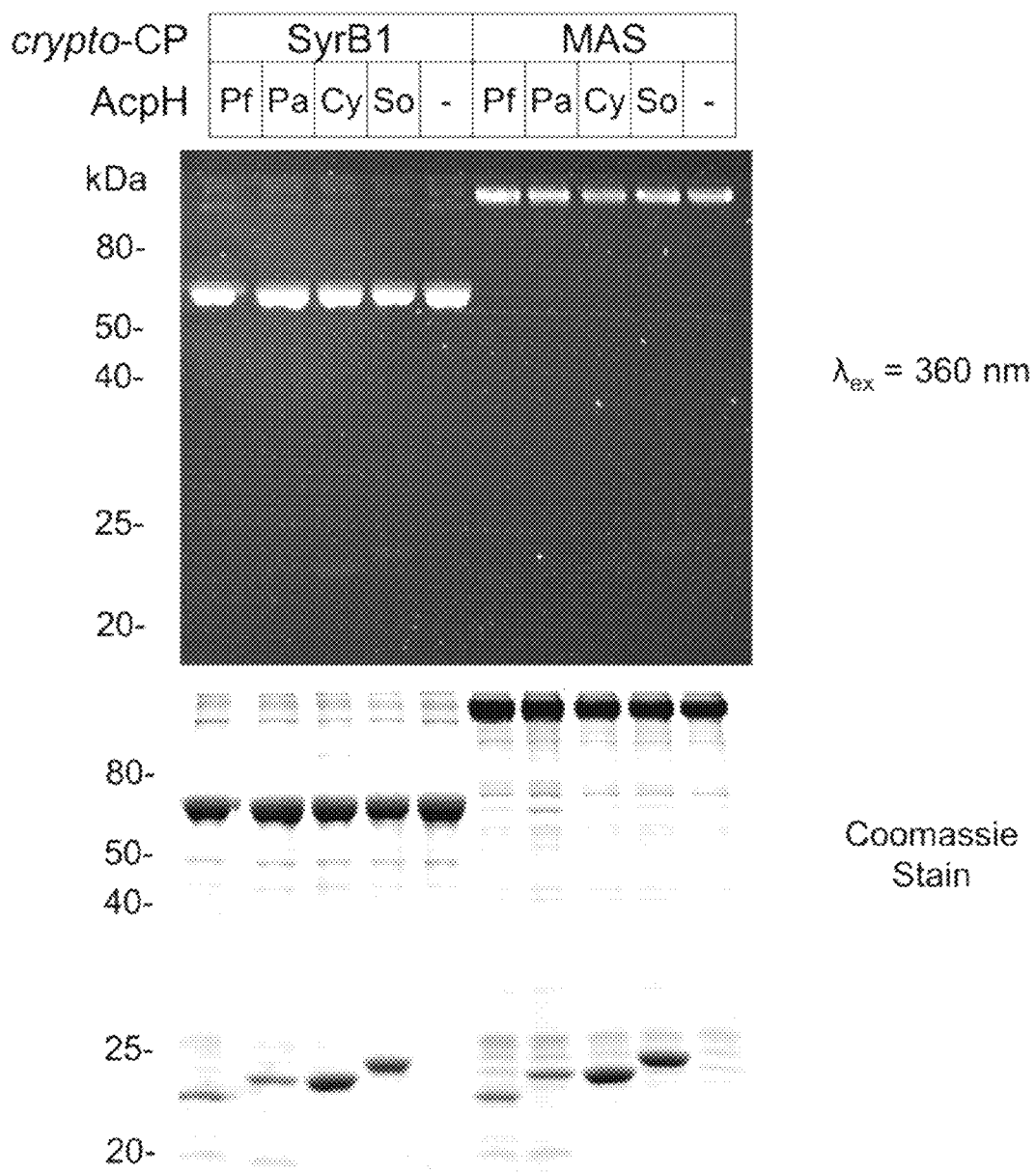
FIG. 7: Analysis of AcpH homolog activity with SyrB1 and MAS: AcpH homologs from P. fluorescens (Pf), P. aeruginosa (Pa), Cyanothece PCC 7822 (Cy) and S. oneidensis (So) are evaluated by SDS-PAGE with various crypto-CP (+) compared to buffer blanks (−) after overnight incubation at 37° C.
Figure 8:
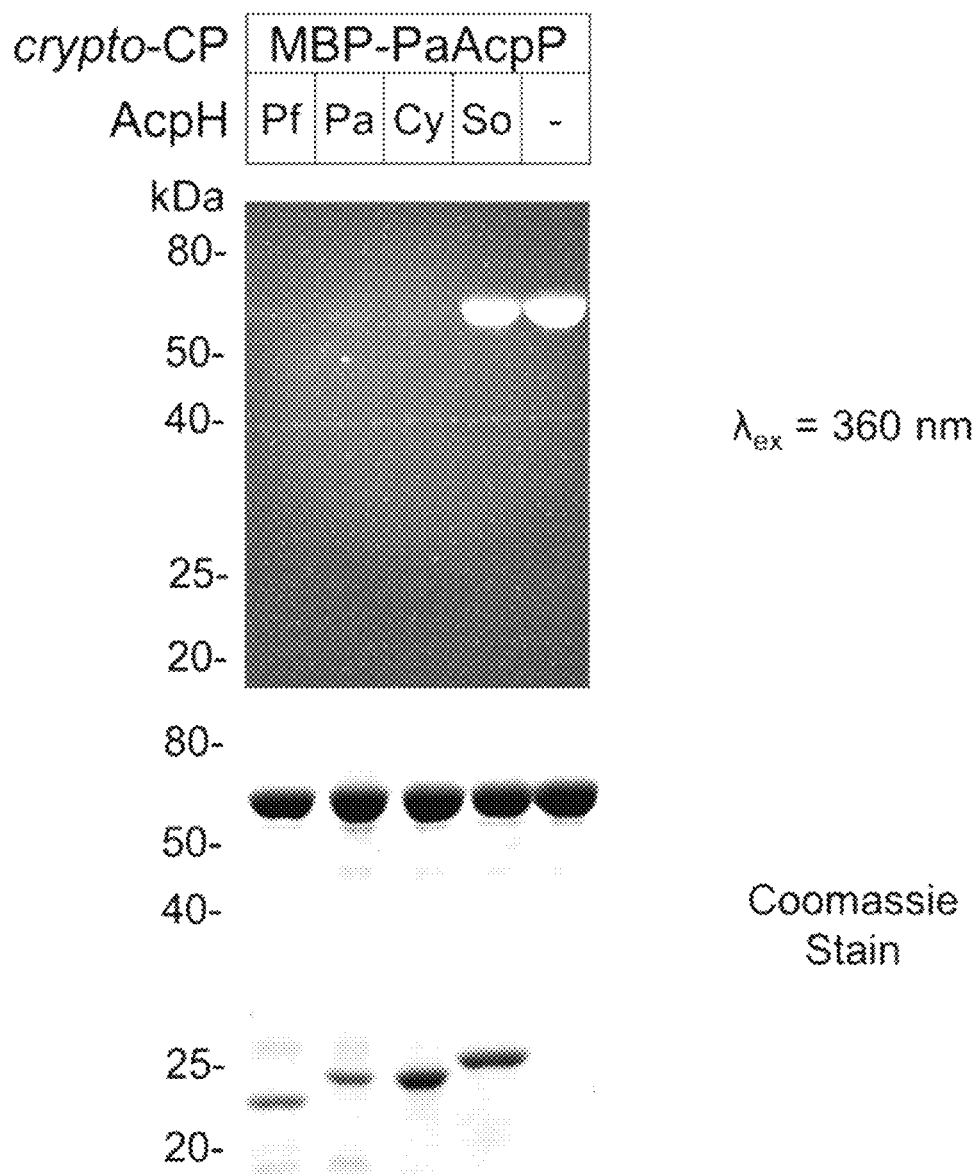
FIG. 8: Analysis of AcpH homolog activity with MBP-PaAcpP: AcpH homologs from P. fluorescens (Pf), P. aeruginosa (Pa), Cyanothece PCC 7822 (Cy) and S. oneidensis (So) are evaluated by SDS-PAGE with various crypto-CP (+) compared to buffer blanks (−) after overnight incubation at 37° C.
Figure 9:
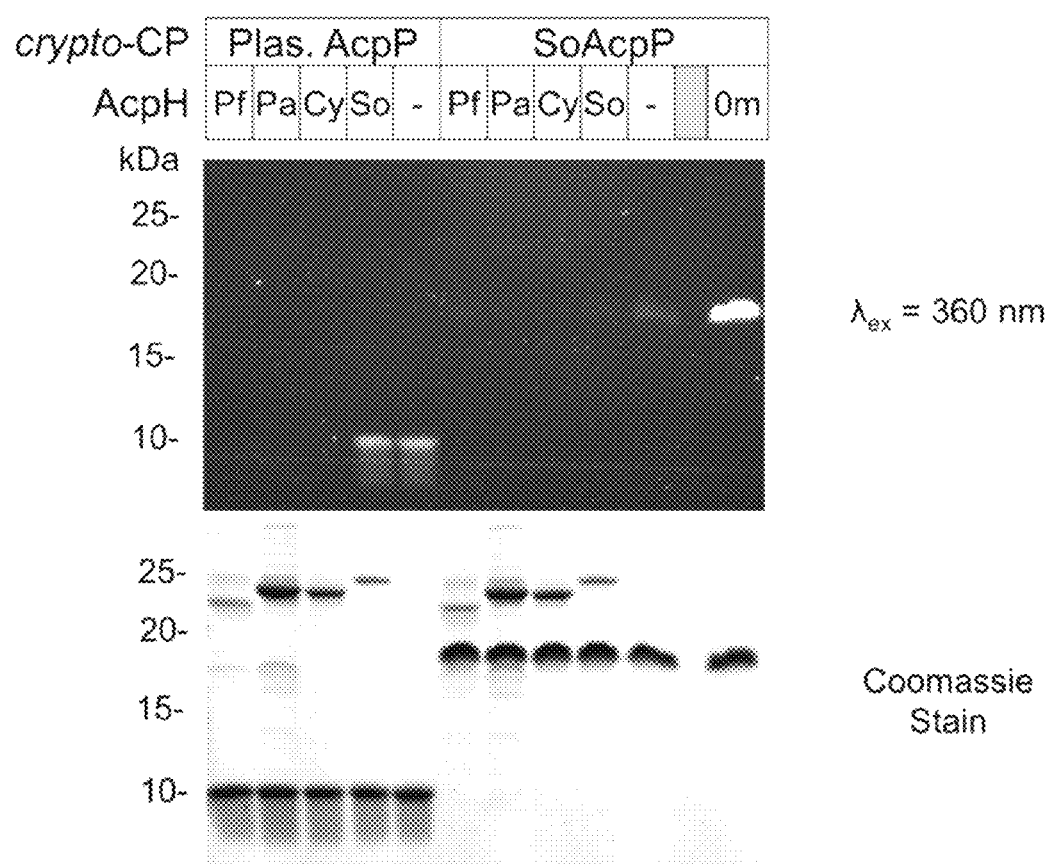
FIG. 9: Analysis of AcpH homolog activity with Plasmodium AcpP and SoAcpP: AcpH homologs from P. fluorescens (Pf), P. aeruginosa (Pa), Cyanothece PCC 7822 (Cy) and S. oneidensis (So) are evaluated by SDS-PAGE with various crypto-CP (+) compared to buffer blanks (−) after overnight incubation at 37° C.; Coumarin-PPant from SoAcpP appeared to hydrolyze overnight in incubated samples compared to non-incubated sample "0m
Figure 10:
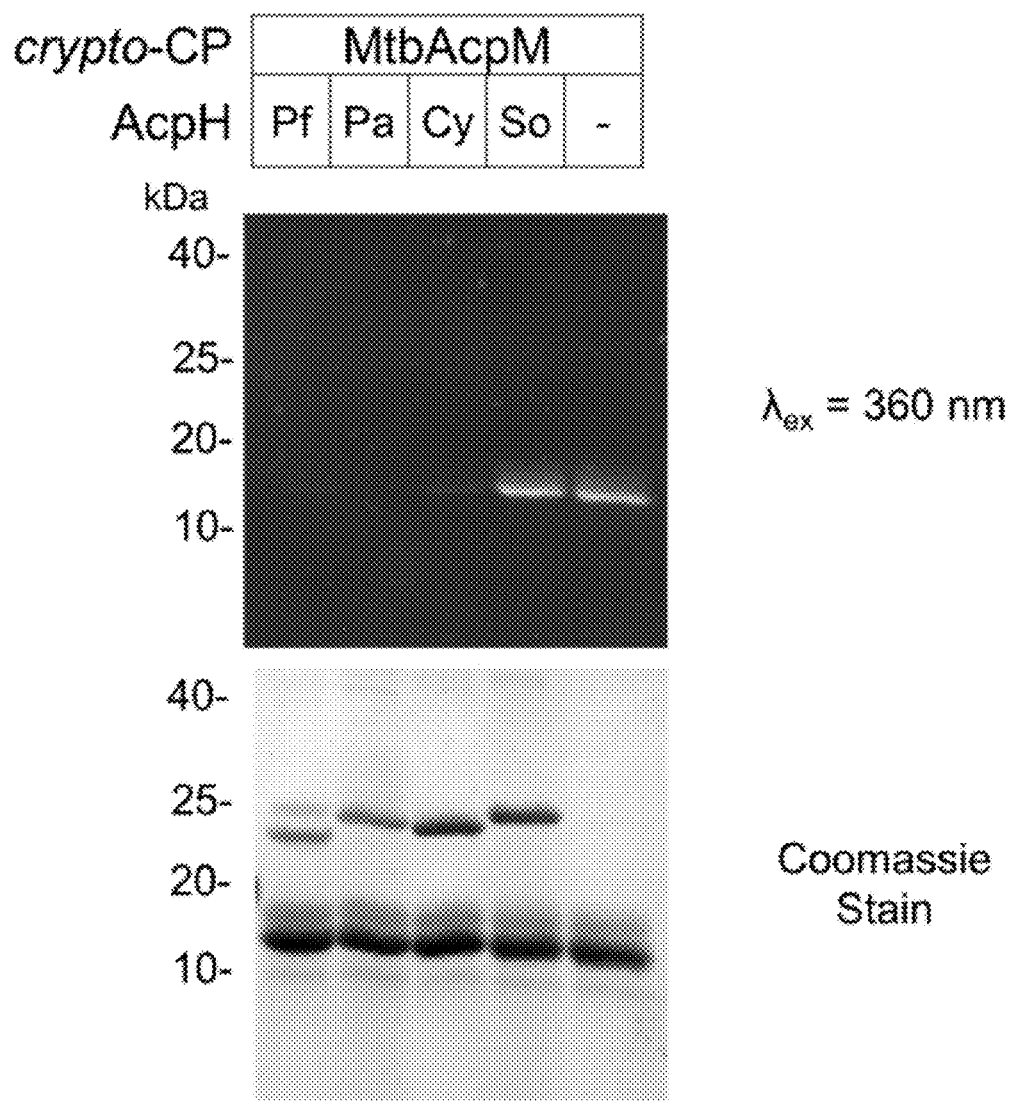
FIG. 10: Analysis of AcpH homolog activity with MtbAcpM: AcpH homologs from P. fluorescens (Pf), P. aeruginosa (Pa), Cyanothece PCC 7822 (Cy) and S. oneidensis (So) are evaluated by SDS-PAGE with various crypto-CP (+) compared to buffer blanks (−) after overnight incubation at 37° C.
Figure 11:
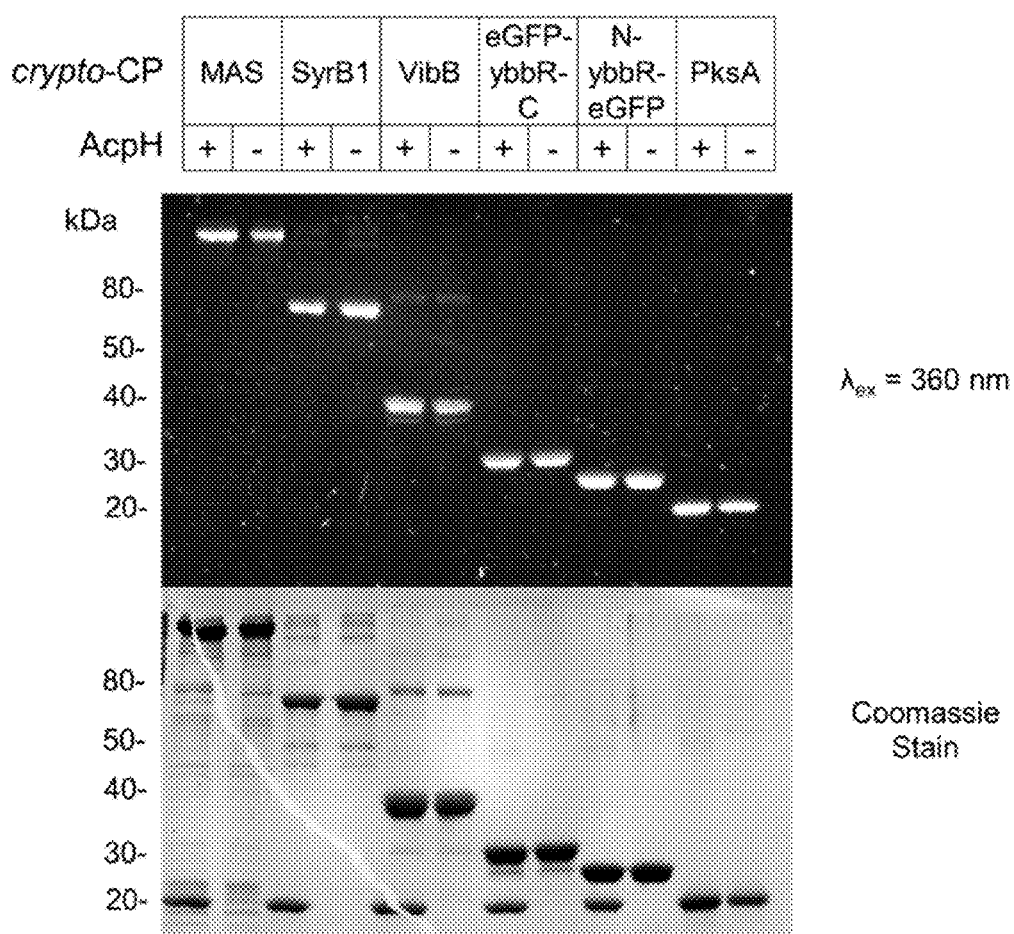
FIG. 11: Analysis of SoAcpH activity with various CP #1: AcpH homolog from S. oneidensis (So) is evaluated by SDS-PAGE with various crypto-CP (+) compared to buffer blanks (−) after overnight incubation at 37° C.: (Sequences in (a) and (b) are identified in SEQ ID NO: 1).
Figure 12:
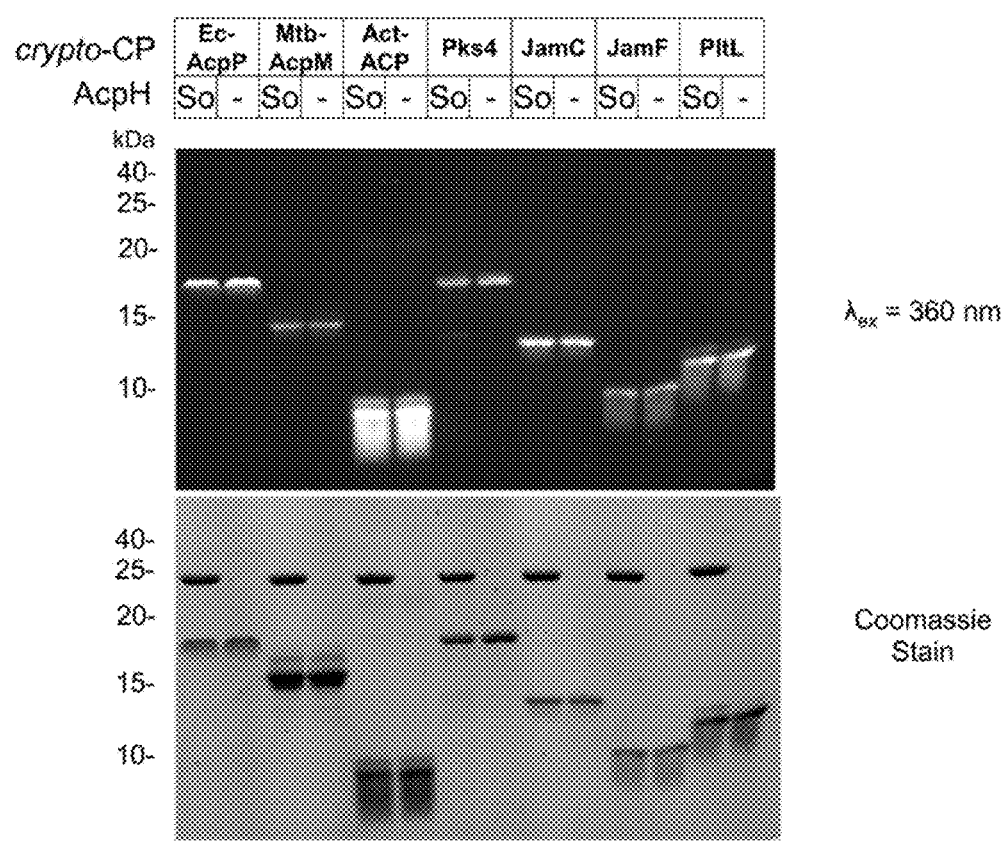
FIG. 12: Analysis of SoAcpH activity with various CP #2: AcpH homolog from S. oneidensis (So) are evaluated by SDS-PAGE with various crypto-CP (+) compared to buffer blanks (−) after overnight incubation at 37° C.
Figure 13A:
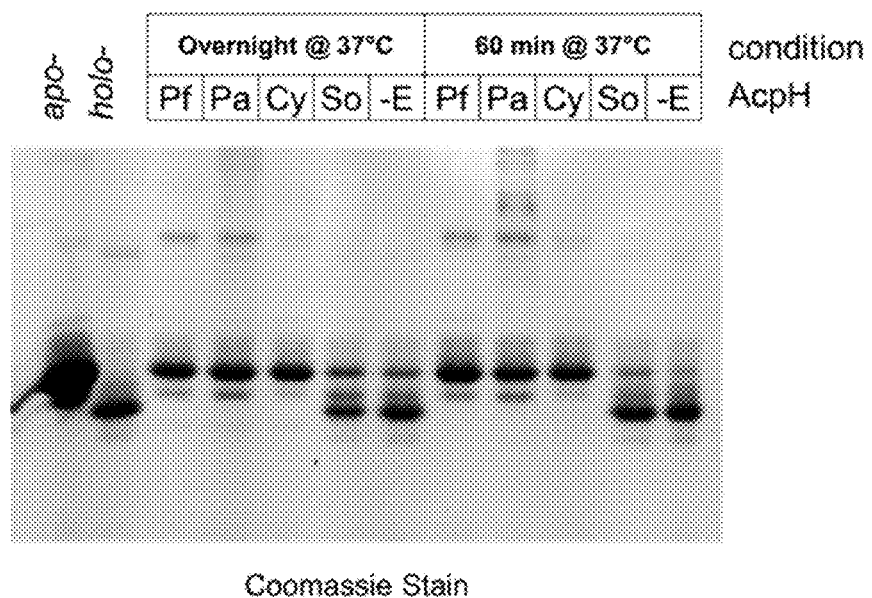
FIGS. 13A-13B.
Figure 13B:
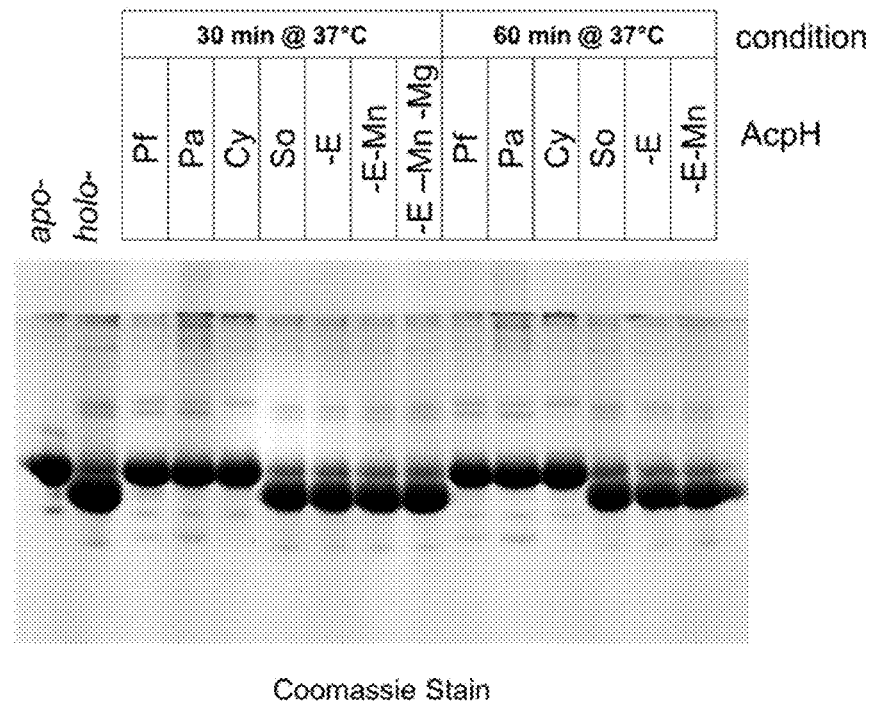
Figure 14:
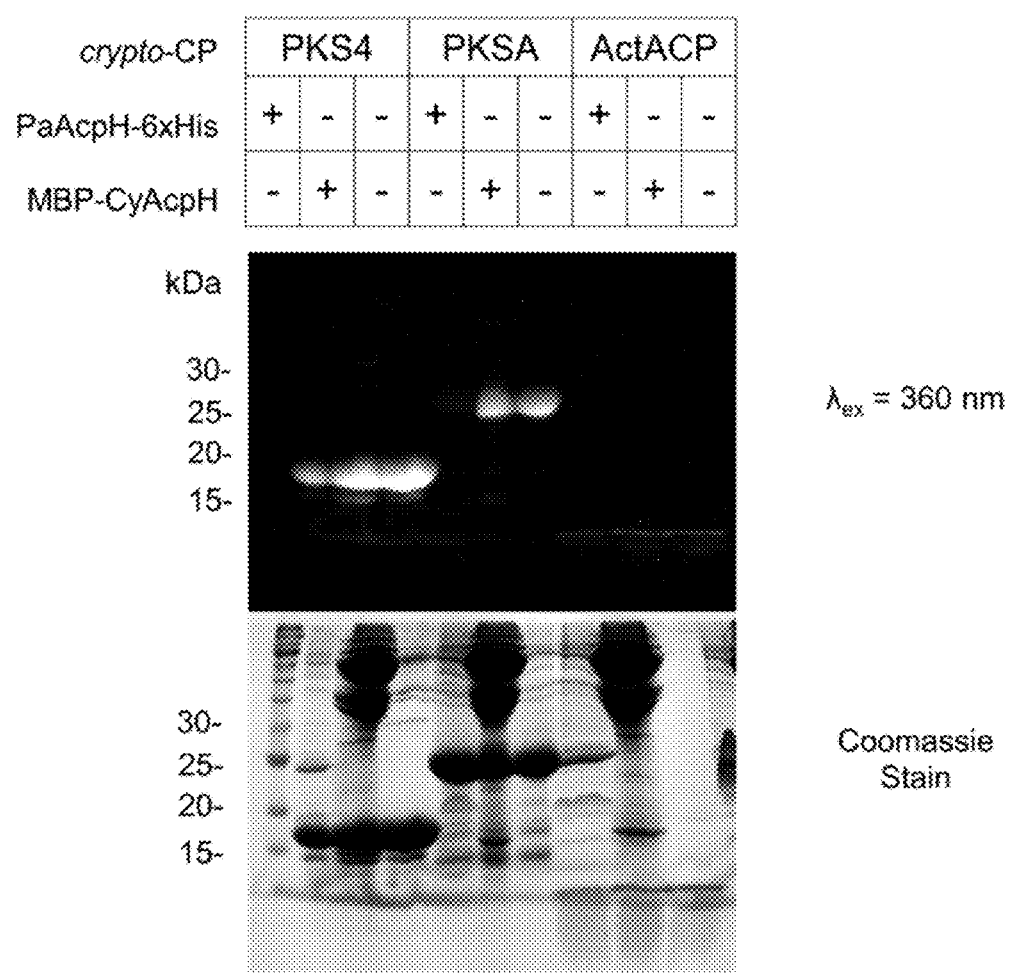
FIG. 14: Analysis of PaAcpH and MBP-CyAcpH with PKS-ACP activity: AcpH homologs from P. aeruginosa (Pa) and MBP-fusion AcpH homolog from Cyanothece PCC7822 (MBP-CyAcpH) are evaluated by SDS-PAGE with various crypto-CP (+) compared to buffer blanks (−) after overnight incubation at 37° C.
Figure 15:
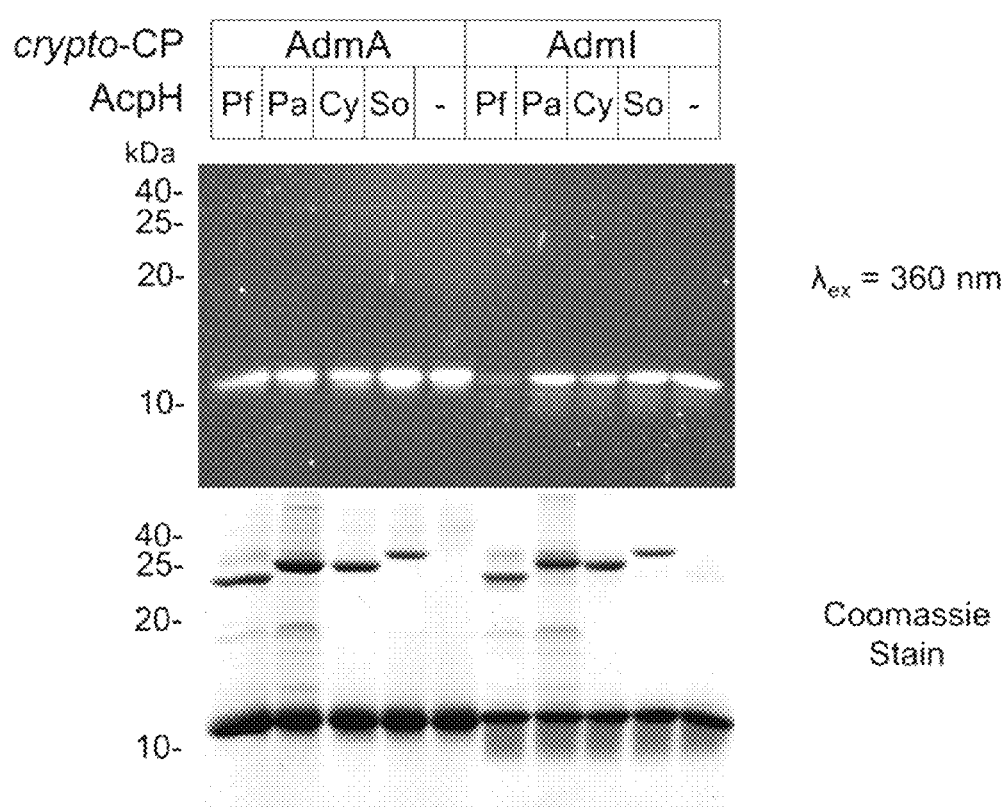
FIG. 15: Analysis of AcpH homolog activity with AdmA and AdmI: AcpH homologs from P. fluorescens (Pf), P. aeruginosa (Pa), Cyanothece PCC 7822 (Cy) and S. oneidensis (So) are evaluated by SDS-PAGE with various crypto-CP (+) compared to buffer blanks (−) after overnight incubation at 37° C.
Figure 16:
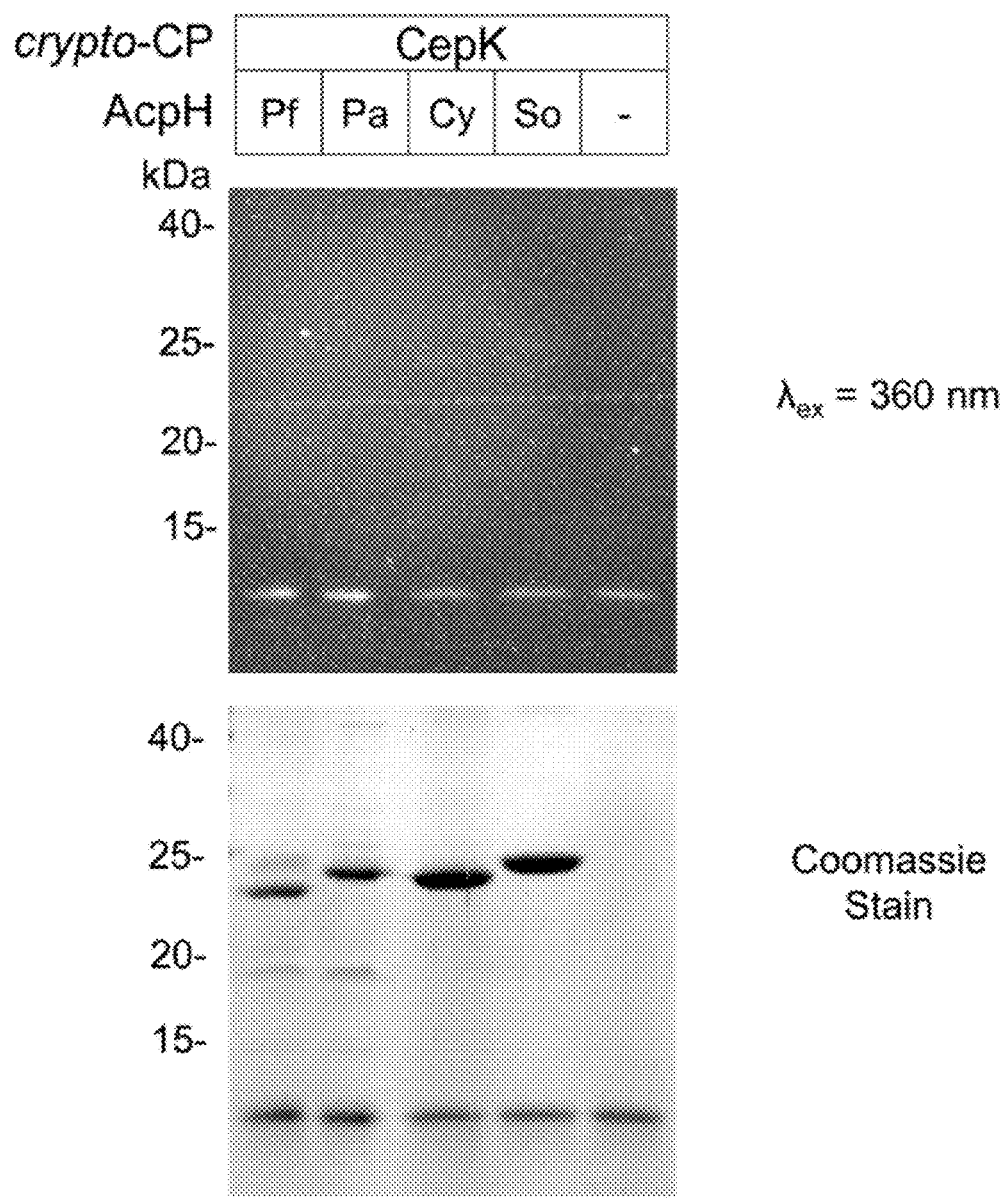
FIG. 16: Analysis of AcpH homolog activity with CepK: AcpH homologs from P. fluorescens (Pf), P. aeruginosa (Pa), Cyanothece PCC 7822 (Cy) and S. oneidensis (So) are evaluated by SDS-PAGE with various crypto-CP (+) compared to buffer blanks (−) after overnight incubation at 37° C.
Figure 17:
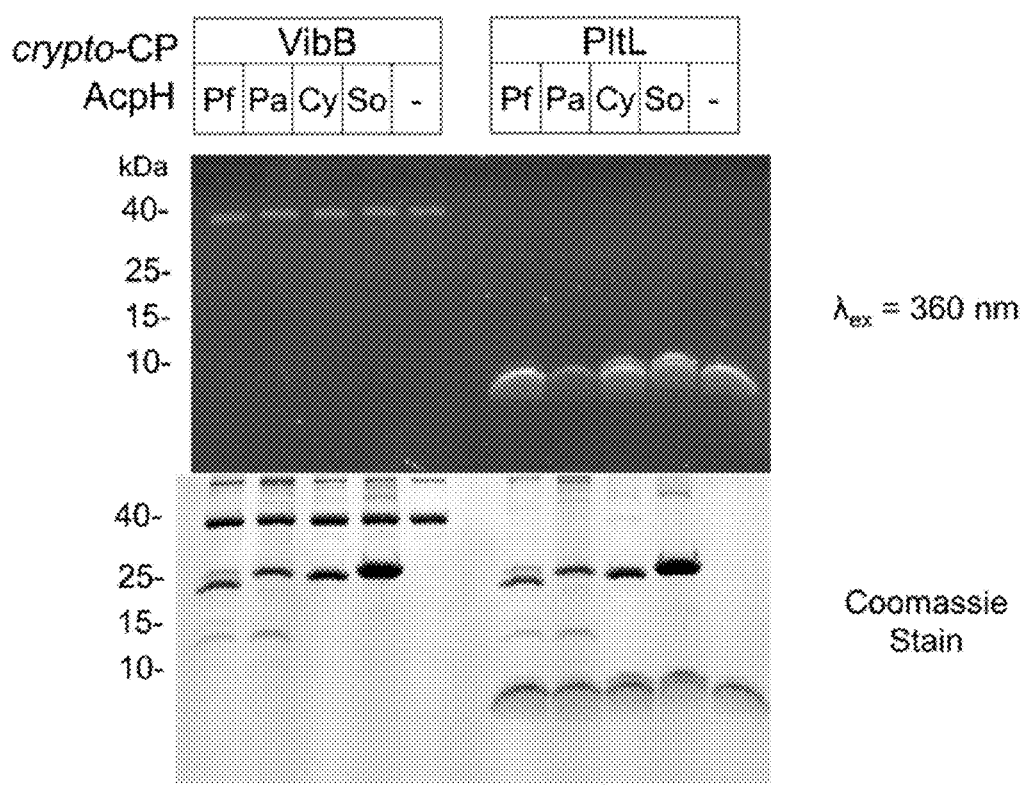
FIG. 17: Analysis of AcpH homolog activity with VibB and PltL: AcpH homologs from P. fluorescens (Pf), P. aeruginosa (Pa), Cyanothece PCC 7822 (Cy) and S. oneidensis (So) are evaluated by SDS-PAGE with various crypto-CP (+) compared to buffer blanks (−) after overnight incubation at 37° C.
Figure 18:
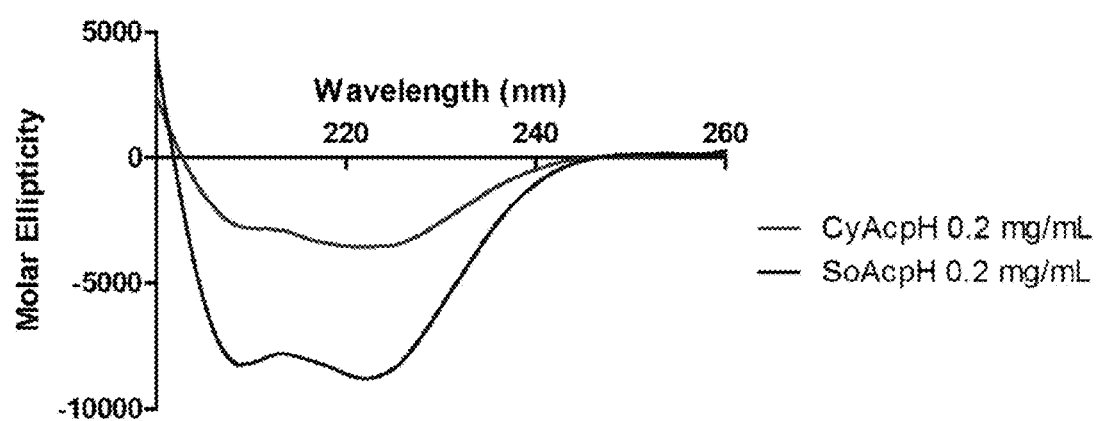
FIG. 18: Circular dichroism analysis of CyAcpH and SoAcpH: Circular dichroism analysis of suspected inactive S. oneidensis AcpH (SoAcpH) compared to known active Cyanothece PCC7822 (CyAcpH) reveals strong alpha-helical character in SoAcpH at similar protein concentrations suggesting that SoAcpH maintains consistent secondary structure.
Figure 20A:
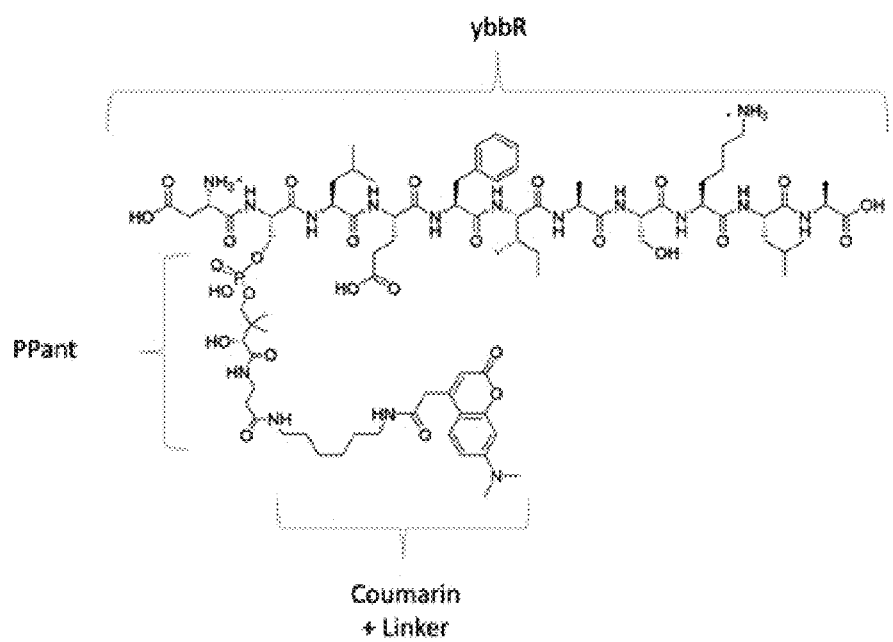
FIGS. 20A-20C: Chemical structures of non-fusion ybbR peptide substrates: Variations of ybbR subjected to coumarin-PPant labeling AcpH activity Urea-PAGE analysis include (FIG. 20A) free peptide (SEQ ID NO:78), (FIG. 20B) FITC-conjugated peptide (SEQ ID NO:79)
Figure 20B:
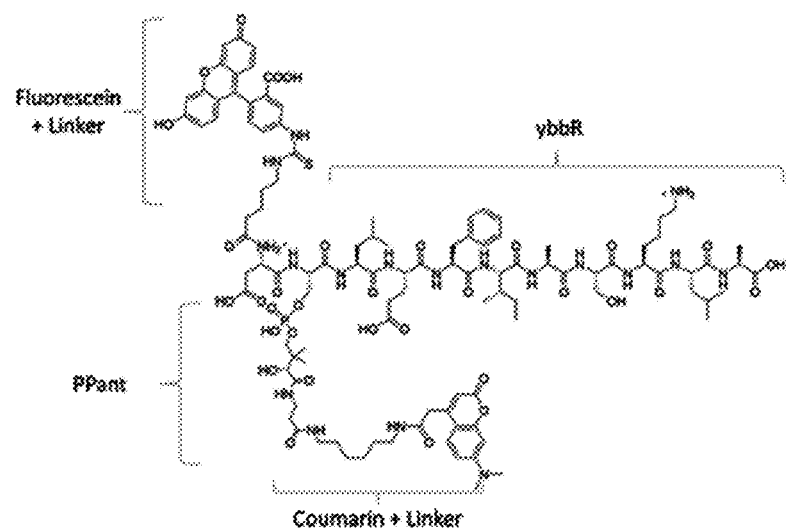
Figure 20C:
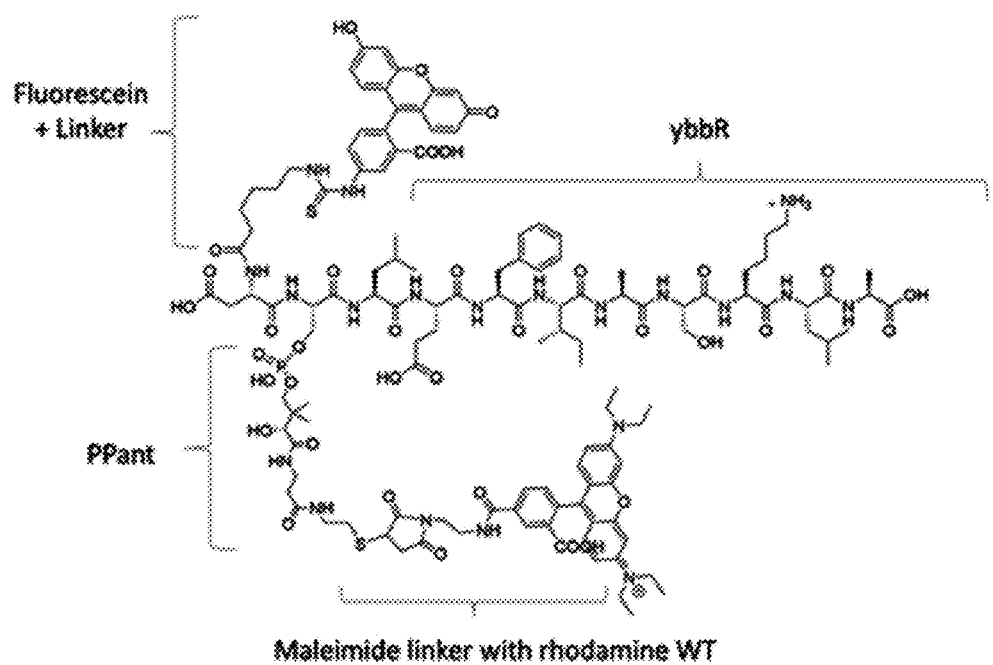
Figure 21:
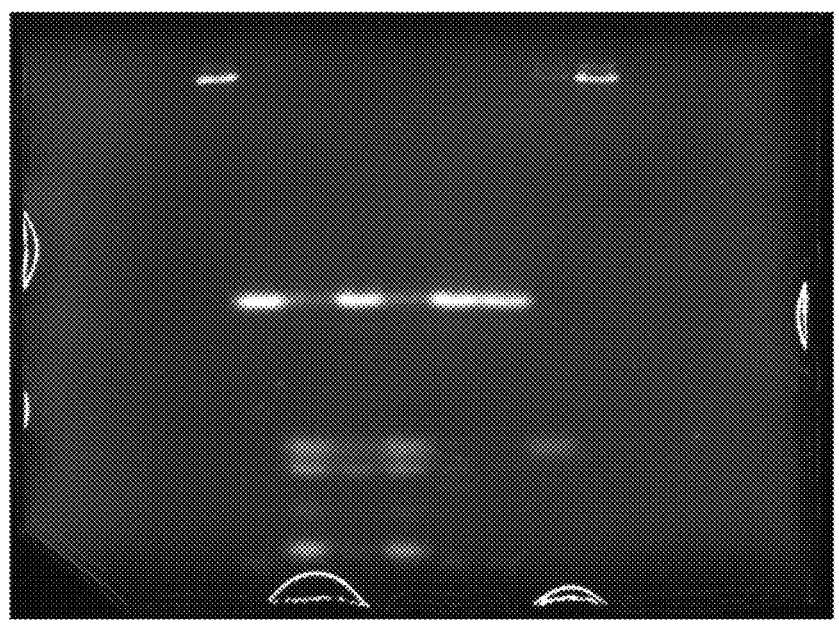
FIG. 21: Analysis of AcpH activity with coumarin-ybbR: AcpH homologs from P. fluorescens (Pf), P. aeruginosa (Pa), Cyanothece PCC 7822 (Cy) and S. oneidensis (So) are evaluated by Urea-PAGE with crypto-ybbR and crypto-PksA (P) compared to buffer blanks (−) after overnight incubation at 37° C. (+) or non-incubation (−).
Figure 22:
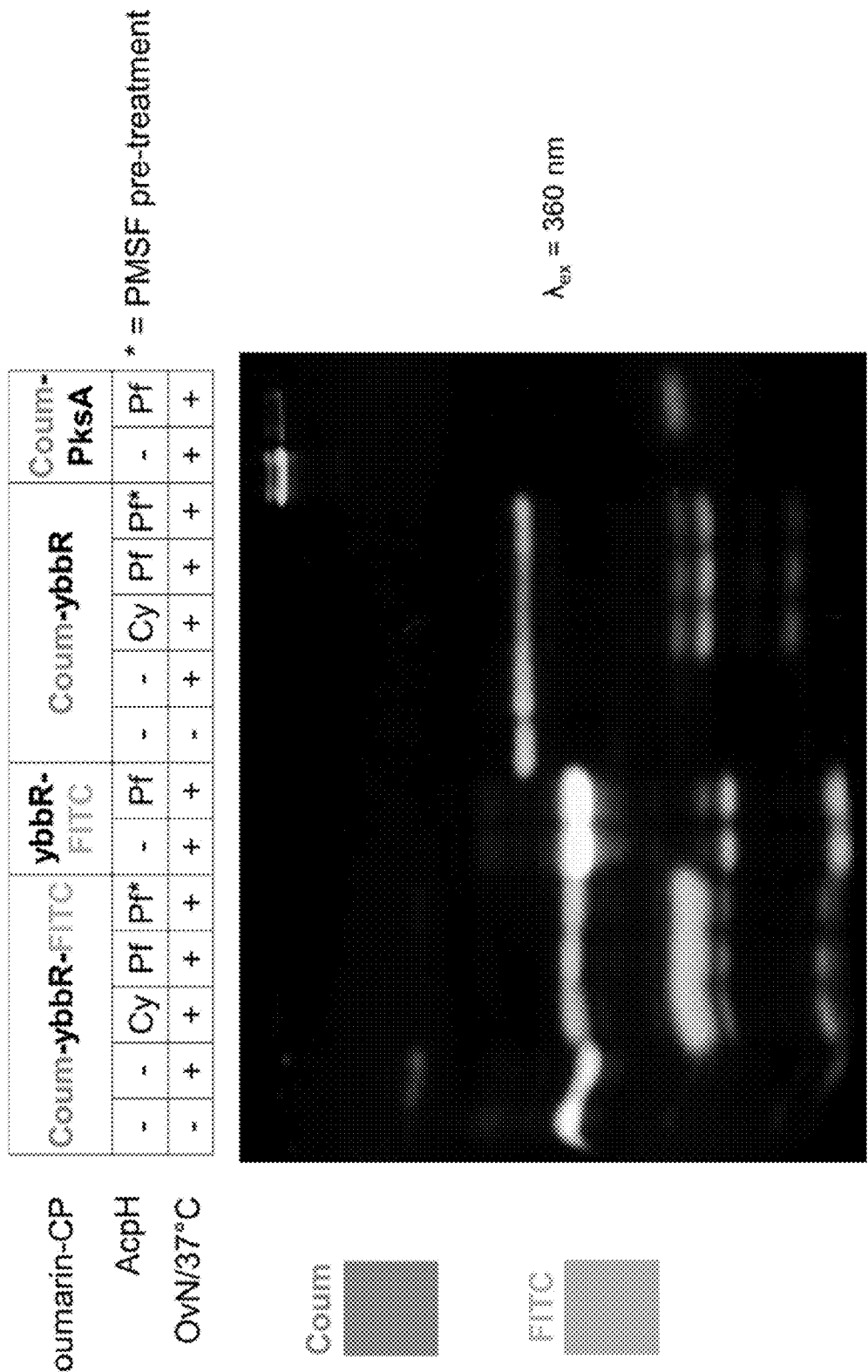
FIG. 22: Analysis of AcpH activity with coumarin-labeled ybbR and FITC-ybbR: AcpH homologs from P. fluorescens (Pf), and Cyanothece PCC 7822 (Cy) are evaluated by Urea-PAGE with crypto-ybbR and crypto-PksA compared to buffer blanks (−) after overnight incubation at 37° C. (+) or non-incubation (−); PMSF is also used to pretreat a PfAcpH sample to ensure that probe hydrolysis is not due to serine-protease.
Figure 23:
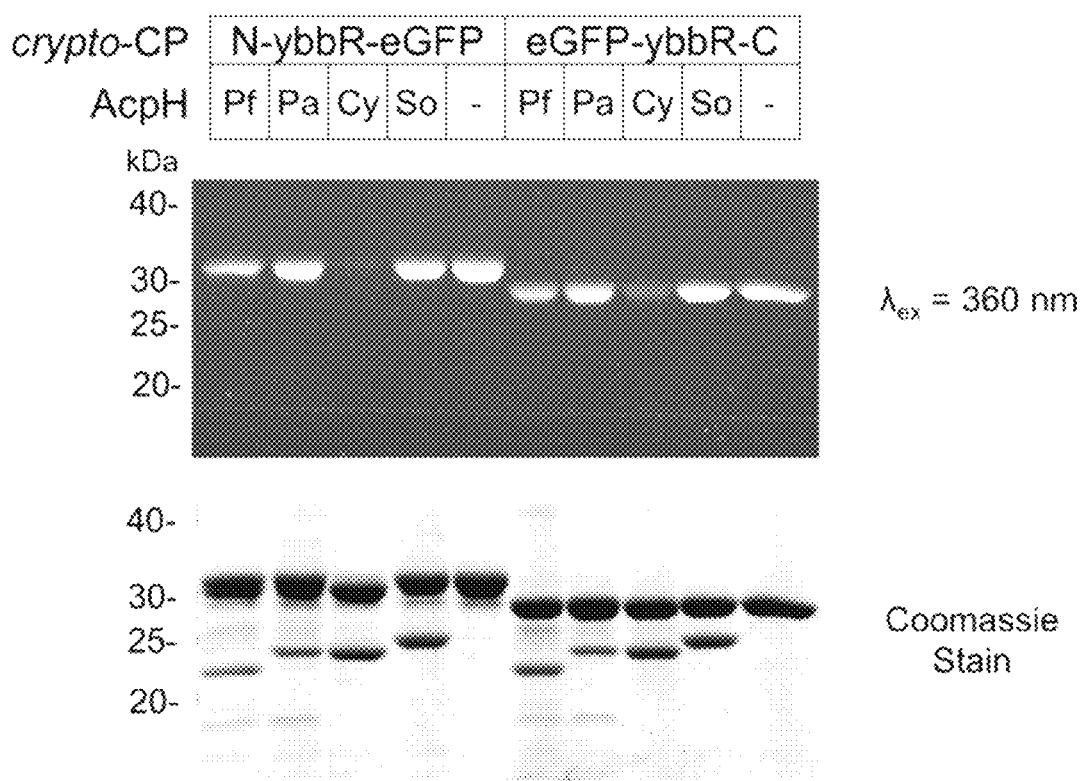
FIG. 23: Analysis of AcpH homolog activity with ybbR-eGFP fusions: AcpH homologs from P. fluorescens (Pf), P. aeruginosa (Pa), Cyanothece PCC 7822 (Cy) and S. oneidensis (So) are evaluated by SDS-PAGE with crypto-ybbR-eGFP N- and C-terminal fusions compared to buffer blanks (−) after overnight incubation at 37° C.
Figure 24:
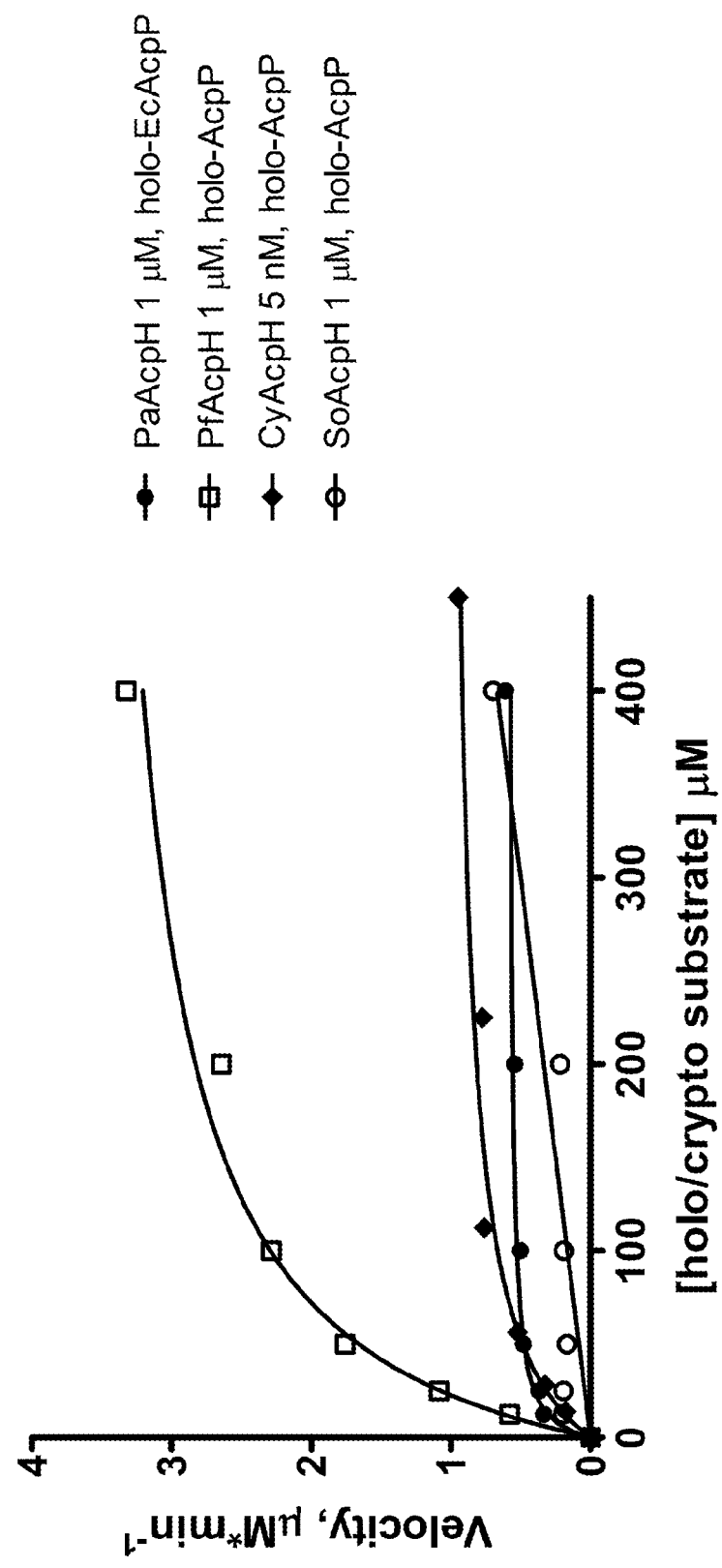
FIG. 24: Analysis of AcpH homolog kinetics with holo-EcAcpP: Reaction of AcpH homologs from *P. fluorescens* (Pf), *P. aeruginosa* (Pa), *Cyanothece* PCC 7822 (Cy) and *S. oneidensis* (So) with holo-EcAcpP, and subsequent EDTA-quenching allow derivation of HPLC kinetic values; CyAcpH demonstrated significantly higher turnover, and required a lower enzyme concentration of 5 nM, compared to 1 μM utilized for other AcpH homologs
Figure 25:
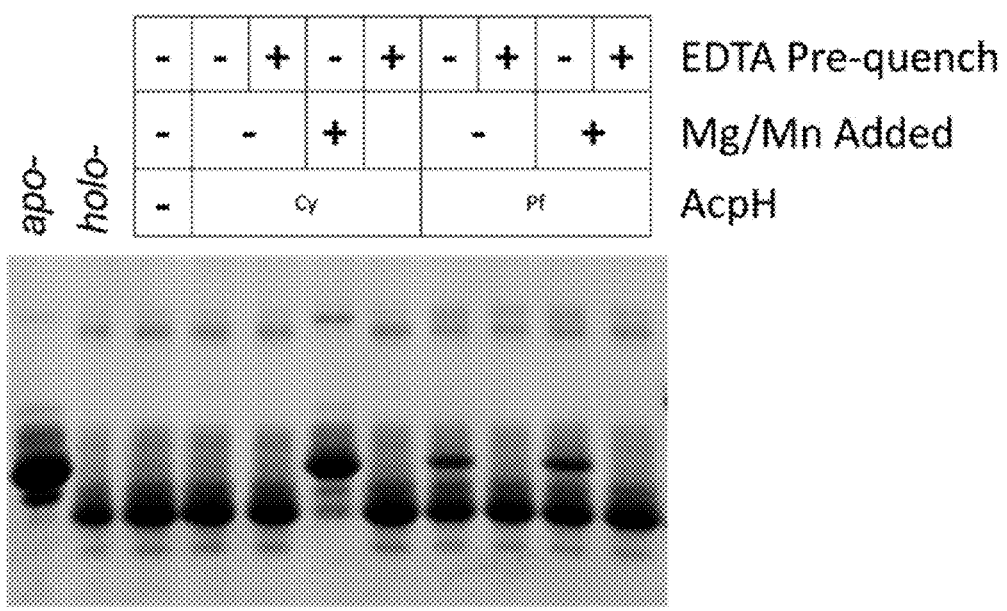
FIG. 25: Verification of EDTA quench method: AcpH homologs from *P. fluorescens* (Pf), and *Cyanothece* PCC 7822 (Cy) are evaluated to verify the holo-*E. coli* AcpP reaction termination expected by EDTA addition prior to evaluating HPLC kinetic samples; No conversion of holo- to apo-AcpP was observed following a10 minute incubation at 37° C., followed by overnight incubation at room temperature
Figure 26:
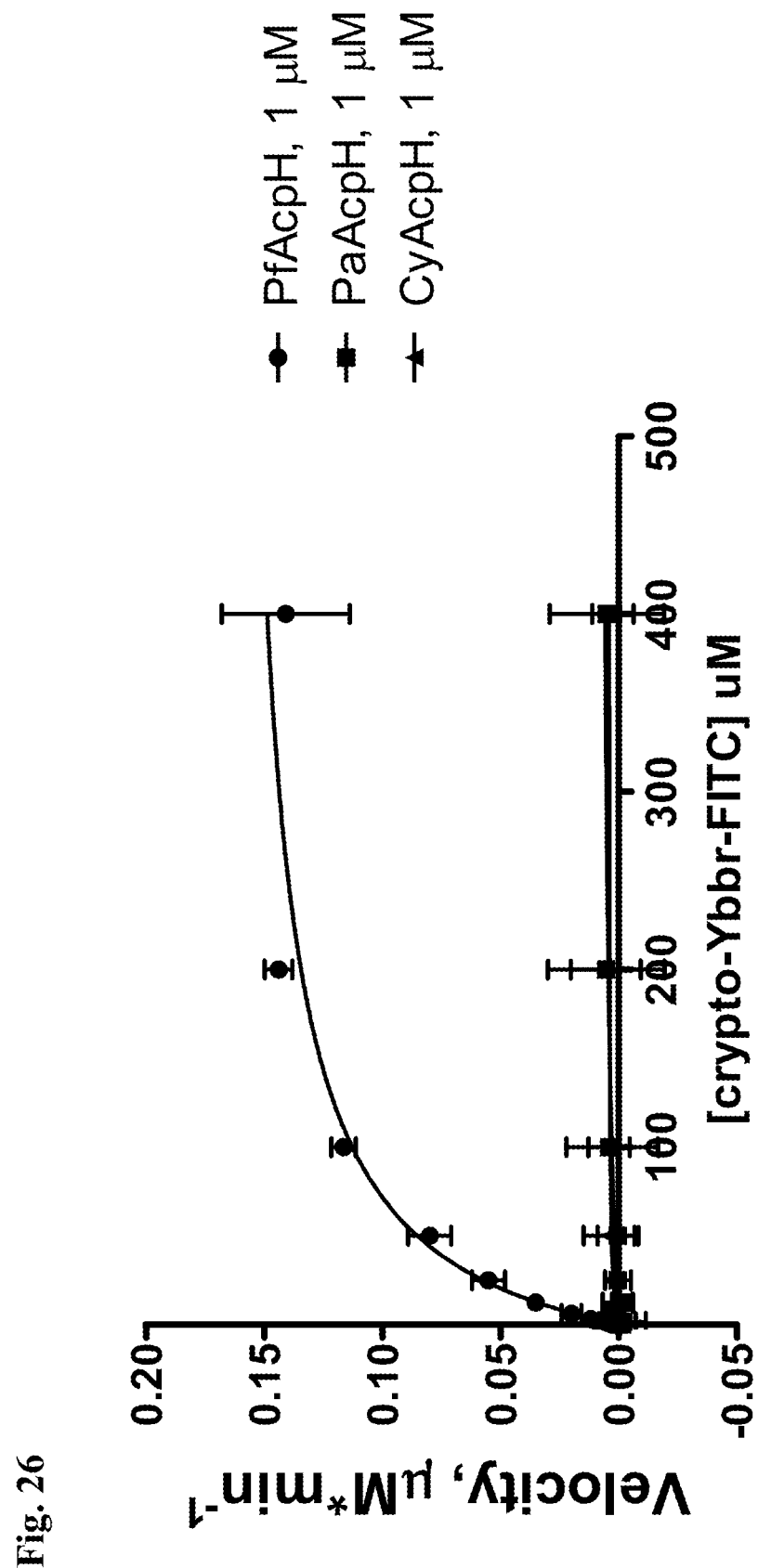
FIG. 26: Analysis of AcpH homolog kinetics with crypto-ybbR-FITC: Reaction of AcpH homologs from *P. fluorescens* (Pf), *P. aeruginosa* (Pa), and *Cyanothece* PCC 7822 (Cy) in microwell format with crypto-yBBR-FITC allows derivation of HPLC kinetic values; while PaAcpH and CyAcpH appeared to demonstrate signal above background, PfAcpH demonstrated clear signal indicating substrate turnover.
Figure 27A:
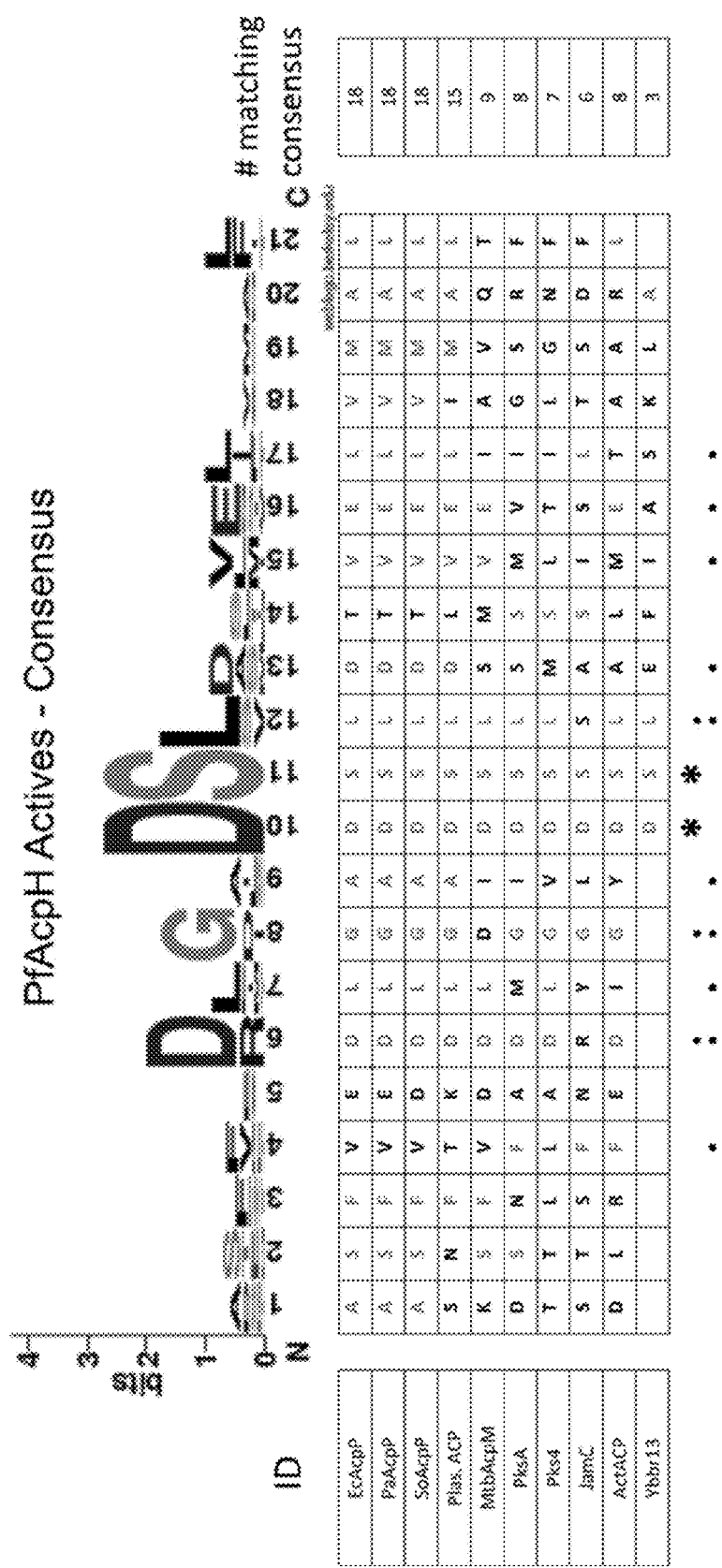
FIGS. 27A-27B: PfAcpH consensus substrate sequence and CP alignments: The consensus sequence of all PfAcpH active carrier protein sequences was generated using WebLogo (at website weblogo.berkeley.edu); The consensus demonstrates several residues matching those of the type II FAS ACPs as being particularly pervasive across active substrates (FIG. 27A); Inactive substrates contain 6 or fewer residues matching the consensus.
Figure 27B:
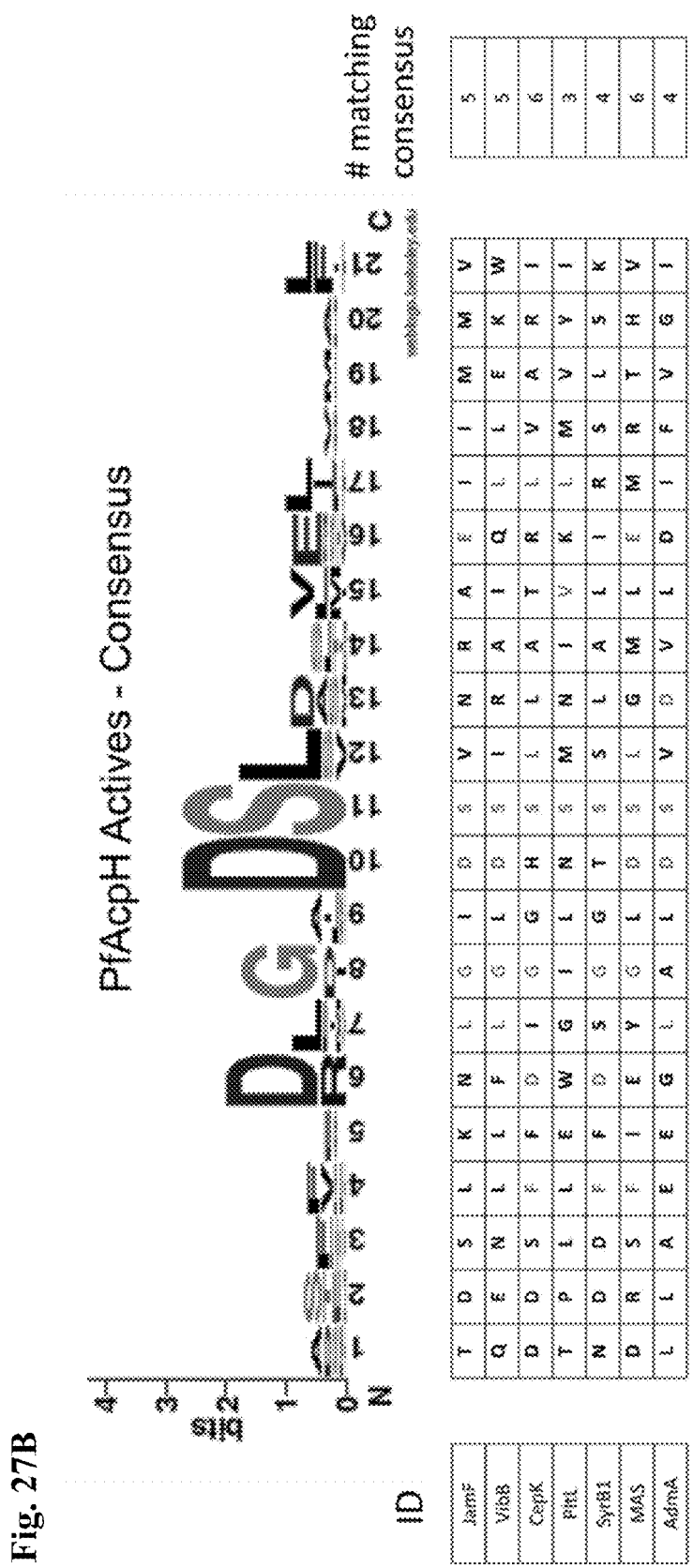

(FIG. 27B), while only one active substrate, ybbR, contains fewer than 6 residues matching the consensus:

```
JamF:
                                 (SEQ ID NO: 90)
TDSLKNLGIDSVNRAEIIMMV

VibB:
                                 (SEQ ID NO: 91)
QENLLFLGLDSIRAIQLLEKW

CepK:
                                 (SEQ ID NO: 92)
DDSFFDIGGHSLLATRLVARI

PltL:
                                 (SEQ ID NO: 93)
TPLLEWGILNSMNIVKLMVYI

SyrB1:
                                 (SEQ ID NO: 94)
NDDFFDSGGTSSLALIRSLSK

MAS:
                                 (SEQ ID NO: 95)
DRSFIEYGLDSLGMLEMRTHV

AdmA:
                                 (SEQ ID NO: 96)
LLAEEGLALDSVDVLDIFVGI.
```

Figure 28A:
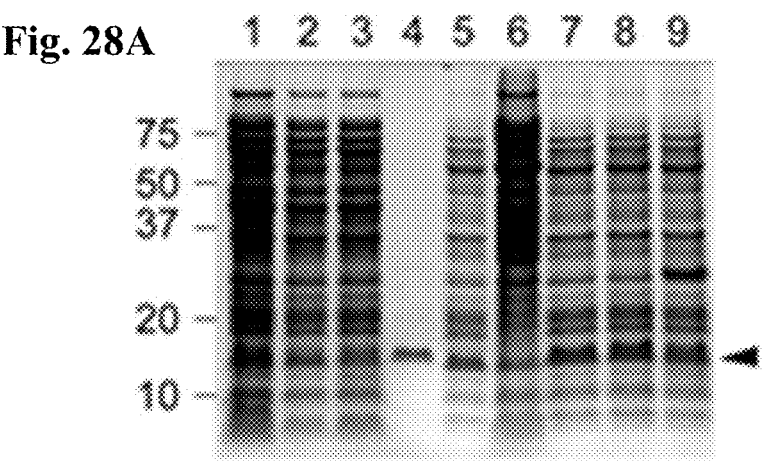
Figure 28B:
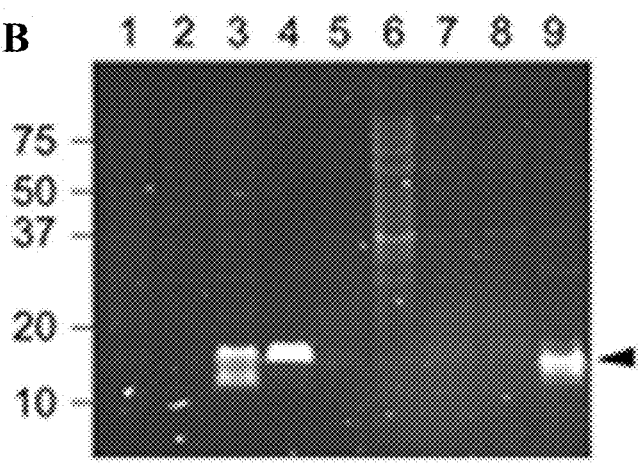
Figure 28C:
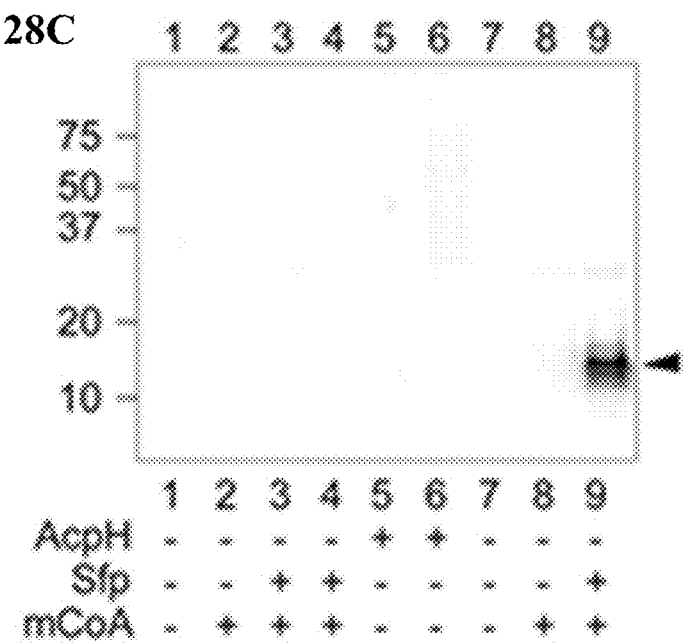
Figure 28D:
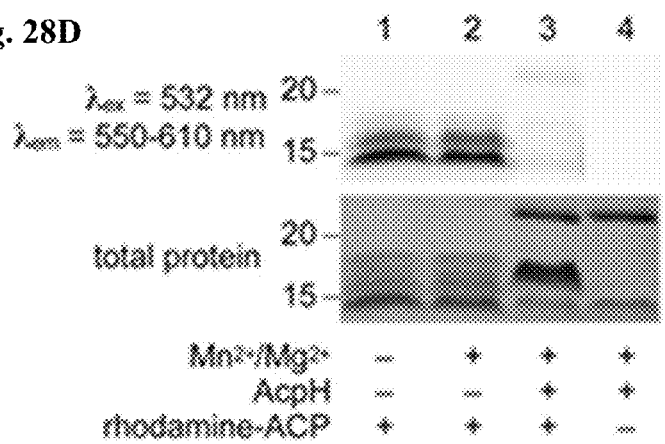
Figure 28E:
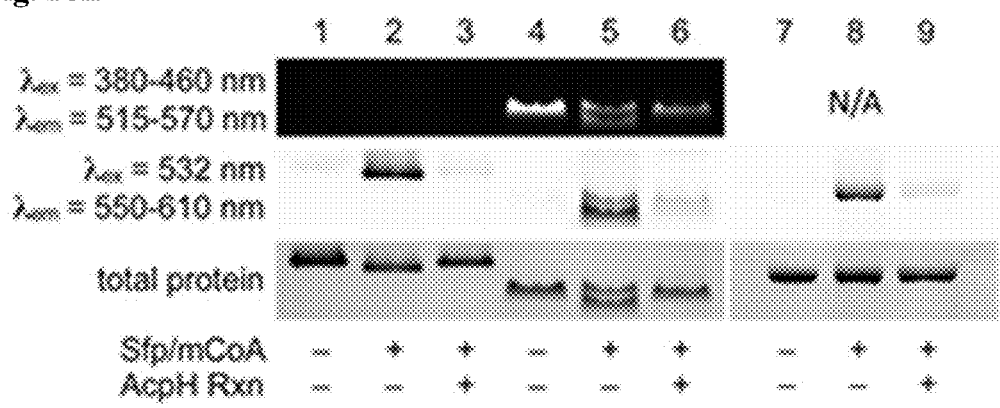
Figure 28F:
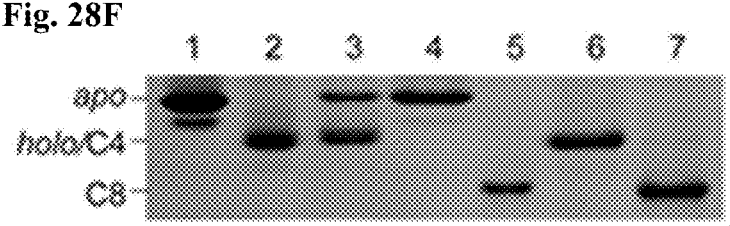

FIGS. 28A-28F: Labeling of native *E. coli* ACP in DK554 cellular lysate: (FIGS. 28A-28C) Apo-ACP produced through over-expression with *E. coli* DK554 is present in cell lysate as monitored with (FIG. 28A) Coomassie stain, (FIG. 28B) 254 nm, and (FIG. 28C) 532 nm excitation 550-610 nm emission fluorescence. ACP is labeled using coumarin-CoA and Sfp but not without Sfp; Coumarin-labeled ACP co-migrates and fluoresces like purified coumarin-ACP standard; AcpH treatment results in the complete removal of the fluorescent coumarin from ACP in the soluble fraction "s", and non-ACP insoluble precipitate "i" is observed in the last coumarin sample; further treatment of the lysate now removed of coumarin with rhodamine-CoA and Sfp results in rhodamine-labeling visible under both 532 and 254 nm excitation (Arrows indicate ACP). FIG. 28D: Fluorescence and total protein results as function of varying $Mn^{2+}/Mg^{2+}$, AcpH and rhodamine-ACP. FIG. 28E: Fluorescence and total protein results as function of Sfp/mCoA and AcpH Rxn. FIG. 28F: Results for apo, holo/C4 and C8.

Figure 29B:
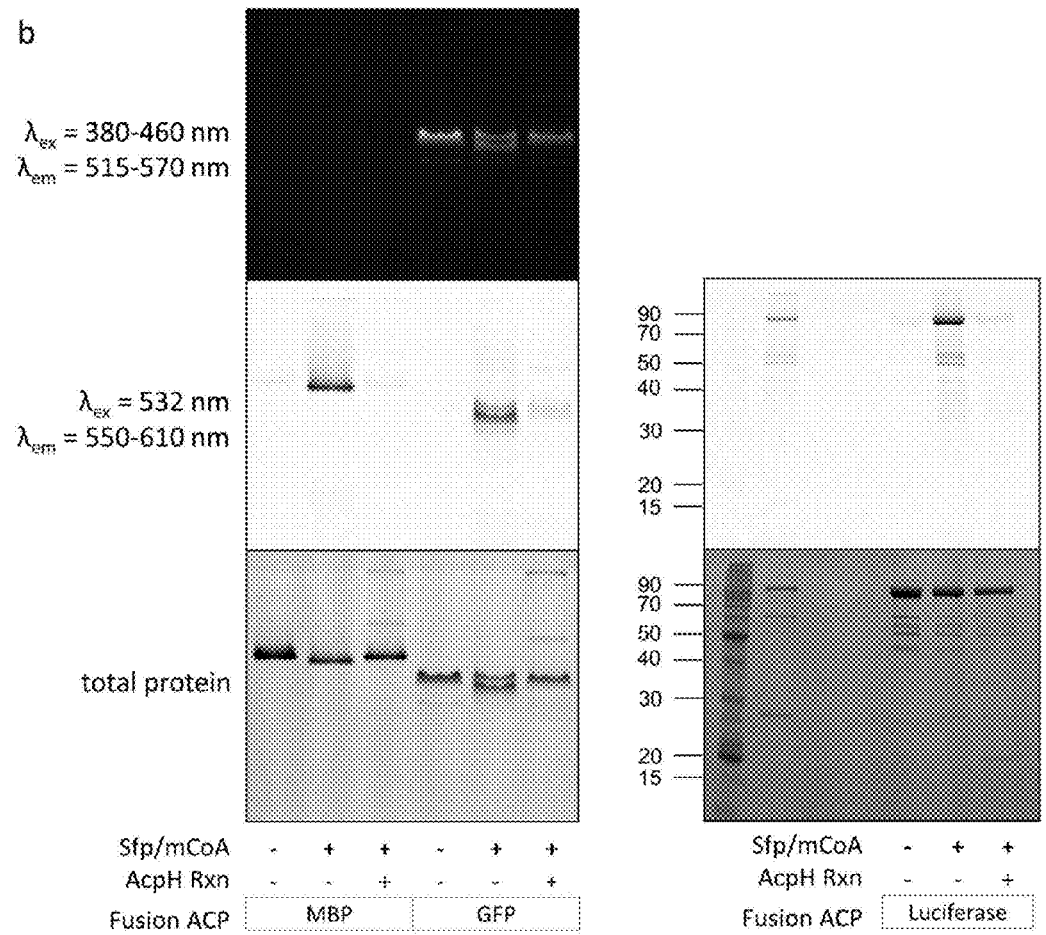
Figure 29C:
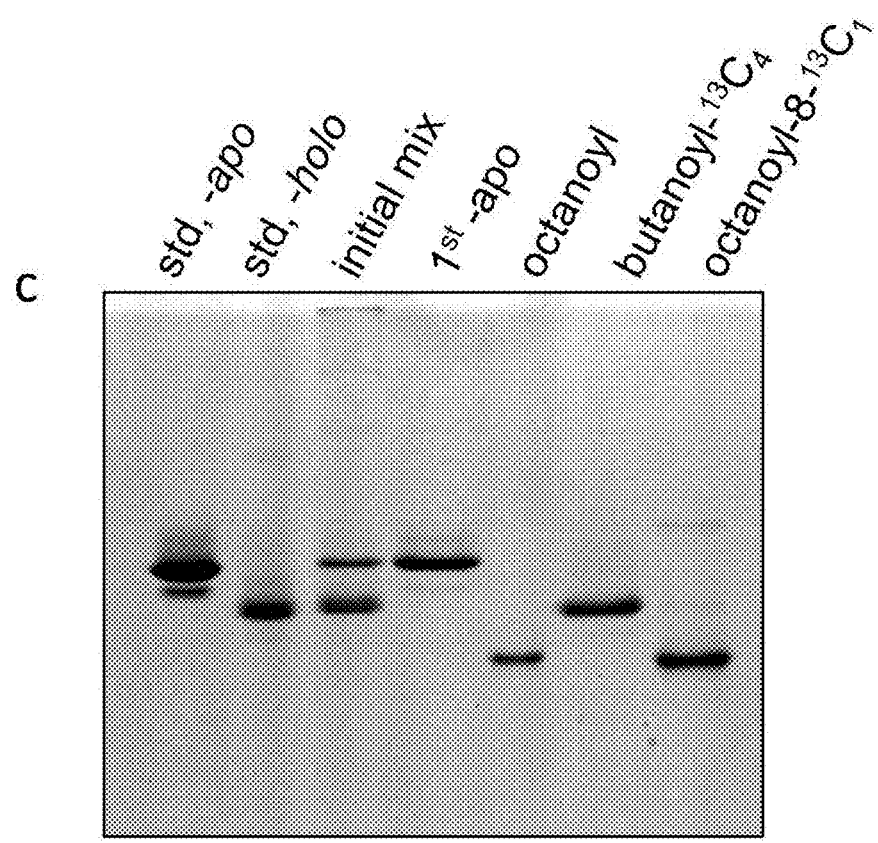

FIGS. 29A-29C: Gel Detection of Reversible ACP Labeling. (a-c) Apo-ACP produced through over-expression with *E. coli* DK554 is present in cell lysate (lane 1) as monitored with (FIG. 29A) Coomassie stain, (FIG. 29B) 254 nm, and (FIG. 29C) 532 nm/550-610 nm excitation/emission fluorescence; the ACP sample is labeled within the lysate using coumarin-CoA and Sfp (lane 3) but not without Sfp (lane 2); Coumarin-ACP within the lysate co-migrates and fluoresces similarly to a purified coumarin-ACP standard (lane 4); AcpH treatment results in the complete removal of the fluorescent coumarin from ACP in the soluble (lane 5) and some precipitate is observed as the insoluble fraction (lane 6) fractions; further treatment of the lysate with Sfp and rhodamine-CoA results in the labeling of the new apo-ACP with a red-fluorescent band (lane 9) visible under both green and UV excitation; (d) Additional analysis of a separate rhodamine-pantetheine labeled crypto-ACP sample (lane 1 & 2) confirms that AcpH is able to remove the fluorescent rhodamine-pantetheine from crypto-ACP (lane 3); (e) Application of Sfp/AcpH reversible labeling methodology to fusion-ACPs: MBP-PaACP (lanes 1-3), GFP-ACP (lanes 4-6), and LuxAB-ACP (lanes 7-9); Apo-carrier protein fusions (lanes 1, 4, & 7) are treated with rhodamine-CoA "mCoA" and Sfp to generate crypto-variants (lanes 2, 5, &

8) and subsequently removed with AcpH treatment (lanes 3, 6, & 9); (f) Acyl-pantetheine analogs were installed on the $^{15}$N-ACP used for NMR analysis. ACP standards for apo—(lane 1) and holo—(lane 2) allow evaluation of modified ACP; $^{15}$N-ACP is initially obtained as a mixture of apo/holo (lane 3) that is readily converted to full apo—(lane 4) with AcpH. Conversion to octanoyl-ACP (lane 5) proceeds with "One-Pot" Sfp methodology; subsequent butanoyl-$^{13}$C-ACP (lane 6) and octanoyl-8-$^{13}$C-ACP (lane 7) samples are produced with apo-$^{15}$N-ACP regenerated by AcpH.

Figure 30A:
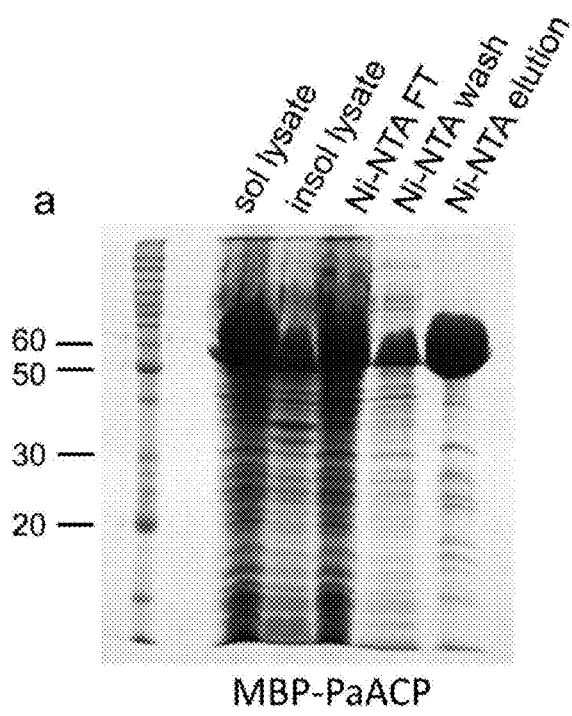
Figure 30B:
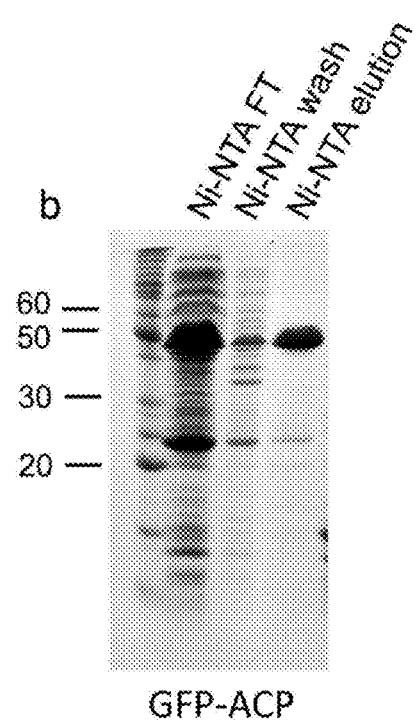

FIGS. 30A-30B: MBP- & GFP-ACP Ni-NTA purification pel: SDS-PAGE and coomassie staining was performed to estimate fusion ACP purity; MBP-PaACP (FIG. 30A) and GFP-ACP (FIG. 30B) were both purified separately by Ni-NTA resin and DEAE anion exchange resin (following initial AcpH treatment) prior to labeling experiments utilizing rhodamine-CoA.

Figure 31:
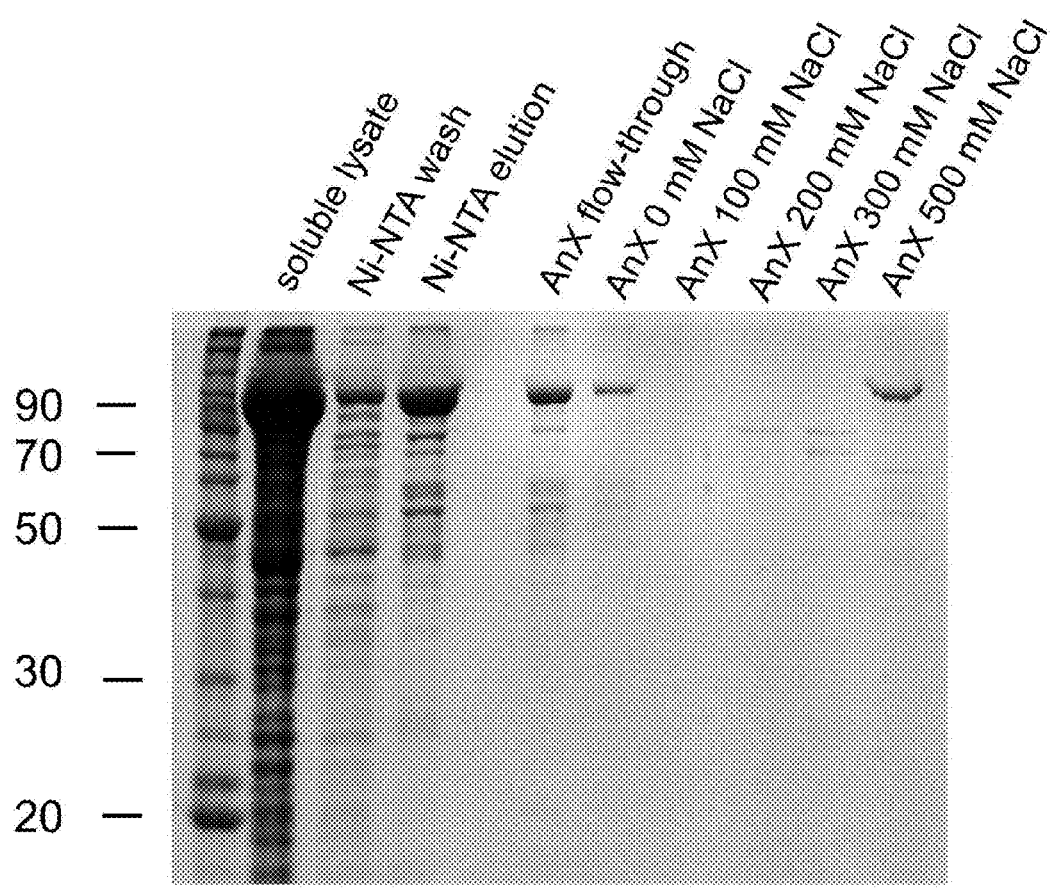

FIG. 31: Fusion luciferase-ACP purification gel: Purification of luciferase-ACP fusion was conducted with Ni-NTA resin affinity purification from the soluble lysate, followed with a 30 mM imidazole wash, and a 300 mM imidazole elution; Following preparative AcpH treatment and desalting into anion exchange ("AnX") buffer, the protein was applied to a DEAE column resulting in unbound protein in flow-through and subsequent washes various NaCl concentrations further purified the sample with a final 500 mM NaCl elution resulted in protein used for labeling and activity analysis.

Figure 32:
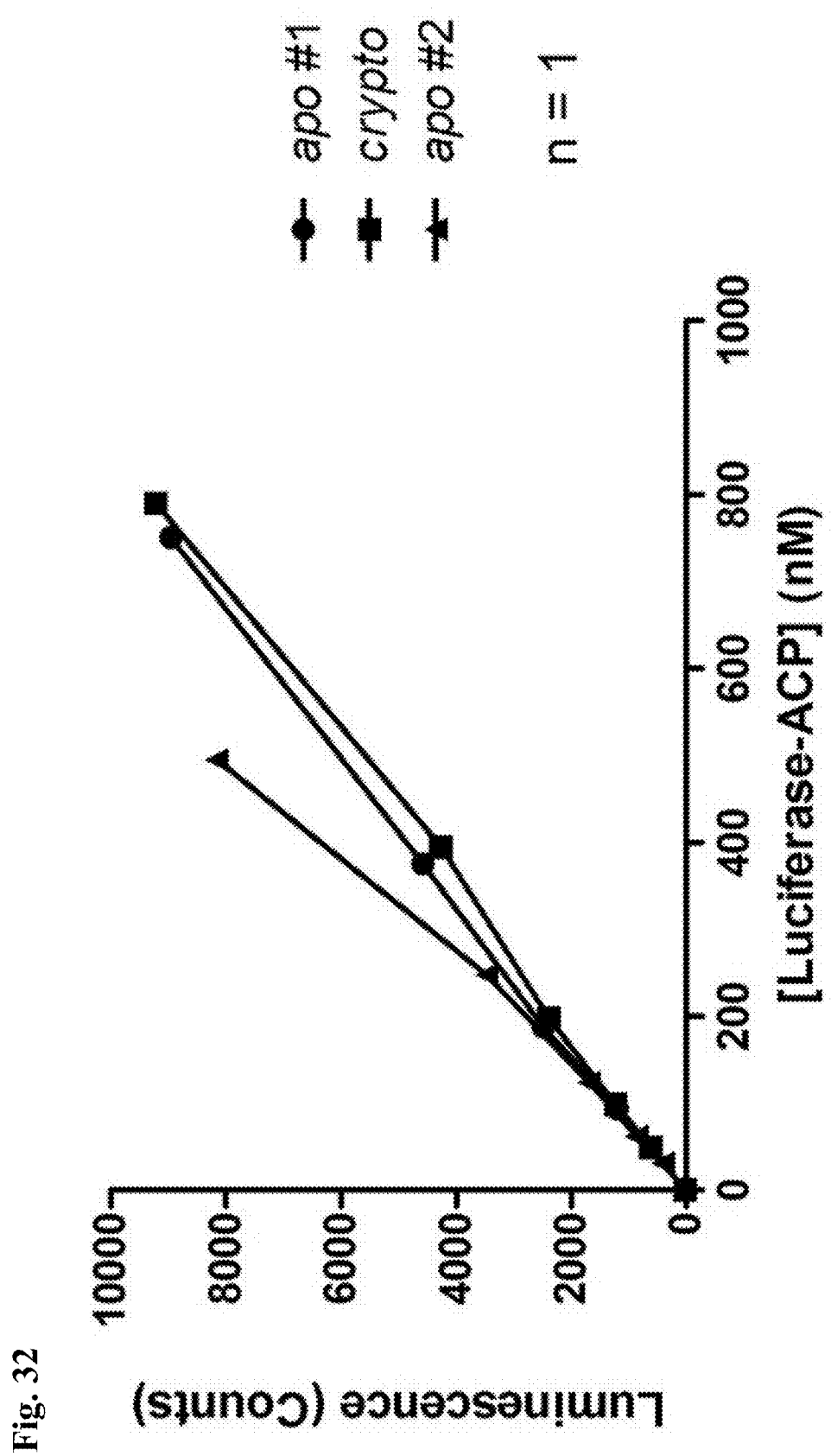

FIG. 32: Luciferase-ACP activity assay: Bacterial luciferase was expressed as an ACP fusion (Lux-ACP), purified, and subjected to ACP labeling and unlabeling techniques. The original apo-Lux-ACP was generated and purified, followed by labeling with rhodamine-CoA and Sfp to generate crypto-Lux-ACP; the crypto-Lux-ACP was subsequently reacted with AcpH to remove the rhodamine-pantetheine and regenerate the apo-Lux-ACP and activity assays with Lux-ACP were conducted with each discrete sample to ensure no significant loss of activity.

Figure 33:
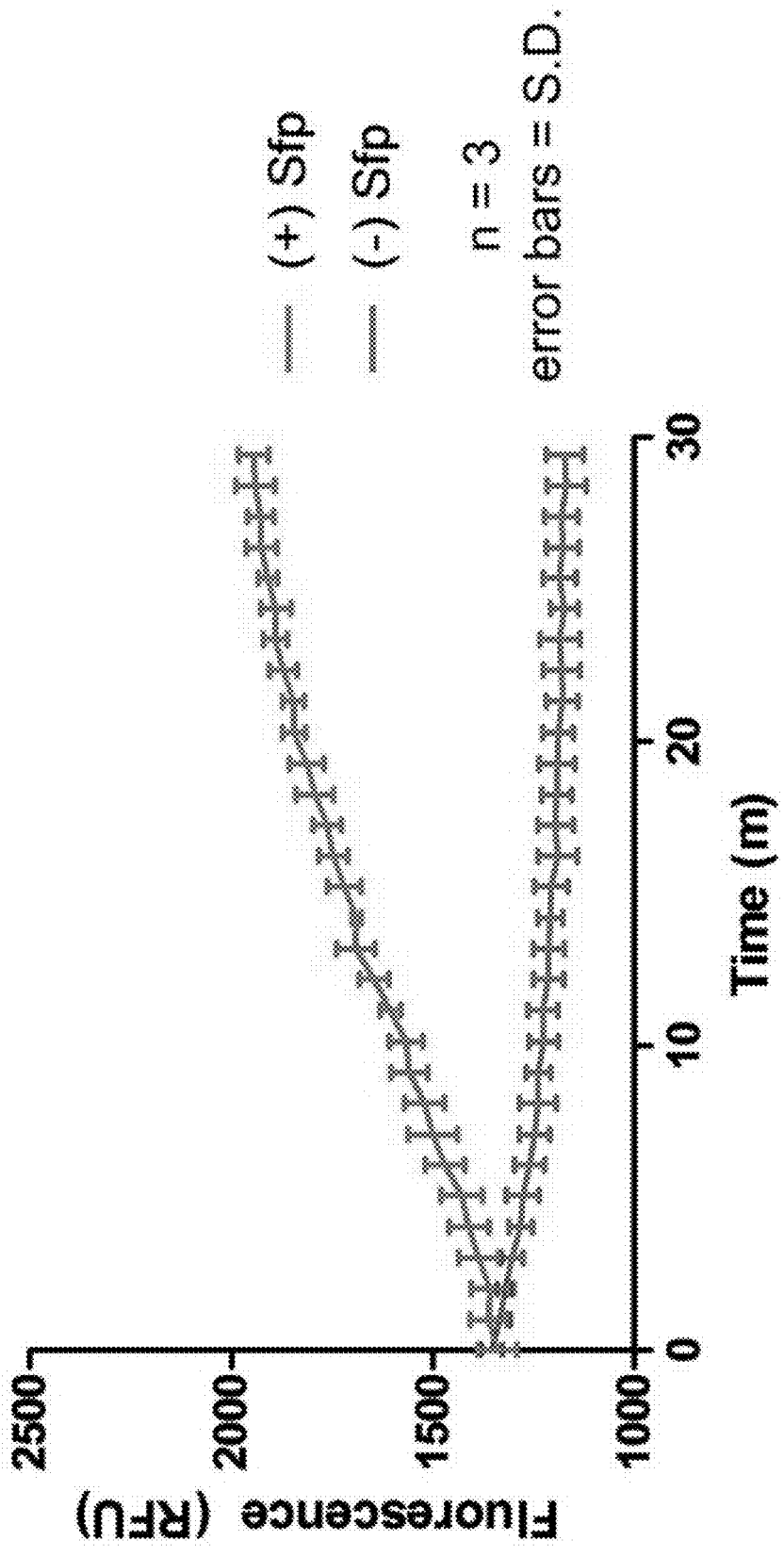

FIG. 33: GFP-ACP: rhodamine-CoA labeling & FRET evaluation: Labeling of 10 μM apo-GFP-ACP with 20 μM rhodamine-CoA & 1 μM Sfp generates a distinguished FRET effect when excited with 405 nm light, and monitoring rhodamine emission at 595 nm.

FIGS. 34A-34F: [$^{15}$N]ACP acyl-pantetheine analog Urea-PAGE: Labeling and regeneration of all AcpH and Sfp-mediated reactions were monitored via Urea-PAGE analysis and compared to pure apo- and holo-ACP standards (std); (FIG. 34A) Initially expressed/purified [$^{15}$N]ACP is a mixture of apo- and holo-carrier protein which is converted to apo-[$^{15}$N]ACP using AcpH. AcpH reaction insoluble fraction did not contain a significant amount of ACP-$^{15}$N; (FIG. 34B) Conversion of apo-[$^{15}$N]ACP to octanoyl-[$^{15}$N]ACP proceeded via "one-pot" Sfp methodology applying octanoyl-pantetheinamide; (FIG. 34C) AcpH is used to regenerate the apo-form of carrier protein from previous octanoyl-[$^{15}$N]ACP; (FIG. 34D) Regenerated apo-[$^{15}$N]ACP is converted to [$^{13}$C$_4$]butanoyl-[$^{15}$N]ACP using [$^{13}$C$_4$]butanoyl-pantetheine oxoester with "one-pot" Sfp methodology; (FIG. 34E) apo-[$^{15}$N]ACP is regenerated from [$^{13}$C$_4$]butanoyl-[$^{15}$N]ACP using an AcpH reaction; (FIG. 34F) Regenerated apo-[$^{15}$N]ACP is converted to [8-$^{13}$C$_1$]octanoyl-[$^{15}$N]ACP using [8-$^{13}$C$_1$]octanoyl-pantetheine oxoester with "one-pot" Sfp methodology.

FIGS. 35A-35F: [$^{15}$N]ACP purification, SDS-PAGE: (FIG. 35A) SDS-PAGE analysis of [$^{15}$N]ACP purity following expression/purification/AcpH reaction of [$^{15}$N]ACP from E. coli to generate apo-[$^{15}$N]ACP and subsequent DEAE ion exchange prior to generate NMR-ready sample (NaCl elution); (FIG. 35B) Ni-NTA resin purification of octanoyl-[$^{15}$N]ACP from crude one-pot reaction results in NMR-ready sample; (FIG. 35C) DEAE purification of the regenerated/NMR-ready apo-[$^{15}$N]ACP; (FIG. 35D) Ni-NTA resin purification of [$^{13}$C$_4$]butanoyl-[$^{15}$N]ACP from "one-pot" crude reaction allows for NMR analysis; (FIG. 35E) DEAE purification of the second regenerated apo-[$^{15}$N]ACP from AcpH crude reaction precedes the next labeling step; (FIG. 35F) Ni-NTA resin purification of labeled [8-$^{13}$C$_1$]octanoyl-[$^{15}$N]ACP prior to NMR analysis.

Figure 36:
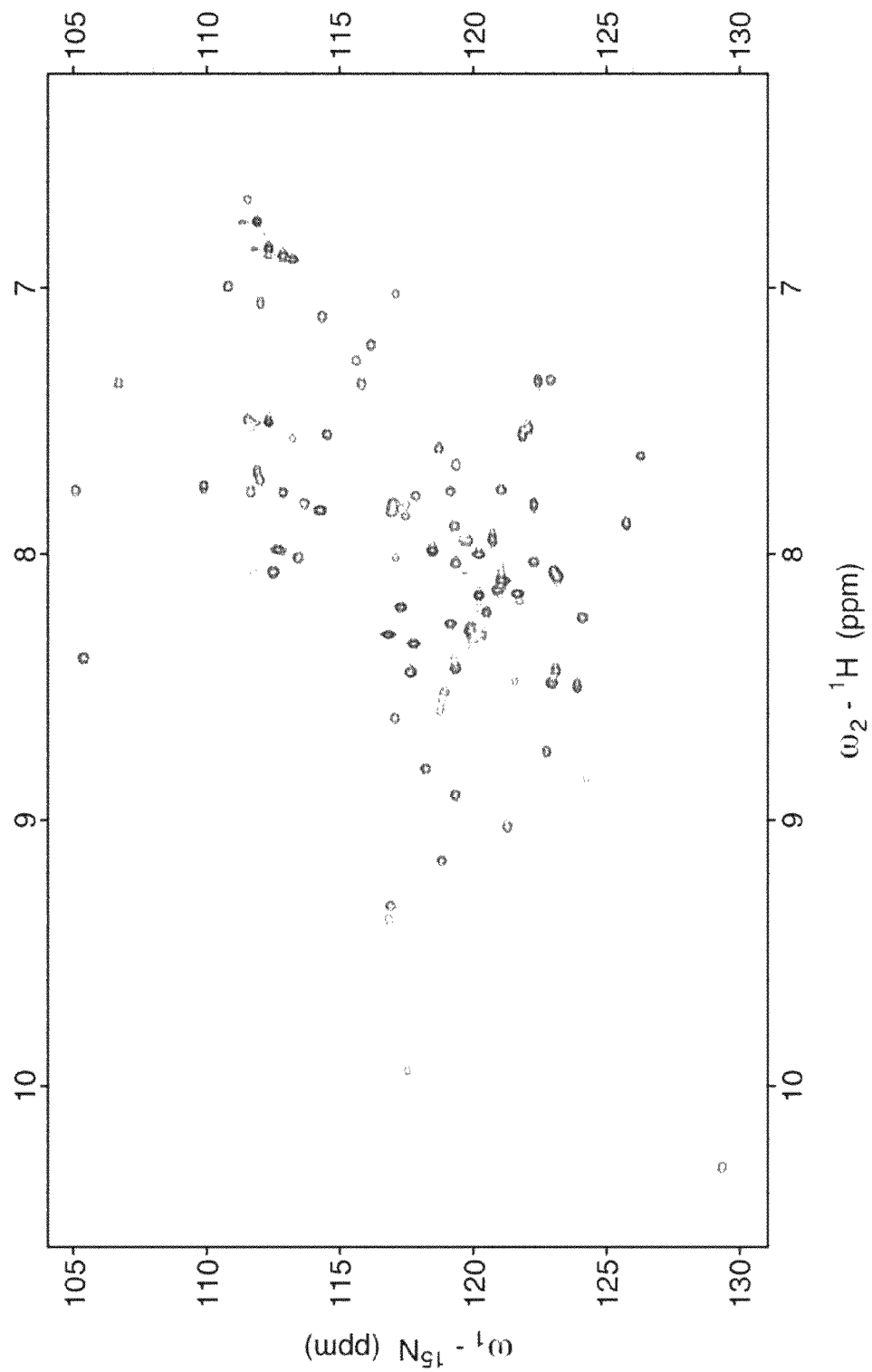

FIG. 36: 1$^{st}$ apo-[$^{15}$N]ACP HSQC spectrum.

Figure 37:
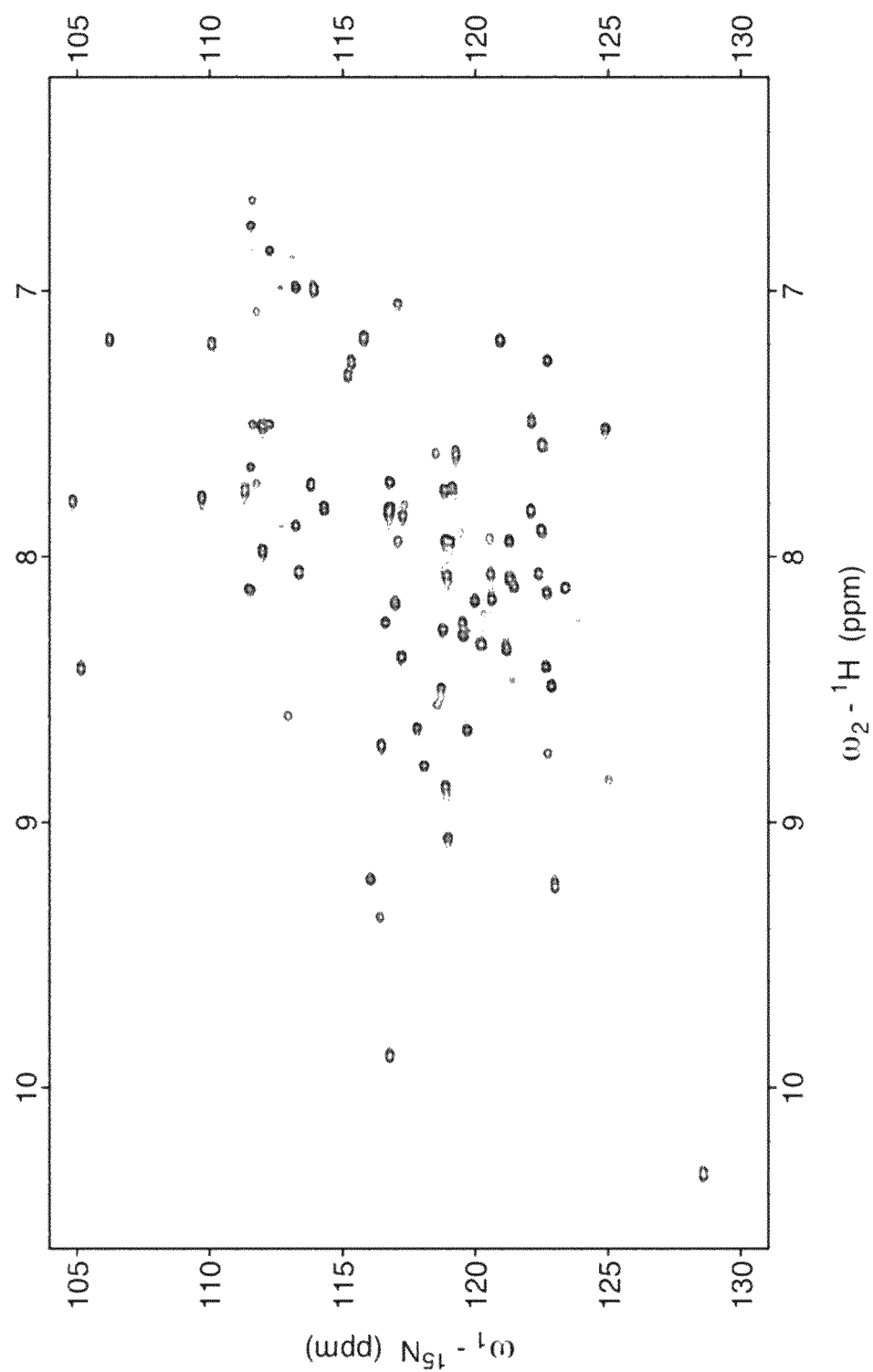

FIG. 37: Octanoyl-[$^{15}$N]ACP HSQC spectrum.

Figure 38:
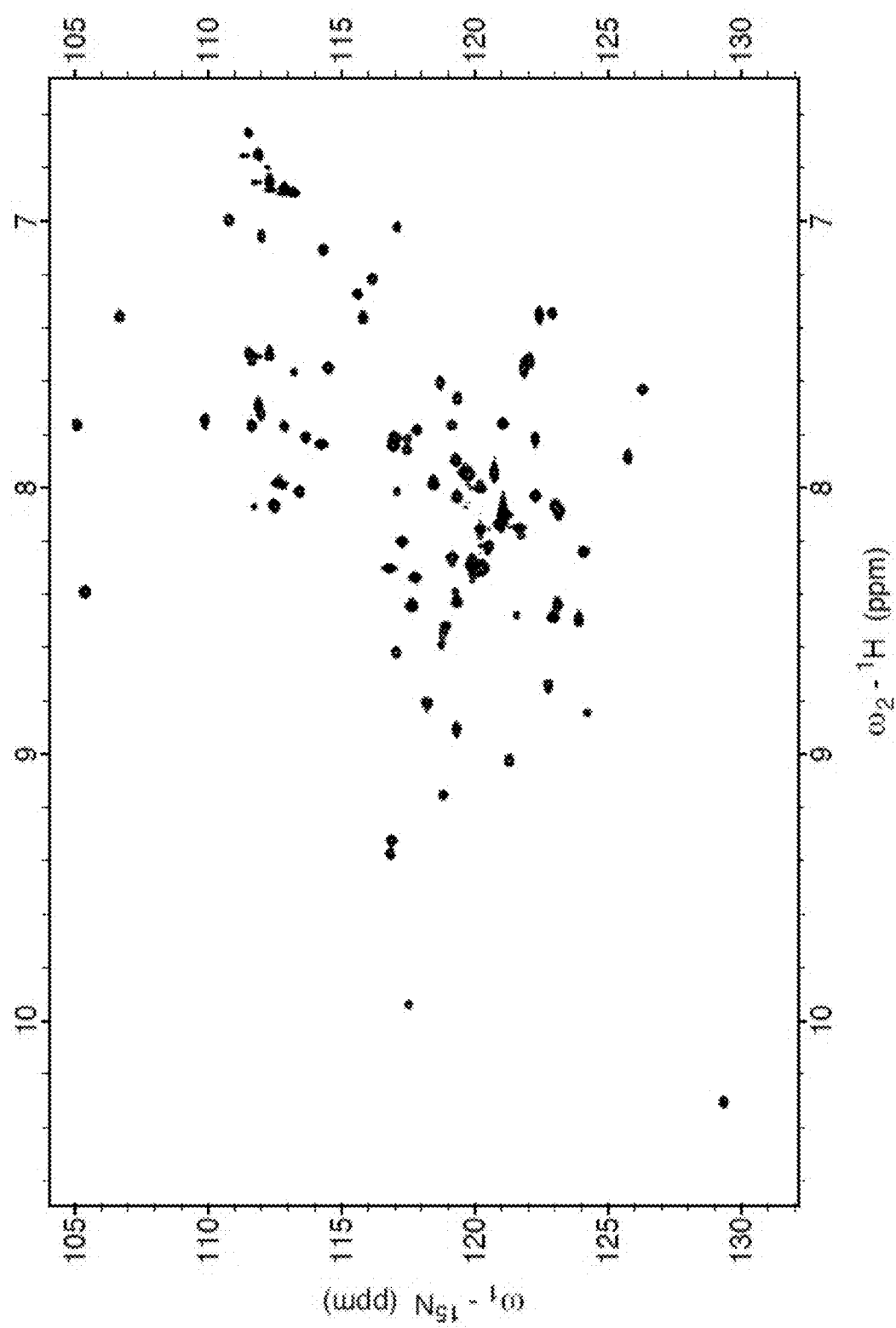

FIG. 38: 2$^{nd}$ apo-[$^{15}$N]ACP HSQC spectrum.

Figure 39:
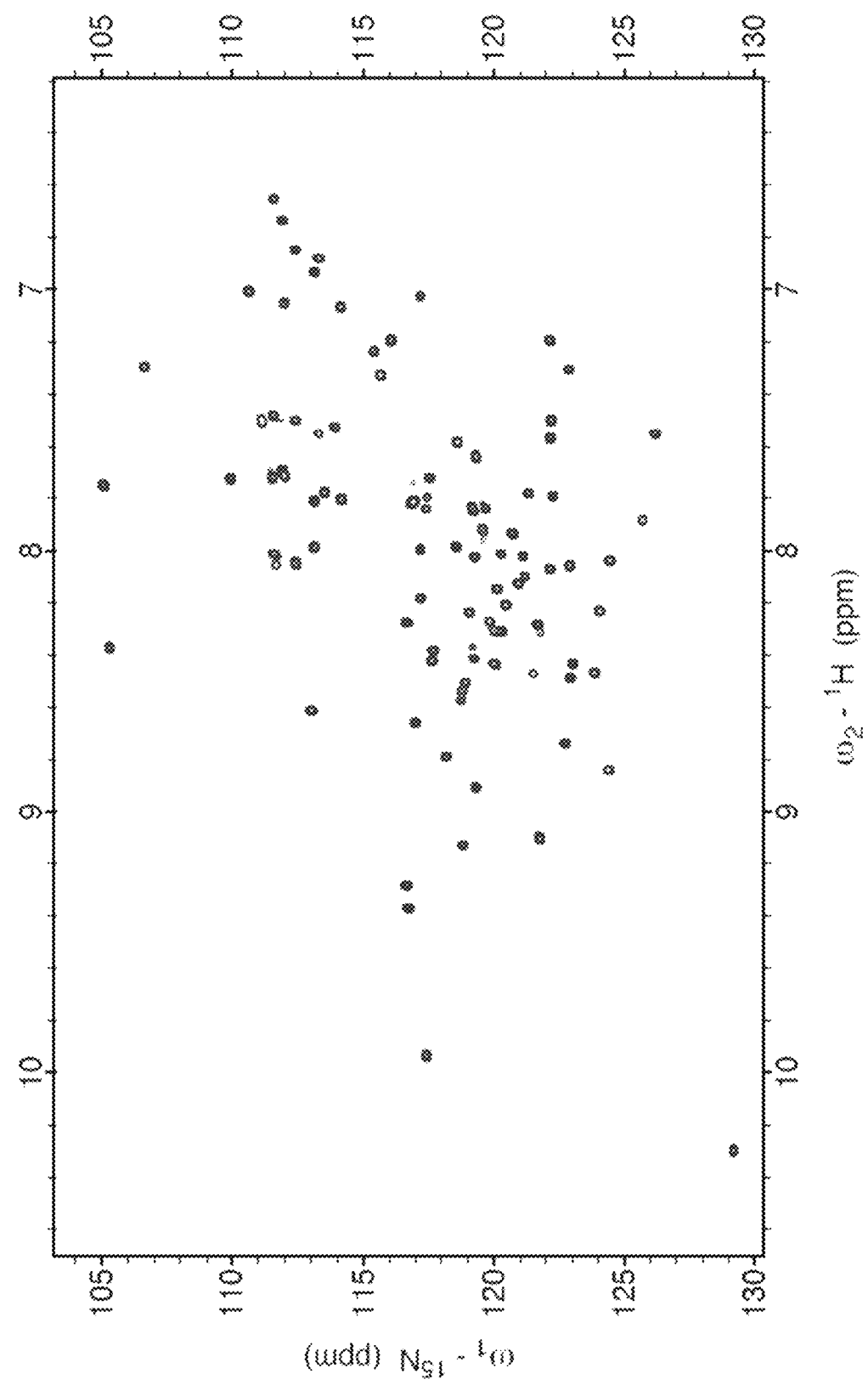

FIG. 39: [$^{13}$C$_4$]Butanoyl-[$^{15}$N]ACP HSQC spectrum.

Figure 40:
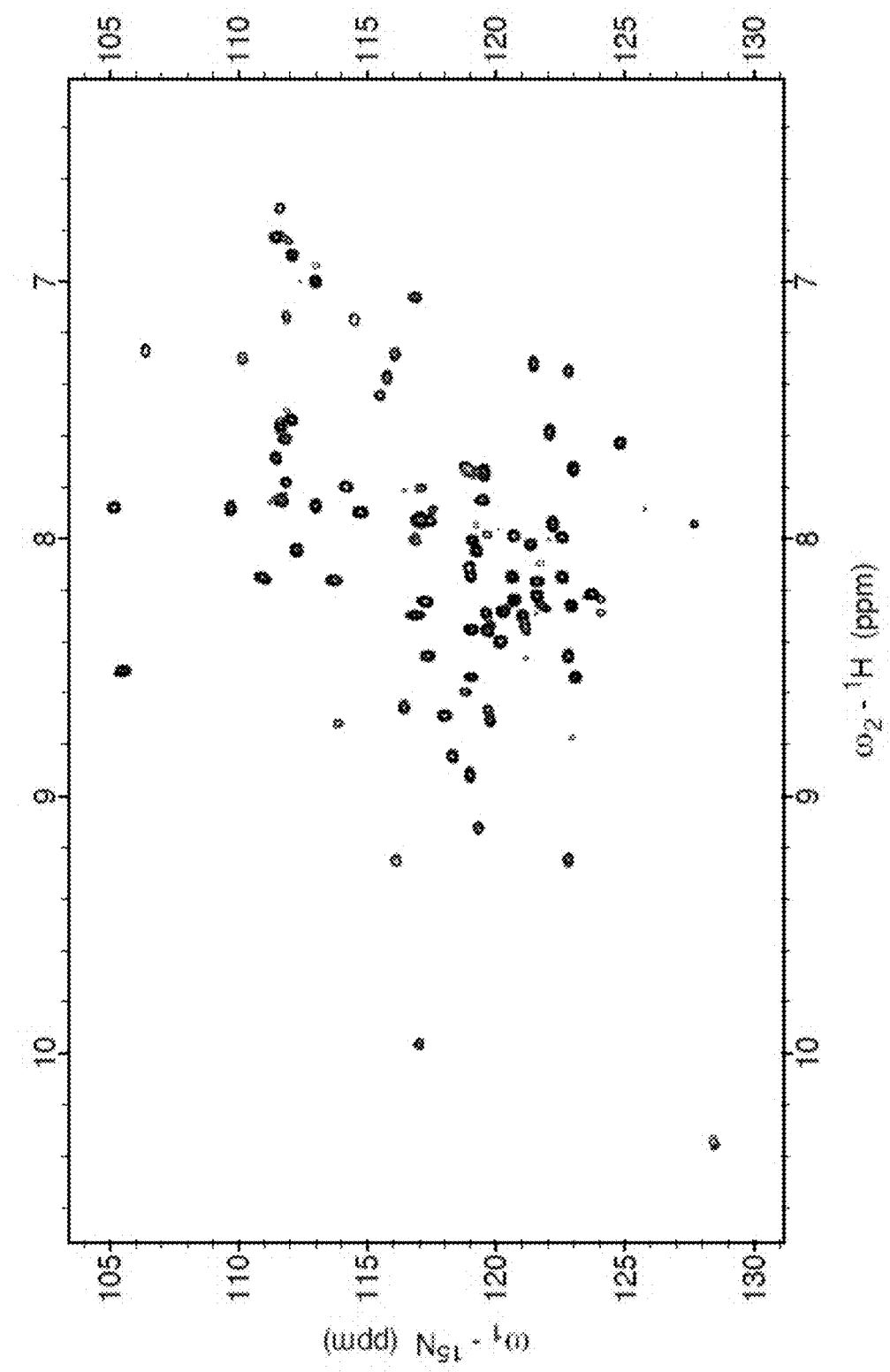

FIG. 40: [8-$^{13}$C$_1$]Octanoyl-[$^{15}$N]ACP HSQC spectrum.

Figure 41:
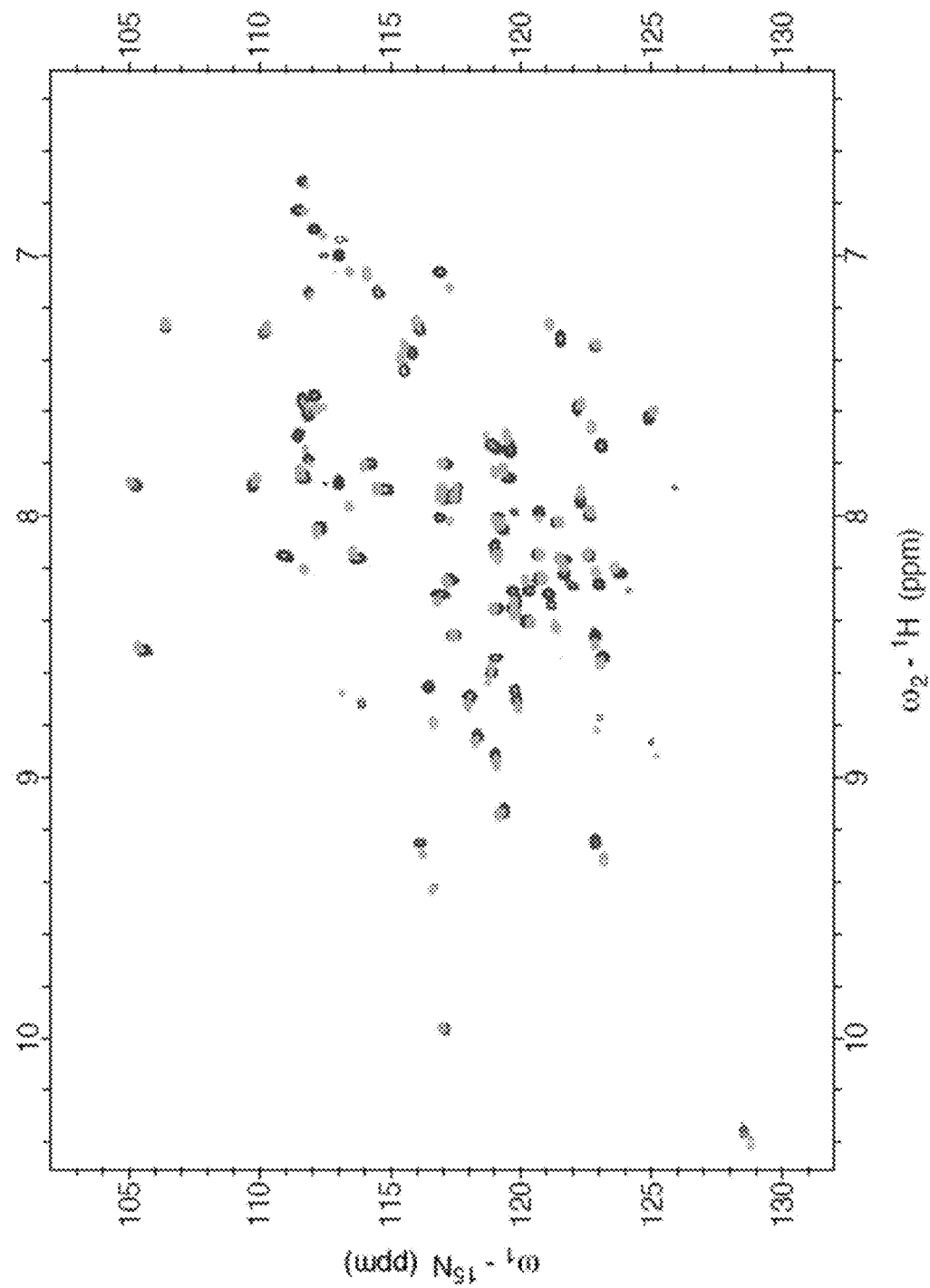

FIG. 41: Octanoyl-[$^{15}$N]ACP/[8-$^{13}$C$_1$]octanoyl-[$^{15}$N]ACP HSQC spectrum overlay.

Figure 42A:
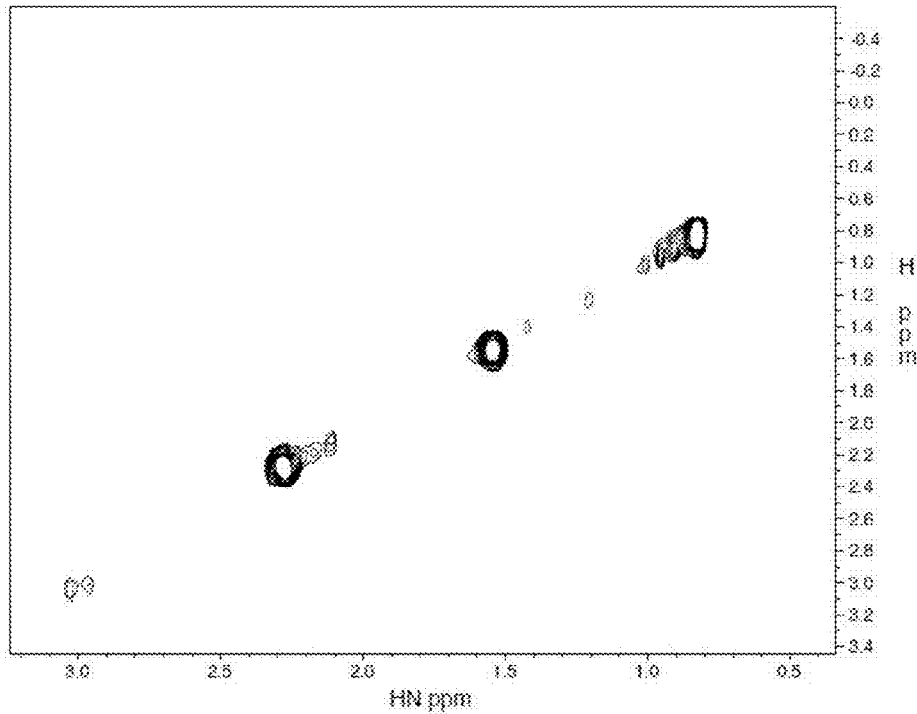
Figure 42B:
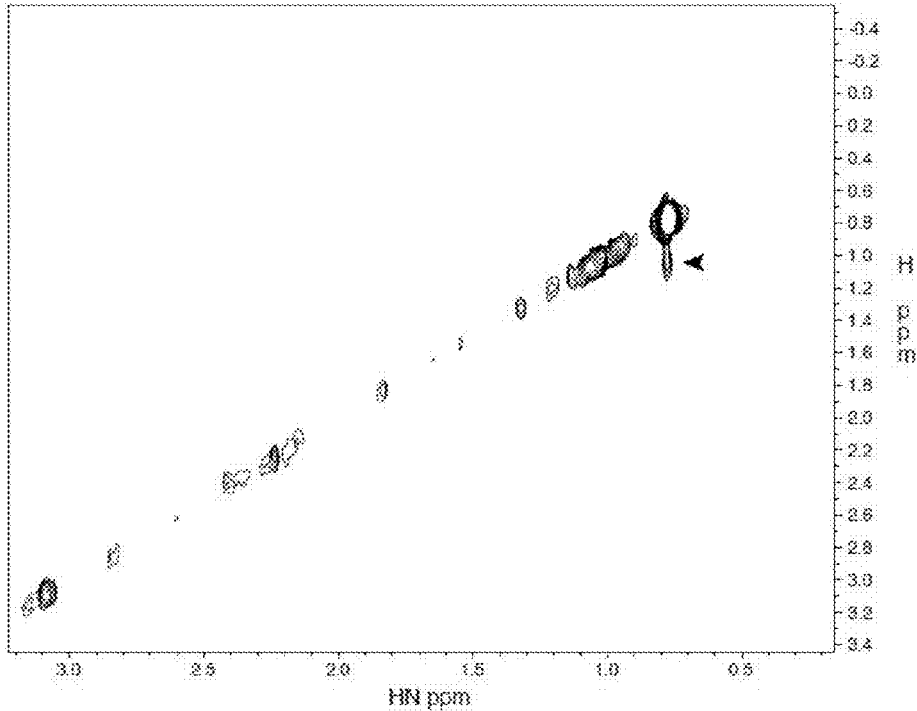

FIGS. 42A-42B 42: [$^{15}$N]ACP NOE spectra: [$^{13}$C$_4$]butanoyl- vs. [8-$^{13}$C$_1$]octanoyl-[$^{15}$N]ACP: (FIG. 42A) NOE spectrum utilizing [$^{13}$C$_4$]butanoyl-oxypantetheine probe appended to [$^{15}$N]ACP. Lack of signal above background provides no evidence for sequestration into [$^{15}$N]ACP while the NOE spectrum for [8-$^{13}$C$_1$]octanoyl-oxypantetheine appended to [$^{15}$N]ACP (FIG. 42B) gives a noticeable signal (arrow) above baseline at approximately 1.0 H$_{ppm}$ and 0.75 H—N$_{ppm}$.

Figure 43A:
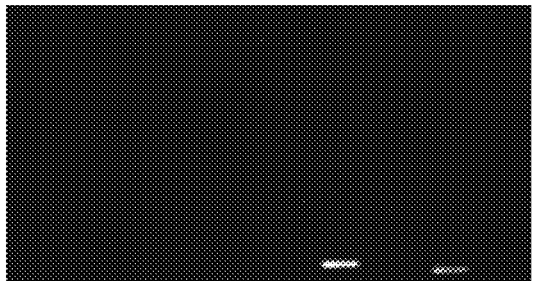
Figure 43B:
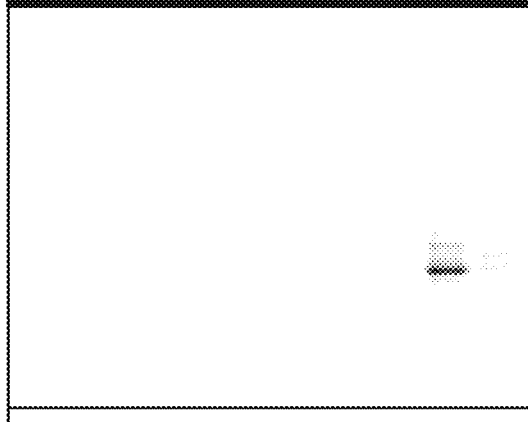
Figure 43C:
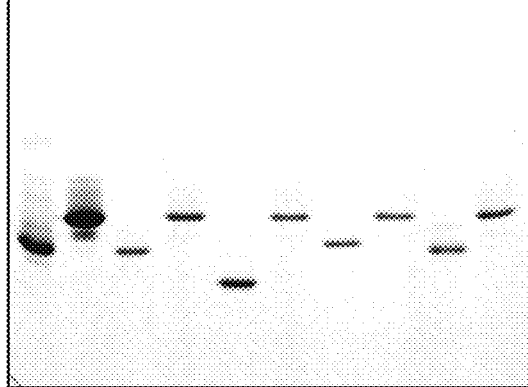

FIGS. 43A-43C: E. coli ACP reaction efficiency gels: Labeling of E. coli apo-ACP proceeded using Sfp and a variety of pantetheine analogs. Butanoyl-pantetheine ("C4") was installed and removed with AcpH; Octanoyl-pantetheine ("C8") was installed and removed with AcpH. Coumarin-pantetheine ("coum.") was installed, giving a UV-fluorescent signal, and subsequently removed with AcpH; lastly, rhodamine-CoA ("rhod.") was installed to give a UV and 532 nm excited fluorescent band, and was removed with AcpH; ACP products were evaluated on conformation-sensitive Urea-PAGE and compared to apo-/holo-ACP standards. FIG. 43A: UV excitation and visible emission; FIG. 43B: 532 nm excitation and 550-610 nm emission; FIG. 43C: total protein.

FIGS. 44A-44D: Fusion-ACP reaction efficiency gels: GFP-ACP, MBP-PaACP, and Luciferase-ACP proceed via Sfp/rhodamine-CoA reaction to convert the apo-ACPs into crypto-ACPs that fluoresce at 532 nm excitation and 550-610 nm emission. All crypto-fusion-ACPs are returned to the apo-form in good yield with AcpH treatment and evaluated by SDS-PAGE. FIG. 44A: 532 nm excitation and 550-610 nm emission results for Fusion ACP for GFP and MBP; FIG. 44B: total protein for Fusion ACP for GFP and MBP; FIG. 44C: 532 nm excitation and 550-610 nm emission results for Fusion ACP for Luciferase; FIG. 44D: total protein for Fusion ACP for Luciferase.

Figure 45:
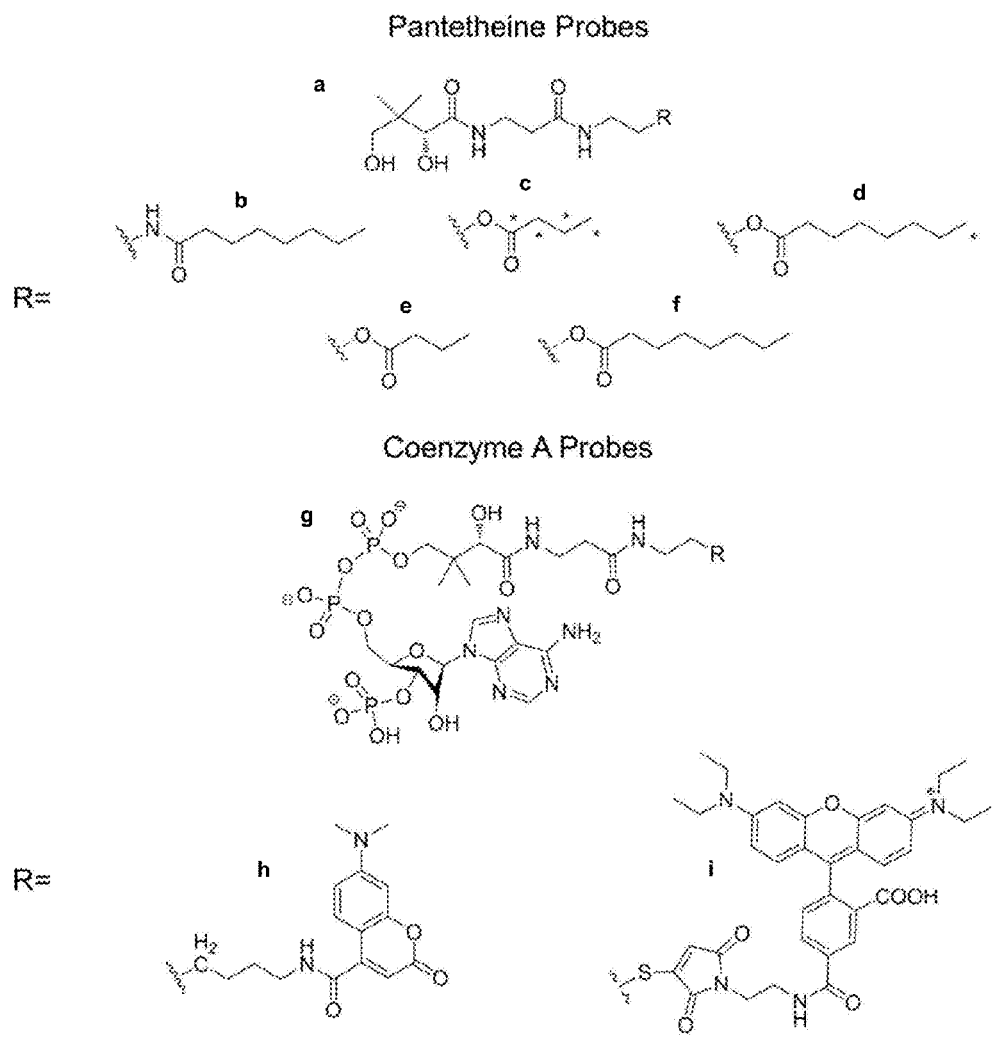
Figure 46A:
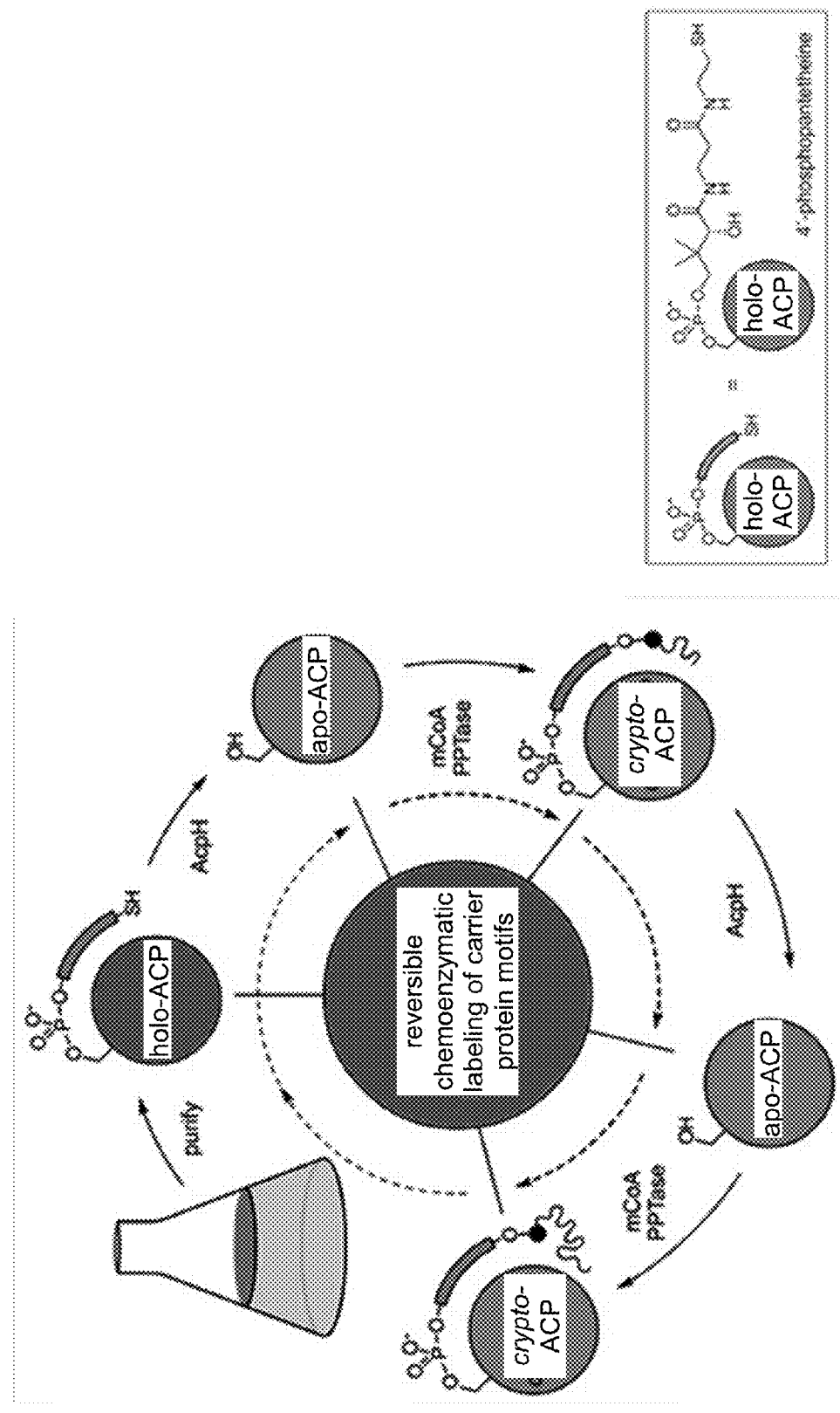
Figure 46B:
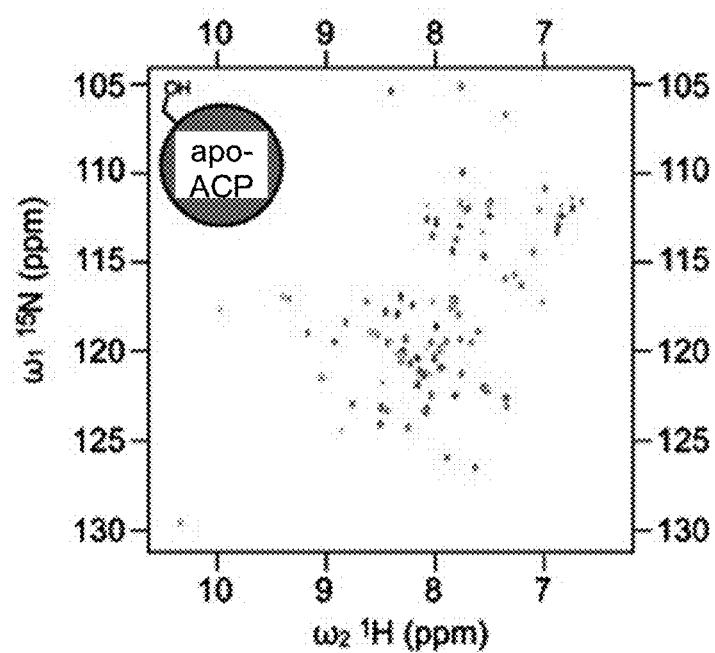
Figure 46C:
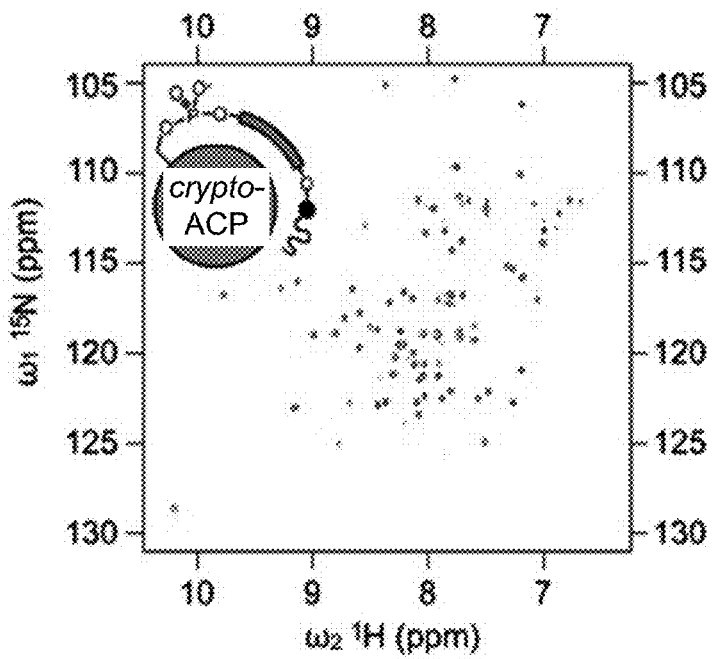
Figure 46D:
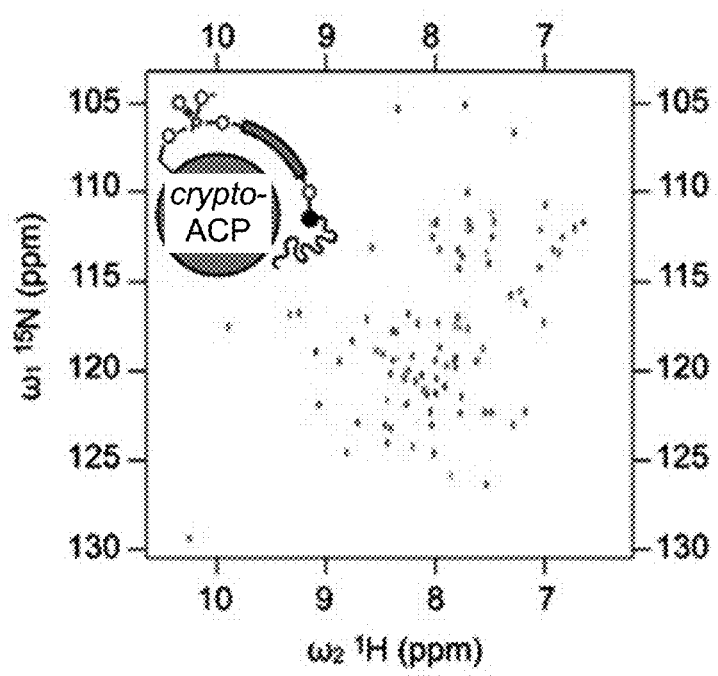
Figure 47A:
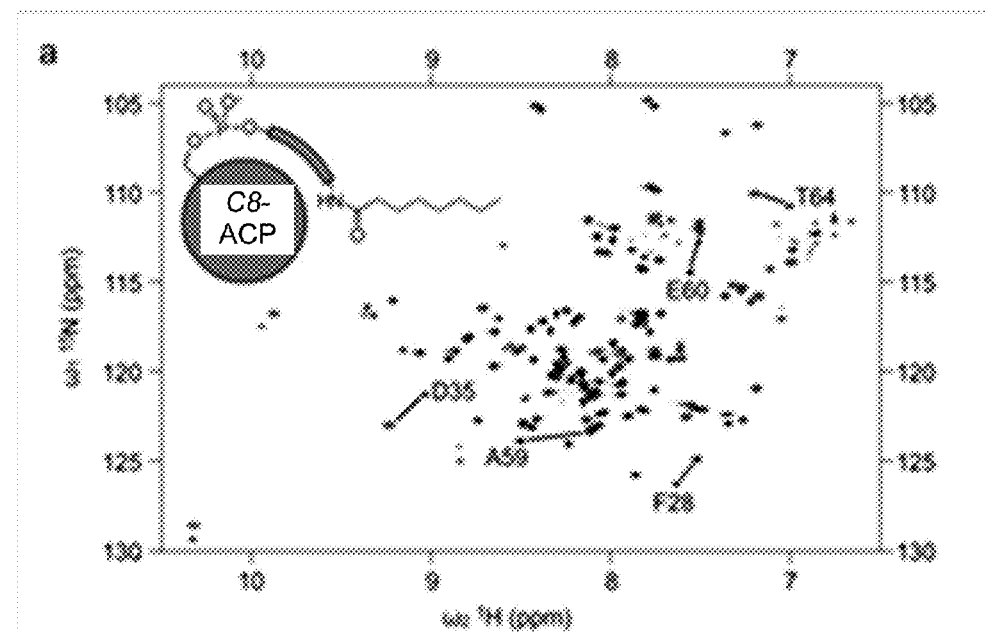
Figure 47B:
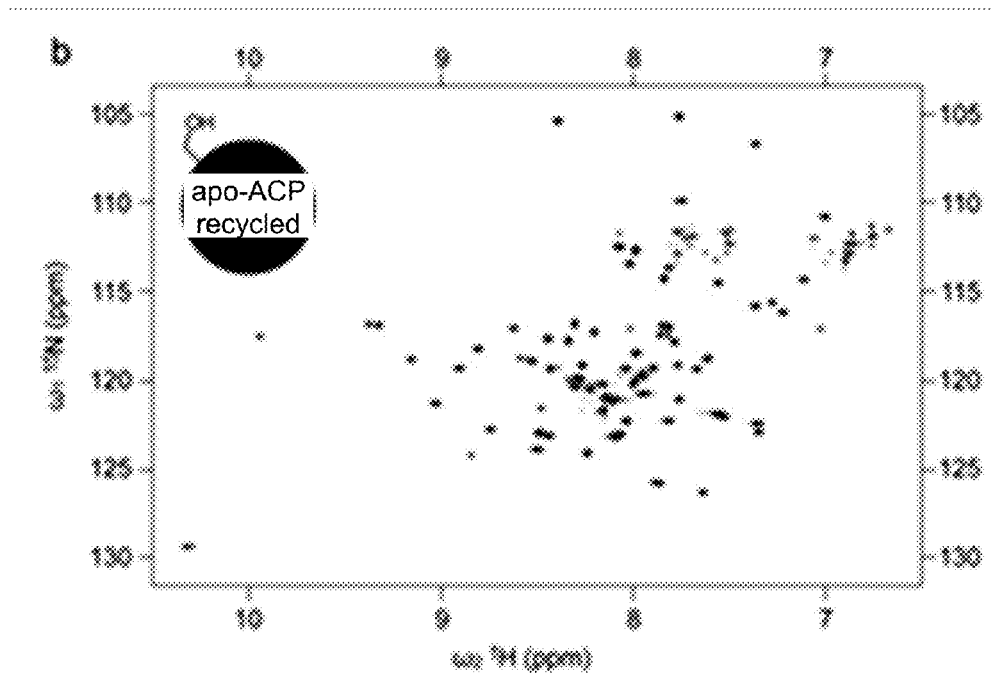
Figure 47C:
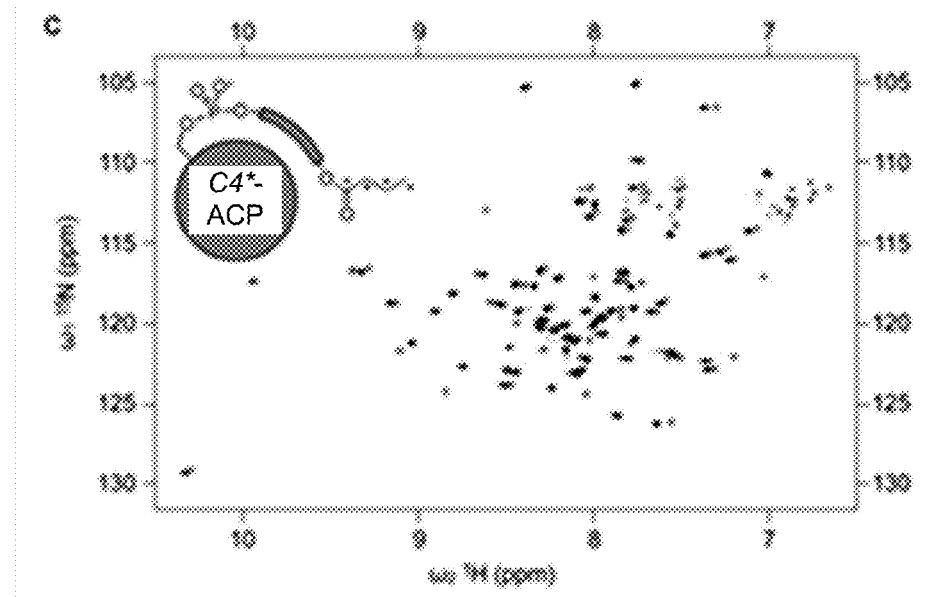
Figure 47D:
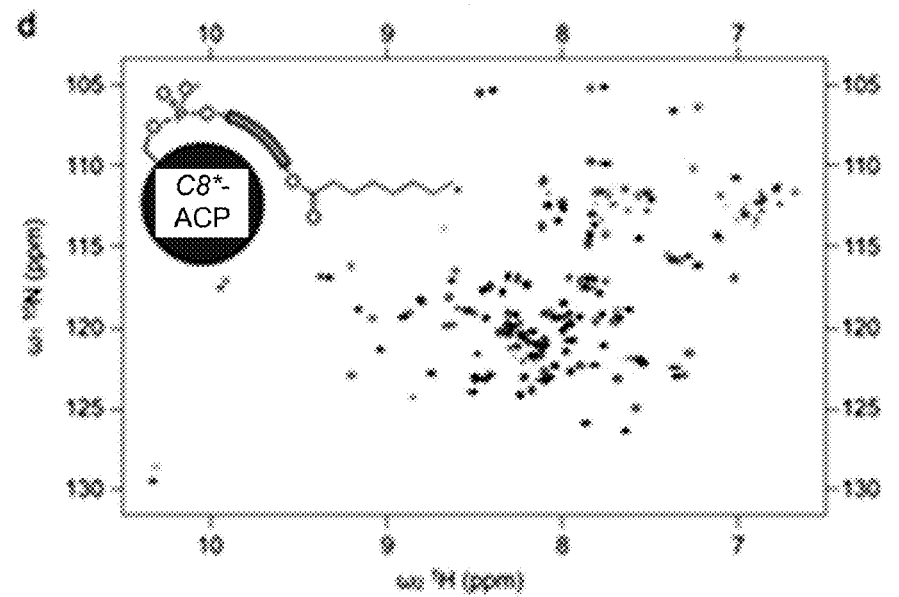

FIG. 45. Utilized ACP probe structures: (element a) The pantetheine moiety served as the basis for attachment of varied acyl groups to [$^{15}$N]ACP, including an octanoyl-group (element b) via an amide linkage, as well as [$^{13}$C$_4$]butanoyl- (element c) and [8-$^{13}$C$_1$]octanoyl- (element d) via oxyester linkage for NMR studies, as well as regular butanoyl (element e) and octanoyl (element f) pantoxy analogs for ACP reaction efficiency studies. (element g) Coenzyme A provided a scaffold for attachment of two different fluorophores for further reaction and linkage to ACP, including coumarin (element h) and rhodamine (element i).

FIG. 46A-46D. Reversible labeling of E. coli ACP for NMR studies: $^{15}$N-ACP expressed in E. coli DE3 (BL-21) is isolated in the holo state (top, FIG. 46A); ACP is prepared for covalent labeling by treatment with AcpH to generate exclusively apo-ACP; Protein purity and modification homogeneity is confirmed by 2D-NMR (FIG. 46B); labeling with acyl pantetheine analogs to the crypto-ACP, or labeled form, proceeds via PPTase/mCoA modification that is analyzed by NMR ((FIG. 46C), (FIG. 46D)); modification is quantitatively reversed by AcpH, returning labeled proteins to the apo form, where this iterative process can be exploited to provide unique structural insights into ACP-substrate interactions.

FIGS. 47A-47D: HSQC spectra of four recycled ACPs in various acyl states overlayed with apo-ACP: (FIG. 47A) $^{15}$N—$^{1}$H-HSQC of the originally prepared apo-ACP is overlayed with the HSQC of octanoyl-ACP; characteristic changes in the chemical shifts of specific residues are observed upon loading of the acyl chain; (FIG. 47B) HSQC of regenerated apo-ACP overlayed with the original apo-ACP preparation; nearly perfect overlap of the two spectra indicates that the regenerated apo-ACP is folded properly; (FIG. 47C) HSQC of butryryl-$^{13}$C-ACP (green) is overlayed with the original apo-ACP; changes observed are more subtle than those observed in 3a because the shorter acyl chain interacts with ACP to a lesser extent than the longer octanoyl chain; (FIG. 47D) HSQC of octanoyl-(8-$^{13}$C)-ACP is overlayed with the original apo-ACP; changes in chemical shifts are nearly identical to the shifts observed in (a), indicating that iterative labeling and unlabeling does not affect substrate sequestration properties of ACP.

Figure 48:
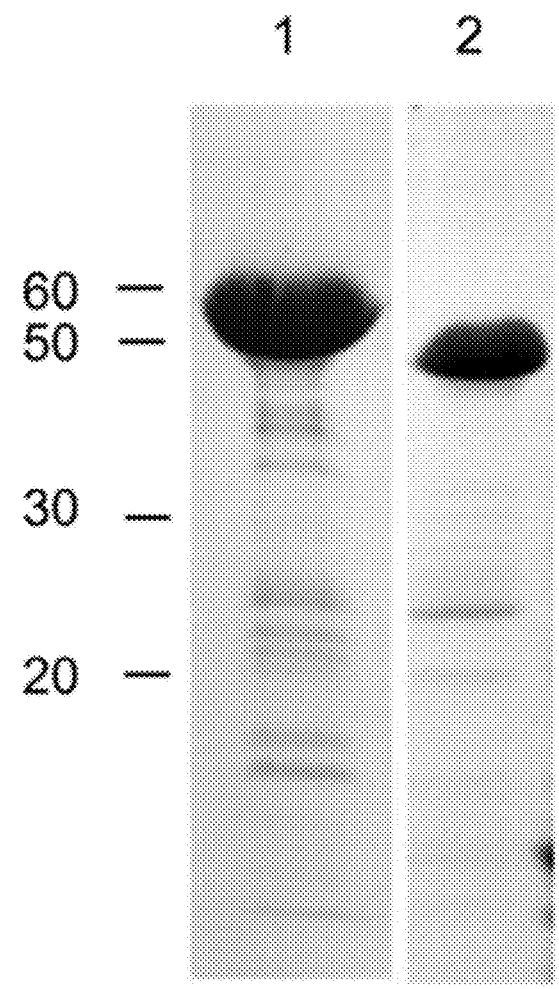

FIG. 48: Fusion ACP Ni-NTA Purification Gel: SDS-PAGE and coomassie staining was performed to ascertain fusion ACP purity; MBP-PaACP (lane 1) and GFP-ACP (lane 2) were both purified by Ni-NTA resin and DEAE anion exchange resin (following initial AcpH treatment) prior to labeling experiments utilizing rhodamine-CoA.

DETAILED DESCRIPTION OF THE INVENTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, S, Se and Si, and wherein the nitrogen, selenium, and sulfur atoms may optionally be oxidized, and the nitrogen heteroatom may optionally be quaternized. The heteroatom(s) O, N, P, S, Se, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si (CH$_3$)$_3$, —CH$_2$—CH=N—OCH$_3$, —CH=CH—N (CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O) NR', —NR'R", —OR', —SeR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, unless otherwise stated, mean, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g. 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom (e.g. N, O, or S), wherein sulfur heteroatoms are optionally oxidized, and the nitrogen heteroatoms are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "alkylsulfonyl," as used herein, means a moiety having the formula —S($O_2$)—R', where R' is an alkyl group as defined above. R' may have a specified number of carbons (e.g., "$C_1$-$C_4$ alkylsulfonyl"). The term "sulfonylalkyne," as used herein, means a moiety have the formula ≡—S($O_2$)—R', where R' is an alkyl group as defined above. R' may have a specified number of carbons (e.g., "$C_1$-$C_4$ sulfonylalkyne").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —$CO_2$R', —CONR'R", —OC(O) NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR)$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_3$-$C_8$ aryl, and each substituted or unsubstituted heteroaryl is a substituted or unsubstituted $C_3$-$C_8$ heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_3$-$C_7$ aryl, and each substituted or unsubstituted heteroaryl is a substituted or unsubstituted $C_3$-$C_7$ heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_3$-$C_8$ arylene, and/or each substituted or unsubstituted heteroaryl is a substituted or unsubstituted $C_3$-$C_8$ heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_3$-$C_7$ aryl, and/or each substituted or unsubstituted heteroaryl is a substituted or unsubstituted $C_3$-$C_7$ heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_3$-$C_7$ arylene, and/or each substituted or unsubstituted heteroarylene is a substituted or unsubstituted $C_3$-$C_7$ heteroarylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

The symbol "~~~" denotes the point of attachment of a chemical moiety to the remainder of a molecule or chemical formula.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue," or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

Conjugates described herein may be synthesized using bioconjugate or conjugate chemistry. Conjugate chemistry includes coupling two molecules together to form an adduct. Conjugation may be a covalent modification. Currently favored classes of conjugate chemistry reactions available with reactive known reactive groups are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

The reactive functional groups can be chosen such that they do not participate in, or interfere with, the chemical stability of the conjugate described herein. Alternatively, a reactive functional group can be protected from participating in the crosslinking reaction by the presence of a protecting group.

The term "fluorescein" as used herein refers to fluorescent derivatization agents for labeling proteins. As used herein, fluorescein includes its derivatives such as, for example, fluorescein isothiocyanate (e.g. FITC), carboxyfluorescsein, succinimidyl esters of carboxyfluorescein (e.g. FAM, 6-JOE)), fluorescein-X-succinimidyl esters (e.g. SFX), and fluorescein dichlorotriazine (e.g. DTAF).

A "reactive probe" as used herein, refers to moiety used for site selective-covalent modification of a target protein. Covalent modification may be accomplished using conjugate chemistry as described herein. Exemplary reactive probes include, for example, thiol-reactive agents that generate stable thioether moieties, azide-alkyne agents used in cycloaddition chemistry, dichlorotriazines, acyl nitriles, hydrazines, hydroxylamines, succinimidyl-alkylene agents used to react with amines), biotin-avidin, or photoreactive crosslinkers (e.g. benzophenone-4-malemide, benzophenone-4-isothiocyanate), chloro-acrylate, sulfonyl-alkynes, or alpha-bromo-amides as described, for example in Worthington, et al. ACS Chem Biol. 2006 Dec. 20; 1(11):687-91; Ishikawa, et al. J Am Chem Soc. 2013 Jun. 19; 135(24): 8846-9; and Blatti, et al. PLoS One. 2012; 7(9):e42949.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^1$ substituent may be distinguished as $R^{1.1}$, $R^{1.2}$, $R^{1.3}$, $R^{1.4}$, etc., wherein each of $R^{1.1}$, $R^{1.2}$, $R^{1.3}$, $R^{1.4}$ etc. is defined within the scope of the definition of $R^1$ and optionally differently.

A "detectable moiety" as used herein refers to a moiety that can be detected using techniques known in the art. In embodiments, the detectable moiety is covalently attached.

The detectable moiety may provide for imaging of the attached compound or biomolecule. The detectable moiety may indicate the contacting between two compounds. Exemplary detectable moieties are fluorophores, antibodies, reactive dies, radio-labeled moieties, magnetic contrast agents, and quantum dots. Exemplary fluorophores include fluorescein, rhodamine, GFP, coumarin, FITC, AlExa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As used herein, "expression vector" refers to polynucleotide elements that are used to introduce recombinant nucleic acid into cells for either expression or replication. Selection and use of such vehicles is routine in the art. One skilled in the art would readily understand that a variety of recombinant vectors may be utilized in the practice of embodiments of the invention. An expression vector includes vectors capable of expressing nucleic acids operatively linked to regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid.

ACP nucleotide sequences, or a mixture of such sequences, can be cloned into one or more recombinant vectors as individual cassettes, with separate control elements or under the control of a single promoter. The ACP cassette can include flanking restriction sites to allow for the easy deletion and insertion of other proteins so that hybrid or chimeric ACPs can be generated. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

The phrase "supplied as" and the like, refers to how a particular component of a kit is provided within the kit (e.g. a peptide is provided as a solid or dissolved in a liquid). When supplied as a solid, the component may be a, for example, a powder a gel, or a tablet. When supplied as a liquid, the component may be dissolved in any liquid suitable for dissolving the component therein (e.g. water, buffers, organic solvents, mixtures of organic solvents and water such as DMSO/water).

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Amino acids may alternatively be designated as "Aaa1," "Aaa2," "Aaa3" where Aaa represents the three letter symbol of an amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid, which encodes a polypeptide, is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A nucleic acid (such as a polynucleotide), a polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Identity" or "percent identity," in the context of two or more polynucleotide sequences or polypeptide sequences, refers to two or more sequences or subsequences that are the same or have a specified percentage of nucleic acids or amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection.

Optimal alignment of sequences for comparison and determination of sequence identity can be determined by a sequence comparison algorithm or by visual inspection (see, generally, Ausubel et al., infra). When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters as known in the art, for example BLAST or BLAST 2.0. For example, comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Nat'l. Acad. Sci. USA* 85:2444, or by computerized implementations of these algorithms (GAP, BESTFIT, FASTA, and TFASTA in the Wisconsin Genetics Software Package, Genetics Computer Group, 575 Science Dr., Madison, Wis.). Thus alignment can be carried out for sequences that have deletions and/or additions, as well as those that have substitutions, as well as naturally occurring, e.g., polymorphic or allelic variants, and man-made variants.

The phrase "substantial sequence identity" or "substantial identity," in the context of two polynucleotide sequences or polypeptide sequences, refers to a sequence that has at least 70% identity to a reference sequence. Percent identity can be any integer from 70% to 100%. Two polynucleotide sequences or polypeptide sequences that have 100% sequence identity are said to be "identical." A polynucleotide sequences or polypeptide sequence is said to have "substantial sequence identity" to a reference sequence when the sequences have at least about 70%, at least about 75%, at least 80%, at least 85%, at least 90%, at least 91%, at least 92%, at least 93%, at least 94%, at least 95%, at least 96%, at least 97%, at least 98%, or at least 99% or greater sequence identity as determined using the methods described herein, such as BLAST using standard parameters as described above.

The terms "ACP," "acyl carrier protein," and "ACP protein moiety" as used herein, refer to carrier proteins (or moieties thereof in the case of an ACP protein moiety) recognizable by (i.e. capable of being catalyzed by) either an ACP hydrolase or a phosphopantethienyl transferase. In vivo, endogenous cellular ACP's are involved in the synthesis (e.g. biosynthesis) of fatty acids, polyketides, and/or non-ribosomal peptide synthesis and typically bind to a phosphopantetheine, which acts as a linker to anchor growing fatty acids, polyketides or peptides. The term ACP includes proteins of the same or similar names and functional fragments and homologs thereof recognizeable by either an ACP hydrolase or phosphopantethienyl transferase. Typically, an ACP includes a "-DSL-" conserved sequence. The term ACP includes recombinant or naturally-occuring forms of an ACP (e.g. ACP preprotein), or variants or homologs therof that are recognized by either an ACP hydrolase or phosphopantethienyl transferase. In embodiments, an ACP is a full-length ACP protein. In embodiments, an ACP has a sequence length of at least 10 amino acids. In embodiments, an ACP has a sequence length of at least 20 amino acids. In embodiments, ACPs and ACP homologs are proteins with known involvement in acylation of fatty acids, polyketides, or peptides. Accordingly, an ACP may be a Fatty Acid ACP (i.e. a carrier protein or functional fragment thereof that is capable of participating in the fatty acid synthesis pathway involved in acylation of fatty acids). An ACP may be a Polyketide ACP (i.e. a carrier protein or functional fragment thereof that is capable of participating in the acylation of polyketides). An ACP may be a Peptide ACP (i.e. a carrier protein or functional fragment thereof that is capable of participating in the acylation of peptides and/or amino acids). In embodiments, the ACP is a protein, or functional fragment or homologs thereof, identified in Table 1 (SEQ ID NOs: 33, 34, 35, 36, 37, 38, 39, 40, 41, 42, 43, 44, 45, 46, 47, or 48).

An "ACP protein fusion moiety" as used herein refers an ACP protein moiety covalently bound to a second protein (e.g. a full length protein or protein domain), which may serve variety of functions. Exemplary second proteins include but are not limited to proteins with unique physical properties, such as GFP; proteins with catalytic activity, such as luciferase; and proteins with distinct cellular localization, such as the cell-surface protein the beta-2 adrenergic receptor. One skilled in the art would readily recognize the second protein can include classes of proteins such kinases, proteases, ligases, reductases, cell signaling proteins, ligand binding proteins (e.g. ion channels and transporters, oxidases), and structural proteins.

An "Apo-ACP" refers to an ACP not covalently bound to a phosphopantetheine moiety or analogue, as described herein. A "holo-ACP" refers to an ACP covalently bound to a phosphopantetheine moiety. A "ACP-phosphopantetheine conjugate" refers to an ACP protein moiety or ACP fused protein moiety covalently bound to a phosphopantetheine analogue moiety, as described herein. An ACP may be characterized as an ACP derived from a particular organism. For example, a P. aeruginosa ACP is an ACP, or functional fragment thereof, found in P. aeruginosa.

"ACP-hydrolase," "AcpH," or "acyl carrier protein hydrolase" are herein used interchangeably and refer to proteins having phosphodiesterase activity that are capable of cleaving a phosphopantethiene moiety or analogue from an ACP. An AcpH may be characterized as an AcpH derived from a particular organism. For example, a P. aeruginosa AcpH is an AcpH, or functional fragment thereof, found in P. aeruginosa. In embodiments, the AcpH is a protein, or functional fragment or homologs thereof, having identified by the following accession numbers or SEQ ID NOs: (SEQ ID NO:73), NP$_{13}$ 253043.1 (P. aeruginosa PAO1) (SEQ ID NO:74), (P. fluorescens NCIMB 10586) (SEQ ID NO:75), and YP$_{13}$ 003888700.1 (Cyanothece PCC 7822) (SEQ ID NO:76).

"Phosphopantetheinyl transferase," "phosphopantetheine transferase," "PPTase," or "Sfp" are herein used interchangeably and refer to proteins capable of transferring a phosphopantetheine moiety or analogue to an ACP. In embodiments, a phosphopantetheine moiety or phosphopantetheine analogue moiety is transferred from a phosphopantetheinyl transferase to a serine on an ACP. A PPTase may be characterized as a PPTase derived from a particular organism. For example, a B. subtilis PPTase is a PPTase, or functional fragment thereof, found in B. subtilis). In embodiments, the PPTase is a protein, or functional fragment or homologs thereof, having identified by the following accession numbers: YP$_{13}$ 004206313 (SEQ ID NO:104), YP$_{13}$ 007210795 (SEQ ID NO:105) (B. subtilis), AAG04554 (SEQ ID NO:106) (P. aeruginosa), EDV65312 (SEQ ID NO:107) and EDV67052 (SEQ ID NO:108).

An "ACP-phosphopantetheine conjugate" as used herein refers to a phosphopantetheiene analogue moiety covalently bound to an ACP protein moiety or ACP protein fusion moiety via a phosphodiester linker. In embodiments, a ACP-phosphopantetheine conjugate has the formula:

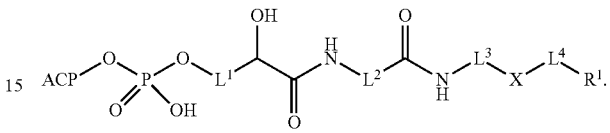

$L^1$, $L^2$, $L^3$, $L^4$, X, and $R^1$ are as described herein.

A "phosphopantetheine analogue moiety" or "phosphopantetheinyl analogue moiety" as used herein refers to a pantetheine analogue moiety attached to a phosphodiester linker. In embodiments, a phosphopantetheine analogue moiety has the formula:

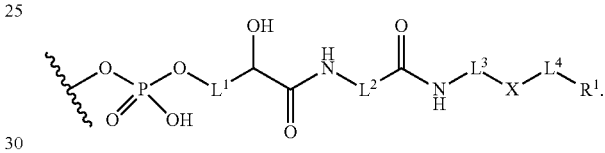

$L^1$, $L^2$, $L^3$, $L^4$, X, and $R^1$ are as described herein.

A "CoA-phosphopantetheine analogue" or "CoA-phosphopantetheinyl analogue" as used herein refers to a phosphopantetheine analogue moiety covalently attached to a phosphoadenosine moiety. In embodiments, a ACP-CoA-phosphopantetheine analogue has the formula:

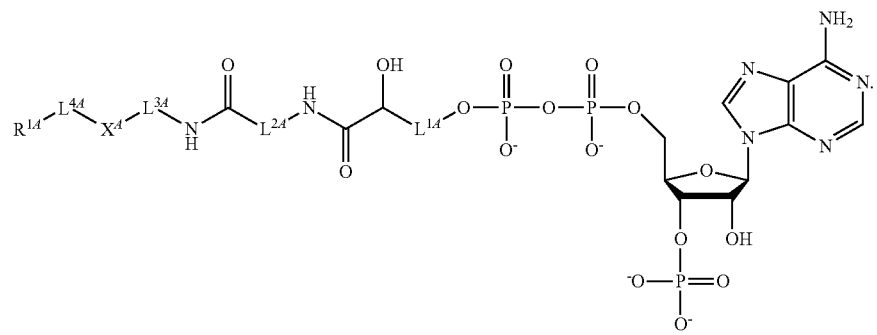

$L^{1A}$, $L^{2A}$, $L^{3A}$, $L^{4A}$, $X^A$, and $R^{1A}$ are as described herein.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

II. Methods

In a first aspect is a method of forming an Apo-ACP from an ACP-phosphopantetheine conjugate. The method includes contacting an ACP-phosphopantetheine conjugate with an ACP hydrolase. The ACP-phosphopantetheine conjugate includes a phosphopantetheine analogue moiety covalently bonded to an ACP through a phosphodiester linker. The ACP hydrolase is allowed to cleave the phosphodiester linker thereby forming an Apo-ACP. The ACP-phosphopantetheine conjugate has the formula:

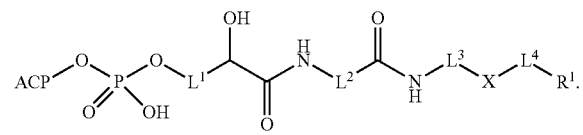

ACP is an ACP protein moiety or an ACP protein fusion moiety. $L^1$, $L^2$ and $L^3$ are independently substituted or unsubstituted alkylene. $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. X is —S—, —NH— or —O—. $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, a detectable moiety or a reactive probe.

The ACP may be an ACP protein moiety. When the ACP is an ACP protein moiety, the ACP protein moiety may be a Fatty Acid ACP protein moiety, a polyketide ACP protein moiety, a peptide ACP protein moiety. The ACP may be a Fatty Acid ACP protein moiety. The ACP may be a polyketide ACP protein moiety. The ACP may be a peptide ACP protein moiety. The ACP may be an ACP protein fusion moiety. When the ACP is an ACP protein fusion moiety, the ACP protein moiety portion of the ACP protein fusion moiety may be a Fatty Acid ACP protein moiety, a Polyketide ACP protein moiety, or a Peptide ACP protein moiety (i.e. a second protein moiety covalently bound to a Fatty Acid ACP protein moiety, a Polyketide ACP protein moiety, or a Peptide ACP protein moiety). In embodiments, the ACP protein moiety portion of the ACP protein fusion moiety is a Fatty Acid ACP protein moiety. In embodiments, the ACP protein moiety portion of the ACP protein fusion moiety is a Polyketide ACP moiety. In embodiments, the ACP protein moiety portion of the ACP protein fusion moiety is a Peptide ACP protein moiety. One skilled in the art would appreciate that the ACP proteins described herein share common functionality (e.g. involvement in acylation of a product) and may share substantial sequence identity.

In embodiments, the ACP protein moiety is an *E. coli* ACP protein moiety, *P. aeruginosa* ACP protein moiety, *S. oneidensis* ACP protein moiety, *P. falciparum* ACP protein moiety, *M. tuberculosis* ACP protein moiety, *S. coelicolor* ACP protein moiety, *A. parasiticus* ACP protein moiety, *G. fujikuroi* ACP protein moiety, *L. majuscule* ACP protein moiety or *P. fluorescens* apo-ACP. The ACP protein moiety may be an *E. coli* apo-ACP. When the ACP protein moiety is an *E. coli* ACP protein moiety, it may be *E. coli* ACpP (type II). The ACP protein moiety may be a *P. aeruginosa* apo-ACP. The ACP protein moiety may be a *S. oneidensis* apo-ACP. The ACP protein moiety may be a *P. falciparum* ACP protein moiety. The ACP protein moiety may be a *M. tuberculosis* apo-ACP. The ACP protein moiety may be a *S. coelicolor* ACP protein moiety. The ACP protein moiety may be an *A. parasiticus* ACP protein moiety. The ACP protein moiety may be a *G. fujikuroi* apo-ACP. The ACP protein moiety may be a *L. majuscule* ACP protein moiety. The ACP protein moiety may be a *P. fluorescens* ACP protein moiety. The ACP protein moiety may be a protein moiety having an amino acid sequence identity having at least 60%, 65%, 70%, 75%, 80%, 85%, 90%, 95%, 99% or 100% identity to the entire portion or a functional fragment thereof of SEQ ID NOs: 33, 34, 35, 36, 37, 38, 39, 40, 41, 42, 43, 44, 45, 46, 47, or 48, wherein the functional fragment is recognizable by either an ACP hydrolase or a phosphopantethienyl tranferase.

An ACP protein moiety may also encompass amino acid sequence mutants of an ACP. The amino acid sequence mutants may be substitutional, deletional, or insertional mutants. Substitutional mutants may include conservatively modified variants as described herein, including embodiments thereof. Deletional mutants include the deletion of amino acids at a non-terminal endpoint in the protein. Insertional mutants include the addition of amino acids at a non-terminal endpoint in the protein. In embodiments, the ACP protein moiety is a protein having a substitutional mutation in SEQ ID NOs: 33, 34, 35, 36, 37, 38, 39, 40, 41, 42, 43, 44, 45, 46, 47, or 48. In embodiments, the ACP protein moiety is a protein having a deletional mutation in SEQ ID NOs: 33, 34, 35, 36, 37, 38, 39, 40, 41, 42, 43, 44, 45, 46, 47, or 48. In embodiments, the ACP protein moiety is a protein having an insertional mutation in SEQ ID NOs: 33, 34, 35, 36, 37, 38, 39, 40, 41, 42, 43, 44, 45, 46, 47, or 48. In embodiments, the ACP protein moiety may include non-proteinogenic amino acids. ACP protein moiety mutants described herein are recognizable by either an ACP hydrolase or a phosphopantethienyl tranferase. The ACP protein moiety may be a fragment of the full-length ACP recognizable by either an ACP hydrolase or a phosphopantethienyl tranferase. The fragment may include amino acid substitutions, deletions, or insertions. Substitutional mutants may include conservatively modified variants as described herein, including embodiments thereof. Insertional mutants include the addition of amino acids at a non-terminal endpoint in the fragment. Deletional mutants include the deletion of amino acids at a non-terminal endpoint in the fragment. In embodiments, the ACP protein moiety fragment may include non-proteinogenic amino acids. ACP fragment is recognizable by either an ACP hydrolase or a phosphopantethienyl tranferase.

TABLE 1

| Source Organism | Accession Number |
| --- | --- |
| E. coli | NP_287228 (SEQ ID NO: 33) |
| P. aeruginosa | NP_251656 (SEQ ID NO: 34) |
| S. oneidensis | NP_718356 (SEQ ID NO: 35) |
| P. falciparum | 3GZL_A (SEQ ID NO: 36) |
| M. tuberculosis | NP_216760 (SEQ ID NO: 37) |
| M. tuberculosis | YP_006516394 (SEQ ID NO: 38) |
| S. coelicolor | NP_629239 (SEQ ID NO: 39) |
| A. parasiticus | 2KR5_A (SEQ ID NO: 40) |
| G. fujikuroi | CAB92399 (SEQ ID NO: 41) |
| L. majuscula | AAS98798 (SEQ ID NO: 42) |
| L. majuscula | CAB46501 (SEQ ID NO: 43) |
| P. agglomerans | AAO39095 (SEQ ID NO: 44) |
| P. agglomerans | AAO39103 (SEQ ID NO: 45) |
| V. cholerae | AAC45926 (SEQ ID NO: 46) |
| P. fluorescens | AAD24885 (SEQ ID NO: 47) |
| P. syringae | AAZ99831 (SEQ ID NO: 48) |

One skilled in the art would readily recognize a P. fluorescens ACP (e.g. SEQ ID NO:47) may be also be referred to as a P. protogens ACP as P. fluorescens has been recently reclassified to P. protogens. Accordingly, herein, "P. protogens" and "P. fluorescens" are used interchangeably.

An ACP protein moiety may also include sequences having the formula:

-DSL(Aaa1)(Aaa2)(Aaa3)(Aaa4)(Aaa5)(Aaa6)-.

Aaa1 is D, E, or S. Aaa2 is T, F, or W. Aaa3 is V, L, or I. Aaa4 is E, A, or L. Aaa5 is A, S, R, or L. Aaa6 is V, K, or L.

In embodiments, the compound may have an amino acid sequence of SEQ ID NOs: 1, 2, 3, 4, 5, 6, 7, or 8.

TABLE 2

| SEQ ID NO: 1. | DSLEFIASKLA |
| SEQ ID NO: 2. | GDSLSWLLRLLN |
| SEQ ID NO: 3. | DSLEFIAAKLA |
| SEQ ID NO: 4. | DSAEFIASKLA |
| SEQ ID NO: 5. | ASLEFIASKLA |
| SEQ ID NO: 6. | ASFVEDLGADSLDTVELVMALEEEF |
| SEQ ID NO: 7. | DSLDTVELVMA |
| SEQ ID NO: 8. | DSLDTVELVMALEEEFDTEIPDEEAEKI |

The ACP protein moiety includes ACP protein sequences as described herein, including Apo-ACP protein sequences and fragments thereof recognizable by either an ACP hydrolase or a phosphopantethienyl tranferase. The ACP protein moiety may be a full-length APC protein. The ACP protein moiety may be a fragment of a full length ACP protein. The ACP protein moiety may be at least 10 amino acids to at least 100 amino acids in length. The ACP protein moiety may be at least 10 amino acids to at least 90 amino acids in length. The ACP protein moiety may be at least 10 amino acids to at least 80 amino acids in length. The ACP protein moiety may be at least 10 amino acids to at least 70 amino acids in length. The ACP protein moiety may be at least 10 amino acids to at least 60 amino acids in length. The ACP protein moiety may be at least 10 amino acids to at least 50 amino acids in length. The ACP protein moiety may be at least 10 amino acids to at least 40 amino acids in length. The ACP protein moiety may be at least 10 amino acids to at least 30 amino acids in length. The ACP protein moiety may be at least 10 amino acids to at least 25 amino acids in length. The ACP protein moiety may be at least 10 amino acids to at least 20 amino acids in length. The ACP protein moiety may be at least 10 amino acids to at least 15 amino acids in length.

The ACP protein moiety may be at least 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 amino acids in length. The ACP protein moiety may be about 10 amino acids in length. The ACP protein moiety may be about 11 amino acids in length. The ACP protein moiety may be about 12 amino acids in length. The ACP protein moiety may be about 13 amino acids in length. The ACP protein moiety may be about 14 amino acids in length. The ACP protein moiety may be about 15 amino acids in length. The ACP protein moiety may be about 16 amino acids in length. The ACP protein moiety may be about 17 amino acids in length. The ACP protein moiety may be about 18 amino acids in length. The ACP protein moiety may be about 19 amino acids in length. The ACP protein moiety may be about 20 amino acids in length. The ACP protein moiety may be about 21 amino acids in length. The apo-ACP may be about 22 amino acids in length. The ACP protein moiety may include a -DSLsequence. In embodiments, the amino acid sequence of the ACP protein moiety has the same amino acid sequence as the apo-ACP and the ACP-phosphopantetheine conjugate.

The ACP protein moiety includes functional fragments of an ACP. Functional fragments may include a -DSLsequence (alternatively referred to herein as a "DSL sequence") or a sequence including amino acids corresponding to the -DSLsequence in a natural ACP protein (referred to herein as a DSL-corresponding sequence"). In embodiments, a functional fragment is about 110, 100, 90, 80, 70, 65, 60, 55, 50, 45, 40, 35, 30, 25, 20, 15, or 10 amino acids and contains a -DSL-sequence or DSL-corresponding sequence. In embodiments, a functional fragment is about 110 amino acids and contains a -DSLsequence DSL-corresponding sequence. In embodiments, a functional fragment is about 100 amino acids and contains a -DSLsequence DSL-corresponding sequence. In embodiments, a functional fragment is about 90 amino acids and contains a -DSL-sequence DSL-corresponding sequence. In embodiments, a functional fragment is about 80 amino acids and contains a -DSLsequence DSL-corresponding sequence. In embodiments, a functional fragment is about 70 amino acids and contains a -DSLsequence DSL-corresponding sequence. In embodiments, a functional fragment is about 60 amino acids and contains a -DSLsequence DSL-corresponding sequence. In embodiments, a functional fragment is about 50 amino acids and contains a -DSLsequence DSL-corresponding sequence. In embodiments, a functional fragment is about 40 amino acids and contains a -DSLsequence DSL-corresponding sequence. In embodiments, a functional fragment is about 30 amino acids and contains a -DSLsequence DSL-corresponding sequence. In embodiments, a functional fragment is about 25 amino acids and contains a -DSLsequence DSL-corresponding sequence. In embodiments, a functional fragment is about 20 amino acids and contains a -DSLsequence DSL-corresponding sequence. In embodiments, a functional fragment is about 15 amino acids and contains a -DSLsequence DSL-corresponding sequence. In embodiments, a functional fragment is about 10 amino acids and contains a -DSLsequence or DSL-corresponding sequence. In embodiments, the functional fragment is a fragment of an ACP having SEQ ID NO: 1, 2, 3, 4, 5, 6, 7, 8, 33, 34, 35, 36, 37, 38, 39, 40, 41, 42, 43, 44, 45, 46, 47, or 48.

Functional fragments of an ACP may include peptides in which a -DSLsequence or a DSL-corresponding sequence is flanked by an equal number of amino acids (e.g. e.g. -XXX-DSL-XXX-, where X represents an amino acid.) In embodiments, the functional fragment is a peptide having about 50 amino acids on each side of a -DSLsequence or a DSL-corresponding sequence. In embodiments, the functional fragment is a peptide having about 45 amino acids on each side of a -DSLsequence or a DSL-corresponding sequence. In embodiments, the functional fragment is a peptide having about 40 amino acids on each side of a -DSLsequence or a DSL-corresponding sequence. In embodiments, the functional fragment is a peptide having about 35 amino acids on each side of a -DSLsequence or a DSL-corresponding sequence. In embodiments, the functional fragment is a peptide having about 30 amino acids on each side of a -DSLsequence or a DSL-corresponding sequence. In embodiments the functional fragment is a peptide having about 29, 28, 27, 26, 25, 24, 23, 22, or 21 amino acids on each side of a -DSLsequence or a DSL-corresponding sequence. In embodiments, the functional fragment is a peptide having about 20 amino acids on each side of a -DSLsequence or a DSL-corresponding sequence. In embodiments, the functional fragment is a peptide having about 19, 18, 17, or 16 amino acids on each side of a -DSLsequence or a DSL-corresponding sequence. In embodiments, the functional fragment is a peptide having about 15 amino acids on each side of a -DSLsequence or a DSL-corresponding sequence. In embodiments, the functional fragment is a peptide having about 14, 13, 12, or 11 amino acids on each side of a -DSLsequence or a DSL-corresponding sequence. In embodiments, the functional fragment is a peptide having about 10 amino acids on each side of a -DSLsequence or a DSL-corresponding sequence. In embodiments, the functional fragment is a peptide having about 9, 8, 7, or 6 amino acids on each side of a -DSLsequence or a DSL-corresponding sequence. In embodiments, the functional fragment is a peptide having about 5 amino acids on each side of a -DSLsequence or a DSL-corresponding sequence. In embodiments, the functional fragment is a fragment of an ACP having SEQ ID NO: 1, 2, 3, 4, 5, 6, 7, 8, 33, 34, 35, 36, 37, 38, 39, 40, 41, 42, 43, 44, 45, 46, 47, or 48.

Functional fragments of an ACP include peptides may include peptides wherein the -DSLsequence or a DSL-corresponding sequence is flanked by an unequal number of amino acids (e.g. -XXXXX-DSL-XXX-, where X represents an amino acid). In embodiments, the functional fragment is a peptide having about 45, 40, 35, 30, 25, 20, 15, or about 10 amino acids upstream (e.g. -XXX-DSL-, where X represents an amino acid) of a -DSLsequence or a DSL-corresponding sequence and about 50 amino acids downstream (e.g. -DSL-XXX-, where X represents an amino acid) of the -DSLsequence or a DSL-corresponding sequence. In embodiments, the functional fragment is a peptide having about 50, 40, 35, 30, 25, 20, 15, or about 10 amino acids upstream of a -DSLsequence or a DSL-corresponding sequence and about 45 amino acids downstream of the -DSLsequence or a DSL-corresponding sequence. In embodiments, the functional fragment is a peptide having about 50, 45, 35, 30, 25, 20, 15, or about 10 amino acids upstream of a -DSL-sequence or a DSL-corresponding sequence and about 40 amino acids downstream of the -DSL-sequence or a DSL-corresponding sequence. In embodiments, the functional fragment is a peptide having about 50, 45, 40, 30, 25, 20, 15, or about 10 amino acids upstream of a -DSLsequence or a DSL-corresponding sequence and about 35 amino acids downstream of the -DSLsequence or a DSL-corresponding sequence. In embodiments, the functional fragment is a peptide having about 50, 45, 40, 35, 25, 20, 15, or about 10 amino acids upstream of a -DSLsequence or a DSL-corresponding sequence and about 30 amino acids downstream of the -DSLsequence or a DSL-corresponding sequence. In embodiments, the functional fragment is a peptide having about 50, 45, 40, 35, 30, 20, 15, or about 10 amino acids upstream of a -DSLsequence or a DSL-corresponding sequence and about 25 amino acids downstream of the -DSLsequence or a DSL-corresponding sequence. In embodiments, the functional fragment is a peptide having about 50, 45, 40, 35, 30, 25, 15, or about 10 amino acids upstream of a -DSLsequence or a DSL-corresponding sequence and about 20 amino acids downstream of the -DSLsequence or a DSL-corresponding sequence. In embodiments, the functional fragment is a peptide having about 50, 45, 40, 35, 30, 25, 20, or about 10 amino acids upstream of a -DSLsequence or a DSL-corresponding sequence and about 15 amino acids downstream of the -DSLsequence or a DSL-corresponding sequence. In embodiments, the functional fragment is a peptide having about 50, 45, 40, 35, 30, 25, 20, or about 15 amino acids upstream of a -DSLsequence or a DSL-corresponding sequence and about 10 amino acids downstream of the -DSLsequence or a DSL-corresponding sequence. In embodiments, the functional fragment is a fragment of an ACP having SEQ ID NO: 1, 2, 3, 4, 5, 6, 7, 8, 33, 34, 35, 36, 37, 38, 39, 40, 41, 42, 43, 44, 45, 46, 47, or 48.

In embodiments, the functional fragment is a peptide having about 1, 2, 3, 4; 5, 6, 7, 8, 9, 10, 11, 12, 13, 14, 15, 16, 17, 18, 19, 20, 21, 22, 23, or about 24 amino acids upstream of a -DSL-sequence or a DSL-corresponding sequence and about 25 amino acids downstream of the -DSL-sequence or a DSL-corresponding sequence. In embodiments, the functional fragment is a peptide having about 1, 2, 3, 4; 5, 6, 7, 8, 9, 10, 11, 12, 13, 14, 15, 16, 17, 18, 19, 20, 21, 22, 23, or about 25 amino acids upstream of a -DSLsequence or a DSL-corresponding sequence and about 24 amino acids downstream of the -DSLsequence or a DSL-corresponding sequence. In embodiments, the functional fragment is a peptide having about 1, 2, 3, 4; 5, 6, 7, 8, 9, 10, 11, 12, 13, 14, 15, 16, 17, 18, 19, 20, 21, 22, 24, or about 25 amino acids upstream of a -DSLsequence or a DSL-corresponding sequence and about 23 amino acids downstream of the -DSLsequence or a DSL-corresponding sequence. In embodiments, the functional fragment is a peptide having about 1, 2, 3, 4; 5, 6, 7, 8, 9, 10, 11, 12, 13, 14, 15, 16, 17, 18, 19, 20, 21, 23, 24, or about 25 amino acids upstream of a -DSLsequence or a DSL-corresponding sequence and about 22 amino acids downstream of the -DSLsequence or a DSL-corresponding sequence. In embodiments, the functional fragment is a peptide having about 1, 2, 3, 4; 5, 6, 7, 8, 9, 10, 11, 12, 13, 14, 15, 16, 17, 18, 19, 20, 22, 23, 24, or about 25 amino acids upstream of a -DSLsequence or a DSL-corresponding sequence and about 21 amino acids downstream of the -DSLsequence or a DSL-corresponding sequence. In embodiments, the functional fragment is a peptide having about 1, 2, 3, 4; 5, 6, 7, 8, 9, 10, 11, 12, 13, 14, 15, 16, 17, 18, 19, 21, 22, 23, 24, or about 25 amino acids upstream of a -DSLsequence or a DSL-corresponding sequence and about 20 amino acids downstream of the -DSL sequence or a DSL-corresponding sequence. In embodiments, the functional fragment is a peptide having about 1, 2, 3, 4; 5, 6, 7, 8, 9, 10, 11, 12, 13, 14, 15, 16, 17, 18, 20, 21, 22, 23, 24, or about 25 amino acids upstream of a -DSL sequence or a DSL-corresponding sequence and about 19 amino acids downstream of the -DSL sequence or a DSL-corresponding sequence. In embodiments, the functional fragment is a peptide having about 1, 2, 3, 4; 5, 6, 7, 8, 9, 10, 11, 12, 13, 14, 15, 16, 17, 19, 20, 21, 22, 23, 24, or about 25 amino acids upstream of a -DSL sequence or a DSL-corresponding sequence and about 18 amino acids downstream of the -DSL sequence or a DSL-corresponding sequence. In embodiments, the functional fragment is a peptide having about 1, 2, 3, 4; 5, 6, 7, 8, 9, 10, 11, 12, 13, 14, 15, 16, 18, 19, 20, 21, 22, 23, 24, or about 25 amino acids upstream of a -DSL sequence or a DSL-corresponding sequence and about 17 amino acids downstream of the -DSL sequence or a DSL-corresponding sequence. In embodiments, the functional fragment is a peptide having about 1, 2, 3, 4; 5, 6, 7, 8, 9, 10, 11, 12, 13, 14, 15, 17, 18, 19, 20, 21, 22, 23, 24, or about 25 amino acids upstream of a -DSL sequence or a DSL-corresponding sequence and about 16 amino acids downstream of the -DSL sequence or a DSL-corresponding sequence. In embodiments, the functional fragment is a peptide having about 1, 2, 3, 4; 5, 6, 7, 8, 9, 10, 11, 12, 13, 14, 16, 17, 18, 19, 20, 21, 22, 23, 24, or about 25 amino acids upstream of a -DSL sequence or a DSL-corresponding sequence and about 15 amino acids downstream of the -DSL sequence or a DSL-corresponding sequence. In embodiments, the functional fragment is a peptide having about 1, 2, 3, 4; 5, 6, 7, 8, 9, 10, 11, 12, 13, 15, 16, 17, 18, 19, 20, 21, 22, 23, 24, or about 25 amino acids upstream of a -DSL sequence or a DSL-corresponding sequence and about 14 amino acids downstream of the -DSL sequence or a DSL-corresponding sequence. In embodiments, the functional fragment is a peptide having about 1, 2, 3, 4; 5, 6, 7, 8, 9, 10, 11, 12, 14, 15, 16, 17, 18, 19, 20, 21, 22, 23, 24, or about 25 amino acids upstream of a -DSL sequence or a DSL-corresponding sequence and about 13 amino acids downstream of the -DSL sequence or a DSL-corresponding sequence. In embodiments, the functional fragment is a peptide having about 1, 2, 3, 4; 5, 6, 7, 8, 9, 10, 11, 13, 14, 15, 16, 17, 18, 19, 20, 21, 22, 23, 24, or about 25 amino acids upstream of a -DSL sequence or a DSL-corresponding sequence and about 12 amino acids downstream of the -DSL sequence or a DSL-corresponding sequence. In embodiments, the functional fragment is a peptide having about 1, 2, 3, 4; 5, 6, 7, 8, 9, 10, 12, 13, 14, 15, 16, 17, 18, 19, 20, 21, 22, 23, 24, or about 25 amino acids upstream of a -DSL sequence or a DSL-corresponding sequence and about 11 amino acids downstream of the -DSL sequence or a DSL-corresponding sequence. In embodiments, the functional fragment is a peptide having about 1, 2, 3, 4; 5, 6, 7, 8, 9, 11, 12, 13, 14, 15, 16, 17, 18, 19, 20, 21, 22, 23, 24, or about 25 amino acids upstream of a -DSL sequence or a DSL-corresponding sequence and about 10 amino acids downstream of the -DSL sequence or a DSL-corresponding sequence. In embodiments, the functional fragment is a peptide having about 1, 2, 3, 4; 5, 6, 7, 8, 10, 11, 12, 13, 14, 15, 16, 17, 18, 19, 20, 21, 22, 23, 24, or about 25 amino acids upstream of a -DSL sequence or a DSL-corresponding sequence and about 9 amino acids downstream of the -DSL sequence or a DSL-corresponding sequence. In embodiments, the functional fragment is a peptide having about 1, 2, 3, 4; 5, 6, 7, 9, 10, 11, 12, 13, 14, 15, 16, 17, 18, 19, 20, 21, 22, 23, 24, or about 25 amino acids upstream of a -DSL sequence or a DSL-corresponding sequence and about 8 amino acids downstream of the -DSL sequence or a DSL-corresponding sequence. In embodiments, the functional fragment is a peptide having about 1, 2, 3, 4; 5, 6, 8, 9, 10, 11, 12, 13, 14, 15, 16, 17, 18, 19, 20, 21, 22, 23, 24, or about 25 amino acids upstream of a -DSL sequence or a DSL-corresponding sequence and about 7 amino acids downstream of the -DSL sequence or a DSL-corresponding sequence. In embodiments, the functional fragment is a peptide having about 1, 2, 3, 4; 5, 7, 8, 9, 10, 11, 12, 13, 14, 15, 16, 17, 18, 19, 20, 21, 22, 23, 24, or about 25 amino acids upstream of a -DSL sequence or a DSL-corresponding sequence and about 6 amino acids downstream of the -DSL sequence or a DSL-corresponding sequence. In embodiments, the functional fragment is a peptide having about 1, 2, 3, 4; 6, 7, 8, 9, 10, 11, 12, 13, 14, 15, 16, 17, 18, 19, 20, 21, 22, 23, 24, or about 25 amino acids upstream of a -DSL sequence or a DSL-corresponding sequence and about 5 amino acids downstream of the -DSL sequence or a DSL-corresponding sequence. In embodiments, the functional fragment is a peptide having about 1, 2, 3, 5, 6, 7, 8, 9, 10, 11, 12, 13, 14, 15, 16, 17, 18, 19, 20, 21, 22, 23, 24, or about 25 amino acids upstream of a -DSL sequence or a DSL-corresponding sequence and about 4 amino acids downstream of the -DSL sequence or a DSL-corresponding sequence. In embodiments, the functional fragment is a peptide having about 1, 2, 4; 5, 6, 7, 8, 9, 10, 11, 12, 13, 14, 15, 16, 17, 18, 19, 20, 21, 22, 23, 24, or about 25 amino acids upstream of a -DSL sequence or a DSL-corresponding sequence and about 3 amino acids downstream of the -DSL sequence or a DSL-corresponding sequence. In embodiments, the functional fragment is a fragment of an ACP having SEQ ID NO: 1, 2, 3, 4, 5, 6, 7, 8, 33, 34, 35, 36, 37, 38, 39, 40, 41, 42, 43, 44, 45, 46, 47, or 48.

In embodiments, the functional fragment is a peptide having a -DSL sequence or a DSL-corresponding sequence flanked downstream by about 1, 2, 4; 5, 6, 7, 8, 9, 10, 11, 12, 13, 14, 15, 16, 17, 18, 19, 20, 21, 22, 23, 24, 25, 30, 35, 40, 45, or 50 amino acids (e.g. -DSL-XXX, where X represents an amino acid). In embodiments, the functional fragment is a peptide having a -DSL-sequence or a DSL-corresponding sequence flanked upstream (e.g. XXX-DSL-, were X represents an amino acid) by about 1, 2, 4; 5, 6, 7, 8, 9, 10, 11, 12, 13, 14, 15, 16, 17, 18, 19, 20, 21, 22, 23, 24, 25, 30, 35, 40, 45, or 50 amino acids. In embodiments, the functional fragment is a fragment of an ACP having SEQ ID NO: 1, 2, 3, 4, 5, 6, 7, 8, 33, 34, 35, 36, 37, 38, 39, 40, 41, 42, 43, 44, 45, 46, 47, or 48.

In embodiments, an ACP protein moiety as described herein, including embodiments thereof, a support bound ACP-protein moiety. An ACP-protein moiety may be covalently attached to a solid support at the carboxy terminus of the ACP protein moiety or ACP protein fusion moiety thereby forming a support bound ACP-protein moiety:

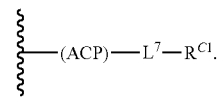

$R^{C1}$ is a solid support (e.g. comprising a cellulose membrane, a nanoparticle, or a resin). ACP is an ACP protein moiety defined as herein, including embodiments thereof. $L^7$ is a solid support linker. In embodiments, $L^7$ is a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. In embodiments, $L^7$ is substituted or unsubstituted alkylene, substituted or unsubstituted heteroalkylene. $L^7$ may also include a PEG linker moiety. In embodiments, $L^7$ is -$L^5$-PEG-$L^6$-$R^{C1}$, wherein $L^5$ and $L^6$ are independently —O—, —S—, —NH—, —NHC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments $L^5$ and $L^6$ are independently —O—, —S—, —NH—, —NHC(O)—, substituted or unsubstituted alkylene, substituted or unsubstituted heteroalkylene.

PEG may be a moiety of branched or unbranched polyethylene glycol moieties, e.g. having formula:

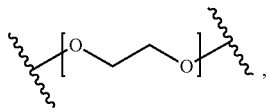

where n is an integer of about 5 to about 100.

The symbol n may be about 5 to about 100. The symbol n may be about 5 to about 90. n may be about 5 to about 80. The symbol n may be about 5 to about 70. The symbol n may be about 5 to about 60. The symbol n may be about 5 to about 50. The symbol n may be about 5 to about 40. The symbol n may be about 5 to about 30. The symbol n may be about 5 to about 20. The symbol n may be about 5 to about 10. The symbol n may be about 10 to about 30. The symbol n may be about 10 to about 20.

The solid support may be a cellulose membrane (e.g. a nitrocellulose membrane). The solid support may be an Au nanoparticle or a gold monolayer. The solid support may be a resin. The resin may be a polystyrene resin. The polystyrene resin may be crosslinked polystyrene. The resin may be a polyamine resin.

In embodiments, $L^1$ is substituted or unsubstituted $C_1$-$C_5$ alkylene. $L^1$ may be $C_1$-$C_3$ alkylene. $L^1$ may be —CH$_2$C(CH$_3$)$_2$—. $L^2$ may be substituted or unsubstituted $C_1$-$C_5$ alkylene. In embodiments, $L^2$ is —CH$_2$—. $L^3$ may be substituted or unsubstituted $C_1$-$C_5$ alkylene. In embodiments, $L^3$ is —CH$_2$—.

$L^4$ may be a bond, substituted or unsubstituted $C_1$-$C_{20}$ alkylene, or substituted or unsubstituted 2 to 20 membered heteroalkylene. $L^4$ may be substituted or unsubstituted $C_1$-$C_{10}$ alkylene or substituted or unsubstituted 2 to 10 membered heteroalkylene. $L^4$ may be substituted or unsubstituted $C_1$-$C_5$ alkylene or substituted or unsubstituted 2 to 5 membered heteroalkylene.

$L^4$ substituted or unsubstituted 3 to 6 membered cycloalkylene, substituted or unsubstituted 3 to 6 membered heterocycloalkylene, substituted or unsubstituted 5 or 6 membered arylene or substituted or unsubstituted 5 or 6 membered heteroarylene.

X may be —S—. X may be —NH—. X may be —O—. $R^1$ may be substituted or unsubstituted $C_1$-$C_{20}$ alkylene, substituted or unsubstituted $C_1$-$C_{10}$ alkylene, or substituted or unsubstituted $C_1$-$C_5$ alkylene. $R^1$ may be $R^{1.1}$-substituted $C_1$-$C_{20}$ alkylene, $R^{1.1}$-substituted $C_1$-$C_{10}$ alkylene, or $R^{1.1}$-substituted $C_1$-$C_5$ alkylene. $R^1$ may be or substituted or unsubstituted 2 to 20 membered heteroalkylene, substituted or unsubstituted 2 to 10 membered heteroalkylene, or substituted or unsubstituted 2 to 5 membered heteroalkylene. $R^1$ may be $R^{1.1}$-substituted 2 to 20 membered heteroalkylene, $R^{1.1}$-substituted 2 to 10 membered heteroalkylene, or $R^{1.1}$-substituted 2 to 5 membered heteroalkylene. $R^1$ may be substituted or unsubstituted 3 to 6 membered cycloalkylene, substituted or unsubstituted 3 to 6 membered heterocycloalkylene, substituted or unsubstituted 5 or 6 membered arylene or substituted or unsubstituted 5 or 6 membered heteroarylene. $R^1$ may be $R^{1.1}$-substituted 3 to 6 membered cycloalkylene, $R^{1.1}$-substituted 3 to 6 membered heterocycloalkylene, $R^{1.1}$-substituted 5 or 6 membered arylene or $R^{1.1}$-substituted 5 or 6 membered heteroarylene. $R^{1.1}$ is hydrogen, halogen, —N$_3$, CF$_3$, —CCl$_3$, —CBr$_3$, —CI$_3$, CN, —CHO, —OH, NH$_2$, COOH, —CONH$_2$, NO$_2$, SH, —SO$_2$, —SO$_2$Cl, —SO$_3$H, —SO$_4$H, —SO$_2$NH$_2$, —NHNH$_2$, —ONH$_2$, —NHC(O)NHNH$_2$, unsubstituted $C_1$-$C_5$ alkyl, unsubstituted 2 to 5 membered heteroalkyl, unsubstituted 3 to 6 membered cycloalkyl, unsubstituted 3 to 6 membered heterocycloalkyl, unsubstituted 5 or 6 membered aryl, or unsubstituted 5 or 6 membered heteroalkyl.

$R^1$ may be a detectable moiety or a reactive probe.

$R^1$ may be a detectable moiety. The detectable moiety may be a fluorophore. The fluorophore may be fluorescein, coumarin, rhodamine, or GFP. The fluorophore may be fluorescein. The fluorophore may be coumarin. The fluorophore may be rhodamine. The fluorophore may be GFP. $R^1$ may be a reactive probe. The reactive probe may be a reactive moiety used for bioconjugation as described herein, including embodiments thereof.

The ACP protein moiety or ACP protein fusion moiety may be bonded to the phosphopantetheine analogue moiety at an internal serine residue within the amino acid sequence of the ACP protein moiety. The ACP protein moiety or ACP protein fusion moiety is as described herein, including embodiments thereof. The ACP protein fusion moiety may include an ACP protein moiety bound to an amino terminus or a carboxy terminus of a second fusion protein moiety. The ACP protein fusion moiety may include an ACP protein moiety bound to an internal amino acid residue of a second fusion protein moiety. The ACP protein moiety is as described herein, including embodiments thereof.

Also provided herein is a support bound ACP-phosphopantetheine conjugate. An ACP-phosphopantetheine conjugate may be covalently attached to a solid support at the carboxy terminus of the ACP protein moiety or ACP protein fusion moiety thereby forming a support bound ACP-phosphopantetheine conjugate:

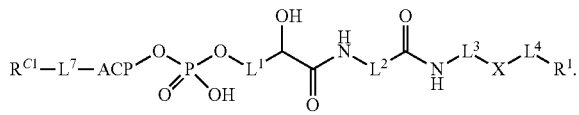

ACP is as described herein, including embodiments thereof. $L^1$, $L^2$, $L^3$, $L^4$, $L^5$, $L^6$, $L^7$, $R^1$, $R^{C1}$ and PEG are as defined herein including embodiments thereof.

The Apo-ACP may be a Fatty Acid Apo-ACP, a Polyketide Apo-ACP, or a Peptide Apo-ACP. The Apo-ACP may be a Fatty Acid Apo-ACP. The Apo-ACP may be a polyketide Apo-. The Apo-ACP may be a peptide Apo-ACP. One skilled in the art would appreciate that the ACP proteins described herein share common functionality (e.g. involvement in acylation of a product) and may share substantial sequence identity.

In embodiments, the Apo-ACP is an *E. coli* apo-ACP, *P. aeruginosa* apo-ACP, *S. oneidensis* apo-ACP, *P. falciparum* apo-ACP, *M. tuberculosis* apo-ACP, *S. coelicolor* apo-ACP, *A. parasiticus* apo-ACP, *G. fujikuroi* apo-ACP, *L. majuscule* apo-ACP or *P. fluorescens* apo-ACP. The Apo-ACP may be an *E. coli* apo-ACP. When the apo-APC is an *E. coli* apo-ACP, it may be *E. coli* ACpP (type II). The Apo-ACP may be a *P. aeruginosa* apo-ACP. The Apo-ACP may be a *S. oneidensis* apo-ACP. The Apo-ACP may be a *P. falciparum* apo-ACP. The Apo-ACP may be a *M. tuberculosis* apo-ACP. The Apo-ACP may be a *S. coelicolor* apo-ACP. The Apo-ACP may be an *A. parasiticus* apo-ACP. The Apo-ACP may be a *G. fujikuroi* apo-ACP. The Apo-ACP may be a *L. majuscule* apo-ACP. The Apo-ACP may be a *P. fluorescens* apo-ACP. The Apo-ACP may be a protein moiety having an amino acid sequence identity having at least 60%, 65%, 70%, 75%, 80%, 85%, 90%, 95%, 99% or 100% identity to the entire portion or a functional fragment thereof of SEQ ID NOs: 33, 34, 35, 36, 37, 38, 39, 40, 41, 42, 43, 44, 45, 46, 47, or 48, wherein the functional fragment is recognizable by either an ACP hydrolase or a phosphopantetheinyl tranferase.

An Apo-ACP may also encompass amino acid sequence mutants of an ACP. The amino acid sequence mutants may be substitutional mutants deletional, or insertional mutants. Substitutional mutants may include conservatively modified variants as described herein, including embodiments thereof. Deletional mutants include the deletion of amino acids at a non-terminal endpoint in the protein. Insertional mutants include the addition of amino acids at a non-terminal endpoint in the protein. In embodiments, the Apo-ACP is a protein having a substitutional mutation in SEQ ID NOs: 33, 34, 35, 36, 37, 38, 39, 40, 41, 42, 43, 44, 45, 46, 47, or 48. In embodiments, the Apo-ACP is a protein having a deletional mutation in SEQ ID NOs: 33, 34, 35, 36, 37, 38, 39, 40, 41, 42, 43, 44, 45, 46, 47, or 48. In embodiments, the Apo-ACP is a protein having an insertional mutation in SEQ ID NOs: 33, 34, 35, 36, 37, 38, 39, 40, 41, 42, 43, 44, 45, 46, 47, or 48. In embodiments, the ACP Apo-ACP may include non-proteinogenic amino acids. All Apo-ACP mutants described herein retain activity. The Apo-ACP may be a fragment of the full-length ACP, wherein the fragment is recognizable by either an AcpH or a PPTase. The fragment may include amino acid substitutions, deletions, or insertions. Substitutional mutants may include conservatively modified variants as described herein, including embodiments thereof. Insertional mutants include the addition of amino acids at a non-terminal endpoint in the fragment. Deletional mutants include the deletion of amino acids at a non-terminal endpoint in the fragment. In embodiments, the Apo-ACP may include non-proteinogenic amino acids. Apo-ACP fragments having mutations described herein are recognizable by either an AcpH or a PPTase.

The apo-ACP may be a full-length APC protein. The apo-ACP may be a fragment of an apo-ACP. The apo-ACP may be at least 10 amino acids to at least 100 amino acids in length. The apo-ACP may be at least 10 amino acids to at least 90 amino acids in length. The apo-ACP may be at least 10 amino acids to at least 80 amino acids in length. The apo-ACP may be at least 10 amino acids to at least 70 amino acids in length. The apo-ACP may be at least 10 amino acids to at least 60 amino acids in length. The apo-ACP may be at least 10 amino acids to at least 50 amino acids in length. The apo-ACP may be at least 10 amino acids to at least 40 amino acids in length. The apo-ACP may be at least 10 amino acids to at least 30 amino acids in length. The apo-ACP may be at least 10 amino acids to at least 25 amino acids in length. The apo-ACP may be at least 10 amino acids to at least 20 amino acids in length. The apo-ACP may be at least 10 amino acids to at least 15 amino acids in length.

The apo-ACP may be at least 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 amino acids in length. The apo-ACP may be about 10 amino acids in length. The apo-ACP may be about 11 amino acids in length. The apo-ACP may be about 12 amino acids in length. The apo-ACP may be about 13 amino acids in length. The apo-ACP may be about 14 amino acids in length. The apo-ACP may be about 15 amino acids in length. The apo-ACP may be about 16 amino acids in length. The apo-ACP may be about 17 amino acids in length. The apo-ACP may be about 18 amino acids in length. The apo-ACP may be about 19 amino acids in length. The apo-ACP may be about 20 amino acids in length. The Apo-ACP may be about 21 amino acids in length. The apo-ACP may be about 22 amino acids in length. The Apo-ACP may include a -DSLsequence or a DSL-corresponding sequence.

Also provided herein is a support bound Apo-ACP. The Apo-ACP may be covalently attached to a solid support at its carboxy terminus. The apo-ACP may be bound to the solid support using a PEG linker having the formula:

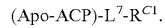

$$(\text{Apo-ACP})\text{-}L^7\text{-}R^{C1}.$$

The Apo-ACP is as described herein, including embodiments thereof. $L^5$, $L^6$, $L^7$, $R^{C1}$ and PEG are as defined herein including embodiments thereof.

The ACP hydrolase may be a *P. aeruginosa* ACP hydrolase, *Cyanothece* sp. ACP hydrolase, or *P. fluorescens* ACP hydrolase. The ACP hydrolase may be a *P. aeruginosa* ACP hydrolase. The ACP hydrolase may be a *Cyanothece* sp. ACP hydrolase. The ACP hydrolase may be a *P. fluorescens* ACP hydrolase. The ACP hydrolase may not be an *E. coli* ACP hydrolase (e.g. an AcpH found in *E. coli*). The ACP hydrolase may be a recombinant ACP hydrolase. In embodiments, an ACP hydrolase includes an AcpH having at least 60, 70, 80, 90, 95, 96, 97, 98, 99, or 100% sequence homology to a wildtype AcpH so long as the ACP hydrolase retains phosphodiesterase activity. An AcpH may also encompass amino acid sequence mutants of an AcpH. The amino acid sequence mutants may be substitutional mutants deletional, or insertional mutants. Substitutional mutants may include conservatively modified variants as described herein, including embodiments thereof. Deletional mutants include the deletion of amino acids at a non-terminal endpoint in the protein. Insertional mutants include the addition of amino acids at a non-terminal endpoint in the protein. In embodiments, the AcpH may include non-proteinogenic amino acids. All AcpH mutants described herein retain phosphodiesterase activity. The hydrolase may be a fragment of the full-length ACP hydrolase, so long as the fragment retains phosphodiesterase activity. The fragment may include amino acid substitutions, deletions, or insertions. Substitutional mutants may include conservatively modified variants as described herein, including embodiments thereof. Insertional mutants include the addition of amino acids at a non-terminal endpoint in the fragment. Deletional mutants include the deletion of amino acids at a non-terminal endpoint in the fragment. In embodiments, the AcpH fragment may include non-proteinogenic amino acids. AcpH fragment having mutations described herein retain phosphodiesterase activity.

The method may further include contacting the Apo-ACP with a CoA-phosphopantetheine analogue and a phosphopantetheinyl transferase. The CoA-phosphopantetheine analogue includes a phosphopantetheine analogue moiety covalently bonded to a phosphoadenosine moiety through a phosphodiester linkage. The phosphopantetheinyl transferase is allowed to cleave the phosphodiester linkage and bind the phosphopantetheine analogue moiety to the apo-ACP through a phosphodiester linker forming a second ACP-phosphopantetheine conjugate. The CoA-phosphopantetheine analogue has the formula:

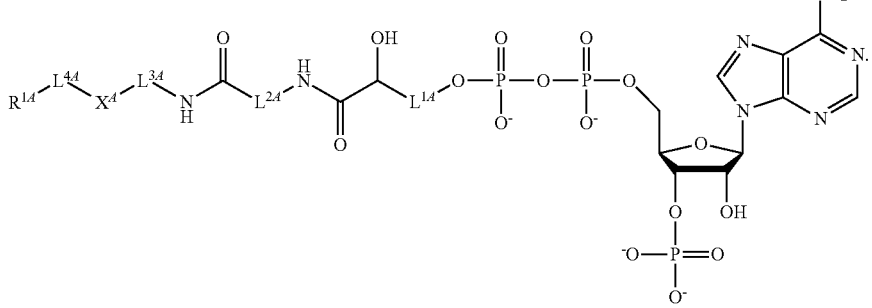

$L^{1A}$, $L^{2A}$ and $L^{3A}$ are independently substituted or unsubstituted alkylene. $L^{4A}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. $X^A$ is —S—, —NH— or —O—. $R^{1A}$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, a detectable moiety or a reactive probe.

The second ACP-phosphopantetheine conjugate has the formula:

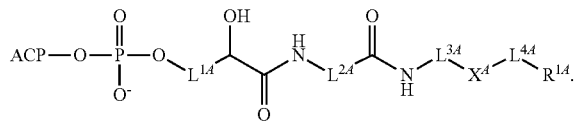

$L^{1A}$, $L^{2A}$, $L^{3A}$, $L^{4A}$, $X^A$ and $R^{1A}$ are as described herein, including embodiments thereof.

In embodiments phosphopantetheinyl transferase is a *B. subtilis* phosphopantetheinyl transferase. In embodiments a phosphopantetheinyl transferase includes phosphopantetheinyl transferase at least 60, 70, 80, 90, 95, 96, 97, 98, 99, or 100% sequence homology to a wildtype PPTase so long as the phosphopantetheinyl transferase retains activity. The phosphopantetheinyl transferase may be a fragment of the full-length phosphopantetheinyl transferase, so long as the fragment retains activity.

In embodiments, the method includes contacting the second ACP-phosphopantetheine conjugate with a second ACP hydrolase and allowing the second ACP hydrolase to cleave the phosphodiester linker thereby forming the Apo-ACP. In embodiments, the method may be iteratively repeated such that the Apo-ACP and ACP-phosphopantetheine conjugate may be intercoverted using the methods described herein. The method may be repeated 10 times without substantial degradation of the ACP protein. The method may be repeated at least 9, 8, 7, 6, 5, 4, 3, 2, or 1 times without substantial degradation of the ACP protein.

In embodiments, the methods described herein are performed in vitro. In embodiments, the methods described herein are performed in vivo.

III. Compounds

In another aspect is provided a compound including an amino acid sequence having the formula:

-DSL(Aaa1)(Aaa2)(Aaa3)(Aaa4)(Aaa5)(Aaa6)-.

Aaa1 is D, E, or S. Aaa2 is T, F, or W. Aaa3 is I, L, or V. Aaa4 is E, A, or L. Aaa5 is A, S, L, or R. Aaa6 is V, K or L. In one embodiment, the sequence is not -DSLDTVELV- (SEQ ID NO:97). In one embodiment, the sequence is not -DSLDTVELVMA-(SEQ ID NO:98). In one embodiment, the sequence is not -ADSLDTVELV- (SEQ ID NO:99). In one embodiment, the sequence is not -GADSLDTVELV- (SEQ ID NO:100). In one embodiment, the sequence is not -VEDLGADSLDTVELV- (SEQ ID NO:101). In one embodiment, the sequence is not -NSASFVEDLGAD-SLDTVELV- (SEQ ID NO:102).

In embodiments, the compounds has the amino acid sequence:

```
                                          (SEQ ID NO: 1)
R^N-DSL(Aaa1)(Aaa2)(Aaa3)(Aaa4)(Aaa5)(Aaa6)-R^C,

R^N-DSLEFIASKLA-R^C
or
                                          (SEQ ID NO: 2)
R^N-GDSLSWLLRLLN-R^C.
```

Aa1-Aa6 is as defined above. $R^N$ is —NH$_2$, a detectable moiety, or a reactive probe. $R^C$ is —COOH, a detectable moiety, a reactive probe, or -$L^7$-$R^{C1}$. $L^7$ is a solid support linker. In embodiments, $L^7$ is a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. $L^7$ may also include a PEG linker moiety. In embodiments, $L^7$ is -$L^5$-PEG-$L^6$-$R^{C1}$, wherein $L^5$ and $L^6$ are independently —O—, —S—, —NH—, —NHC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{C1}$ is a solid support comprising a cellulose membrane, a nanoparticle, or a resin.

$R^N$ may be —$NH_2$. $R^N$ may a detectable moiety. $R^N$ may be a reactive probe. When $R^N$ is a detectable moiety, the detectable moiety may be a fluorophore. The fluorophore may be fluorescein, coumarin, rhodamine, or GFP. The fluorophore may be FITC. $R^C$ may be —COOH. $R^C$ may be a detectable moiety. $R^C$ may be a reactive probe. $R^C$ may be $L^5$-PEG-$L^6$-$R^{C1}$. In embodiments, when $R^N$ is —$NH_2$, $R^C$ is —COOH, a detectable moiety, a reactive probe, or -$L^5$-PEG-$L^6$-$R^{C1}$. When $R^N$ is —$NH_2$, $R^C$ may be a detectable moiety. When $R^N$ is —$NH_2$, $R^C$ may be a reactive probe, or -$L^5$-PEG-$L^6$-$R^{C1}$. When $R^N$ is —$NH_2$, $R^C$ may be -$L^5$-PEG-$L^6$-$R^{C1}$. When $R^N$ is detectable moiety, $R^C$ may be —COOH, a detectable moiety, a reactive probe, or -$L^5$-PEG-$L^6$-$R^{C1}$.

$L^5$ and $L^6$ may independently be —O—. —S—. —NH—, or —NHC(O)—. $L^5$ and $L^6$ may independently be substituted or unsubstituted $C_1$-$C_{20}$ alkylene, or substituted or unsubstituted 2 to 20 membered heteroalkylene. $L^5$ and $L^6$ may independently be substituted or unsubstituted $C_1$-$C_{10}$ alkylene, or substituted or unsubstituted 2 to 10 membered heteroalkylene. $L^5$ and $L^6$ may independently be substituted or unsubstituted $C_1$-$C_5$ alkylene, or substituted or unsubstituted 2 to 5 membered heteroalkylene. $L^5$ and $L^6$ may independently be substituted or unsubstituted 3 to 6 membered cycloalkylene, substituted or unsubstituted 3 to 6 membered heterocycloalkylene, substituted or unsubstituted 5 or 6 membered arylene or substituted or unsubstituted 5 or 6 membered heteroarylene. PEG is as described herein, including embodiments thereof. PEG may have a molecular weight of about PEG50 to about PEG5000. PEG may have a molecular weight of about PEG50 to about PEG4000. PEG may have a molecular weight of about PEG50 to about PEG3000. PEG may have a molecular weight of about PEG50 to about PEG2000. PEG may have a molecular weight of about PEG50 to about PEG1000. $R^{C1}$ may be a cellulose membrane (e.g. a nitrocellulose membrane). $R^{C1}$ may be a resin. The resin may be a polystyrene resin or a polyamine resin. When the resin is a polystyrene resin, the resin may be a crosslinked polystyrene resin. $R^{C1}$ may be a nanoparticle. The nanoparticle may be a Au nanoparticle.

In embodiments the compound is covalently bonded to a phosphopantetheine analogue moiety using the methods provided herein. In embodiments, the phosphopantetheine analogue moiety is bound to the compound at a serine. In embodiments, a phosphopantetheine analogue moiety bound to the compound is removed from the compound using the methods provided herein.

In embodiments, a compound having SEQ ID NO 1, 2, 3, 4, 5, 6, 7, or 8 may be covalently bonded to a phosphopantetheine analogue moiety using the methods provided herein. In embodiments a phosphopantetheine analogue moiety bound to a compound having SEQ ID NO 1, 2, 3, 4, 5, 6, 7, or 8 is removed from the compound using the methods provided herein.

The compound may have the formula:

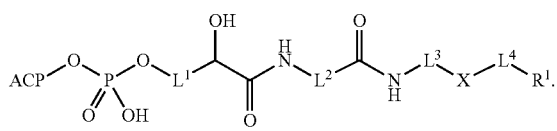

(III)

ACP is an ACP protein moiety or an ACP protein fusion moiety including the amino acid sequences described above in this section (Section III. Compounds), including embodiments thereof. $L^1$, $L^2$, $L^3$, $L^4$, and X are as described above, including embodiments thereof. $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, a detectable moiety or a reactive probe. $R^1$ may be hydrogen. $R^1$ may be a detectable moiety. The detectable moiety is as described herein, including embodiments thereof.

$R^1$ may be substituted or unsubstituted $C_1$-$C_{20}$ alkylene, substituted or unsubstituted $C_1$-$C_{10}$ alkylene, or substituted or unsubstituted $C_1$-$C_5$ alkylene. $R^1$ may be $R^{1.1}$-substituted $C_1$-$C_{20}$ alkylene, $R^{1.1}$-substituted $C_1$-$C_{10}$ alkylene, or $R^{1.1}$-substituted $C_1$-$C_5$ alkylene. $R^1$ may be or substituted or unsubstituted 2 to 20 membered heteroalkylene, substituted or unsubstituted 2 to 10 membered heteroalkylene, or substituted or unsubstituted 2 to 5 membered heteroalkylene. $R^1$ may be $R^{1.1}$-substituted 2 to 20 membered heteroalkylene, $R^{1.1}$-substituted 2 to 10 membered heteroalkylene, or $R^{1.1}$-substituted 2 to 5 membered heteroalkylene. $R^1$ may be substituted or unsubstituted 3 to 6 membered cycloalkylene, substituted or unsubstituted 3 to 6 membered heterocycloalkylene, substituted or unsubstituted 5 or 6 membered arylene or substituted or unsubstituted 5 or 6 membered heteroarylene. $R^1$ may be $R^{1.1}$-substituted 3 to 6 membered cycloalkylene, $R^{1.1}$-substituted 3 to 6 membered heterocycloalkylene, $R^{1.1}$-substituted 5 or 6 membered arylene or $R^{1.1}$-substituted 5 or 6 membered heteroarylene. $R^{1.1}$ is hydrogen, halogen, —$N_3$, $CF_3$, —$CCl_3$, —$CBr_3$, —$CI_3$, CN, —CHO, —OH, $NH_2$, COOH, —$CONH_2$, $NO_2$, SH, —$SO_2$, —$SO_2Cl$, —$SO_3H$, —$SO_4H$, —$SO_2NH_2$, —$NHNH_2$, —$ONH_2$, —NHC(O)$NHNH_2$, unsubstituted $C_1$-$C_5$ alkyl, unsubstituted 2 to 5 membered heteroalkyl, unsubstituted 3 to 6 membered cycloalkyl, unsubstituted 3 to 6 membered heterocycloalkyl, unsubstituted 5 or 6 membered aryl, or unsubstituted 5 or 6 membered heteroalkyl.

In another aspect is a compound having formula:

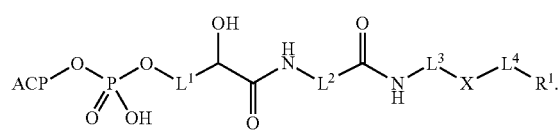

(IV)

ACP is an ACP protein moiety or an ACP protein fusion moiety, including embodiments thereof. $L^1$, $L^2$, $L^3$, $L^4$, and X are as described above, including embodiments thereof. $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, a detectable moiety or a reactive probe. $R^1$ may be a detectable moiety. The detectable moiety may be a fluorophore. The fluorophore may be fluorescein, coumarin, rhodamine, or GFP. $R^1$ may be a reactive probe as described herein, including embodiments thereof. In embodiments when the ACP is an ACP protein moiety or an ACP protein fusion including the amino acid sequences described above in this section (Section III. Compounds), $R^1$ may be hydrogen.

IV. Kits

In another aspect is a kit for reversibly labeling an ACP. The kit includes an ACP hydrolase and a phosphopantetheinyl transferase. The ACP hydrolase may be a *P. aeruginosa* ACP hydrolase, *Cyanothece* sp. ACP hydrolase, or *P. fluorescens* ACP hydrolase. The hydrolase may be a *P. aeruginosa* ACP hydrolase. The hydrolase may be a *Cyanothece* sp. ACP hydrolase. The hydrolase may be a *P. fluorescens* ACP hydrolase. The hydrolase may have at least 60, 70, 80, 90, 95, 96, 97, 98, 99, or 100% sequence homology to a wildtype AcpH. The hydrolase may be a fragment of the full-length ACP hydrolase, such that the fragment retains phosphodiesterase activity. The ACP hydrolase of the kit may be supplied as a protein. When supplied as a protein, the ACP hydrolase may be supplied as a powder, a liquid, or a gel. The ACP hydrolase may be supplied on an expression vector as described herein, including embodiments thereof. When supplied as an expression vector, the ACP hydrolase may be a solid, such as a powder, a gel, or pre-dissolved in a liquid. When pre-dissolved, the expression vector may be at a pre-determined concentration.

The phosphopantetheinyl transferase may be a *B. subtilis* phosphopantetheinyl transferase (i.e. a phosphopantetheinyl transferase found in *B. subtilis*). The phosphopantetheinyl transferase may have at least 60, 70, 80, 90, 95, 96, 97, 98, 99, or 100% sequence homology to a wildtype PPTase. The phosphopantetheinyl transferase may be a fragment of the full-length phosphopantetheinyl transferase, such that the fragment retains transferase activity. The phosphopantetheinyl transferase of the kit may be supplied as a protein. When supplied as a protein, the phosphopantetheinyl transferase may be supplied as a powder, a liquid, or a gel. The phosphopantetheinyl transferase may be supplied on an expression vector as described herein, including embodiments thereof. When supplied as an expression vector, the phosphopantetheinyl transferase may be a solid such as a powder, a gel, or pre-dissolved in a liquid. When pre-dissolved, the expression vector may be at a pre-determined concentration. The phosphopantetheinyl transferase may be supplied on a different expression vector than the ACP hydrolase. In embodiments, the phosphopantetheinyl transferase and ACP hydrolase are supplied on the same expression vector.

The kit may include an Apo-ACP. The Apo-ACP is as described herein, including embodiments thereof. The Apo-ACP may be an *E. Coli* Apo-ACP. The Apo-ACP may be supplied as a polypeptide. The Apo-ACP may be supplied as a solid such as a powder, a liquid, or as a gel. Alternatively, the Apo-ACP may be supplied as a component of an expression vector. The Apo-ACP may be supplied on its own expression vector. The expression vector may have an inducible promoter. The inducible promoter may be different from an inducible promoter on another expression vector in the kit. The Apo-ACP may be supplied on a single expression vector with at least one of a ACP hydrolase or a phosphopantetheinyl transferase.

The kit may include an ACP-phosphopantetheine conjugate. The ACP-phosphopantetheine conjugate is as described herein, including embodiments thereof.

The kit may include a compound as described herein, including embodiments thereof. The compound may have an amino acid sequence as set forth by SEQ ID NO: 1, 2, 3, 4, 5, 6, 7, or 8. The peptide may be supplied as a solid, in a liquid, or as a gel, as described herein, including embodiments thereof. The peptide may be supplied as a component of an expression vector. The expression vector may be different from the other expression vectors included in the kit. The expression vector may be the same as at least one of the other expression vectors in the kit. The peptide may include at least one phosphopantetheine analogue moiety as described herein, including embodiments thereof. The phosphopantetheine analogue moiety may have the formula:

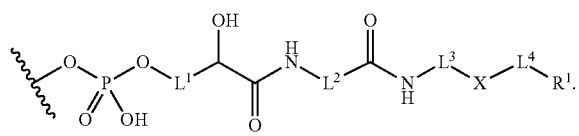

$L^1$, $L^2$, $L^3$, $L^4$, X, and $R^1$ are as described herein, including embodiments thereof.

The kit may include an CoA-phosphopantetheine analogue as described herein, including embodiments thereof. The CoA-phosphopantetheine analogue may have the formula:

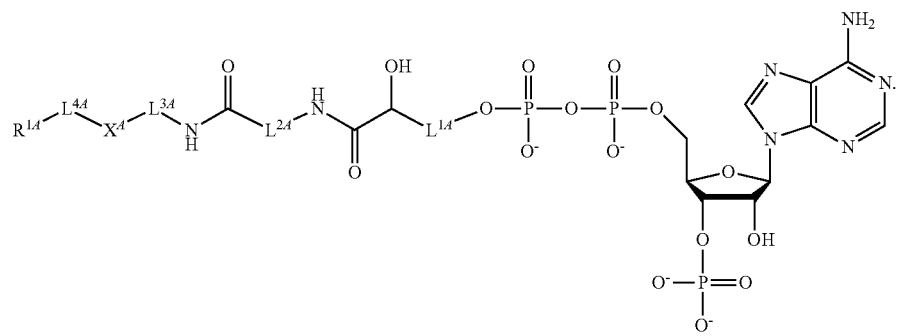

$L^1$, $L^2$, $L^3$, $L^4$, $X^A$, and $R^{1A}$ are as described herein, including embodiments thereof.

The kit may include an ACP hydrolase, a phosphopantetheinyl transferase, an Apo-ACP, and an CoA-phosphopantetheine analogue. The kit may include an ACP hydrolase, a phosphopantetheinyl transferase, and an ACP-phosphopantetheine conjugate. The kit may include an ACP hydrolase, a phosphopantetheinyl transferase, and a compound as described herein, including embodiments thereof. The kit may include an ACP hydrolase, a phosphopantetheinyl transferase, an Apo-ACP, an CoA-phosphopantetheine analogue, an ACP-phosphopantetheine conjugate, a com-

43 pound as described herein, including embodiments thereof or a combination thereof. The kit may further include a detectable moiety.

One skilled in the art would recognize that kits set forth herein could include buffers and other solutions necessary for example, for conjugation reactions, for hydrolase activity, or for phosphopantetheinyl transferase activity. One skilled in the art would recognize that kits including expression vectors could include additional reagents necessary for PCR amplification of the gene products. Such additions would be trivial and do not deviate from the inventive aspect of the kits provided herein.

V. Embodiments

Embodiment 1

A method of forming an Apo-ACP from an ACP-phosphopantetheine conjugate, said method comprising:
(i) contacting an ACP-phosphopantetheine conjugate with an ACP hydrolase, wherein said ACP-phosphopantetheine conjugate comprises an phosphopantetheine analogue moiety covalently bonded to an ACP through a phosphodiester linker; and
(ii) allowing said ACP hydrolase to cleave said phosphodiester linker thereby forming an Apo-ACP,
wherein said ACP-phosphopantetheine conjugate has the formula:

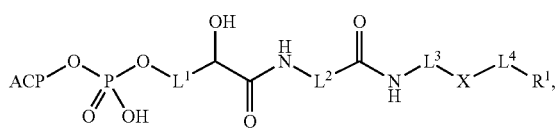

wherein;
ACP is an ACP protein moiety or an ACP protein fusion moiety;
$L^1$, $L^2$ and $L^3$ are independently substituted or unsubstituted alkylene;
$L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
X is —S—, —NH— or —O—;
$R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, a detectable moiety or a reactive probe.

Embodiment 2

The method of embodiment 1, wherein said ACP is an ACP protein fusion moiety.

Embodiment 3

The method of embodiment 2, wherein said ACP protein fusion moiety comprises an ACP protein moiety bound to an amino terminus or a carboxy terminus of a second fusion protein moiety.

44

Embodiment 4

The method of embodiment 2, wherein said ACP protein fusion moiety comprises an ACP protein moiety bound to an internal amino acid residue of a second fusion protein moiety.

Embodiment 5

The method of embodiment 1, wherein $R^1$ is a detectable moiety

Embodiment 6

The method of embodiment 5, wherein said detectable moiety is a fluorophore

Embodiment 7

The method of embodiment 6, wherein said fluorophore is fluorescein, coumarin, rhodamine, or GFP Embodiment 8

The method of embodiment 1, wherein $R^1$ is a reactive probe

Embodiment 9

The method of embodiment 1, wherein $L^1$ is —CH$_2$C(CH$_3$)$_2$—, $L^2$, is —CH$_2$—, and $L^3$ is —CH$_2$—.

Embodiment 10

The method of embodiment 1, wherein said ACP hydrolase is a P. aeruginosa ACP hydrolase, Cyanothece sp. ACP hydrolase, or P. fluorescens ACP hydrolase.

Embodiment 11

The method of embodiment 1, wherein said ACP hydrolase is not an E. coli ACP hydrolase.

Embodiment 12

The method of embodiment 1, wherein said apo-ACP is a Fatty Acid ACP, Polyketide ACP, or Peptide ACP.

Embodiment 13

The method of embodiment 12, wherein said apo-ACP is a E. coli apo-ACP, P. aeruginosa apo-ACP, S. oneidensis apo-ACP, P. falciparum apo-ACP, M. tuberculosis apo-ACP, S. coelicolor apo-ACP, A. parasiticus apo-ACP, G. fujikuroi apo-ACP, L. majuscule apo-ACP or P. fluorescens apo-ACP.

Embodiment 14

The method of embodiment 13, wherein said apo-ACP is E. coli AcpP (type II).

Embodiment 15

The method of embodiment 1, further comprising:
(i) contacting said Apo-ACP with a CoA-phosphopantetheine analogue and a phosphopantetheinyl transferase, wherein said CoA-phosphopantetheine analogue comprises a phosphopantetheine analogue moiety covalently bonded to a phosphoadenosine moiety through a phosphodiester linkage;
(ii) allowing said phosphopantetheinyl transferase to cleave said phosphodiester linkage and bind said phosphopantetheine analogue moiety to said apo-ACP through a phosphodiester linker thereby forming a second ACP-phosphopantetheine conjugate;
wherein said CoA-phosphopantetheine analogue has the formula:

$$R^{1A}\text{-}L^{4A}\text{-}X^A\text{-}L^{3A}\text{-}NH\text{-}C(O)\text{-}L^{2A}\text{-}NH\text{-}C(O)\text{-}CH(OH)\text{-}L^{1A}\text{-}O\text{-}P(O)(O^-)\text{-}O\text{-}P(O)(O^-)\text{-}O\text{-}\text{Adenosine-}3'\text{-}OP(O)(O^-)_2$$

wherein;
$L^{1A}$, $L^{2A}$ and $L^{3A}$ are independently substituted or unsubstituted alkylene;
$L^{4A}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
$X^A$ is —S—, —NH— or —O—;
$R^{1A}$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, a detectable moiety or a reactive probe.

Embodiment 16

The method of embodiment 15, further comprising
(i) contacting said second ACP-phosphopantetheine conjugate with a second ACP hydrolase; and
(ii) allowing said second ACP hydrolase to cleave said phosphodiester linker thereby forming said Apo-ACP.

Embodiment 17

The method of embodiment 15, wherein said phosphopantetheinyl transferase is a *B. subtilis* phosphopantetheinyl transferase.

Embodiment 17

A compound comprising an amino acid sequence having the formula:

-DSL(Aaa1)(Aaa2)(Aaa3)(Aaa4)(Aaa5)(Aaa6)-, wherein;
Aaa1 is D, E, or S;
Aaa2 is T, F, or W;
Aaa3 is V, L, or I;
Aaa4 is E, A, or L;
Aaa5 is A, S, R, or L;
Aaa6 is V, K, or L; and
wherein said sequence is not -DSLDTVELV- (SEQ ID NO:97).

Embodiment 18

The compound of embodiment 17, having the formula:

$R^N$-DSL(Aaa1)(Aaa2)(Aaa3)(Aaa4)(Aaa5)(Aaa6)-$R^C$, $R^N$-DSLEFIASKLA-$R^C$ (SEQ ID NO:1) or $R^N$-GD-SLSWLLRLLN-$R^C$ (SEQ ID NO:2), wherein;
$R^N$ is —NH$_2$, a detectable moiety, or a reactive probe; and
$R^C$ is —COOH, a detectable moiety, a reactive probe, or -$L^7$-$R^{C1}$, wherein
$L^7$ is a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene -$L^5$-PEG-$L^6$-$R^{C1}$,
$L^5$ and $L^6$ independently —O—, —S—, —NH—, —NHC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^{C1}$ is a solid support comprising a cellulose membrane or a resin.

Embodiment 19

The compound of embodiment 18, wherein said solid support is a cellulose membrane.

Embodiment 20

The compound of embodiment 18, wherein said solid support is a resin.

Embodiment 21

The compound of embodiment 20, wherein said resin polystyrene resin or a polyamine resin.

Embodiment 22

The compound of embodiment 17 having the formula:

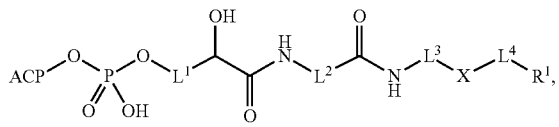

wherein;

ACP is an ACP protein moiety or ACP fusion protein moiety comprising said amino acid sequence;

$L^1$, $L^2$ and $L^3$ are independently substituted or unsubstituted alkylene;

$L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

X is —S—, —NH— or —O—;

$R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, a detectable moiety or a reactive probe.

Embodiment 23

The compound of embodiment 22, wherein said ACP protein fusion moiety comprises an ACP protein moiety bound to an amino terminus or a carboxy terminus of a second fusion protein moiety.

Embodiment 24

The compound of embodiment 22, wherein said ACP protein fusion moiety comprises an ACP protein moiety bound to an internal amino acid residue of a second fusion protein moiety.

Embodiment 25

The compound of embodiment 22, wherein $R^1$ is a detectable moiety.

Embodiment 26

The compound of embodiment 25, wherein said detectable moiety is a fluorophore.

Embodiment 27

The compound of embodiment 26, wherein said fluorophore is fluorescein, coumarin, rhodamine, or GFP.

Embodiment 28

The compound of embodiment 22, wherein $R^1$ is a reactive probe.

Embodiment 29

A compound having the formula:

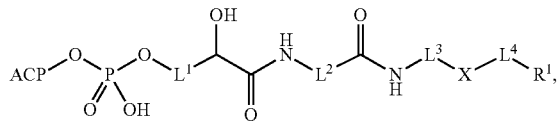

wherein;

ACP is an ACP protein moiety or an ACP protein fusion moiety;

$L^1$, $L^2$ and $L^3$ are independently substituted or unsubstituted alkylene;

$L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

X is —S—, —NH— or —O—;

$R^1$ is substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene, a detectable moiety or a reactive probe.

Embodiment 30

The compound of embodiment 29, wherein X is —NH—.

Embodiment 31

The compound of embodiment 29, wherein X is —O—.

Embodiment 32

A kit for reversibly labeling an ACP, said kit comprising;
(i) an ACP hydrolase; and
(ii) a phosphopantetheinyl transferase.

Embodiment 33

The kit of embodiment 32, wherein said ACP hydrolase is supplied as a protein.

Embodiment 34

The kit of embodiment 32, wherein said ACP hydrolase is supplied on an expression vector.

Embodiment 35

The kit of embodiment 32, wherein said ACP hydrolase is a *P. aeruginosa* ACP hydrolase, *Cyanothece* sp. ACP hydrolase, or *P. fluorescens* ACP hydrolase.

Embodiment 36

The kit of embodiment 32, wherein said phosphopantetheinyl transferase is supplied as a protein.

Embodiment 37

The kit of embodiment 32, wherein said phosphopantetheinyl transferase is supplied on an expression vector.

Embodiment 38

The kit of embodiment 32, wherein said phosphopantetheinyl transferase is a *B. subtilis* phosphopantetheinyl transferase.

Embodiment 39

The kit of embodiment 32, further comprising an Apo-ACP.

Embodiment 40

The kit of embodiment 39, wherein said Apo-ACP is supplied as a protein.

Embodiment 41

The kit of embodiment 39, wherein said Apo-ACP is supplied on an expression vector.

Embodiment 42

The kit of embodiment 39, wherein said Apo-ACP is an *E. Coli* Apo-ACP, *P. aeruginosa* Apo-ACP, *S oneidensis* Apo-ACP, *P. falciparum* Apo-ACP, *M tuberculosis* Apo-ACP, *S. coelicolor* Apo-ACP, *A. parasiticus* Apo-ACP, *G. fujikuroi* Apo-ACP, *L. majuscule* Apo-ACP.

Embodiment 43

The kit of embodiment 32, further comprising an ACP-phosphopantetheine conjugate having the formula:

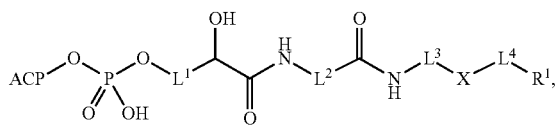

wherein;
ACP is an ACP protein moiety or an ACP protein fusion moiety;
$L^1$, $L^2$ and $L^3$ are independently substituted or unsubstituted alkylene;
$L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
X is —S—, —NH— or —O—;
$R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, a detectable moiety or a reactive probe.

Embodiment 44

The kit of embodiment 32, further comprising a compound of embodiment 17 having the formula:

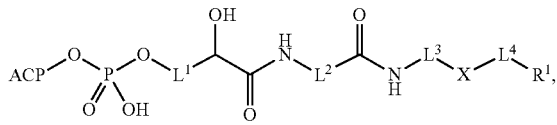

wherein;
ACP is an ACP protein moiety or an ACP protein fusion moiety comprising said amino acid sequence;
$L^1$, $L^2$ and $L^3$ are independently substituted or unsubstituted alkylene;
$L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

X is —S—, —NH— or —O—;

$R^1$ is hydrogen substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, a detectable moiety or a reactive probe.

Embodiment 45

The kit of embodiment 44, wherein said compound is supplied as a polypeptide.

Embodiment 46

The kit of embodiment 44, wherein said compound is supplied on an expression vector.

Embodiment 47

The kit of embodiment 45, wherein $R^{1.4}$ is a detectable moiety.

Embodiment 48

The kit of embodiment 47, wherein said detectable moiety is a fluorophore.

Embodiment 49

The kit of embodiment 48, wherein said fluorophore is fluorescein, coumarin, rhodamine, or GFP.

Embodiment 50

A method for labeling an acyl carrier protein (ACP), said method comprising
contacting an ACP having a first pantetheine-conjugated moiety attached thereto with an acyl carrier protein hydrolase (AcpH), under conditions suitable to remove said first pantetheine-conjugated moiety, thereby providing an apo-form of said ACP (apo-ACP); and
contacting said apo-ACP with a phosphopantetheinyl transferase (PPTase) and a second pantetheine-conjugated small molecule under conditions suitable to allow conjugation of said pantetheine-conjugated small molecule with said apo-ACP, thereby labeling said ACP Embodiment 51

The method according to embodiment 53, wherein said ACP is free ACP or an ACP fusion protein.

Embodiment 52

The method according to embodiment 54, wherein said AcpH is from *Pseudomonas aeruginosa*.

Embodiment 53

The method according to embodiment 53, wherein said PPTase is from *Bacillus subtilis*.

Embodiment 54

A method for labeling an apo-form of an acyl carrier protein (apo-ACP), said method comprising
contacting an apo-ACP with a phosphopantetheinyl transferase (PPTase) and a pantetheine-conjugated small molecule under conditions suitable to allow conjugation of said pantetheine-conjugated small molecule with said apo-ACP, thereby labeling said apo-ACP.

Embodiment 55

The method according to embodiment 54, wherein said apo-ACP is free apo-ACP or an apo-ACP fusion protein.

Embodiment 56

A labeled acyl carrier protein produced according to one of embodiments 49 to 53.

Embodiment 57

A labeled apo-form of an apo-ACP produced according to one of embodiments 54 or 55.

VI. Examples

1. Example 1

The cloning, expression, and evaluation of new acyl carrier protein hydrolase homologs from *Pseudomonas fluorescens, Cyanothece*, and *Shewanella oneidensis* reveals remarkable variation in substrate recognition and kinetic parameters for phosphopantetheine hydrolysis when compared to that from *Pseudomonas aeruginosa*. Study of FAS, PKS, and NRPS carrier proteins reveals an overall preference for acyl carrier protein substrates from type II FAS pathways as well as variable activity for PKS types, with NRPS carrier proteins being the least active substrate. *Cyanothece* AcpH possesses a remarkable kinetic superiority over past reported AcpH enzymes for *E. coli* ACP.

Post-translational protein modification allows engineering of extra utility into biochemical systems for a variety of medically and scientifically useful purposes.[1-4] A particularly useful post-translational modification of the acyl carrier protein (ACP) accommodates a variety of phosphopantetheine (PPant) analogs that may also be specifically removed.[6] More recently, labeling of free and fusion small peptides has opened the door to expanded bio-conjugation applications.[7-10] However, these methods face difficulties in either the kinetics of probe application, or in non-specific label removal. Various minimal peptides have been discovered that accommodate PPant labeling,[11,12] but have not yet been shown to be specifically and enzymatically reversible. Here is demonstrated acyl carrier protein hydrolase (AcpH) homologs not only display superior kinetics for PPant removal from *E. coli* ACP, but also demonstrate specific hydrolase activity against the 11-amino acid ybbR peptide substrate.

Since the first identification of AcpH activity and characterization in *E. coli*,[13,14] ways to broadly incorporate a specific biocompatible hydrolase activity into the world of versatile phosphopantetheine labeling pioneered with the phosphopantetheinyl transferase (PPTase) Sfp have been searched.[11,12,15,16] The identification of a more stable AcpH from *P. aeruginosa*[17] and its subsequent characterization using free and fusion-ACP with phosphopantetheine analogs[6] enabled discovery of a more promiscuous AcpH for establishing a complete and robust reversible labeling strategy. However, the AcpH has primarily demonstrated promiscuity for various modified phosphopantetheines appended to the *E. coli* ACP from type II fatty acid synthesis (FAS). While some limited non-FAS carrier proteins have been tested with AcpH,[17] the results served to highlight the need for a broader carrier protein substrate compatibility analysis.

To this end, a more thorough evaluation of carrier protein substrates recognized not only by AcpH from *P. aeruginosa* PAO1 (PaAcpH, $NP_{13}$ 253043.1), but also annotated hypothetical AcpH homologs from *Cyanothece* PCC 7822 (CyAcpH, $YP_{13}$ 003888700.1), *S. oneidensis* MR-1 (SoAcpH, NP_718678.1), and an AcpH suspected resided within *P. fluorescens* NCIMB 10586 due to AcpH annotation in other *P. fluorescens* strains such as *P. fluorescens* SBW25 (YP_002871039.1) was sought. We chose these additional organisms as AcpH sources to represent a snapshot of selected currently annotated AcpH homologs, comparing proximal phylogenetic relations (*P. fluorescens*), and more distal relationships (*Cyanothece, S. oneidensis*). We also believed the broad sequence variation between these AcpH homologs would serve to provide additional confirmation for previous predictions of active site residues.[18] However, to truly cement Sfp/AcpH methodology as a site-specific reversible labeling tool, we evaluated function with a minimal 11 amino acid (AA) peptide discovered for PPant labeling, ybbR.[11,12]

Cloning and Expression Produced Soluble Protein for all Constructs.

Our initial goal was to establish the AcpH substrate preference with regards to carrier proteins from fatty acid synthesis (FAS), polyketide synthesis (PKS), and non-ribosomal peptide synthesis (NRPS) pathways (Table 1a). To facilitate this goal with so many sample reactions, we took to labeling all carrier proteins with a coumarin-pantetheine analog using one-pot methodology,[16,19] and qualifying AcpH activity by significant reduction of visible protein band fluorescence in AcpH test reactions. FAS ACPs were derived from bacterial protein targets with the exception of the apicoplast ACP from *P. falciparum*. Carrier proteins included *E. coli* AcpP (type II), *P. aeruginosa* AcpP (type II), *S. oneidensis* AcpP (type II), *P. falciparum* apicoplast ACP (Type II),[20] *M. tuberculosis* AcpM (Type II) and MAS (FAS/PKS hybrid). PaAcpH, PfAcpH, and CyAcpH were active against all FAS ACPs with the exception of the atypical MAS (Table 1a). Interesting, both crypto-SoAcpP and holo-SoAcpP demonstrated PPant hydrolysis overnight, requiring the subsequent holo-SoAcpP analysis be conducted on a shorter timescale.

tion of activity against phosphopantetheine-labeled ybbR was determined. Considering that the reversible phospho- TABLE 1a AcpH qualitative CP activity. AcpH homolog activity was determined through overnight reaction with crypto-CP except in the case of holo-SoAcpP. A significant reduction in fluorescence of AcpH-treated CP from controls or Urea-PAGE gel-shift are labeled as active "YES".

| | Carrier Protein | | Enzyme | | | |
|---|---|---|---|---|---|---|
| | Organism | Name | PaAcpH | PfAcpH | CyAcpH | SoAcpH |
| FAS | E. coli | AcpP | YES | YES | YES | no |
| | P. aeruginosa | AcpP | YES | YES | YES | no |
| | S. oneidensis | AcpP | YES† | YES† | YES† | no |
| | P. falciparum | ACP‡ | YES | YES | YES | no |
| | M. tuberculosis | AcpM | YES | YES | YES | no |
| | M. tuberculosis | MAS | no | no | no | no |
| PKS | S. coelicolor | ActACP | no | YES | no | no |
| | A. parasiticus | PksA | YES | YES | YES | no |
| | G. fujikuroi | Pks4 | no | YES | no | no |
| | L majuscula | JamC | YES | YES | YES | no |
| | L majuscula | JamF | no | no | no | no |
| | P. agglomerans | AdmI | no | YES | no | no |
| NRPS | P. agglomerans | AdmA | no | no | no | no |
| | V. cholerae | VibB | no | no | no | no |
| | A. orientalis | CepK | no | no | no | no |
| | P. fluorescens | PltL | YES | no | no | no |
| | P. syringae | SyrB1 | no | no | no | no |

PKS-type ACPs were derived from a mixture of bacterial and fungal targets. Carrier proteins included S. coelicolor ActACP,[21] A. parasiticus PksA,[22] G. fujikuroi Pks4,[23] L. majuscula JamC and JamF,[24] and P. agglomerans AdmI.[25] Activity is displayed in Table a1, with PfAcpH demonstrating the only activity with crypto-ActACP and Pks4, while all other AcpH except SoAcpH were capable of activity with crypto-PksA and JamC.

NRPS-type peptidyl carrier proteins (PCP) FAS ACPs were derived from bacterial protein targets. Carrier proteins included P. agglomerans AdmA,[25] V. cholerae VibB,[26] A. orientalis CepK, P. fluorescens PltL, P. syringae SyrB1.[27] The observed partial activity resulted from PaAcpH with PltL (Table 1a). It is particularly interesting that an AcpH from P. aeruginosa worked with a PCP from P. protogens, which is closely related to P. fluorescens, while the P. fluorescens AcpH did not. Without wishing to be bound by theory, knowing the true overall role of AcpH within each organism, renders it difficult to predict when AcpH activity is desired or triggered. However, in analyzing the sequence variation between P. fluorescens NCIMB 10586 from which our PfAcpH was derived, and P. fluorescens Pf-5 from which PltL was derived, we find that the amino acid sequence of PaAcpH to the Pf-5 PfAcpH version (not studied) is 70%, while the PfAcpH from strain NCIMB 10586 to Pf-5 is 82%.

Improved substrate promiscuity of the PfAcpH and CyAcpH was observed. To further investigate its lower activity, we evaluated the secondary structure of SoAcpH compared to the known active CyAcpH. Circular dichroism revealed strong alpha helical character, indicating a consistent protein fold. Additionally, we aligned the SoAcpH protein sequence to those of PaAcpH, PfAcpH, CyAcpH, and EcAcpH for comparison to the existing EcAcpH analysis based off SPoT.[18] This analysis reveals predicted aspartate active site $Mn^{2+}$ binding residues in the case of all AcpH except SoAcpH, lending additional support to our results demonstrating the S. oneidensis protein is inactive as an AcpH.

Due to the observations of improved activity of PfAcpH and CyAcpH from the original PaAcpH, next characterizapantetheinylation labeling is positioned as a direct competitor to existing techniques allowing labeling of short peptides used by sortase (5AA),[7, 28] farnesyl-transferase (4AA),[8] and transglutaminase (5AA)[9, 10] methodologie, variations of the ybbR (11AA) free peptide, fluoresceinisothiocyanate (FITC)-ybbR conjugate,[29] and eGFP-ybbR fusion were evaluated[11]. Coumarin-PPant was conjugated to all ybbR variations with one-pot methodology and analyzed with Urea-PAGE using all AcpH homologs, demonstrating qualitative activity for all ybbR constructs with PfAcpH and CyAcpH and no activity for SoAcpH (Table 2a). These observations open the door to a wide variety of bioconjugation applications using ybbR and phosphopantetheine analogs and provides potential advantages for increased substrate variety and experimental flexibility when applied to existing bioconjugation methods utilizing a larger ACP. Areas which can benefit from this include in vitro protein labeling, protein immobilization, tissue engineering,[30] and even cell labeling.[31]

TABLE 2a

AcpH activity with modified ybbR peptide. Various ybbR peptide substrate variations were evaluated for AcpH activity qualitatively. AcpH from both P. fluorescens and Cyanothece PCC7822 demonstrated detectable activity.

| | Fusion Modification | | Enzyme | | | |
|---|---|---|---|---|---|---|
| | N-term | C-term | PaAcpH | PfAcpH | CyAcpH | SoAcpH |
| YbbR13 | N/A | N/A | no | YES | YES | no |
| | FITC | N/A | no | YES | YES | no |
| | GFP | 6xHis | no | YES | YES | no |
| | 6xHis | GFP | no | YES | YES | no |

Given the demonstrated variation in AcpH substrate compatibility for both full carrier proteins and variations of the 11-mer ybbR substrate, we sought to further distinguish the new AcpH homologs with kinetic evaluation using the representative E. coli AcpP and ybbR substrates. Kinetic analysis of the AcpH homologs with holo-*E. coli* AcpP at 37° C. resulted in truly superior kinetic values for CyAcpH compared to PaAcpH and PfAcpH (Table 3). $K_{cat}$ values obtained were 211 min$^{-1}$ for CyAcpH, 3.7 min$^{-1}$ for PfAcpH, and 0.6 min$^{-1}$ for PaAcpH, with $k_{cat}/K_m$ values of 3.6 min$^{-1}$*μM$^{-1}$ for CyAcpH, 0.06 min$^{-1}$*μM$^{-1}$ for PfAcpH, and 0.05 min$^{-1}$*μM$^{-1}$ for PaAcpH. The high apparent turnover for CyAcpH, was confirmed via a EDTA quench to terminate the hydrolysis reaction. The quench did indeed result in enzyme arrest while awaiting HPLC analysis. These results are significant, as this reveals CyAcpH's turnover of holo-*E. coli* AcpP surpassing the kinetic parameters of Sfp for apo-*E. coli* AcpP of $k_{cat}$=5.8 min$^{-1}$ and $k_{cat}/K_m$=1 min$^{-1}$*μM$^{-1}$.[32]. While the CyAcpH kinetic results are derived from free *E. coli* AcpP, this result implies an uncanny advantage for this newly characterized enzyme in designing reversible labeling scenarios with AcpP as a protein handle.

TABLE 3

AcpH homolog AcpP and ybbR kinetics. AcpH homolog activity was determined at 37° C. with holo- *E. coli* AcpP using HPLC detection, as well as crypto-FITC-ybbR in a FRET-quench microwell plate assay. Best in-class kinetics for evaluated substrates are CyAcpH for holo-AcpP, and PfAcpH for crypto- FITC-ybbR.

| Enzyme | Substrate | [AcpH], μm | $V_{max}$ (min$^{-1}$) | $K_m$ (μM) | $k_{cat}$ (min$^{-1}$) | $k_{cat}/K_M$ (min$^{-1}$*μM$^{-1}$) |
|---|---|---|---|---|---|---|
| PaAcpH | holo-ACP | 1 | 0.59 ± 0.02 | 12 ± 2 | 0.59 ± 0.02 | 0.049 |
| PfAcpH | (*E. coli*) | 1 | 3.7 ± 0.1 | 61 ± 7 | 3.7 ± 0.1 | 0.060 |
| CyAcpH |  | 0.005 | 1.1 ± 0.1 | 58 ± 9 | 211 ± 11 | 3.6 |
| SoAcpH |  | 1 | NC† |  |  |  |
| PaAcpH | crypto-FITC- | 1 | 0.008 ± 0.016 | 177 ± 744 | 0.008 ± 0.016 | 4.7E−05 |
| PfAcpH | YbbR (3) | 1 | 0.17 ± 0.01 | 48 ± 5 | 0.17 ± 0.01 | 0.003 |
| CyAcpH |  | 1 | 0.004 ± 0.004 | 21 ± 68 | 0.004 ± 0.004 | 2.0E−04 |

†SoAcpH activity data could not be calculated "NC" due to low turnover

Kinetics of the AcpH homologs against ybbR substrate utilized a FRET-reporter system with rhodamine WT PPant-labeled FITC-ybbR previously used to monitor Sfp activity.[29, 33] FITC-ybbR was conjugated with Rhodamine-CoA[33] to generate the crypto-FITC-ybbR material. HPLC purification and lyophilization of the crypto-FITC-ybbR resulted in quantitative yield and supplied the substrate necessary for AcpH kinetic analysis. SoAcpH was not analyzed for kinetics, as it did not display activity in the qualitative ybbR activity analysis. Real-time analysis of AcpH homologs at 37° C. in 96-well format provided kinetic data favoring the activity of PfAcpH for crypto-FITC-ybbR. $K_{cat}$ values obtained were 0.17 min$^{-1}$ for PfAcpH with $k_{cat}/K_m$ of 0.003 min$^{-1}$*μM$^{-1}$. While PaAcpH and CyAcpH demonstrated nonzero kinetic values for the crypto-FITC-ybbR, the kinetic value standard deviation included zero (Table 3). Compared to Sfp's kcat of 11 and $k_{cat}/K_m$ of 0.091 for ybbR,[11] the PfAcpH demonstrated two orders of magnitude slower reaction rates. However, this distinguished activity still provides advantages compared to sortase and farnesyl transferase systems. First, the labeling step utilizing Sfp and a coenzyme A analog still possesses good kinetics, even if AcpH PPant removal is slower. Additionally, both the Sfp and AcpH reactions are favored towards product formation due to the energy released by breaking a phosphodiester bond in both cases, unlike the constant equilibrium experienced by a sortase reaction and the consequently high substrate concentrations required to achieve efficient labeling. Compared to farnesyl-transferase, the Sfp labeling step possesses a similar $k_{cat}$, but allows flexible ybbR placement on the amino/carboxy-terminus or internal to the target protein.[11] In comparison, the farnesyl prosthetic attachment site must be on the C-terminus of a protein and removal of the farnesyl group requires an irreversible carboxypetidase protease cleavage of the transfer site sequence. Thus, in bio-conjugation applications requiring a fusion sequence smaller than the 80 amino acid AcpP, truly reversible and site-specific labeling can be implemented with the 11 amino acid ybbR using combined Sfp/PfAcpH methodology. The incidental activity of PfAcpH with a peptide discovered originally for Sfp[11] implies that there is significant room for AcpH activity improvement, either by modification of the ybbR sequence, or discovery of a new dual-purpose peptide that possesses desirable kinetics for both Sfp and AcpH activity.

Following the completion of our substrate panels and the identification of our most promiscuous AcpH from *P. fluorescens*, we wanted to identify any particularly important consensus residues from active protein sequences and derive a conclusion that may guide future substrate prediction. The sequences from 10 amino acids on either side of the active site serine were aligned and used to generate a consensus sequence from all carrier proteins active with PfAcpH. This procedure generated a core consensus of "DLGXD-SLDXVEL" (SEQ ID NO:103) which displays a strong preference for particular amino acids residing in type II FAS ACP. This absolute sequence is not required for activity, but our results indicate that carrier proteins with 5 or fewer matching amino acids are inactive. The "DSL" portion appears to be especially important, as only one PKS ACP, JamC, is active with the variation "DSS". In comparison, none of the inactive NRPS PCPs contain the "DSL" active site sequence except MAS, or possess more than 6 matching identical amino acids surrounding the active site.

In conclusion, analysis of three new AcpH gene products and comparison to existing *P. aeruginosa* AcpH reveals a remarkable array of information regarding substrate compatibility. Despite the apparent inactivity of the hypothetical *S. oneidensis* AcpH, the AcpH homologs from *P. fluorescens* and *Cyanothece* present superior alternative to the existing methods for phosphopantetheine removal, with CyAcpH demonstrating remarkable kinetic values for holo-AcpP hydrolysis, while PfAcpH possesses the best available kinetics for crypto-ybbR hydrolysis, as well as the broadest apparent substrate promiscuity versus the evaluated carrier proteins. These new enzymes demonstrate substantial potential for further substrate truncation and peptide sequence modification, as well as ready implementation with established reversible ACP labeling methods.

Methods:

General.

Protein concentrations were determined using UV absorbance at 280 nm, with extinction coefficients calculated using ExPASy[34] online tool for each protein.

Cloning.

The *P. aeruginosa* PAO1 AcpH gene [geniD: 881435] identified previously[17] was cloned as described previously.[6] All primers used for cloning are located in supplemental information (Table 4) *Cyanothece* PCC 7822 AcpH gene [genID: 9739974], and *Shewanella oneidensis* AcpH gene [genID: 1170805] were cloned from genomic DNA using standard techniques. *P. fluorescens* NCIMB 10586 AcpH gene was cloned using homology primers designed from *P. fluorescens* SBW25 AcpH gene [7817947]. Sequencing of intermediate PCR product allowed design of more specific primers and production of final PCR gene product. MtbAcpM was subcloned from an alternate vector to remove the stop codon. All AcpH gene and AcpM PCR products were treated with restriction endonuclease and ligated into pET29b plasmids containing a C-terminal 6×His tag.

TABLE 4

Primers used for cloning

| Primer Name | Primer Sequence (5' → 3') |
|---|---|
| PfAcpH F1 | AAAACATATGAATTATCTCGCACATCTGCACC (SEQ ID NO: 49) |
| PfAcpH R1 | AAAACTCGAGTGCAAAGGCCTGCAACTCTGG (SEQ ID NO: 50) |
| PfAcpH R2 | AAAACTCGAGTTAAAATTGGAGTGCAAAGGCCTGC (SEQ ID NO: 51) |
| PfAcpH R3 | AAAACTCGAGAAATTGGAGTGCAAAGGCCTGCAAC (SEQ ID NO: 52) |
| CyAcpH F1 | AAAACATATGAATTATCTGGCTCATTTATTTTAGC (SEQ ID NO: 53) |
| CyAcpH R1 | AAAACTCGAGAGCCAAGTTAACATAATCAATCAGTTG (SEQ ID NO: 54) |
| SoAcpH F1 | AAAACATATGAACATTCTTACACACTTACATCTGG (SEQ ID NO: 55) |
| SoAcpH R1 | AAAACTCGAGCTCGGGTAAGTAGTCAATTGGAG (SEQ ID NO: 56) |
| MtbAcpM F1 | AAAACATATGGTGCCTGTCACTCAGGAAGAAATC (SEQ ID NO: 57) |
| MtbAcpM R1 | AAAAAAGCTTCTTGGACTCGGCCTCAAGC (SEQ ID NO: 58) |

Protein Expression.

All AcpH growth, and purification procedures are previously described.[6] TesA was expressed and purified in the same manner as AcpH. Lysis buffer for CyAcpH and PfAcpH are excepted in that they utilized higher glycerol content. CyAcpH and PfAcpH were purified and desalted in the presence of 50 mM TrisCl pH 8.0, 250 mM NaCl, and 25% glycerol. The additional glycerol contributed significantly to higher perceived protein recovery and prolonged stability. *E. coli* AcpP, and *P. aeruginosa* MBP-AcpP were prepared as previously described. *S. oneidensis* AcpP was prepared in the same manner as *E. coli* AcpP. MtbAcpM, ActACP, JamC, JamF, AdmA, AdmI, SyrB1-AT, PltL, CepK, VibB, and MAS containing cells were grown in LB with appropriate antibiotic at 37° C. until they reached an optical density of 0.6. IPTG was added to 1 mM, and the cells were incubated with shaking at 16° C. overnight. *Plasmodium* ACP was grown as previously described.[20] All ACP constructs were grown in antibiotics appropriate for the contained plasmid. All cells were centrifuged to obtain a pellet, which was re-dissolved in lysis buffer. MtbAcpM expressed as an apo/holo/acyl mixture, and required overnight treatment with Affigel-25 conjugates of TesA thioesterase[ref] and PfAcpH prior to labeling. *Plasmodium* ACP expressed as holo- and was treated with PaAcpH conjugated to Affigel-25 prior to labeling. Spin concentration of ACP with 3 kDa Millipore centrifugal filters (EMD Millipore, Billerica, Mass.) resulted in a stock One-Pot Carrier Protein Coumarin-Labeling Strategy.

Unless otherwise noted, all coumarin-PPant labeling proceeded as follows: apo-carrier protein or peptide at 50-200 µM were labeled in 50 mM Na-HEPES pH 7.5, 10 mM $MgCl_2$, 8 mM ATP, 0.1 µM MBP-CoaA/D/E, 0.1 µM native Sfp, and 1.1 equivalents of coumarin-pantetheine at 37° C. overnight. Crypto-protein samples were repurified using standard IMAC techniques in pH 8 lysis buffer with Ni-NTA resin, and spin-concentrated/buffer exchanged to remove imidazole and concentrate with 0.5 mL 3 kDa MWCO cellulose filters. Crypto-peptide samples were purified with HPLC, lyophilized, and redissolved in 50 mM TrisCl pH 8.0 prior to analysis.

General AcpH Gel-Based Activity.

Specific procedures for AcpH activity are described previously.[6] Briefly, qualitative analysis of crypto-carrier protein or peptide samples proceeded at 37° C. overnight reaction with 1 µM AcpH homolog. Following AcpH treatment, an equal volume of 2×SDS-PAGE loading dye was added to crypto-carrier proteins samples and heated 5 min at 90° C., and run on 12% or 15% SDS-PAGE. Gels were fixed in 50/40/10% water/methanol/acetic acid for 30 minutes, and washed with water three times before UV imaging. Holo-carrier protein reactions were analyzed with Urea-PAGE as previously described.[6] All protein gels were Coomassie stained for evaluating total protein. Crypto-peptides were evaluated on Urea-PAGE, and were imaged immediately after running with no gel fixing.

FITC-ybbR Labeling & Purification.

Preparation of rhodamine-labeled FITC-ybbR proceeded via reaction of 200 µM FITC-ybbR with 200 µM rhodamine WT-CoA synthesized as described previously[33] with 1 µM Sfp in 50 mM HEPES pH 7.5 and 10 mM $MgCl_2$ for 2 hours at 37° C. Crypto-peptide samples were purified with HPLC, lyophilized, and redissolved in 50 mM TrisCl pH 0.08 at 4 mM prior to analysis.

HPLC AcpH Kinetics.

Holo-*E. coli* AcpP was prepared as a serial dilution in 50 mM TrisCl, 250 mM NaCl, 30 mM $MgCl_2$, and 2 mM $MnCl_2$. PaAcpH, PfAcpH, and SoAcpH were prepared at 2 µM in similar buffer with 10% glycerol but lacking Mg/Mn. CyAcpH was prepared at 10 nM in the same AcpH buffer. Addition of AcpH into holo-AcpP samples provided final top concentrations of 400, 200, 100, 50, 25, 12.5 µM for PaAcpH/PfAcpH/SoAcpH, and 900, 450, 225, 112.5, 56.25, 28.1, 14 µM for CyAcpH. Reactions were transferred to prewarmed shaker at 37° C. and were quenched with 100 mM EDTA after 10 minutes. Samples were centrifuged and evaluated at 210 nm with HPLC using an acetonitrile gradient to determine apo-AcpP product formation. Michaelis-Menten kinetics were calculated using GraphPad Prism (GraphPad Software, La Jolla, Calif.).

FRET AcpH Kinetics:

Rhodamine-labeled FITC-Ybbr as well as standard 1:1 apo-FITC-ybbR:rhodamine-CoA was subjected to an 11-point serial dilution in 50 mM TrisCl pH 8.0 to achieve final concentrations of 400-0.4 µM. PfAcpH, CyAcpH, PaAcpH and buffer blank were prepared to give a final solution added concentration of 1 or 0 µM AcpH, 50 mM TrisCl pH 8.0, 15 mM $MgCl_2$, 1 mM $MnCl_2$, and 1 mg/mL BSA. Total reaction volumes were 50 µL and utilized a 96-well Costar 3694 plate (Corning, Lowell, Mass.). Following mixing, reactions were centrifuged for 2 minutes at 1500 rpm, and incubated at 37° C. over 4 hours in a HTS 7000 plus Bioassay Reader (Perkin Elmer, Waltham, Mass.) in kinetic mode. Comparison of enzyme reactions to buffer blank and 1:1 apo-FITC-ybbR:rhodamine-CoA standard allowed calculation of product formation and determination of Michaelis-Menten kinetics using GraphPad Prism.

General Methods.

All protein concentrations were determined using UV spectroscopy at 280 nM with the extinction coefficient calculated from derived amino acid sequences with the ExPASy ProtParam tool.

Cloning of AcpH Constructs.

The *Pseudomonas aeruginosa* PAO1 AcpH gene [PA4353] identified previously (Murugan, 2010) was cloned as described previously. (Kosa, 2012). *Cyanothece* PCC7822 AcpH (CyAcpH) PCR product was generated from genomic DNA using forward primer "CyAcpH F1" and reverse primer "CyAcpH R1" with Phusion polymerase (New England Biolabs, City, State). *Shewanella oneidensis* MR-1 AcpH (SoAcpH) PCR product was generated from genomic DNA using forward primer "SoAcpH F1" and reverse primer "SoAcpH R1" with Phusion polymerase. *Pseudomonas fluorescens* NCIMB 10586 AcpH (PfAcpH) primers were designed using the AcpH homolog sequence from *Pseudomonas fluorescens* SBW25, as it is the closest strain phylogenetically. PCR product was first generated from genomic DNA using forward primer "PfAcpH F1" and reverse primer "PfAcpH R1" using Phusion polymerase, generating low amounts of ~600 bp and ~1000 bp products. Both ~600 bp and ~1000 bp products were submitted for sequencing using "PfAcpH F1" and "PfAcpH R1" and the 1000 bp product contained a gene coding for a homologous AcpH. Reverse primer "PfAcpH R2" containing the stop codon and "PfAcpH R3" without the stop codon were designed from the derived PCR product sequence and used with forward primer "PfAcpH F1 to generate a new ~600 bp band using nested PCR with Pfu polymerase, as Phusion did not generate product with the new primers. All final PCR products and template plasmid pET29b (Novagen, city, state) were treated with NdeI and XhoI restriction endonucleases (New England Biolabs, City, State), gel-purified, ligated, transformed into *E. coli* DH5a, and sequenced for confirmation.

AcpH Holo-ACP Kinetics Sample Preparation.

*E. coli* holo-ACP was diluted into 50 mM TrisCl pH 8.0, 250 mM NaCl, 10% glycerol, 30 mM MgCl2 and 2 mM MnCl2 buffer to a concentration of 800 µM. Serial dilution of holo-ACP resulted in a final concentration range of 800-25 µM. AcpH was diluted from MOPS lysis buffer into 50 mM TrisCl pH 8.0, 250 mM NaCl, 10% glycerol and added to an equal volume of the holo-ACP serial dilution to initiate the reaction. Reaction tubes were transferred to a pre-warmed rack at 37° C. and shaken for the duration of the experiment. Time points were collected at 10 minutes for Cy and PfAcpH and 60 minutes for SoAcpH by addition of reaction contents to 100 mM EDTA (pH 8.0). All samples were frozen at -80° C. until evaluated by HPLC.

Verification of EDTA Quench with PfAcpH and CyAcpH.

PfAcpH and CyAcpH were prepared in the same buffer conditions as the HPLC assay format in a 20 µL reaction volume, with the following alterations. Holo-*E. coli* AcpP was utilized at a final concentration of 150 µM. Each AcpH was prepared in four different manners: with no $Mg^{2+}/Mn^{2+}$, no $Mg^{2+}/Mn^{2+}$ EDTA pre-quench, $Mg^{2+}/Mn^{2+}$, and $Mg^{2+}/Mn^{2+}$+EDTA pre-quench. EDTA quench involved an equal volume addition of 100 mM EDTA pH 7.5. Samples were incubated 10 minutes at 37° C. and then quenched with EDTA if not already pre-quenched. Samples were then incubated overnight at room temperature to simulate the conditions experienced by HPLC samples while awaiting injection. One fourth volume of 5× Native-PAGE loading dye was added to samples, and 10 µL of that mixture was run on 20% Urea-PAGE for analysis.

HPLC Detection Method.

Kinetics samples were mixed briefly with finger flicking, and centrifuged at 13000 rpm for 10 minutes at room temperature prior to transferring contents into HPLC vials. 20 µL of each reaction time point was injected on an Agilent 1100 series HPLC with column (Burdick & Jackson OD5 #9575, 25 cm×4.6 mm ID) using an acetonitrile/water gradient. Both water and acetonitrile contained 0.05% TFA. Method gradient for each injection: 0-5 min with 10% acetonitrile, 5-30 min with 10-100% acetonitrile, 30-35 min with 100% acetonitrile, 35-37 min with 100-10% acetonitrile, 37-40 min with 10% acetonitrile. HPLC-grade solvents (J. T. Baker, Phillipsburg, N.J.) were used exclusively. Apo- & holo-ACP protein standards were used to validate the retention times identified using 210 nm UV light at approximately 21 and 19 minutes, respectively. Peak integration was performed for all samples, and substrate turnover was calculated from the ratio of apo- to holo-ACP present in the HPLC trace and the known concentration of total ACP in reaction samples. Calculated rates for AcpH versus substrate concentration were obtained through Excel data analysis and graphed in Prism GraphPad using the "Michaelis-Menten" function for enzyme kinetics, with a zero data point added for substrate concentration of 0 µM*min-1 and 0 µM substrate for AcpH graphs.

Circular Dichroism Analysis of Select AcpH Homologs.

CyAcpH and SoAcpH protein preparations in Tris lysis buffer were desalted with PD-10 desalting columns (GE Healthcare, city, state) into 0.2 µm filtered 50 mM $K_2HPO_4$ pH 8.0, and subsequently diluted to 0.2 mg/mL. Samples were kept on ice until transfer to 2 mm width quartz cuvette for analysis at 25° C. Scans were acquired in 0.5 nm increments averaged over 5 seconds from 260 nm to 200 nm. Sample data was subjected to smooth and raw ellipticity was used in conjunction with specific protein residue number and molecular weight to calculate molar ellipticity using established procedures.

References for Example 1

1. Bertozzi, J. A. P. C. R. Chemistry in living systems. Nature chemical biology 1, 13-21 (2005).
2. Sarah J. Luchansky, S. A., Bradley K. Hayes, and Carolyn R. Bertozzi Metabolic Functionalization of Recombinant Glycoproteins. Biochemistry 43, 12358-12366 (2004).
3. Batra, G. et al. Expression, purification and characterization of in vivo biotinylated dengue virus envelope domain III based tetravalent antigen. Protein expression and purification 74, 99-105 (2010).

4. Stachler, M. D., Chen, I., Ting, A. Y. & Bartlett, J. S. Site-specific modification of AAV vector particles with biophysical probes and targeting ligands using biotin ligase. Molecular therapy: the journal of the American Society of Gene Therapy 16, 1467-1473 (2008).
5. Dereeper, A. et al. Phylogeny.fr: robust phylogenetic analysis for the non-specialist. Nucleic acids research 36, W465-469 (2008).
6. Kosa, N. M., Haushalter, R. W., Smith, A. R. & Burkart, M. D. Reversible labeling of native and fusion-protein motifs. Nature methods 9, 981-984 (2012).
7. Williamson, D. J., Fascione, M. A., Webb, M. E. & Turnbull, W. B. Efficient N-terminal labeling of proteins by use of sortase. Angewandte Chemie 51, 9377-9380 (2012).
8. Rashidian, M., Song, J. M., Pricer, R. E. & Distefano, M. D. Chemoenzymatic reversible immobilization and labeling of proteins without prior purification. Journal of the American Chemical Society 134, 8455-8467 (2012).
9. Jae-Hun Lee, C. S., Do-Hyun Kim, Il-Hyang Park, Sun-Gu Lee, & Yoon-Sik Lee, a.B.-G.K. Glutamine (Q)-Peptide Screening for Transglutaminase Reaction Using mRNA Display. Biotechnology and Bioengineering 110, 353-362 (2012).
10. Takahara, M., Hayashi, K., Goto, M. & Kamiya, N. Tailing DNA aptamers with a functional protein by two-step enzymatic reaction. Journal of bioscience and bioengineering (2013).
11. Yin, J. et al. Genetically encoded short peptide tag for versatile protein labeling by Sfp phosphopantetheinyl transferase. Proceedings of the National Academy of Sciences of the United States of America 102, 15815-15820 (2005).
12. Yin, J., Lin, A. J., Golan, D. E. & Walsh, C. T. Site-specific protein labeling by Sfp phosphopantetheinyl transferase. Nature Protocols 1, 280-285 (2006).
13. Thomas, J. & Cronan, J. E. The enigmatic acyl carrier protein phosphodiesterase of *Escherichia coli*: genetic and enzymological characterization. The Journal of biological chemistry 280, 34675-34683 (2005).
14. Larrabee, P.R.V.a.A.R. Acyl carrier protein. The Journal of biological chemistry 242, 1776-1781 (1967).
15. Luis E. N. Quadri, P. H. W., Ming Lei, Michiko M. Nakano, Peter Zuber, and Christopher T. Walsh Characterization of Sfp, a *Bacillus subtilis* Phosphopantetheinyl Transferase for Peptidyl Carrier Protein Domains in Peptide Synthetases. Biochemistry 37, 1585-1595 (1998).
16. Worthington, A. S. & Burkart, M. D. One-pot chemoenzymatic synthesis of reporter-modified proteins. Organic & biomolecular chemistry 4, 44-46 (2006).
17. Murugan, E., Kong, R., Sun, H., Rao, F. & Liang, Z. X. Expression, purification and characterization of the acyl carrier protein phosphodiesterase from *Pseudomonas Aeruginosa*. Protein expression and purification 71, 132-138 (2010).
18. Jacob Thomas, D. J. R., and John E. Cronan Acyl Carrier Protein Phosphodiesterase (AcpH) of *Escherichia coli* is a Non-Canonical Member of the HD Phosphatase/Phosphodiesterase Family. Biochemistry 46, 129-136 (2007).
19. Kristine M. Clarke, A. C. M., James J. La Clair, and Michael D. Burkart In Vivo Reporter Labeling of Proteins via Metabolic Delivery of Coenzyme A Analogues. JACS Communications 127, 11234-11235 (2005).
20. Sean T. Prigge, X. H., Lucia Gerena, Norman C. Waters, and Kevin A. Reynolds The Initiating Steps of a Type II Fatty Acid Synthase in *Plasmodium falciparum* are Catalyzed by pfACP, pfMCAT, and pfKASIII. Biochemistry 42, 1160-1169 (2003).
21. Haushalter, R. W. et al. Binding and "pKa" modulation of a polycyclic substrate analogue in a type II polyketide acyl carrier protein. ACS chemical biology 6, 413-418 (2011).
22. Crawford, J. M. et al. Structural basis for biosynthetic programming of fungal aromatic polyketide cyclization. Nature 461, 1139-1143 (2009).
23. Pia Linnemannstons, J. S., Maria del Mar Prado, Robert H. Proctor, Javier Avalos, and Bettina Tudzynski The polyketide synthase gene pks4 from *Gibberella fujikuroi* encodes a key enzyme in the biosynthesis of the red pigment bikaverin. Fungal genetics and biology: FG & B 37, 134-148 (2002).
24. Edwards, D. J. et al. Structure and biosynthesis of the jamaicamides, new mixed polyketide-peptide neurotoxins from the marine *cyanobacterium* Lyngbya majuscula. Chemistry & biology 11, 817-833 (2004).
25. Fortin, P. D., Walsh, C. T. & Magarvey, N. A. A transglutaminase homologue as a condensation catalyst in antibiotic assembly lines. Nature 448, 824-827 (2007).
26. C. Gary Marshall, M. D. B., Robin K. Meray, and Christopher T. Walsh Carrier Protein Recognition in Siderophore-Producing Nonribosomal Peptide Synthetases. 8429-8437 (2002).
27. Matthews, M. L. et al. Substrate-triggered formation and remarkable stability of the C—H bond-cleaving chloroferryl intermediate in the aliphatic halogenase, SyrB2. Biochemistry 48, 4331-4343 (2009).
28. Hidehiko Hirakawa, S. I., and Teruyuki Nagamune Design of Ca2R-Independent *Staphylococcus aureus* Sortase A Mutants. Biotechnology and Bioengineering 109, 2955-2961 (2012).
29. Foley, T. L. & Burkart, M. D. A homogeneous resonance energy transfer assay for phosphopantetheinyl transferase. Analytical biochemistry 394, 39-47 (2009).
30. Katarzyna A. Mosiewicz, K. J., and Matthias P. Lutolf Phosphopantetheinyl Transferase-Catalyzed Formation of Bioactive Hydrogels for Tissue Engineering. JACS Communications 132, 5972-5974 (2010).
31. Nathalie George, H. P., Horst Vogel, Nils Johnsson, and Kai Johnsson Specific Labeling of Cell Surface Proteins with Chemically Diverse Compounds. JACS Communications 126, 8896-8897 (2004).
32. Quadri, L. E. N. Characterization of Sfp, a *Bacillus subtilis* phosphopantetheinyl transferase for peptidyl carrier protein domains in peptide synthetases. Biochemistry 37, 1585-1595 (1998).
33. Foley, T. L. et al. Preparation of FRET reporters to support chemical probe development. Organic & biomolecular chemistry 8, 4601-4606 (2010).
34. ExPASy ProtParam Tool.

2. Example 2

The reversible covalent attachment of chemical probes to proteins has long been sought as a means to visualize and manipulate proteins. Here we demonstrate the full reversibility of post-translational custom pantetheine modification of *E. coli* acyl carrier protein (ACP) for visualization and functional studies. We utilize this iterative enzymatic methodology in vitro for reversible labeling variants and apply these tools to Nuclear Magnetic Resonance (NMR) structural studies of protein-substrate interactions.

Post-translational protein modification is important for adding functions to proteins that can be exploited for therapeutics[1], protein engineering,[2] affinity design[3,4], and enzyme immobilization[5], among other applications[6]. Acyl carrier protein (ACP) labeling with 4'-phosphopantetheine (PPT), conjugated to a tag of choice by its transferase (PPTase) represents one of the most flexible covalent protein labeling methods, as illustrated by the application of ACP tagged peptides', for bio-gel formation[8], and ACP-dependent protein immobilization[9]. Labeling ACP and ACP fusion proteins with PPT analogs is also successfully leveraged for visualization[10,11], isolation[12], functional[13], and structural[14,15] studies of carrier protein-dependent biosynthetic enzymes[16]. Yet further advancement of these tools is hampered by an inability to easily reverse PPT attachment. Indeed, naturally occurring ACPs, often isolated in holo-form (including a native PPT modification), cannot be further modified directly with another PPT tag. To overcome these difficulties, an AcpH (acyl carrier protein hydrolase), a phosphodiesterase from *Pseudomonas aeruginosa*[17] and Sfp, a PPTase from *Bacillus subtilis*[18] was used to swap different PPT-conjugated small molecules on free ACP and ACP fusion proteins. This reversible tagging system offers the ability to connect synthetic and biological chemistry with ease and provides uniformly labeled, high quality ACP and ACP fusion proteins, as demonstrated here through fluorescent labeling and solution-phase protein NMR.

For evaluation of iterative labeling, fluorescent ACP labeling directly in cellular lysate from *E. coli* strain DK554, which overexpresses native fatty acid ACP (AcpP) in predominantly apo-form was performed[19]. Treatment of this lysate with coumarin-CoA[20] and Sfp generated a blue-fluorescent band upon excitation of sodium-dodecyl sulfate polyacrylamide gel electrophoresis (SDS-PAGE) samples at 254 nm that co-migrated with a coumarin-labeled ACP standard. Subsequent treatment of coumarin-labeled lysate with recombinant AcpH uniformly removed the coumarin-PPT from ACP, as demonstrated by disappearance of the blue band. Subsequent treatment of the sample with Sfp and rhodamine-CoA[21] generated a new red-fluorescent SDS-PAGE band upon excitation at 532 nm; this label can also be removed with AcpH.

After demonstrating the compatibility of AcpH in removing various PPT analogs, the flexibility of our technique was demonstrated by evaluating interaction with ACP fusion proteins. AcpH removed rhodamine-PPT from ACP attached to three different fusion partners, an N-terminal maltose binding protein (MBP), a C-terminal green fluorescent protein (GFP) and an N-terminal bacterial luciferase fusion (Lux-ACP). The luciferase-ACP fusion's activity did not change notably following label manipulation. Additionally labeling of the ACP-GFP fusion with rhodamine-CoA was found to generate an observable Förster resonance energy transfer (FRET) signal, lending itself to observing AcpH or PPTase activity in a simple and scalable assay format.

Recent studies of fatty acid and polyketide pathways focus on the extent and function of substrate sequestration by ACP, where the growing acyl chain is covalently attached via a thioester linkage to the terminus of post-translationally added 4'-phosphopantetheine[22]. Biosynthetic intermediates with varied chemical structures participate in intermolecular interactions with ACP that modulate substrate dynamics and ACP structure[9,15]. The nature of these ACP-substrate interactions depends on the chemical structure of the biosynthetic intermediate and can vary with respect to chain length and oxidation state[23]. Furthermore, observations of this phenomenon appear to vary depending on the analytical method used. X-ray crystallography of hexanoyl-, heptanoyl-, and decanoyl-ACPs from *E. coli* fatty acid biosynthesis all show the acyl chain clearly buried in ACP, while two crystal forms of butanoyl-ACP have the acyl chain in different positions both inside and outside of the protein[24,25]. NMR studies have shown that short-chain polyketide analogs protrude into solution when appended to *S. coelicolor* actinorhodin ACP (actACP), while saturated acyl chains of 4-8 carbons associate more closely with this polyketide ACP[15]. Variations in substrate dynamics must clearly play a role in the catalytic processivity of these synthases, and we hypothesize that the dynamics of substrate binding serves a critical function in substrate specificity.

In order to evaluate substrate dynamics with respect to substrate identity, it is necessary to perform multiple studies on the same protein with varying acyl substrates covalently attached. Given the labor and expense of preparing uniformly labeled, isotope-enriched proteins for nuclear magnetic resonance (NMR) structural studies, the use of AcpH was investigated as a means to recycle $^{15}N$ enriched ACP. A single sample of $^{15}N$ enriched *E. coli* ACP was labeled with several acyl pantetheine analogs and characterized the dynamics of the appended acyl-ACP-$^{15}N$ species by NMR spectroscopy. By incorporating fatty-acyl pantetheines with $^{13}C$ labels within the alkyl chain, we directly observed intramolecular interactions with the pendant acyl chain using NOE measurements.

ACP-$^{15}N$ was evaluated at each labeling conformation via gel and NMR analysis. An initial apo and holo mixture was obtained following *E. coli* expression, requiring full conversion to the apo-form using AcpH. Subsequent conversion to octanoyl-ACP-$^{15}N$ utilized the chemo-enzymatic synthesis of octanoyl-CoA[14] with Sfp labeling. After NMR evaluation, the ACP-$^{15}N$ was converted back to the apo-form with AcpH for subsequent relabeling. $^{15}N$—$^{1}H$ heteronuclear single quantum coherence (HSQC) spectra was acquired of all three ACP-$^{15}N$ species (apo-, octanoyl-, and regenerated apo). Comparing apo-ACP-$^{15}N$ to the octanoyl-ACP-$^{15}N$, chemical shift perturbations characteristic of acyl chain sequestration in the hydrophobic binding pocket were observed[26]. Conversion from this acylated form back to the apo-form by AcpH provided uniformly unlabeled apo-ACP-$^{15}N$, as confirmed by an HSQC spectrum of the regenerated protein that identically matched that of the original. This validated the feasibility of reversible ACP labeling, as it demonstrated that the regenerated apo-ACP-$^{15}N$ is properly folded and ready for subsequent modification.

This regenerated apo-ACP-$^{15}N$ was labeled with butanoyl-$^{13}C_4$-CoA that contained $^{13}C$ labels from carbons one through four. Butanoyl-$^{13}C_4$-ACP-$^{15}N$ demonstrated weaker HSQC chemical shift perturbations compared to octanoyl-ACP-$^{15}N$. Further sample treatment involved one last conversion to the apo-form by AcpH, followed by labeling with octanoyl-8-$^{13}C_1$-CoA containing a single $^{13}C$ label at carbon eight. $^{13}C$-selective nuclear overhauser effect (NOE) experiments were performed, in which NMR signals for other protons within 5 angstroms from the $^{13}C$ label, were observed on the butanoyl-$^{13}C_4$-ACP-$^{15}N$ and octanoyl-8-$^{13}C_1$-ACP-$^{15}N$ as a means to gain structural information about substrate-protein interactions. In collecting $^{13}C$-edited NOE spectra of the $^{13}C$-labeled acyl pantetheines, no NOE signal for butanoyl-$^{13}C_4$-ACP-$^{15}N$ was observed, whereas octanoyl-8-$^{13}C_1$-ACP produced a notable signal. This result was likely produced from spatial proximity of an aliphatic proton in an ACP-$^{15}N$ sidechain and the $^{13}CH_3$ group in the octanoyl-$^{13}C_1$-acyl chain, indicating that the longer acyl chain is immobilized in the protein binding pocket. This finding indicates a lack of dynamic mobility and sequestration of the acyl chain on the NMR time scale. Conversely, the negative result from butanoyl-$^{13}C_4$-ACP-$^{15}N$ indicates that the shorter acyl chain is notably more dynamic in solution. The X-ray crystal structure indicates two states for a tethered butanoyl substrate, one sequestered and one outside the protein[24]. NMR-based finding highlights the differences between solution and crystalline structures, in which the behavior of substrate-tethered ACPs varies substantially in different physical states. We conclude that analysis of ACP-substrate dynamics must necessarily be performed in solution state.

In addition to observing the dynamics of tethered acyl substrates, these NMR studies provide a quantitative evaluation for protein quality after repeated labeling and unlabeling steps. This demonstration offered an ideal testing ground for the reversible labeling method, as we used only one isotope-enriched protein sample for the entire experiment. Any protein degradation or incomplete reactivity would severely compromise the quality of resulting NMR spectra. To provide quality control, HSQC spectra of purified ACP-$^{15}N$ were acquired at each discrete step throughout the process and compared to the original apo-ACP-$^{15}N$ sample, which revealed predominant protein integrity retention throughout the experiment. Through tracking the ultraviolet absorbance of ACP-$^{15}N$ throughout all conversions (Table 5), a final recovery of 27% protein was observed after 5 discrete enzymatic reaction steps. The reaction efficiency for all presented reactions was further evaluated, demonstrating that two-step yields above 60% are feasible for most ACP constructs.

TABLE 5

Recovery of [$^{15}N$]ACP from NMR experiments
Purified [$^{15}N$]ACP Sample Recovery

|  | apo #1 | octanoyl | apo #2 | [$^{13}C_4$] butanoyl | [8-$^{13}C_1$] octanoyl |
|---|---|---|---|---|---|
| Calculated Mass, A280 (mg) | 4.6 | 2.7 | 2.0 | 1.6 | 1.2 |
| Step Yield (%) | — | 59% | 74% | 80% | 75%† |

UV absorbance measurements were conducted on the [$^{15}N$]ACP sample conducted at several discrete steps to track protein quantity. While sample recovery is not complete at each step, this method is well suited to apo-[$^{15}N$]ACP regeneration with slight modifications enhancing protein retention.
†Note: Two-step yield is calculated for [8-$^{13}C_1$]octanoyl-[$^{15}N$]ACP, as the concentration was not determined for the intermediate apo-[$^{15}N$]ACP.

This work suggests that AcpH is capable of removing a broad variety of covalently-tethered labels beyond those studied here, in addition to accommodating N and C-terminal ACP fusion partners with ease. Given the multitude of existing opportunities for ACP labeling, particularly in work involving fusion protein applications and natural product biosynthetic studies, providing a reversible methodology will provide markedly improved flexibility for rapid modification of protein species. Additionally, the cost-saving measure of recovering valuable apo-ACP substrates cannot be overlooked. Due to the wide pantetheine substrate acceptance demonstrated by a combined Sfp and AcpH methodology, various fluorescent and functional tags can be exchanged on a single protein with robustness not offered by previous enzymatic methods.

Determination of Protein Concentration, Protein Gels, Miscellaneous.

ACP concentrations were determined by UV absorbance measurements at 280 nm unless otherwise noted. Extinction coefficients were calculated using Expasy "ProtParam" tool: E. coli free ACP=1490 M$^{-1}$ cm$^{-1}$, GFP-ACP=69000 M$^{-1}$ cm$^{-1}$, MBP-PaACP=66000 M$^{-1}$ cm$^{-1}$, Lux-ACP=85720 M$^{-1}$ cm$^{-1}$. Non-ACP protein concentrations and fusion-ACPs used in the efficiency analysis were determined using the Bradford method against a BSA standard. ACP was run on 20% 2M Urea-PAGE to resolve apo/holo/crypto conversions, and 12% SDS-PAGE to evaluate overall purity during NMR workup. ACP fusions MBP-PaACP and GFP-ACP samples were run on 15% acrylamide 2 M Urea-PAGE for fluorescent imaging experiments. Electrophoresis of fluorescent coumarin and rhodamine non-fusion E. coli ACP modifications utilized 10% Tris-Tricine SDS-PAGE.

Gel Imaging.

Coomassie stained gels were imaged on a Fluor-S MultiImager (Bio-Rad) using visible light exposure. Coomassie gel images were acquired as ".tiff" and excess white was discarded using the "Auto Levels" feature of Photoshop (Adobe). UV acquisition was also performed on the Fluor-S MultiImager, with short/long wave UV and a 520LP filter, excess black was discarded using the "Auto Levels" feature of Photoshop (Adobe). GFP-fluorescent imaging performed prior to gel fixing was performed on a UVP BioSpectrum (UVP LLC) system with SYBR Green 515 nm-570 nm emission filter, exciting with trans-illumination from a UVP BioLite with 420BP40 filter. GFP-fluorescent images were collected as ".tiff" and had gray input levels adjusted using Photoshop (Adobe) from "0,1.00,255" to "0,1.00,150" to discard excess black. Rhodamine-labeled protein gels were imaged on a Typhoon (GE Healthcare) gel scanner at 50 μm resolution with a photomultiplier tube (PMT) setting of 450, using 532 nm (green laser) excitation, and 580BP30 emission filter. Typhoon gel images were collected as ".gel" files, converted to ".tiff" in ImageJ (NIH), exported to Photoshop (Adobe) and had gray input levels adjusted from "0,1.00, 255" to "80,1.00,255" to discard excess whites collected from the ".gel" file. All gels, with the exception of GFP-ACP containing gels, were fixed with 10% acetic acid, 40% methanol, and 50% water for 1 hour, then rinsed 3 times with water for prior to UV fluorescent imaging and subsequent staining GFP-ACP images were acquired prior to gel fixing, after which they were fixed and imaged as other gels.

Production of AcpH and Recombinant ACP Constructs. Cloning methods and primers are contained in Supplementary Information (Table 6). For expression of E. coli ACP-$^{15}N$, E. coli BL21 (DE3) cells containing plasmid pET22b encoding C-terminal 6xHis tagged E. coli ACP was cultured in 1 L M9 minimal media supplemented with 1 g/L of N$^{15}$ enriched ammonium chloride and 100 mg/L ampicillin. Culture was grown to OD$_{600}$=0.6, induced with 1 mM IPTG and incubated 4 hours at 37° C. E. coli BL-21(DE3) cells containing the MBP-AcpH plasmid were grown in 1 L LB, 0.2% D-glucose and 50 μg/mL kanamycin sulfate at 37° C. to OD=0.6, induced with 1 mM of isopropyl β-D-1-thiogalactopyranoside (IPTG), and grown at 16° C. overnight. Media was centrifuged 30 minutes at 2000 rpm to pellet cells. Cell pellets were stored at −20° C. overnight. AcpH-6xHis construct was grown similarly without glucose. Cells were thawed on ice and suspended in lysis buffer (50 mM TrisCl pH 8, 500 mM NaCl, 10% glycerol) with additional ingredients 0.1 mg/mL lysozyme, 0.1 mM DTT, 5 μg/mL DNase I, 5 μg/mL RNAse A and passed twice through a French pressure device at 1000 psi. Lysate was centrifuged 45 minutes at 10,000 rpm, and supernatant was incubated with amylose resin (New England Biolabs) for MBP-AcpH or Ni-NTA (Novagen) for AcpH-6xHis according to manufacturer protocols. Eluted MBP-AcpH was then concentrated to 10 mg/mL and MBP-AcpH was FPLC-purified with 50 mM TrisCl, 250 mM TrisCl, pH 8.0 buffer to remove contaminating native E. coli MBP. MBP-AcpH was concentrated with 10 kDa Amicon spin filter (Millipore Corp) stored in 40% glycerol at −80° C. after flash freezing aliquots in liquid nitrogen. 6×His-AcpH was lysed in a similar manner, but purified with Ni-NTA resin (Novagen). Ni-NTA resin with bound protein was washed with 10 mM imidazole and eluted with 300 mM imidazole in lysis buffer. 6×His-AcpH was desalted to remove imidazole, and flash frozen at −80° C. at 1 mg/mL without further modification. MBP-PaACP and Lux-ACP were expressed in E. coli BL-21 (DE3) in LB with 50 µg/mL kanamycin. GFP-ACP (6×His-tagged in pCA24N vector)[27] was expressed in K-12 strain AG1 (ASKA library) cells, in LB with 20 µg/mL chloramphenicol. Cells containing fusion ACPs were grown, induced, and purified in an otherwise identical manner to 6×His-tagged AcpH. MBP- and GFP-fusion ACP 300 mM imidazole elutions were dialyzed into AcpH reaction buffer without $Mg^{2+}$ and $Mn^{2+}$ cofactors overnight. Lux-ACP was buffer exchanged using a PD-10 desalting column (GE Healthcare) into AcpH reaction buffer, flash frozen, and stored overnight at −80° C. Lux-ACP was thawed on ice and AcpH was added to 5 µM, and the reaction incubated at 37° C. for 4 hours. Dialyzed ACP fusions next had appropriate amounts of 1M $MgCl_2$ and $MnCl_2$ added to achieve 15 mM and 1 mM final concentrations, respectively. Free AcpH was added to free ACP and MBP/GFP fusion ACPs at 5 µM final concentration, and the mixture was incubated overnight at 37° C. in a rotary wheel. Lux-ACP was reacted for 4 hours at 37° C. ACP reactions were centrifuged to remove any precipitate, and purified by anion exchange chromatography. Purity evaluation was conducted on MBP-PaACP and GFP-ACP, as well as Lux-ACP with SDS-PAGE.

TABLE 6

Primers used for ACP/AcpH cloning

| Primer Name | Primer Sequence (5' → 3') |
|---|---|
| AcpH F1 | AAAAAACATATGAACTACCTCGC (SEQ ID NO: 59) |
| AcpH R1 | AAAAAACTCGAGTCAGCGCTGGCTCAG (SEQ ID NO: 60) |
| AcpH F2 | AAAAAACATATGAACTATCTGGCACACC (SEQ ID NO: 61) |
| AcpH R2 | AAAAAACTCGAGTTAGCGCTGAGACAG (SEQ ID NO: 62) |
| AcpH F3 | GTCTCAGCGCGGACTCGAGCACCACCACCACC (SEQ ID NO: 63) |
| AcpH R3 | GTGCTCGAGTCCGCGCTGAGACAGGGCAAATGC (SEQ ID NO: 64) |
| PaACP F1 | AAAAAACATATGAGCACCATCG (SEQ ID NO: 65) |
| PaACP R1 | AAAAAACTCGAGTTGCTGGTGAG (SEQ ID NO: 66) |
| EcACP F1 | AAAAGGATCCAGCACTATCGAAGAACGCGTTAAG (SEQ ID NO: 67) |
| EcACP R1 | AAAACTCGAGCGCCTGGTGGCCGTTGATGTAATC (SEQ ID NO: 68) |
| LuxCt F1 | AAAACATATGAAATTTGGTAACTTCCTTTTAACTTATC (SEQ ID NO: 69) |
| LuxCt R1 | AAAAGGATCCTGAATGATATTTAACAATGTTAGCATTTACTAC (SEQ ID NO: 70) |

TABLE 6-continued

Primers used for ACP/AcpH cloning

| Primer Name | Primer Sequence (5' → 3') |
|---|---|
| LuxCt 695bp | CAGTTGATCACGATTCAAACAAAGC (SEQ ID NO: 71) |
| LuxCt 1390bp | CTTGATCAAATGAGTGAAGGTCG (SEQ ID NO: 72) |

Primers used in cloning/subcloning for gene products used in this manuscript.
Intentionally placed restriction sites are underlined.

Preparation of Coumarin-ACP Standard.

DK554 cells were grown, induced, and prepared to generate predominantly apo-ACP. Isopropanol supernatant containing ACP was applied to DEAE resin, and eluted with a sodium chloride gradient. ACP was then labeled using 6×His-Sfp and coumarin-CoA. Sfp was removed with Ni-NTA resin, and excess coumarin-CoA was removed with size exclusion chromatography on G25 sephadex resin.

Preparation of E. coli DK554 Lysate.

50 mL LB media supplemented with 25 µM calcium D-pantothenate, 50 mM D-glucose, and 50 µg/mL kanamycin utilized previously. Media was inoculated with 1 mL of overnight DK554 starter culture and grown to OD=0.4. IPTG was added at a concentration of 1 mM to the media and was shaken for 5 hours at 37° C. Media was centrifuged at 4000 rpm at 4° C. for 30 minutes to pellet cells. Cell pellets were resuspended in 25 mM TrisCl pH 7.5, 250 mM NaCl, 0.1 mg/mL lysozyme, 10 µM pepstatin, 10 µM leupeptin and passed twice through a French pressure device at 1000 psi. Removal of coumarin-pantetheine from ACP in 5 mL lysate used 10 µM MBP-AcpH fusion in 600 mL AcpH reaction buffer (50 mM TrisCl, pH 8.0, 100 mM NaCl, 10% glycerol, 15 mM $MgCl_2$, 1 mM $MnCl_2$) within a 3 kDa MWCO dialysis bag at 37° C. overnight.

Fluorescent Labeling of E. coli DK554 Lysate with Modified Coenzyme A.

E. coli DK554 cell lysate with total protein concentration of approximately 2 mg/mL was added to the volume of premade 10×PPTase reaction buffer (500 mM Na-HEPES, 100 mM $MgCl_2$, pH 7.4) that brought the total reaction concentration to 50 mM Na-HEPES pH 7.4, 10 mM $MgCl_2$, 5 µM of coumarin-CoA, and 2 µM Sfp. Samples were incubated at 37° C. for 1 hour, followed by centrifugation to remove precipitate, supernatant passage over an equilibrated G50 Sephadex (GE Healthcare) desalting column, and dialysis of the lysate into 50 mM TrisCl pH 8.0, 100 mM NaCl, 10% glycerol to further remove unreacted CoA analog.

AcpH Treatment of Coumarin-ACP in Lysate.

Coumarin-labeled DK554 cell lysate supernatant was added to a freshly-prepared 10× AcpH reaction buffer to generate the following reaction concentrations: 50 mM TrisCl pH 8, 150 mM NaCl, 15 mM $MgCl_2$, 1 mM $MnCl_2$. MBP-AcpH was added to 2 µM. Reaction contents were placed in a 3.5 kD MWCO dialysis membrane and dialyzed against 50-fold volume of reaction buffer stirred overnight at 37° C. No remaining coumarin-ACP fluorescence was observed, and a significant amount of MBP-AcpH appeared as precipitate afterwards, as determined by SDS-PAGE analysis (not shown). Post-reaction contents were centrifuged 30 minutes at 4000 rpm at 6° C. Supernatant was dialyzed back into 50 mM TrisCl pH 7.5, 250 mM NaCl in preparation for rhodamine-labeling.

Sfp & AcpH Treatment of Purified Rhodamine-ACP.

The demonstrated activity of AcpH on rhodamine-ACP was performed with previously purified 6×His-tagged apo-ACP. 7 nmol of apo-ACP was treated with 5 µM native Sfp and 24 nmol of rhodamine-CoA in 50 mM TrisCl pH 8, 100 mM NaCl, 10 mM $MgCl_2$ at 37° C. for 1 hour. Rhodamine-ACP was re-purified with Ni-NTA resin to remove excess rhodamine-CoA and Sfp, and dialyzed to remove imidazole. Dialyzed rhodamine-ACP was then incubated with and without 7 µM AcpH at 37° C. for 2 hours, and the resulting crude reactions were run on SDS-PAGE and imaged to illustrate fluorescent label removal with AcpH.

AcpH Treatment of ACP-$^{15}$N for NMR Study.

An AcpH reaction was conducted to generate each apo-$^{15}$N-ACP sample prior to labeling and/or analysis. Following NMR acquisition of each sample, ACP was dialyzed into AcpH reaction buffer without cofactors (50 mM TrisCl pH 8.0, 100 mM NaCl). Glycerol was found to be unnecessary for desired AcpH activity and was omitted. Following dialysis, $MgCl_2$ and $MnCl_2$ were added to achieve a final concentration of 15 mM and 1 mM, respectively. Free 6×His AcpH was added to a concentration of 5-10 µM, and the mixture was incubated at 37° C. for 8 hours. Reaction completion was determined by Urea-PAGE analysis. The completed reactions were centrifuged 30 minutes at 4,000 rpm at 6° C. to remove precipitate.

Labeling of ACP-$^{15}$N Using "One-Pot" Sfp Methodology.

Apo-ACP-$^{15}$N was mixed with CoA-A, D, & E, ATP disodium salt, native Sfp, and octanoyl-pantethenamide in a one-pot chemoenzymatic reaction[27] to selectively generate octanoyl-ACP-$^{15}$N in vitro. Additional generation of butanoyl-$^{13}C_4$-ACP-$^{15}$N and octanoyl-8-$^{13}C_1$-ACP-$^{15}$N analogs was conducted with the same methodology, except using regenerated apo-ACP-$^{15}$N with butanoyl-$^{13}$C-oxypantetheine and oxtanoyl-8-$^{13}C_1$-oxypantetheine. Ni-NTA resin was used to re-purify the ACP-$^{15}$N after each labeling reaction. Apo/holo/crypto ACP-$^{15}$N monitoring was conducted with separation on conformationally sensitive Urea-PAGE.

ACP Anion Exchange Purification.

All preparative ACP samples were dialyzed into low salt buffer. *E. coli* ACP and MBP-PaACP ion exchange running buffer was 25 mM L-Histidine pH 6.0. GFP-ACP and Lux-ACP ion exchange buffer was 25 mM bis-Tris, pH 6.0. Supernatants were then applied to a DEAE HiTrap (GE Healthcare) 1 mL or 5 mL column. Free ACP, MBP-ACP, and GFP-ACP were loaded onto columns and washed with 10 mL of 25 mM buffer and 25 mM NaCl and eluted with 5 mL of 25 mM buffer and 500 mM NaCl. LuxACP was loaded onto a 5 mL DEAE HiTrap and washed with a step gradient of 0, 100, 200, 300, and 500 mM NaCl in 25 mM bis-Tris pH 6.0. NMR *E. coli* ACP-$^{15}$N samples were then dialyzed into 100 mM sodium phosphate, 1 mM DTT, pH 7.4, and concentrated to 450 µL prior to NMR acquisition. *E. coli* ACP-$^{15}$N NMR sample purity was evaluated by SDS-PAGE analysis. Following ion exchange, fusion ACPs were dialyzed or desalted, spin concentrated, and stored at −80° C. prior to further use.

Fusion-ACP Rhodamine-CoA Labeling and Label Removal.

Purified apo-MBP-PaACP at 200 µM was labeled with 1 mM rhodamine-CoA and 13 µM native Sfp in a reaction volume of 20 µL for 3 hours at 37° C. Purified apo-GFP-ACP at 150 µM was labeled with 1 mM rhodamine-CoA and 7 µM native Sfp in a reaction volume of 35 µL for 3 hours at 37° C. Purified apo-Lux-ACP at 12 µM was labeled with 50 µM rhodamine-CoA and 3 µM native Sfp for 1 hour at 37° C. Fusion ACPs were then re-purified from excess rhodamine-CoA and native Sfp using Ni-NTA resin, and buffer exchanged and concentrated using 10 kDa MWCO 0.5 mL Amicon spin filters (Millipore). Label removal of MBP-ACP and GFP-ACP proceeded with 4 µL of the concentrated crypto-fusion ACPs with 10 µM AcpH in 10 µL of AcpH reaction buffer for 3 hours at 37° C. 6 µM crypto-Lux-ACP was reacted with 5 µM AcpH for 3 hours at 37° C. AcpH reaction samples were run immediately afterwards on Urea-PAGE (MBP-ACP and GFP-ACP) or SDS-PAGE (Lux-ACP) with no further purification.

Sfp & AcpH Treatment of *E. coli* ACP and Fusion-ACPs for Efficiency Analysis.

Labeling of butanoyl, octanoyl, and coumarin ACP proceeded via Sfp and CoA A-D-E "one-pot methodology". Labeling of free ACP and fusion-ACPs with rhodamine proceeded via Sfp and rhodamine-CoA. Free *E. coli* ACP reactions were conducted overnight at 37° C. MBP-PaACP labeling proceeded via native Sfp; GFP-ACP and luciferase-ACP reactions using Sfp-conjugate proceeded for 6 hours at 37° C. MBP-PaACP was repurified using Ni-NTA and desalted with PD-10 desalting column (GE Healthcare) to remove imidazole. GFP-ACP and luciferase-ACP were separated from solids with a fitted spin column and desalted to remove excess CoA analog. Non-fluorescent *E. coli* ACPs were quantified using UV spectrometry. Label removal proceeded in AcpH reaction buffer with 10% glycerol via reaction with an AcpH-conjugate for *E. coli* ACP at 37° C. overnight, and room temperature overnight for MBP-PaACP and GFP-ACP. Due to precipitation induced by extended incubation, luciferase ACP was reacted with AcpH at 37° C. for 2 hours. Reaction completion was monitored by gel-shifts and/or fluorescence depletion in 20% Urea-PAGE for free ACPs, and 10% SDS-PAGE for the fusion ACPs. Final apo-ACP samples were then desalted into AcpH reaction buffer lacking $Mg^{2+}/Mn^{2+}$ and subsequently quantified.

GFP-ACP: Rhodamine-CoA & Sfp Labeling Monitoring by FRET

Apo-GFP-ACP and rhodamine-CoA were diluted to 100 µM and 200 µM, respectively, in 10 mM TrisCl pH 7.5. 5 µL of this 10× substrate mix was added to 6 wells of a costar 3694 96-well plate (Corning Inc) in triplicate. 10 µL of milliQ water diluent was added to adjust final concentrations. 35 µL of 1.43 µM Sfp in 71.5 mM HEPES pH 7.6, 14.3 mM $MgCl_2$, 1.43 mg/mL BSA (stabilizer) was added to initiate the reaction, with reaction buffer lacking Sfp added to the control. Final 50 µL enzyme reactions contained 10 µM apo-GFP-ACP, 20 µM rhodamine-CoA, 1 µM Sfp, 50 mM HEPES pH 7.6, 10 mM $MgCl_2$. The 96-well plate was centrifuged 2 minutes at 1000 rpm, and fluorescence was monitored at 405 nm excitation and 595 nm emission for 30 minutes at in a Perkin-Elmer HTS 7000 Plus plate reader at room temperature.

Pantetheine Probe Synthesis.

All CoA-related probes are depicted in Supplementary Information. Pantetheine probe synthetic methods and chemical spectra are also contained within Supplementary Information.

Cloning of MBP-AcpH, AcpH-6×his, MBP-PaACP, and Lux-ACP Constructs.

The AcpH gene [PA4353] identified previously[1] was PCR-amplified from *P. aeruginosa* PAO1 genomic DNA using forward primer "AcpH F1" and reverse primer "AcpH R1" (Supplementary Table 2). NdeI/XhoI restriction-digested AcpH insert was then ligated into a pET24b vector modified with an N-terminal MBP fusion tag originally from pMALc2 according to procedure described elsewhere[2] for increased solubility and orthogonal purification purposes. A 'free' 6×His-tagged version was also constructed using an *E. coli*-optimized sequence of PA4353 purchased in a pUC57 vector (GeneWiz Inc, South Plainfield, N.J.). All attempts to sub-clone the gene into vectors providing N-terminal 6×His tags produced insoluble protein (pET28b, pCDF-2, pBAD-HisC). The gene was subcloned into pET29b using NdeI/XhoI primers "AcpH F2" and "AcpH R2", restriction digested, and ligated to generate a native construct (not used in this experiment). The native construct was then subjected to site directed mutagenesis with forward primer "AcpH F3" and reverse primer "AcpH R3" to remove the stop codon to allow translation of the C-terminal 6×His tag. This final construct was transformed into *E. coli* BL-21(DE3) for soluble expression of a free C-terminal 6×His-tagged construct. The ACP gene [PA2966] used to generate MBP-PaACP was PCR-amplified from *P. aeruginosa* PAO1 genomic DNA using forward primer "PaACP F1" and reverse primer "PaACP R1". NdeI/XhoI restriction-digested PaACP was ligated into the same MBP pET24b-based vector as described for AcpH, except the ACP stop codon was omitted to generate a C-terminal 6×His affinity tag. For construction of the luciferase-ACP fusion, *E. coli* ACP was cloned from stock plasmid encoding wild-type ACP using forward primer "EcACP F1" and reverse primer "EcACP R1". *E. coli* ACP PCR product was then restriction digested with BamHI/XhoI and inserted into pET29a. This *E. coli* ACP plasmid was sequenced for verification and subjected to NdeI/BamHI restriction digestion in preparation for luciferase gene insertion. Bacterial luciferase (*V. harveyi* luxAB fusion) was cloned from a synthetic construct termed luxCt[3] using forward primer "LuxCt F1" and reverse primer "LuxCt R1". The luxCt PCR product was restriction digested with NdeI/BamHI and ligated into the pET29 containing *E. coli* ACP. Sequence verification was performed using T7 promoter/terminator primers, as well as internal luxCt primers "LuxCt 695 bp" and "LuxCt 1390 bp".

Luciferase-ACP Activity Assay.

The luciferase assay was conducted under the same parameters as reported previously[3], however with reduced well volume of 200 µL in 96-well plate Costar 3694 (Corning Inc, Lowell, Mass.) from 357.5 µL and substitution of 1 mM dithiothreitol (DTT) for 50 mM β-mercaptoethanol. All luciferase-ACP, including original/regenerated apo and crypto, were buffer exchanged into 50 mM $NaH_2PO_4$ pH 7.0, 400 mM sucrose, 1 mM DTT prior to analysis in the assay. Generation and purification of apo/crypto luciferase-ACP were conducted with the same methods as for other ACPs. The 96-well plate was centrifuged 2 minutes and evaluated on a Perkin-Elmer HTS 7000 Plus plate reader at room temperature with 1 second integration time per well using a gain of 150.

General Coupling Scheme of PMP Oxypantethiene to $^{13}$C-Labeled Fatty Acids (PMP Oxypantethiene [$^{13}C_4$]Butyl Ester, PMP Oxypantethiene Butyl Ester, [8-$^{13}C_1$]Caprylic-Acid, Caprylic Acid).

In a 50 ml round bottom reaction flask DCM was added as to generate a solution which was 0.1M with respect to the Fatty Acids. The solution was cooled to 0° C. and the reagents added in the following order. 1.6 molar equivalents of Dicyclohexylcarbodiimide were added followed by 1.0 molar equivalent of 4-Dimethylaminopyridine and 0.5 molar equivalence of Camphorsulfonic acid. The solution was allowed to stir momentarily before the addition of 1.1 molar equivalent of the PMP Oxypantethiene prepared previously[10]. The reaction was allowed to proceed over night and was quenched with a sufficient amount of water as to remove any existing carbodimide. The solution was filtered to remove the precipitated dicyclohexyl urea. Solvents were removed via vacuum followed by flash chromatography (elution conditions, 2:1, Hexanes:EtoAC to EtoAC neat) to give the analogues as a yellow oil (90-98% yield).

General Deprotection Scheme of PMP Oxypantethiene Esters.

Deprotection was performed in a 25 ml round bottom flask which contained sufficient THF to generate a 0.05M solution with respect to the Oxypantethiene Ester. A catalytic amount of 1M HCl was added to the solution and the reaction was allowed to proceed overnight. Solvent was reduced under vacuum followed by flash chromatography (elution conditions, Column charged with DCM increase MeOH gradient 10% until product elutes) to afford the analogues as a yellow oil. (80-85% yield)

Protein NMR Parameters.

HSQC spectra were acquired on a Varian 500 MHz or a Varian 800 MHz spectrometer. The spectra of both apo-[15N]ACP preparations were acquired with identical parameters. The spectra were processed with NMRpipe and analyzed with Sparky.

Mass Spectrometry.

Samples evaluated by mass spectrometry utilized electron spray ionization (ESI) in positive ion mode.

PMP-Oxypantethiene[8-$^{13}C_1$]Caprylic Ester & PMP-Oxypantethiene Caprylic Ester.

$^1$H NMR (300 MHz, $CDCl_3$) δ 7.48-7.38 (m, 2H, HAr), 7.02 (t, J=5.9 Hz, 1H, NH), 6.97-6.86 (m, 2H, HAr), 6.12 (s, 1H, NH), 5.45 (s, 1H, ($CH_2O)_2CHAr$), 4.18-4.08 (m, 2H, (CO)$OCH_2CH2$), 4.06 (s, 1H, CCHOH(CO)), 3.82 (s, 3H, $OCH_3$), 3.68 (dd, J=22.6, 11.4 Hz, 2H, $NHCH_2CH_2$), 3.61-3.41 (m, 4H, (CO)$NHCH_2CH_2$, $OCH_2C$), 2.43 (t, J6.3 Hz, 2H, $CH_2CH_2CO$), 2.36-2.26 (m, 2H, $COCH_2CH_2$), 1.68-1.52 (m, 2H, $COCH_2CH_2CH_2$), 1.29 (tq, J=14.4, 7.3 Hz, 8H, $CH_2CH_2CH_2$), 1.09 (d, J=1.9 Hz, 6H, $C(CH_3)_2$), 0.94-0.82 (m, 3H, $CH_2CH_3$)$^{13}$C NMR (300 MHz, $CDCl_3$) δ 174.15, 171.27, 169.89, 160.49, 130.36, 127.77, 113.99, 101.61, 84.03, 78.71, 63.21, 55.57, 38.93, 36.22, 35.17, 34.39, 33.33, 31.92, 29.36, 29.17, 25.13, 22.63, 22.12, 19.39, 14.36; PMP-Oxypantethiene [8-$^{13}C_1$]caprylic ester LRMS exact mass calculated for [M+Na] ($C_{27}H_{42}N_2O_7$) requires m/z 530.29, found m/z 530.39; Oxypantethienecaprylic ester LRMS exact mass calculated for [M+Na] ($C_{27}H_{42}N_2O_7$) requires m/z 529.29, found m/z 529.36.

Oxypantethienediol [8-$^{13}C_1$]caprylic ester & Oxypantethienediol caprylic ester $^1$H NMR (400 MHz, $CDCl_3$) δ 7.40 (s, 1H. $CONHCH_2$), 6.36 (s, 1H, $CONHCH_2$), 4.15 (m, 2H, $CH_2CH_2(CO)$), 3.99 (s, 1H, CCHOH(CO)), 3.57-3.38 (m, 6H, $HOCH_2C$, (CO)$NCH_2CH_2$, (CO)$NCH_2CH_2$), 2.51-2.38 (m, 2H, $CH_2CH_2$(CO)), 2.32 (t, J=7.6 Hz, 2H, (COO)$CH_2CH_2$), 1.69-1.52 (m, 2H, (CO)$CH_2CH_2CH_2$), 1.28 (s, 6H, $CH_2CH_2CH_2CH_2$), 1.07 (d, J=6.6 Hz, 2H, $CH_2CH_2CH_3$), 1.00 (s, 3H, $CCH_3$), 0.91 (s, 3H, $CCH_3$), 0.66 (t, J=6.5 Hz, 3H, $CH_2CH_3$); $^{13}$C NMR (300 MHz, $CDCl_3$) δ 174.48, 174.40, 172.09, 77.63, 70.94, 63.08, 39.57, 39.08, 36.01, 35.51, 34.42, 31.94, 29.38, 29.19, 25.14, 22.65, 21.54, 20.75, 14.37; Oxypantethienediol[8-$^{13}C_1$]caprylic ester LRMS exact mass calculated for [M+Na]$^+$ m/z ($C_{19}H_{36}N_2O_6$) requires 412.26, found m/z 412.34; Oxypantethienediol caprylic ester LRMS exact mass calculated for [M+Na]+ m/z ($C_{19}H_{36}N_2O_6$) requires 411.25, found m/z 411.33.

PMP-Oxypantethiene [$^{13}C_4$]butyl ester & PMP-Oxypantethiene butyl ester $^1$H NMR (400 MHz, CDCl$_3$) δ 7.44-7.37 (m, 2H, ArH), 7.03 (t, J=6.0 Hz, 1H, CONHCH$_2$), 6.93-6.86 (m, 2H, ArH), 6.28 (d, J=4.9 Hz, 1H, CONHCH$_2$), 5.44 (s, 1H, (CH$_2$O)$_2$CHAr), 4.10 (td, J=5.4, 3.2 Hz, 2H, (CO)OCH$_2$CH2), 4.05 (s, 1H, CCHOH(CO)), 3.80 (s, 3H, OCH$_3$), 3.66 (q, J=11.5 Hz, 2H, CONHCH$_2$CH$_2$), 3.59-3.39 (m, 4H, CONHCH$_2$CH$_2$, OCH$_2$C), 2.49-2.36 (m, 3H, CH$_2$CH$_2$CONH, (CO)OCH$_2$CH$_2$), 2.10 (m, 2H, CH$_2$CH$_2$CONH), 1.75 (m, 2H, COOCH$_2$CH$_2$), 1.46 (m, 2H, CH$_2$CH$_2$CH$_3$), 0.78 (m, 3H, CH$_2$CH$_2$CH$_3$); PMP-Oxypantethiene [$^{13}C_4$]butyl ester $^{13}$C NMR (300 MHz, CDCl$_3$) δ 174.24, 174.22, 174.21, 173.69, 173.67, 173.65, 173.64, 171.27, 169.84, 160.51, 130.40, 127.78, 114.02, 101.61, 84.09, 78.74, 63.18, 55.61, 38.95, 36.69, 36.35, 36.12, 35.78, 35.18, 34.29, 33.34, 25.91, 25.24, 22.12, 19.40, 18.96, 18.94, 18.62, 18.60, 18.28, 18.26, 14.12, 14.08, 13.78, 13.74; Oxypantethiene butyl ester $^{13}$C NMR (300 MHz, CDCl$_3$) δ 173.94, 171.27, 169.83, 160.50, 130.39, 127.78, 114.00, 101.60, 84.08, 78.72, 61.18, 55.60, 38.94, 36.24, 35.17, 33.33, 22.11, 19.39, 18.61, 13.94; PMP-Oxypantethiene [$^{13}C_4$]butyl ester LRMS exact mass calculated for [M+Na]+ m/z ($C_{23}H_{34}N_2O_7$) requires 477.23, found m/z 477.31; PMP-Oxypantethiene butyl ester LRMS exact mass calculated for [M+Na]+ m/z ($C_{23}H_{34}N_2O_7$) requires 473.23, found m/z 473.29.

Oxypantethienediol [$^{13}C_4$]butyl ester & Oxypantethienediol Butyl Ester $^1$H NMR (400 MHz, CDCl$_3$) δ 7.47 (t, J=5.9 Hz, 1H, CONHCH$_2$), 6.63 (s, 1H, CONHCH$_2$), 4.55 (s, 1H, OH), 4.24-4.06 (m, 2H, CH$_2$CH$_2$(CO)O), 3.97 (s, 1H, CCHOH(CO)), 3.62-3.39 (m, 6H, HOCH$_2$C, (CO)NCH$_2$CH$_2$), 2.57-2.40 (m, 3H, (CO)NCH$_2$CH$_2$)), 2.16-2.00 (m, 2H, NHCH$_2$CH$_2$), 1.92-1.77 (m, 2H, (CO)CH$_2$CH$_2$), 1.48-1.32 (m, 2H, COO)CH$_2$CH$_2$), 0.97 (s, 3H, CCH$_3$), 0.89 (s, 3H, CCH$_3$), 0.72 (ddd, J=12.5, 7.0, 4.0 Hz, 3H, CH$_2$CH$_3$); Oxypantethienediol [$^{13}C_4$]butyl ester $^{13}$C NMR (300 MHz, CDCl$_3$) δ 174.75, 174.73, 174.70, 174.68, 174.27, 173.99, 173.97, 173.94, 173.92, 172.04, 77.67, 71.14, 63.10, 39.61, 39.17, 36.88, 36.43, 36.12, 35.67, 21.67, 20.70, 19.09, 18.63, 18.18, 14.20, 13.73; Oxypantethienediol butyl ester $^{13}$C NMR (300 MHz, CDCl$_3$) δ 174.46, 174.27, 172.18, 77.45, 70.91, 61.01, 39.53, 39.03, 36.24, 35.94, 35.52, 21.45, 20.71, 18.57, 13.92; Oxypantethienediol [$^{13}C_4$]butyl ester LRMS exact mass calculated for [M+Na]+ m/z ($C_{15}H_{28}N_2O_6$) requires 359.19, found m/z 359.27; Oxypantethienediol butyl ester LRMS exact mass calculated for [M+Na]+ m/z ($C_{15}H_{28}N_2O_6$) requires 355.18, found m/z 355.23.

Example 2 References

Murugan, E., Kong, R., Sun, H., Rao, F. & Liang, Z.-X. *Protein Expres. Pur* 71, 132-138 (2010).
McCafferty, D. G., Lessard, I. A. & Walsh, C. T. *Biochemistry-US* 36, 10498-10505 (1997).
Mayfield, S. P. & Schultz, J. *Plant J.* 37, 449-458 (2004).
Meier, J. L., Haushalter, R. W. & Burkart, M. D. *Bioorgan. Med. Chem. Lett.* 20, 4936-4939 (2010).
16. Meier, J. L. & Burkart, M. D. *Curr. Opin. Chem. Biol.* 15, 48-56 (2011).
17. Murugan, E., Kong, R., Sun, H., Rao, F. & Liang, Z.-X. *Protein Expres. Pur* 71, 132-138 (2010).
18. Quadri, L. E. et al. *Biochemistry-US* 37, 1585-1595 (1998).
19. Lambalot, R. H. & Walsh, C. T. *J. Biol. Chem.* 270, 24658-24661 (1995).
20. Foley, T. L. & Burkart, M. D. *Anal. Biochem.* 394, 39-47 (2009).
21. Foley, T. L. et al. *Org. Biomol. Chem.* 8, 4601-4606 (2010).
22. Chan, D. & Vogel, H. *Biochem. J.* 430, 1-19 (2010).
23. Ploskoń, E. et al. *Chem. Biol.* 17, 776-785 (2010).
24. Roujeinikova, A. et al. *Acta Crystallogr. D* 58, 330-332 (2002).
25. Roujeinikova, A. et al. *J. Mol. Biol.* 365, 135-145 (2007).
26. Upadhyay, S. K. et al. *J. Biol. Chem.* 284, 22390-22400 (2009).
27. Masanari, K. et al. *DNA Res.* 12, 291-299 (2005).
28. Worthington, A. S. & Burkart, M. D. *Org. Biomol. Chem.* 4, 44-46 (2006).

What is claimed is:

1. A method of forming an Apo-acyl carrier protein (ACP) from an ACP-phosphopantetheine conjugate, said method comprising:
   (i) contacting an ACP-phosphopantetheine conjugate with an ACP hydrolase, wherein said ACP-phosphopantetheine conjugate comprises an phosphopantetheine analogue moiety covalently bonded to an ACP through a phosphodiester linker; and
   (ii) allowing said ACP hydrolase to cleave said phosphodiester linker thereby forming an Apo-ACP,
   wherein said ACP-phosphopantetheine conjugate has the formula:

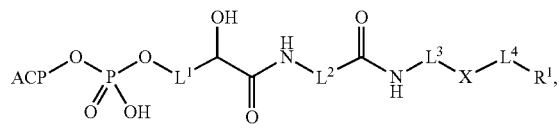

wherein;
   ACP is an ACP protein moiety or an ACP protein fusion moiety;
   $L^1$, $L^2$ and $L^3$ are independently substituted or unsubstituted alkylene;
   $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
   X is —NH— or —O—;
   $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, a detectable moiety or a reactive probe.

2. The method of claim 1, wherein said ACP is an ACP protein fusion moiety.

3. The method of claim 2, wherein said ACP protein fusion moiety comprises an ACP protein moiety bound to an amino terminus or a carboxy terminus of a second fusion protein moiety.

4. The method of claim 2, wherein said ACP protein fusion moiety comprises an ACP protein moiety bound to an internal amino acid residue of a second fusion protein moiety.

5. The method of claim 1, wherein said ACP hydrolase is a P. aeruginosa ACP hydrolase, Cyanothece sp. ACP hydrolase, or P. fluorescens ACP hydrolase.

6. The method of claim 1, wherein said apo-ACP is a Fatty Acid apo-ACP, Polyketide apo-ACP, or Peptide apo-ACP.

7. The method of claim 6, wherein said apo-ACP is a E. coli apo-ACP, P. aeruginosa apo-ACP, S. oneidensis apo-ACP, P. falciparum apo-ACP, M. tuberculosis apo-ACP, S. coelicolor apo-ACP, A. parasiticus apo-ACP, G. fujikuroi apo-ACP, L. majuscule apo-ACP or P. fluorescens apo-ACP.

8. The method of claim 1, further comprising:
   (i) contacting said Apo-ACP with a CoA-phosphopantetheine analogue and a phosphopantetheinyl transferase, wherein said CoA-phosphopantetheine analogue comprises a phosphopantetheine analogue moiety covalently bonded to a phosphoadenosine moiety through a phosphodiester linkage;
   (ii) allowing said phosphopantetheinyl transferase to cleave said phosphodiester linkage and bind said phosphopantetheine analogue moiety to said apo-ACP through a phosphodiester linker thereby forming a second ACP-phosphopantetheine conjugate;
   wherein said CoA-phosphopantetheine analogue has the formula:

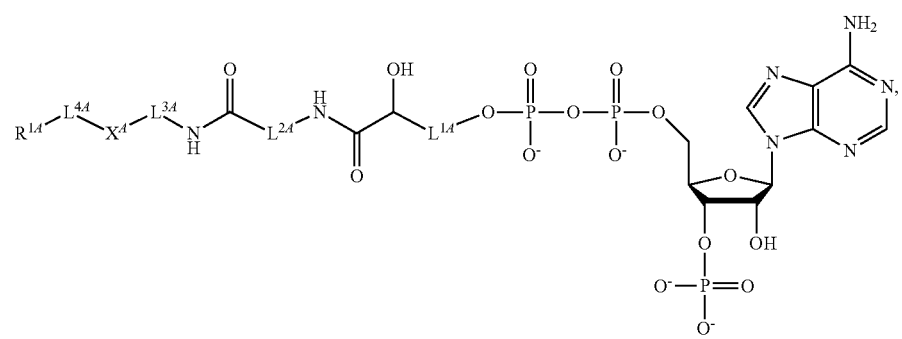

wherein;

$L^{1A}$, $L^{2A}$ and $L^{3A}$ are independently substituted or unsubstituted alkylene;

$L^{4A}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

$X^A$ is —NH— or —O—;

$R^{1A}$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, a detectable moiety or a reactive probe.

9. The method of claim 8, further comprising
    (i) contacting said second ACP-phosphopantetheine conjugate with a second ACP hydrolase; and
    (ii) allowing said second ACP hydrolase to cleave said phosphodiester linker thereby forming said Apo-ACP.

10. The method of claim 8, wherein said phosphopantetheinyl transferase is a *B. subtilis* phosphopantetheinyl transferase.

11. The method of claim 1, wherein the ACP comprises an amino acid sequence having the formula:

-DSL(Aaa1)(Aaa2)(Aaa3)(Aaa4)(Aaa5)(Aaa6)-     (I), wherein;

Aaa1 is D, E, or S;
Aaa2 is T, F, or W;
Aaa3 is V, L, or I;
Aaa4 is E, A, or L;
Aaa5 is A, S, R, or L;
Aaa6 is V, K, or L; and
wherein said sequence is not -DSLDTVELV- (SEQ ID NO:97).

12. The method of claim 11, wherein the ACP has the formula:

$R^N$-DSL(Aaa1)(Aaa2)(Aaa3)(Aaa4)(Aaa5)(Aaa6)-$R^C$ $R^N$-DSLEFIASKLA-$R^C$ (Ia), or $R^N$-GDSLSWLL-RLLN-$R^C$ (Ib) (SEQ ID NO:2), wherein;

$R^N$ is —NH$_2$, a detectable moiety, or a reactive probe; and
$R^C$ is —COOH, a detectable moiety, a reactive probe, or -$L^7$-$R^{C1}$;

$L^7$ is a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene -$L^5$-PEG-$L^6$-$R^{C1}$; wherein $L^5$ and $L^6$ are independently —O—, —S—, —NH—, —NHC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{C1}$ is a solid support comprising a cellulose membrane, a nanoparticle or a resin.

13. The method of claim 1, wherein $R^1$ is a detectable moiety.

14. The method of claim 1, wherein $R^1$ is a reactive probe.

15. The method of claim 1, wherein X is —NH—.

16. The method of claim 1, wherein X is —O—.

* * * * *

UNITED STATES PATENT AND TRADEMARK OFFICE
CERTIFICATE OF CORRECTION

PATENT NO. : 9,823,254 B2
APPLICATION NO. : 14/657221
DATED : November 21, 2017
INVENTOR(S) : Michael D. Burkart, Nicolas M. Kosa and Robert W. Haushalter It is certified that error appears in the above-identified patent and that said Letters Patent is hereby corrected as shown below:

In the Specification

In Column 1, Line 18, delete "This invention was made with Government support under grant number R21AI090213 and R01GM094924 awarded by the National Institutes of Health. The Government may have certain rights in this invention." and insert the following -- This invention was made with government support under AI090213 and GM094924 awarded by the National Institutes of Health. The government has certain rights in the invention. --

Signed and Sealed this
Sixth Day of January, 2026

John A. Squires
*Director of the United States Patent and Trademark Office*

SEQUENCE LISTING

```
<160> NUMBER OF SEQ ID NOS: 108

<210> SEQ ID NO 1
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 1

Asp Ser Leu Glu Phe Ile Ala Ser Lys Leu Ala
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic polypeptide
```

```
<400> SEQUENCE: 2

Gly Asp Ser Leu Ser Trp Leu Leu Arg Leu Leu Asn
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 3

Asp Ser Leu Glu Phe Ile Ala Ala Lys Leu Ala
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 4

Asp Ser Ala Glu Phe Ile Ala Ser Lys Leu Ala
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 5

Ala Ser Leu Glu Phe Ile Ala Ser Lys Leu Ala
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 6

Asp Ser Leu Asp Thr Val Glu Leu Val Met Ala
1               5                   10

<210> SEQ ID NO 7
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 7

Ala Ser Phe Val Glu Asp Leu Gly Ala Asp Ser Leu Asp Thr Val Glu
1               5                   10                  15

Leu Val Met Ala Leu Glu Glu Glu Phe
            20                  25

<210> SEQ ID NO 8
<211> LENGTH: 28
<212> TYPE: PRT
<213> ORGANISM: Artificial Sequence
```

<220> FEATURE:
<223> OTHER INFORMATION: Synthetic polypeptide

<400> SEQUENCE: 8

Asp Ser Leu Asp Thr Val Glu Leu Val Met Ala Leu Glu Glu Glu Phe
1               5                   10                  15

Asp Thr Glu Ile Pro Asp Glu Glu Ala Glu Lys Ile
            20                  25

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33
<211> LENGTH: 78
<212> TYPE: PRT
<213> ORGANISM: Escherichia coli

<400> SEQUENCE: 33

Met Ser Thr Ile Glu Glu Arg Val Lys Lys Ile Ile Gly Glu Gln Leu
1               5                   10                  15

Gly Val Lys Gln Glu Glu Val Thr Asn Asn Ala Ser Phe Val Glu Asp
            20                  25                  30

Leu Gly Ala Asp Ser Leu Asp Thr Val Glu Leu Val Met Ala Leu Glu
        35                  40                  45

Glu Glu Phe Asp Thr Glu Ile Pro Asp Glu Ala Glu Lys Ile Thr
    50                  55                  60

Thr Val Gln Ala Ala Ile Asp Tyr Ile Asn Gly His Gln Ala
65                  70                  75

<210> SEQ ID NO 34
<211> LENGTH: 78
<212> TYPE: PRT
<213> ORGANISM: Pseudomonas aeruginosa

<400> SEQUENCE: 34

Met Ser Thr Ile Glu Glu Arg Val Lys Lys Ile Val Ala Glu Gln Leu
1               5                   10                  15

Gly Val Lys Glu Glu Glu Val Thr Asn Ser Ala Ser Phe Val Glu Asp
            20                  25                  30

Leu Gly Ala Asp Ser Leu Asp Thr Val Glu Leu Val Met Ala Leu Glu
        35                  40                  45

Glu Glu Phe Glu Thr Glu Ile Pro Asp Glu Lys Ala Glu Lys Ile Thr
    50                  55                  60

Thr Val Gln Glu Ala Ile Asp Tyr Ile Val Ala His Gln Gln
65                  70                  75

<210> SEQ ID NO 35
<211> LENGTH: 77
<212> TYPE: PRT
<213> ORGANISM: Shewanella oneidensis

<400> SEQUENCE: 35

Met Ser Asn Ile Glu Glu Arg Val Lys Lys Ile Ile Val Glu Gln Leu
1               5                   10                  15

Gly Val Lys Glu Glu Asp Val Lys Pro Ala Ala Ser Phe Val Asp Asp

```
                    20                  25                  30

Leu Gly Ala Asp Ser Leu Asp Thr Val Glu Leu Val Met Ala Leu Glu
            35                  40                  45

Glu Glu Phe Asp Thr Glu Ile Pro Asp Glu Glu Ala Glu Lys Ile Thr
        50                  55                  60

Thr Val Gln Ala Ala Ile Asp Tyr Val Ser Lys Asn Gln
65                  70                  75

<210> SEQ ID NO 36
<211> LENGTH: 81
<212> TYPE: PRT
<213> ORGANISM: Plasmodium falciparum

<400> SEQUENCE: 36

Ser Ser Leu Lys Ser Thr Phe Asp Asp Ile Lys Lys Ile Ile Ser Lys
1               5                   10                  15

Gln Leu Ser Val Glu Glu Asp Lys Ile Gln Met Asn Ser Asn Phe Thr
            20                  25                  30

Lys Asp Leu Gly Ala Asp Ser Leu Asp Leu Val Glu Leu Ile Met Ala
        35                  40                  45

Leu Glu Glu Lys Phe Asn Val Thr Ile Ser Asp Gln Asp Ala Leu Lys
    50                  55                  60

Ile Asn Thr Val Gln Asp Ala Ile Asp Tyr Ile Glu Lys Asn Asn Lys
65                  70                  75                  80

Gln

<210> SEQ ID NO 37
<211> LENGTH: 115
<212> TYPE: PRT
<213> ORGANISM: Mycobacterium tuberculosis

<400> SEQUENCE: 37

Met Pro Val Thr Gln Glu Glu Ile Ile Ala Gly Ile Ala Glu Ile Ile
1               5                   10                  15

Glu Glu Val Thr Gly Ile Glu Pro Ser Glu Ile Thr Pro Glu Lys Ser
            20                  25                  30

Phe Val Asp Asp Leu Asp Ile Asp Ser Leu Ser Met Val Glu Ile Ala
        35                  40                  45

Val Gln Thr Glu Asp Lys Tyr Gly Val Lys Ile Pro Asp Glu Asp Leu
    50                  55                  60

Ala Gly Leu Arg Thr Val Gly Asp Val Ala Tyr Ile Gln Lys Leu
65                  70                  75                  80

Glu Glu Glu Asn Pro Glu Ala Ala Gln Ala Leu Arg Ala Lys Ile Glu
            85                  90                  95

Ser Glu Asn Pro Asp Ala Val Ala Asn Val Gln Ala Arg Leu Glu Ala
            100                 105                 110

Glu Ser Lys
        115

<210> SEQ ID NO 38
<211> LENGTH: 2111
<212> TYPE: PRT
<213> ORGANISM: Mycobacterium tuberculosis

<400> SEQUENCE: 38

Met Glu Ser Arg Val Thr Pro Val Ala Val Ile Gly Met Gly Cys Arg
1               5                   10                  15
```

Leu Pro Gly Gly Ile Asn Ser Pro Asp Lys Leu Trp Glu Ser Leu Leu
            20                  25                  30

Arg Gly Asp Asp Leu Val Thr Glu Ile Pro Pro Asp Arg Trp Asp Ala
        35                  40                  45

Asp Asp Tyr Tyr Asp Pro Glu Pro Gly Val Pro Gly Arg Ser Val Ser
    50                  55                  60

Arg Trp Gly Gly Phe Leu Asp Asp Val Ala Gly Phe Asp Ala Glu Phe
65                  70                  75                  80

Phe Gly Ile Ser Glu Arg Glu Ala Thr Ser Ile Asp Pro Gln Gln Arg
                85                  90                  95

Leu Leu Leu Glu Thr Ser Trp Glu Ala Ile Glu His Ala Gly Leu Asp
            100                 105                 110

Pro Ala Ser Leu Ala Gly Ser Ser Thr Ala Val Phe Thr Gly Leu Thr
        115                 120                 125

His Glu Asp Tyr Leu Val Leu Thr Thr Thr Ala Gly Gly Leu Ala Ser
    130                 135                 140

Pro Tyr Val Val Thr Gly Leu Asn Asn Ser Val Ala Ser Gly Arg Ile
145                 150                 155                 160

Ala His Thr Leu Gly Leu His Gly Pro Ala Met Thr Phe Asp Thr Ala
                165                 170                 175

Cys Ser Ser Gly Leu Met Ala Val His Leu Ala Cys Arg Ser Leu His
            180                 185                 190

Asp Gly Glu Ala Asp Leu Ala Leu Ala Gly Gly Cys Ala Val Leu Leu
        195                 200                 205

Glu Pro His Ala Ser Val Ala Ala Ser Ala Gln Gly Met Leu Ser Ser
210                 215                 220

Thr Gly Arg Cys His Ser Phe Asp Ala Asp Ala Asp Gly Phe Val Arg
225                 230                 235                 240

Ser Glu Gly Cys Ala Met Val Leu Leu Lys Arg Leu Pro Asp Ala Leu
                245                 250                 255

Arg Asp Gly Asn Arg Ile Phe Ala Val Val Arg Gly Thr Ala Thr Asn
            260                 265                 270

Gln Asp Gly Arg Thr Glu Thr Leu Thr Met Pro Ser Glu Asp Ala Gln
        275                 280                 285

Val Ala Val Tyr Arg Ala Ala Leu Ala Ala Gly Val Gln Pro Glu
    290                 295                 300

Thr Val Gly Val Val Glu Ala His Gly Thr Gly Thr Pro Ile Gly Asp
305                 310                 315                 320

Pro Ile Glu Tyr Arg Ser Leu Ala Arg Val Tyr Gly Ala Gly Thr Pro
                325                 330                 335

Cys Ala Leu Gly Ser Ala Lys Ser Asn Met Gly His Ser Thr Ala Ser
            340                 345                 350

Ala Gly Thr Val Gly Leu Ile Lys Ala Ile Leu Ser Leu Arg His Gly
        355                 360                 365

Val Val Pro Pro Leu Leu His Phe Asn Arg Leu Pro Asp Glu Leu Ser
    370                 375                 380

Asp Val Glu Thr Gly Leu Phe Val Pro Gln Ala Val Thr Pro Trp Pro
385                 390                 395                 400

Asn Gly Asn Asp His Thr Pro Lys Arg Val Ala Val Ser Ser Phe Gly
                405                 410                 415

Met Ser Gly Thr Asn Val His Ala Ile Val Glu Glu Ala Pro Ala Glu
            420                 425                 430

Ala Ser Ala Pro Glu Ser Ser Pro Gly Asp Ala Glu Val Gly Pro Arg

-continued

```
                435                 440                 445
Leu Phe Met Leu Ser Ser Thr Ser Ser Asp Ala Leu Arg Gln Thr Ala
450                 455                 460
Arg Gln Leu Ala Thr Trp Val Glu Glu His Gln Asp Cys Val Ala Ala
465                 470                 475                 480
Ser Asp Leu Ala Tyr Thr Leu Ala Arg Gly Arg Ala His Arg Pro Val
                485                 490                 495
Arg Thr Ala Val Val Ala Ala Asn Leu Pro Glu Leu Val Glu Gly Leu
                500                 505                 510
Arg Glu Val Ala Asp Gly Asp Ala Leu Tyr Asp Ala Val Gly His
                515                 520                 525
Gly Asp Arg Gly Pro Val Trp Val Phe Ser Gly Gln Gly Ser Gln Trp
530                 535                 540
Ala Ala Met Gly Thr Gln Leu Leu Ala Ser Glu Pro Val Phe Ala Ala
545                 550                 555                 560
Thr Ile Ala Lys Leu Glu Pro Val Ile Ala Ala Glu Ser Gly Phe Ser
                565                 570                 575
Val Thr Glu Ala Ile Thr Ala Gln Gln Thr Val Thr Gly Ile Asp Lys
                580                 585                 590
Val Gln Pro Ala Val Phe Ala Val Gln Val Ala Leu Ala Ala Thr Met
                595                 600                 605
Glu Gln Thr Tyr Gly Val Arg Pro Gly Ala Val Val Gly His Ser Met
                610                 615                 620
Gly Glu Ser Ala Ala Val Val Ala Gly Ala Leu Ser Leu Glu Asp
625                 630                 635                 640
Ala Ala Arg Val Ile Cys Arg Arg Ser Lys Leu Met Thr Arg Ile Ala
                645                 650                 655
Gly Ala Gly Ala Met Gly Ser Val Glu Leu Pro Ala Lys Gln Val Asn
                660                 665                 670
Ser Glu Leu Met Ala Arg Gly Ile Asp Asp Val Val Ser Val Val
                675                 680                 685
Ala Ser Pro Gln Ser Thr Val Ile Gly Gly Thr Ser Asp Thr Val Arg
                690                 695                 700
Asp Leu Ile Ala Arg Trp Glu Gln Arg Asp Val Met Ala Arg Glu Val
705                 710                 715                 720
Ala Val Asp Val Ala Ser His Ser Pro Gln Val Asp Pro Ile Leu Asp
                725                 730                 735
Asp Leu Ala Ala Ala Leu Ala Asp Ile Ala Pro Met Thr Pro Lys Val
                740                 745                 750
Pro Tyr Tyr Ser Ala Thr Leu Phe Asp Pro Arg Glu Gln Pro Val Cys
                755                 760                 765
Asp Gly Ala Tyr Trp Val Asp Asn Leu Arg Asn Thr Val Gln Phe Ala
                770                 775                 780
Ala Ala Val Gln Ala Ala Met Glu Asp Gly Tyr Arg Val Phe Ala Glu
785                 790                 795                 800
Leu Ser Pro His Pro Leu Leu Thr His Ala Val Glu Gln Thr Gly Arg
                805                 810                 815
Ser Leu Asp Met Ser Val Ala Leu Ala Gly Met Arg Arg Glu Gln
                820                 825                 830
Pro Leu Pro His Gly Leu Arg Gly Leu Leu Thr Glu Leu His Arg Ala
                835                 840                 845
Gly Ala Ala Leu Asp Tyr Ser Ala Leu Tyr Pro Ala Gly Arg Leu Val
                850                 855                 860
```

-continued

Asp Ala Pro Leu Pro Ala Trp Thr His Ala Arg Leu Phe Ile Asp Asp
865                 870                 875                 880

Asp Gly Gln Glu Gln Arg Ala Gln Gly Ala Cys Thr Ile Thr Val His
            885                 890                 895

Pro Leu Leu Gly Ser His Val Arg Leu Thr Glu Glu Pro Glu Arg His
        900                 905                 910

Val Trp Gln Gly Asp Val Gly Thr Ser Val Leu Ser Trp Leu Ser Asp
    915                 920                 925

His Gln Val His Asn Val Ala Ala Leu Pro Gly Ala Ala Tyr Cys Glu
930                 935                 940

Met Ala Leu Ala Ala Ala Ala Glu Val Phe Gly Glu Ala Ala Glu Val
945                 950                 955                 960

Arg Asp Ile Thr Phe Glu Gln Met Leu Leu Asp Glu Gln Thr Pro
            965                 970                 975

Ile Asp Ala Val Ala Ser Ile Asp Ala Pro Gly Val Val Asn Phe Thr
            980                 985                 990

Val Glu Thr Asn Arg Asp Gly Glu Thr Thr Arg His Ala Thr Ala Ala
        995                 1000                1005

Leu Arg Ala Ala Glu Asp Asp Cys Pro Pro Gly Tyr Asp Ile
    1010                1015                1020

Thr Ala Leu Leu Gln Ala His Pro His Ala Val Asn Gly Thr Ala
    1025                1030                1035

Met Arg Glu Ser Phe Ala Glu Arg Gly Val Thr Leu Gly Ala Ala
    1040                1045                1050

Phe Gly Gly Leu Thr Thr Ala His Thr Ala Glu Ala Gly Ala Ala
    1055                1060                1065

Thr Val Leu Ala Glu Val Ala Leu Pro Ala Ser Ile Arg Phe Gln
    1070                1075                1080

Gln Gly Ala Tyr Arg Ile His Pro Ala Leu Leu Asp Ala Cys Phe
    1085                1090                1095

Gln Ser Val Gly Ala Gly Val Gln Ala Gly Thr Ala Thr Gly Gly
    1100                1105                1110

Leu Leu Leu Pro Leu Gly Val Arg Ser Leu Arg Ala Tyr Gly Pro
    1115                1120                1125

Thr Arg Asn Ala Arg Tyr Cys Tyr Thr Arg Leu Thr Lys Ala Phe
    1130                1135                1140

Asn Asp Gly Thr Arg Gly Gly Glu Ala Asp Leu Asp Val Leu Asp
    1145                1150                1155

Glu His Gly Thr Val Leu Leu Ala Val Arg Gly Leu Arg Met Gly
    1160                1165                1170

Thr Gly Thr Ser Glu Arg Asp Glu Arg Asp Arg Leu Val Ser Glu
    1175                1180                1185

Arg Leu Leu Thr Leu Gly Trp Gln Gln Arg Ala Leu Pro Glu Val
    1190                1195                1200

Gly Asp Gly Glu Ala Gly Ser Trp Leu Leu Ile Asp Thr Ser Asn
    1205                1210                1215

Ala Val Asp Thr Pro Asp Met Leu Ala Ser Thr Leu Thr Asp Ala
    1220                1225                1230

Leu Lys Ser His Gly Pro Gln Gly Thr Glu Cys Ala Ser Leu Ser
    1235                1240                1245

Trp Ser Val Gln Asp Thr Pro Pro Asn Asp Gln Ala Gly Leu Glu
    1250                1255                1260

-continued

Lys Leu Gly Ser Gln Leu Arg Gly Arg Asp Gly Val Val Ile Val
1265                1270                1275

Tyr Gly Pro Arg Val Gly Asp Pro Asp Glu His Ser Leu Leu Ala
1280                1285                1290

Gly Arg Glu Gln Val Arg His Leu Val Arg Ile Thr Arg Glu Leu
1295                1300                1305

Ala Glu Phe Glu Gly Glu Leu Pro Arg Leu Phe Val Val Thr Arg
1310                1315                1320

Gln Ala Gln Ile Val Lys Pro His Asp Ser Gly Glu Arg Ala Asn
1325                1330                1335

Leu Glu Gln Ala Gly Leu Arg Gly Leu Leu Arg Val Ile Ser Ser
1340                1345                1350

Glu His Pro Met Leu Arg Thr Thr Leu Ile Asp Val Asp Glu His
1355                1360                1365

Thr Asp Val Glu Arg Val Ala Gln Gln Leu Leu Ser Gly Ser Glu
1370                1375                1380

Glu Asp Glu Thr Ala Trp Arg Asn Gly Asp Trp Tyr Val Ala Arg
1385                1390                1395

Leu Thr Pro Ser Pro Leu Gly His Glu Glu Arg Arg Thr Ala Val
1400                1405                1410

Leu Asp Pro Asp His Asp Gly Met Arg Val Gln Val Arg Arg Pro
1415                1420                1425

Gly Asp Leu Gln Thr Leu Glu Phe Val Ala Ser Asp Arg Val Pro
1430                1435                1440

Pro Gly Pro Gly Gln Ile Glu Val Ala Val Ser Met Ser Ser Ile
1445                1450                1455

Asn Phe Ala Asp Val Leu Ile Ala Phe Gly Arg Phe Pro Ile Ile
1460                1465                1470

Asp Asp Arg Glu Pro Gln Leu Gly Met Asp Phe Val Gly Val Val
1475                1480                1485

Thr Ala Val Gly Glu Gly Val Thr Gly His Gln Val Gly Asp Arg
1490                1495                1500

Val Gly Gly Phe Ser Glu Gly Gly Cys Trp Arg Thr Phe Leu Thr
1505                1510                1515

Cys Asp Ala Asn Leu Ala Val Thr Leu Pro Pro Gly Leu Thr Asp
1520                1525                1530

Glu Gln Ala Ile Thr Ala Ala Thr Ala His Ala Thr Ala Trp Tyr
1535                1540                1545

Gly Leu Asn Asp Leu Ala Gln Ile Lys Ala Gly Asp Lys Val Leu
1550                1555                1560

Ile His Ser Ala Thr Gly Gly Val Gly Gln Ala Ala Ile Ser Ile
1565                1570                1575

Ala Arg Ala Lys Gly Ala Glu Ile Phe Ala Thr Ala Gly Asn Pro
1580                1585                1590

Ala Lys Arg Ala Met Leu Arg Asp Met Gly Val Glu His Val Tyr
1595                1600                1605

Asp Ser Arg Ser Val Glu Phe Ala Glu Gln Ile Arg Arg Asp Thr
1610                1615                1620

Asp Gly Tyr Gly Val Asp Ile Val Leu Asn Ser Leu Thr Gly Ala
1625                1630                1635

Ala Gln Arg Ala Gly Leu Glu Leu Leu Ala Phe Gly Gly Arg Phe
1640                1645                1650

Val Glu Ile Gly Lys Ala Asp Val Tyr Gly Asn Thr Arg Leu Gly

-continued

```
            1655                1660                1665
Leu Phe Pro Phe Arg Arg Gly Leu Thr Phe Tyr Tyr Leu Asp Leu
        1670                1675                1680
Ala Leu Met Ser Val Thr Gln Pro Asp Arg Val Arg Glu Leu Leu
        1685                1690                1695
Ala Thr Val Phe Lys Leu Thr Ala Asp Gly Val Leu Thr Ala Pro
        1700                1705                1710
Gln Cys Thr His Tyr Pro Leu Ala Glu Ala Ala Asp Ala Ile Arg
        1715                1720                1725
Ala Met Ser Asn Ala Glu His Thr Gly Lys Leu Val Leu Asp Val
        1730                1735                1740
Pro Arg Ser Gly Arg Arg Ser Val Ala Val Thr Pro Glu Gln Ala
        1745                1750                1755
Pro Leu Tyr Arg Arg Asp Gly Ser Tyr Ile Ile Thr Gly Gly Leu
        1760                1765                1770
Gly Gly Leu Gly Leu Phe Phe Ala Ser Lys Leu Ala Ala Ala Gly
        1775                1780                1785
Cys Gly Arg Ile Val Leu Thr Ala Arg Ser Gln Pro Asn Pro Lys
        1790                1795                1800
Ala Arg Gln Thr Ile Glu Gly Leu Arg Ala Ala Gly Ala Asp Ile
        1805                1810                1815
Val Val Glu Cys Gly Asn Ile Ala Glu Pro Asp Thr Ala Asp Arg
        1820                1825                1830
Leu Val Ser Ala Ala Thr Ala Thr Gly Leu Pro Leu Arg Gly Val
        1835                1840                1845
Leu His Ser Ala Ala Val Val Glu Asp Ala Thr Leu Thr Asn Ile
        1850                1855                1860
Thr Asp Glu Leu Ile Asp Arg Asp Trp Ser Pro Lys Val Phe Gly
        1865                1870                1875
Ser Trp Asn Leu His Arg Ala Thr Leu Gly Gln Pro Leu Asp Trp
        1880                1885                1890
Phe Cys Leu Phe Ser Ser Gly Ala Ala Leu Leu Gly Ser Pro Gly
        1895                1900                1905
Gln Gly Ala Tyr Ala Ala Ala Asn Ser Trp Val Asp Val Phe Ala
        1910                1915                1920
His Trp Arg Arg Ala Gln Gly Leu Pro Val Ser Ala Ile Ala Trp
        1925                1930                1935
Gly Ala Trp Gly Glu Val Gly Arg Ala Thr Phe Leu Ala Glu Gly
        1940                1945                1950
Gly Glu Ile Met Ile Thr Pro Glu Glu Gly Ala Tyr Ala Phe Glu
        1955                1960                1965
Thr Leu Val Arg His Asp Arg Ala Tyr Ser Gly Tyr Ile Pro Ile
        1970                1975                1980
Leu Gly Ala Pro Trp Leu Ala Asp Leu Val Arg Arg Ser Pro Trp
        1985                1990                1995
Gly Glu Met Phe Ala Ser Thr Gly Gln Arg Ser Arg Gly Pro Ser
        2000                2005                2010
Lys Phe Arg Met Glu Leu Leu Ser Leu Pro Gln Asp Glu Trp Ala
        2015                2020                2025
Gly Arg Leu Arg Arg Leu Leu Val Glu Gln Ala Ser Val Ile Leu
        2030                2035                2040
Arg Arg Thr Ile Asp Ala Asp Arg Ser Phe Ile Glu Tyr Gly Leu
        2045                2050                2055
```

Asp Ser Leu Gly Met Leu Glu Met Arg Thr His Val Glu Thr Glu
    2060            2065                2070

Thr Gly Ile Arg Leu Thr Pro Lys Val Ile Ala Thr Asn Asn Thr
    2075            2080                2085

Ala Arg Ala Leu Ala Gln Tyr Leu Ala Asp Thr Leu Ala Glu Glu
    2090            2095                2100

Gln Ala Ala Ala Pro Ala Ala Ser
    2105            2110

<210> SEQ ID NO 39
<211> LENGTH: 86
<212> TYPE: PRT
<213> ORGANISM: Streptomyces coelicolor

<400> SEQUENCE: 39

Met Ala Thr Leu Leu Thr Thr Asp Asp Leu Arg Arg Ala Leu Val Glu
1               5                   10                  15

Cys Ala Gly Glu Thr Asp Gly Thr Asp Leu Ser Gly Asp Phe Leu Asp
                20                  25                  30

Leu Arg Phe Glu Asp Ile Gly Tyr Asp Ser Leu Ala Leu Met Glu Thr
            35                  40                  45

Ala Ala Arg Leu Glu Ser Arg Tyr Gly Val Ser Ile Pro Asp Asp Val
        50                  55                  60

Ala Gly Arg Val Asp Thr Pro Arg Glu Leu Leu Asp Leu Ile Asn Gly
65                  70                  75                  80

Ala Leu Ala Glu Ala Ala
                85

<210> SEQ ID NO 40
<211> LENGTH: 89
<212> TYPE: PRT
<213> ORGANISM: Aspergillus parasiticus

<400> SEQUENCE: 40

Ala Met Ala Lys Gly Val Gly Val Ser Asn Glu Lys Leu Asp Ala Val
1               5                   10                  15

Met Arg Val Val Ser Glu Glu Ser Gly Ile Ala Leu Glu Glu Leu Thr
                20                  25                  30

Asp Asp Ser Asn Phe Ala Asp Met Gly Ile Asp Ser Leu Ser Ser Met
            35                  40                  45

Val Ile Gly Ser Arg Phe Arg Glu Asp Leu Gly Leu Asp Leu Gly Pro
        50                  55                  60

Glu Phe Ser Leu Phe Ile Asp Cys Thr Thr Val Arg Ala Leu Lys Asp
65                  70                  75                  80

Phe Met Leu Gly Ser Gly Asp Ala Gly
                85

<210> SEQ ID NO 41
<211> LENGTH: 2009
<212> TYPE: PRT
<213> ORGANISM: Fusarium fujikuroi

<400> SEQUENCE: 41

Met Ala Ser Ser Ala Asp Val Tyr Val Phe Gly Asp Gln Ser Thr Pro
1               5                   10                  15

Val Leu Asp Lys Leu Gln Ala Val Arg Val Lys Asp Asn Ala Leu
                20                  25                  30

Leu Thr Ser Phe Leu Gly Glu Ala Phe Leu Ala Val Arg Glu Ile
            35              40              45

Val Ser Leu Ser Ser Leu Glu Arg Lys Ser Ile Pro Glu Ala Glu Ser
 50              55                      60

Leu Ser Leu Leu Leu Glu Gly Val Arg Arg Ser Glu Pro His Ala Ala
 65              70              75                      80

Leu Asp Ser Ala Phe Val Cys Ile Tyr Glu Ile Gly Tyr Tyr Ile Asp
                85              90              95

Arg Cys Cys His Cys Ala Lys Asp Val Phe Glu Ile Ser Arg Leu Gly
            100             105             110

Val Glu Ala Ala Thr Val Ala Phe Arg Leu Gly Met His Val Arg Arg
            115             120             125

Arg Ala Glu Asn Leu Gly Tyr Ser Thr Pro Ser Ser Trp Ser Met Ile
            130             135             140

Leu Ser Ser Asn Gln Glu Glu Leu Val Ser Glu Ala Leu Lys Glu Phe
145             150             155             160

Ser Lys Glu Lys Asn Leu Thr Tyr Ser Ser Arg Pro Tyr Ile Ser Ala
                165             170             175

Thr Gly Pro Gly Phe Thr Thr Ile Ser Gly Pro Ser Ile Leu Glu
            180             185             190

Ser Val Lys Ser Cys Asp Thr Phe Ser Gly Lys Arg Leu Tyr Pro Ala
            195             200             205

Pro Ile Tyr Gly Pro Tyr His Asn Ser Ser Ser Tyr Ser Glu Ser Ser
            210             215             220

Leu Glu His Gly Leu Ala Ser Ile Leu Glu Asp Val Gly Phe Leu Glu
225             230             235             240

Asn Glu Met Leu Ile Pro Ile Ser Cys Ala Ser Gly Ser Arg Leu
            245             250             255

Asp Gln Leu Ser Phe Gly Asn Leu Leu Lys Asn Val Leu Ser Ser Ala
            260             265             270

Leu Ser Gln Gln Ile Arg Met Asp Leu Val Thr Asp Ala Leu Val Glu
            275             280             285

Thr Val Ser Gly Thr Glu Ala Thr Leu Ile Pro Val Asn Ala Gln Thr
290             295             300

Thr Val Cys Ser Leu Ala Asp Trp Leu Ala Lys Arg Gly Ala Thr Thr
305             310             315             320

Arg Ile Gly Pro Thr Leu Glu Ser Leu Thr Lys Asp Arg Ala Glu Pro
                325             330             335

Asn Leu Ala Pro Gly Asp Glu Asn Lys Ile Ala Ile Gly Phe Ser
            340             345             350

Gly Arg Phe Pro Glu Ala Asp Asn Leu Asp Glu Phe Trp Asp Leu Leu
            355             360             365

Ile Arg Gly Leu Asp Val His Lys Pro Val Pro Glu Glu Arg Phe Ala
            370             375             380

Arg Asp His Tyr Asp Pro Thr Gly Gln Arg Lys Asn Thr Ser Gln Val
385             390             395             400

Gln Tyr Gly Cys Trp Leu Lys Ser Ala Gly Tyr Phe Asp Thr Gln Phe
            405             410             415

Phe His Met Ser Pro Lys Glu Ala Met Gln Thr Asp Pro Ala Gln Arg
            420             425             430

Leu Ala Leu Leu Thr Ala Tyr Glu Ala Leu Glu Met Ala Gly Val Val
            435             440             445

Pro Asp Arg Thr Pro Ser Thr Gln Arg Asn Arg Val Gly Val Tyr Tyr

```
                450           455           460
Gly Thr Thr Ser Asn Asp Trp Gly Glu Val Asn Ser Ser Gln Asp Val
465                 470                 475                 480

Asp Thr Tyr Tyr Ile Pro Gly Ala Asn Arg Ala Phe Ile Pro Gly Arg
                485                 490                 495

Val Asn Tyr Phe Phe Lys Phe Thr Gly Pro Ser Ile Ala Val Asp Thr
                500                 505                 510

Ala Cys Ser Ser Ser Leu Ala Ala Ile Asn Leu Ala Ile Thr Ser Leu
                515                 520                 525

Lys Asn Arg Asp Cys Asn Thr Ala Ile Ala Gly Gly Thr Asn Val Met
530                 535                 540

Thr Asn Pro Asp Asn Phe Ala Gly Leu Asp Arg Gly His Phe Leu Ser
545                 550                 555                 560

Arg Thr Gly Asn Cys Lys Ala Phe Asn Asp Gly Ala Asp Gly Tyr Cys
                565                 570                 575

Arg Ala Asp Gly Ile Gly Thr Leu Ile Leu Lys Arg Leu Pro Asp Ala
                580                 585                 590

Ile Ala Asp Ser Asp Pro Ile Phe Gly Val Ile Leu Gly Ala His Thr
                595                 600                 605

Asn His Ser Ala Glu Ser Val Ser Ile Thr Arg Pro Leu Ala Asp Ala
                610                 615                 620

Gln Glu Tyr Leu Phe Lys Lys Leu Leu Asn Glu Thr Gly Ile His Pro
625                 630                 635                 640

His Asp Val Ser Tyr Val Glu Met His Gly Thr Gly Thr Gln Ala Gly
                645                 650                 655

Asp Ala Val Glu Met Arg Ser Val Leu Asn Ser Phe Ala Phe Asp His
                660                 665                 670

Ser Arg Pro Arg Asp Lys Ser Leu Tyr Leu Gly Ser Val Lys Ala Asn
                675                 680                 685

Val Gly His Ala Glu Ser Ala Ser Gly Val Leu Ala Ile Ile Lys Val
                690                 695                 700

Leu Leu Met Met Gln Lys Asn Thr Ile Pro Pro His Cys Gly Ile Lys
705                 710                 715                 720

Thr Lys Ile Asn Gln Gly Phe Pro Lys Asp Leu Asp His Arg Gly Val
                725                 730                 735

Arg Ile Ala Leu Lys Asp Ser Val Asp Trp Ser Arg Pro Glu Gly Gly
                740                 745                 750

Lys Arg Arg Val Leu Val Asn Asn Phe Ser Ala Ala Gly Gly Asn Thr
                755                 760                 765

Ser Leu Leu Leu Glu Asp Gly Pro Ala Val His Pro Ala Arg Gln His
770                 775                 780

Gln Asp Gly Asp Ala Arg Thr Glu His Val Ala Val Ser Ala Arg
785                 790                 795                 800

Ser Thr Lys Ala Leu Glu Glu Asn Leu Lys Ala Leu Glu Ala Tyr Ile
                805                 810                 815

Ala Asn Ser Trp Ala Pro Glu Gly Glu Leu Leu Ser Gln Leu Ser Tyr
                820                 825                 830

Thr Thr Thr Ala Arg Arg Val His His Ser Arg Arg Val Ala Phe Val
                835                 840                 845

Thr Asn Gly Leu Asp Asp Leu Arg Lys Ser Leu Leu Lys Ala Ala Thr
                850                 855                 860

Asp Ala Gly Gln Val Lys Gly Ile Pro Ala Val Ser Pro Lys Val Gly
865                 870                 875                 880
```

```
Phe Leu Phe Thr Gly Gln Gly Ala Gln Glu Thr Ala Met Ala Ile Gly
            885                 890                 895

Tyr Tyr Lys Ser Phe Ser Ser Phe Arg Ser Asp Ile His Gln Leu Asp
            900                 905                 910

Ser Ile Ala Thr Leu Gln Gly Leu Pro Ser Val Leu Pro Leu Ile His
            915                 920                 925

Gly Thr Thr Pro Val Glu Asp Leu Ser Ala Val Val Gln Leu Gly
        930                 935                 940

Thr Cys Ile Ile Gln Ile Ser Leu Ala Arg Phe Trp Ile Ser Leu Gly
945                 950                 955                 960

Ile Thr Pro Gln Tyr Val Ile Gly His Ser Leu Gly Glu Tyr Ala Ala
            965                 970                 975

Leu Gln Ile Ala Gly Val Leu Ser Val Asn Asp Ala Ile Phe Leu Cys
            980                 985                 990

Gly His Arg Ala Ala Leu Leu Asp Lys Lys Cys Thr Ala Tyr Thr His
            995                 1000                1005

Gly Met Val Ala Val Lys Ala Ala Ala Asp Asp Leu Arg Gln His
        1010                1015                1020

Ile Ser Ser Asp Leu Lys Val Glu Ile Ala Cys Val Asn Gly Ala
        1025                1030                1035

Glu Asp Thr Val Leu Ser Gly Pro Asn Ala Asp Ile Glu Ser Leu
        1040                1045                1050

Cys Gly Lys Leu Thr Gln Ala Gly Tyr Lys Leu His Lys Leu Glu
        1055                1060                1065

Ile Pro Phe Ala Phe His Ser Ser Gln Val Asp Pro Ile Leu Asp
        1070                1075                1080

Asp Leu Glu Glu Leu Ala Ser Gln Val Gly Phe His Glu Pro Lys
        1085                1090                1095

Leu Pro Ile Val Ser Pro Leu Leu Arg Thr Leu Leu Thr Gly Asp
        1100                1105                1110

Thr Leu Gly Pro Gln Tyr Ile Arg Arg His Cys Arg Glu Thr Val
        1115                1120                1125

Asp Phe Leu Gly Ala Ile Lys Met Ala Glu Ser Gln Gly Ile Met
        1130                1135                1140

Asp Arg Ser Gly Met Cys Ile Glu Ile Gly Ala His Pro Ile Leu
        1145                1150                1155

Thr Arg Met Val Lys Ser Ile Ile Gly Gln Asp Phe Arg Cys Leu
        1160                1165                1170

Ala Ser Leu Arg Arg Lys Glu Asp His Phe Lys Thr Leu Ala Asp
        1175                1180                1185

Ser Leu Cys Ala Leu His Leu Ala Gly Phe Ser Val Asn Trp Asp
        1190                1195                1200

Glu Tyr His Arg Asp Phe Ala Ser Ser Arg Asn Val Leu Gln Leu
        1205                1210                1215

Pro Lys Tyr Ser Trp Gln Leu Ala Asn Tyr Trp Met Gln Tyr Lys
        1220                1225                1230

Tyr Ser Trp Cys Leu Thr Lys Gly Asp Ala Pro Val Glu Asn Gly
        1235                1240                1245

Pro Val Gly Ala Val Val Gln Ala Arg Ala Leu Arg Leu Ser Asp
        1250                1255                1260

Ser Val His Asn Val Ile Glu Gln Val His Gly Asp Lys Arg Ser
        1265                1270                1275
```

```
Ser Ile Thr Val Glu Ser Asp Met His Asp Pro Ser Leu Leu Ala
    1280                1285                1290

Ile Ala Gln Asn His Arg Val Asn Gly Leu Thr Met Ala Pro Ser
    1295                1300                1305

Thr Leu Phe Ala Asp Ile Ala Phe Thr Leu Ala Lys His Leu Ile
    1310                1315                1320

Gln Asn His Gly Leu Asp Thr His Thr Asn Leu Pro Ser Ile Asn
    1325                1330                1335

Asn Met Ala Val Glu Lys Ala Leu Ile Val Gly Glu Thr Gly Pro
    1340                1345                1350

Gln Leu Phe Arg Ala Ser Leu Asp Met Asp Trp Thr Thr Met Arg
    1355                1360                1365

Gly Ser Val Arg Ile Phe Ser Val Gly Ala Asn Gly Lys Gln Thr
    1370                1375                1380

Thr Leu His Ala Val Cys Asp Val Ala Val Glu Asn Pro Ser Ser
    1385                1390                1395

His Arg Glu Ser Trp Gln Ser Asn Ala Tyr Leu Ile Gln Arg Gly
    1400                1405                1410

Ile Lys Gln Leu Val Gln Gly Ala Ser Asp Gly Ser Ala His Met
    1415                1420                1425

Met Arg Arg Gly Leu Leu Tyr Lys Ile Phe Ser Asn Ser Val Gln
    1430                1435                1440

Tyr Gly Ser Ala Phe Gln Gly Ile Glu Gln Val Trp Phe Asp Ser
    1445                1450                1455

Glu Gly Leu Glu Gly Thr Gly Lys Val Phe Met Pro Ser Gly Lys
    1460                1465                1470

Asp Thr Phe Ala Leu Asn Pro Tyr Cys Cys Asp Ser Leu Gly His
    1475                1480                1485

Ile Thr Gly Phe Ile Met Asn Cys Ser Asp Ser Leu Asp Leu Asp
    1490                1495                1500

Asp His Val Tyr Ile Asn His Gly Trp Arg Thr Leu Arg Leu Val
    1505                1510                1515

Glu Pro Tyr Gln Cys Asp Val Gln Tyr Gln Thr Tyr Val Lys Met
    1520                1525                1530

Gln Ala Val Gly Ser Asp Asp Ser Thr Tyr Ser Gly Asp Val His
    1535                1540                1545

Val Leu Arg Asp Gly Lys Ile Gly Ile Cys Gly Gly Val Thr
    1550                1555                1560

Phe Lys Lys Val Ala Arg Lys Val Leu Glu Met Leu Leu Pro Lys
    1565                1570                1575

Pro Ser Gly Ala Lys Ala Lys His Gly Val Val Lys His Val Ala
    1580                1585                1590

Pro Glu Pro Val Lys His Val Val Leu Thr Pro Pro Ser Thr Thr
    1595                1600                1605

Ser His Ser Val Gly Thr Thr Ser Pro Pro Glu Pro Thr Glu Ser
    1610                1615                1620

Pro Val Gly Ser Ala Ser Gly Leu Ile Gln Lys Ala Leu Glu Ile
    1625                1630                1635

Ile Ala Asp Glu Ile Gly Val Asp Ile Ser Gln Leu Thr Asp Thr
    1640                1645                1650

Thr Leu Leu Ala Asp Leu Gly Val Asp Ser Leu Met Ser Leu Thr
    1655                1660                1665

Ile Leu Gly Asn Phe Arg Glu Glu Leu Asp Leu Asp Ile Pro Ala
```

-continued

```
                1670                1675                1680

Ala Gln Phe Tyr Glu Phe Ser Thr Val Gln Asp Leu Lys Ser Phe
    1685                1690                1695

Leu Gly Ala Asn Asp Gln Asp Phe Ser Ser Asn Ser Glu Ala
    1700                1705                1710

Glu Ser Ser Ala Ser Ser Ala Ser Thr Ser Pro Ser Asp His
    1715                1720                1725

Gly Asp Asp Val Val Glu Val Lys Pro Val Val Ala Glu Ile
    1730                1735                1740

Pro Arg Ser Thr Ser Thr Ile Leu Gln Gly Thr Lys His Cys Ser
    1745                1750                1755

Gln Thr Leu Phe Leu Phe Pro Asp Gly Ala Gly Ser Ala Thr Ser
    1760                1765                1770

Tyr Val Thr Leu Pro Ser Ile Ser Ser Asp Met Arg Val Ile Gly
    1775                1780                1785

Leu Asn Ser Pro Tyr Leu Thr Lys Pro His Glu Phe Asn Cys Ala
    1790                1795                1800

Leu Gln Asp Ile Thr Gly Ser Tyr Leu Asn Glu Val Arg Arg Arg
    1805                1810                1815

Gln Pro Gln Gly Pro Tyr His Leu Ala Gly Trp Ser Ala Gly Gly
    1820                1825                1830

Val Ser Ala Phe Asp Ala Ala Arg Gln Leu Val Ser Glu Gly Glu
    1835                1840                1845

Val Val Glu Ser Leu Ile Leu Ile Asp Ser Pro Asn Pro Val Gly
    1850                1855                1860

Leu Gly Lys Leu Pro Lys Arg Met Tyr Asp Phe Leu Glu Lys Ser
    1865                1870                1875

Gly Ile Phe Gly Ala Phe Glu Met Gly Glu Glu Ala Gln Ala Pro
    1880                1885                1890

Pro Asp Trp Leu Phe Gln His Phe Cys Val Phe Ile Glu Ala Leu
    1895                1900                1905

Asp Arg Tyr Val Pro Glu Pro Phe Glu His Gly Met Ala Pro Lys
    1910                1915                1920

Thr Thr Ile Ile Trp Ala Ala Asp Gly Val Cys Lys Asn Pro Asp
    1925                1930                1935

Asp Pro Arg Pro Glu Ala Gln Pro Asp Asp Pro Arg Gly Met Asn
    1940                1945                1950

Trp Leu Leu Asn Asn Arg Glu Asp Phe Gly Pro Asn Gly Trp Asp
    1955                1960                1965

Glu Phe Ile Gly Ala Gly Asn Ile Ser Thr Met Ala Ile Glu Asn
    1970                1975                1980

Ala Asn His Phe Thr Met Met Arg Glu Pro Ile Ala Ser Ala Leu
    1985                1990                1995

Cys Ala Lys Ile Arg Glu Thr Met Gly Val Asn
    2000                2005

<210> SEQ ID NO 42
<211> LENGTH: 100
<212> TYPE: PRT
<213> ORGANISM: Lyngbya majuscula

<400> SEQUENCE: 42

Met Glu Asn Leu Thr Val Glu Thr Gln Asn Leu Thr Ser Leu Asp Asn
1               5                   10                  15
```

```
Gly Ser Ile Glu Glu Lys Asn Gly Pro Thr Val Asp Glu Val Gln Glu
             20                  25                  30

Trp Leu Ile Ser Tyr Leu Ser Gln Leu Leu Asp Leu Glu Ile Glu Glu
         35                  40                  45

Ile Ser Thr Ser Thr Ser Phe Asn Arg Tyr Gly Leu Asp Ser Ser Ala
     50                  55                  60

Ser Ile Ser Leu Thr Ser Asp Phe Gly Asp Trp Ile Ser Lys Glu Ile
65                  70                  75                  80

Asp Pro Thr Ile Leu Tyr Ser Tyr Pro Thr Ile Glu Ala Met Ala Glu
                 85                  90                  95

His Phe Gly Ala
            100

<210> SEQ ID NO 43
<211> LENGTH: 79
<212> TYPE: PRT
<213> ORGANISM: Myxococcus xanthus

<400> SEQUENCE: 43

Met Asp Lys Arg Ile Ile Phe Asp Ile Val Thr Ser Ser Val Arg Glu
1               5                   10                  15

Val Val Pro Glu Leu Glu Ser His Pro Phe Glu Pro Glu Asp Asp Leu
             20                  25                  30

Val Gly Leu Gly Ala Asn Ser Leu Asp Arg Ala Glu Ile Val Asn Leu
         35                  40                  45

Thr Leu Glu Lys Leu Ala Leu Asn Ile Pro Arg Val Glu Leu Ile Asp
     50                  55                  60

Ala Lys Thr Ile Gly Gly Leu Val Asp Val Leu His Ala Arg Leu
65                  70                  75

<210> SEQ ID NO 44
<211> LENGTH: 94
<212> TYPE: PRT
<213> ORGANISM: Pantoea agglomerans

<400> SEQUENCE: 44

Met Asn Ile Asn Glu Val Ile Asn His Ile Lys Glu Lys Ile Ile Phe
1               5                   10                  15

Glu Asp Leu Glu Leu Asn Glu Trp Gly His Glu Leu Ser Asp Ile Lys
             20                  25                  30

Asp Asp Thr Pro Leu Leu Ala Glu Glu Gly Leu Ala Leu Asp Ser Val
         35                  40                  45

Asp Val Leu Asp Ile Phe Val Gly Ile Gln Lys Glu Tyr Ser Ile Asp
     50                  55                  60

Leu Gly Glu Ile Thr Ser Glu Leu Met Glu Lys His Cys Gln Ser Pro
65                  70                  75                  80

Leu Thr Leu Ala Glu Leu Val Ile Asp Lys Cys Gly Ala Arg
                 85                  90

<210> SEQ ID NO 45
<211> LENGTH: 87
<212> TYPE: PRT
<213> ORGANISM: Pantoea agglomerans

<400> SEQUENCE: 45

Met Glu Lys Ser Glu Ile Glu Gln Thr Leu Lys Asn Glu Ile Lys Leu
1               5                   10                  15

Ile Asn His Tyr Ser Asp Ser Val Glu Ile Asp Ala Glu Val Lys Leu
```

20                  25                  30
Arg Glu Ile Leu Asp Ser Val Asp Ile Leu Gln Phe Val Tyr Lys Ile
                35                  40                  45

Asn Lys Asp Tyr Gly Leu Ser Phe Gly Ser Asn Ile Gly Asp Glu Lys
         50                  55                  60

Tyr Leu Asp Thr Leu Asp Gly Val Val Ser Trp Val His Ser Ala Ile
 65                  70                  75                  80

Asn Lys Lys Ala Glu Asp Asp
                 85

<210> SEQ ID NO 46
<211> LENGTH: 293
<212> TYPE: PRT
<213> ORGANISM: Vibrio cholerae

<400> SEQUENCE: 46

Met Ala Ile Pro Lys Ile Ala Ser Tyr Pro Leu Pro Val Ser Leu Pro
 1               5                  10                  15

Thr Asn Lys Val Asp Trp Arg Ile Asp Ala Ser Arg Ala Val Leu Leu
                20                  25                  30

Ile His Asp Met Gln Glu Tyr Phe Val His Tyr Phe Ala Ser Gln Ala
             35                  40                  45

Glu Pro Ile Pro Ser Leu Ile Lys His Ile Gln Gln Leu Lys Ala His
         50                  55                  60

Ala Lys Gln Ala Gly Ile Pro Val Val Tyr Thr Ala Gln Pro Ala Asn
 65                  70                  75                  80

Gln Asp Pro Ala Glu Arg Ala Leu Leu Ser Asp Phe Trp Gly Pro Gly
                 85                  90                  95

Leu Ser Glu Glu Thr Ala Ile Ile Ala Pro Leu Ala Pro Glu Ser Gly
                100                 105                 110

Asp Val Gln Leu Thr Lys Trp Arg Tyr Ser Ala Phe Lys Lys Ser Pro
            115                 120                 125

Leu Leu Asp Trp Leu Arg Glu Thr Gly Arg Asp Gln Leu Ile Ile Thr
130                 135                 140

Gly Val Tyr Ala His Ile Gly Ile Leu Ser Thr Ala Leu Asp Ala Phe
145                 150                 155                 160

Met Phe Asp Ile Gln Pro Phe Val Ile Gly Asp Gly Val Ala Asp Phe
                165                 170                 175

Ser Leu Ser Asp His Glu Phe Ser Leu Arg Tyr Ile Ser Gly Arg Thr
            180                 185                 190

Gly Ala Val Lys Ser Thr Gln Gln Ala Cys Leu Glu Ile Ala Ala Gln
        195                 200                 205

His Ser Lys Leu Thr Gly Leu Ser Leu Arg Thr Met Gln His Asp Val
    210                 215                 220

Ala Ala Ala Leu Asn Leu Ser Val Asp Glu Val Asp Val Gln Glu Asn
225                 230                 235                 240

Leu Leu Phe Leu Gly Leu Asp Ser Ile Arg Ala Ile Gln Leu Leu Glu
                245                 250                 255

Lys Trp Lys Ala Gln Gly Ala Asp Ile Ser Phe Ala Gln Leu Met Glu
            260                 265                 270

His Val Thr Leu Gln Gln Trp Trp Gln Thr Ile Gln Ala Asn Leu His
        275                 280                 285

Gln Pro Cys Ser Ala
    290

<210> SEQ ID NO 47
<211> LENGTH: 88
<212> TYPE: PRT
<213> ORGANISM: Pseudomonas protegens

<400> SEQUENCE: 47

Met Asp Gly Glu Glu Val Lys Glu Lys Ile Arg Arg Tyr Ile Met Glu
1               5                   10                  15

Asp Leu Ile Gly Pro Ser Ala Lys Glu Asp Glu Leu Asp Asp Gln Thr
            20                  25                  30

Pro Leu Leu Glu Trp Gly Ile Leu Asn Ser Met Asn Ile Val Lys Leu
        35                  40                  45

Met Val Tyr Ile Arg Asp Glu Met Gly Val Ser Ile Pro Ser Thr His
50                  55                  60

Ile Thr Gly Lys Tyr Phe Lys Asp Leu Asn Ala Ile Ser Arg Thr Val
65                  70                  75                  80

Glu Gln Leu Lys Ala Glu Cys Ala
                85

<210> SEQ ID NO 48
<211> LENGTH: 251
<212> TYPE: PRT
<213> ORGANISM: Pseudomonas syringae

<400> SEQUENCE: 48

Phe Arg Val Leu Asp Glu Ala Asp Arg Gly Asn Thr Ala Pro Leu Ala
1               5                   10                  15

Leu Arg Tyr Val Val Phe Gly Gly Glu Ala Leu Pro Ala Ser Val Leu
            20                  25                  30

Arg Pro Trp Val Glu Arg His Gly Asp Gln Lys Pro Ala Leu Ile Asn
        35                  40                  45

Met Tyr Gly Ile Thr Glu Ala Thr Val His Thr Thr Phe Lys Arg Val
50                  55                  60

Leu Ala Gln Asp Leu Glu Thr Ala Ala Met Val Ser Leu Gly Lys Pro
65                  70                  75                  80

Leu Asp Gly Trp Arg Leu His Leu Leu Asp Ala Ser Leu Ala Pro Val
            85                  90                  95

Ala Ala Gly Thr Thr Gly Glu Leu Tyr Ile Glu Gly Ala Gly Val Ala
            100                 105                 110

Gln Gly Tyr Leu Asn Arg Glu Ala Leu Asn Val Glu Arg Phe Val Glu
        115                 120                 125

Leu Pro Gly Ala Ile Arg Ala Tyr Arg Thr Gly Asp Leu Met Thr Leu
    130                 135                 140

Glu Ser Asn Gly Glu Tyr Ser Tyr Ala Gly Arg Cys Asp Glu Gln Leu
145                 150                 155                 160

Lys Ile Ser Gly Phe Arg Ile Glu Pro Gly Glu Ile Glu Ala Ser Leu
                165                 170                 175

Gln Thr Ser Pro Ser Val Ala Ala His Val Gly Val His Asp Tyr
            180                 185                 190

Gly Asp Gly Asp Leu Arg Leu Val Ala Tyr Val Pro Gly Gln Gly
        195                 200                 205

Val Asp Ala Trp Thr Glu Gln Ala Arg Ser Glu Val Ala Ala Leu Met
    210                 215                 220

Ala Glu Asn Leu Pro Glu Tyr Met Arg Pro Ser Val Tyr Val Pro Leu
225                 230                 235                 240

Val Glu Leu Pro Val Thr His His Gly Lys Ile
              245                 250

<210> SEQ ID NO 49
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 49
aaaacatatg aattatctcg cacatctgca cc                           32

<210> SEQ ID NO 50
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 50
aaaactcgag tgcaaaggcc tgcaactctg g                            31

<210> SEQ ID NO 51
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 51
aaaactcgag ttaaaattgg agtgcaaagg cctgc                        35

<210> SEQ ID NO 52
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 52
aaaactcgag aaattggagt gcaaaggcct gcaac                        35

<210> SEQ ID NO 53
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 53
aaaacatatg aattatctgg ctcatttatt tttagc                       36

<210> SEQ ID NO 54
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 54
aaaactcgag agccaagtta acataatcaa tcagttg                      37

<210> SEQ ID NO 55
<211> LENGTH: 35
<212> TYPE: DNA

```
<213> ORGANISM: Artificial Sequence
<220> FEATURE:
<223> OTHER INFORMATION: Synthetic polynucleotide

<400> SEQUENCE: 55
aaaacatatg aacattctta cacacttaca tctgg                           35

<210> SEQ ID NO 56
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 56
aaaactcgag ctcgggtaag tagtcaattg gag                             33

<210> SEQ ID NO 57
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 57
aaaacatatg gtgcctgtca ctcaggaaga aatc                            34

<210> SEQ ID NO 58
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 58
aaaaaagctt cttggactcg gcctcaagc                                  29

<210> SEQ ID NO 59
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 59
aaaaaacata tgaactacct cgc                                        23

<210> SEQ ID NO 60
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 60
aaaaaactcg agtcagcgct ggctcag                                    27

<210> SEQ ID NO 61
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 61
aaaaaacata tgaactatct ggcacacc                                   28
```

<210> SEQ ID NO 62
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 62
aaaaaactcg agttagcgct gagacag                                    27

<210> SEQ ID NO 63
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 63
gtctcagcgc ggactcgagc accaccacca cc                              32

<210> SEQ ID NO 64
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 64
gtgctcgagt ccgcgctgag acagggcaaa tgc                             33

<210> SEQ ID NO 65
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 65
aaaaaacata tgagcaccat cg                                         22

<210> SEQ ID NO 66
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 66
aaaaaactcg agttgctggt gag                                        23

<210> SEQ ID NO 67
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 67
aaaaggatcc agcactatcg aagaacgcgt taag                            34

<210> SEQ ID NO 68
<211> LENGTH: 34
<212> TYPE: DNA
<213> ORGANISM: Artificial Sequence
<220> FEATURE:

-continued

<223> OTHER INFORMATION: Synthetic polynucleotide

<400> SEQUENCE: 68
aaaactcgag cgcctggtgg ccgttgatgt aatc                               34

<210> SEQ ID NO 69
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 69
aaaacatatg aaatttggta acttcctttt aacttatc                           38

<210> SEQ ID NO 70
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 70
aaaaggatcc tgaatgatat ttaacaatgt tagcatttac tac                     43

<210> SEQ ID NO 71
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 71
cagttgatca cgattcaaac aaagc                                         25

<210> SEQ ID NO 72
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 72
cttgatcaaa tgagtgaagg tcg                                           23

<210> SEQ ID NO 73
<211> LENGTH: 193
<212> TYPE: PRT
<213> ORGANISM: Escherichia coli

<400> SEQUENCE: 73

Met Asn Phe Leu Ala His Leu His Leu Ala His Leu Ala Glu Ser Ser
1               5                   10                  15

Leu Ser Gly Asn Leu Leu Ala Asp Phe Val Arg Gly Asn Pro Glu Glu
            20                  25                  30

Ser Phe Pro Pro Asp Val Val Ala Gly Ile His Met His Arg Arg Ile
        35                  40                  45

Asp Val Leu Thr Asp Asn Leu Pro Glu Val Arg Glu Ala Arg Glu Trp
    50                  55                  60

Phe Arg Asn Glu Thr Arg Arg Val Ala Pro Ile Thr Leu Asp Val Met
65                  70                  75                  80

Trp Asp His Phe Leu Ser Arg His Trp Ser Gln Leu Ser Pro Asp Phe
                85                  90                  95

```
Pro Leu Gln Glu Phe Thr Cys Tyr Ala Arg Glu Gln Val Met Thr Ile
            100                 105                 110

Leu Pro Asp Ser Pro Pro Arg Phe Ile Asn Leu Asn Asn Tyr Leu Trp
            115                 120                 125

Ser Glu Arg Trp Leu Val Arg Tyr Arg Asp Met Asp Phe Ile Gln Ser
        130                 135                 140

Val Leu Asn Gly Met Ala Ser Arg Arg Pro Arg Leu Asp Ala Leu Arg
145                 150                 155                 160

Asp Ser Trp Tyr Asp Leu Asp Ala His Tyr Asp Ala Leu Glu Thr Arg
                165                 170                 175

Phe Trp Gln Phe Tyr Pro Arg Met Met Glu Gln Ala Ser Arg Lys Ala
            180                 185                 190

Leu

<210> SEQ ID NO 74
<211> LENGTH: 193
<212> TYPE: PRT
<213> ORGANISM: Unknown
<220> FEATURE:
<223> OTHER INFORMATION: Cyanothece sp. PCC 7822

<400> SEQUENCE: 74

Met Asn Tyr Leu Ala His Leu Phe Leu Ala Asp Pro Thr Pro Glu Ser
1               5                   10                  15

Gln Ile Gly Asn Leu Leu Gly Asp Phe Val Lys Gly Lys Ile Asp Asn
            20                  25                  30

Leu Ser Ser Ile Tyr Ser Pro Glu Ile Ile Arg Gly Val Lys Thr His
        35                  40                  45

Gln Lys Ile Asp Ile Phe Thr Asp His His Pro Ile Phe Lys Thr Ser
    50                  55                  60

Lys Gln Arg Leu Asn Gln Asn His Arg Lys Phe Ala Gly Val Ile Ile
65                  70                  75                  80

Asp Ile Tyr Tyr Asp His Phe Leu Ala Lys Asn Trp Leu Ile Tyr Ser
                85                  90                  95

Glu Gln Asp Leu Asp Glu Phe Val Ala Asn Thr Tyr Gln Met Leu Glu
            100                 105                 110

Gln His Gln Leu Leu Leu Pro Glu Lys Leu Gln Lys Ala Leu Pro Cys
        115                 120                 125

Met Ile Gln Glu Asp Trp Leu Gly Ser Tyr Arg Tyr Phe Glu Gly Ile
    130                 135                 140

Asp Gln Thr Phe Ser Arg Leu Ser Arg Arg Ile Lys Arg Thr Asn Asn
145                 150                 155                 160

Ile Ala Phe Ala Leu Glu Asp Leu Ile Gln Asn Tyr Ser Gln Leu Glu
                165                 170                 175

Glu Asp Phe Leu Gln Phe Phe Pro Gln Leu Ile Asp Tyr Val Asn Leu
            180                 185                 190

Ala

<210> SEQ ID NO 75
<211> LENGTH: 190
<212> TYPE: PRT
<213> ORGANISM: Psuedomonas aeruginosa

<400> SEQUENCE: 75

Met Asn Tyr Leu Ala His Leu His Leu Gly Gly Pro Gln Pro Ala Gln
1               5                   10                  15
```

Leu Leu Gly Ser Leu Tyr Gly Asp Phe Val Lys Gly Arg Leu Gln Gly
            20                  25                  30

Gln Trp Pro Asp Glu Ile Glu Arg Ala Ile Gln Leu His Arg Arg Ile
        35                  40                  45

Asp Ala Phe Thr Asp Ser His Pro Leu Val His Ala Ala Lys Arg Arg
 50                  55                  60

Phe Pro Leu Glu Arg Arg Phe Ala Gly Val Leu Leu Asp Val Phe
 65                  70                  75                  80

Phe Asp His Cys Leu Ala Arg Asp Trp Asn Asp Tyr Ala Asp Glu Pro
                85                  90                  95

Leu Pro Gln Phe Val Glu Arg Val Tyr Gly Thr Leu Arg Thr Ala Ser
            100                 105                 110

Pro Leu Pro Glu Arg Leu Ala Arg Ile Ala Pro Arg Met Ala Ala Gln
            115                 120                 125

Asp Trp Leu Gly Ser Tyr Arg Glu Phe Ala Val Leu Arg Glu Val Leu
130                 135                 140

Gly Gly Met Ser Arg Arg Leu Ser Arg Pro His Leu Leu Asp Gly Ser
145                 150                 155                 160

Trp Glu Glu Leu Ala Gln Arg Tyr Asp Asp Leu Ser Ala Asp Phe Arg
                165                 170                 175

Ala Phe Tyr Pro Gln Leu Gln Ala Phe Ala Leu Ser Gln Arg
            180                 185                 190

<210> SEQ ID NO 76
<211> LENGTH: 189
<212> TYPE: PRT
<213> ORGANISM: Psuedomonas fluorescens

<400> SEQUENCE: 76

Met Asn Tyr Leu Ala His Leu His Leu Gly Gly Gln Leu Pro Ala Gln
1               5                   10                  15

Leu Leu Gly Ser Leu Tyr Gly Asp Phe Val Lys Gly Arg Leu Gln Gly
            20                  25                  30

Gln Phe Ser Pro Gln Ile Glu Ala Ala Ile Gln Leu His Arg Ser Ile
        35                  40                  45

Asp Arg Phe Thr Asp Ser His Pro Leu Val Gly Glu Ala Leu Ser Arg
 50                  55                  60

Phe Ser Gln Thr Arg Arg Arg Tyr Ala Gly Ile Val Leu Asp Val Phe
 65                  70                  75                  80

Phe Asp His Cys Leu Ala Arg Asp Trp Ala Leu Tyr Ala Asp Gln Pro
                85                  90                  95

Leu Glu Arg Phe Thr Ser His Val Tyr Gln Val Leu Ala Ala Glu Pro
            100                 105                 110

Ala Leu Pro Gly Arg Leu Ala Gln Ile Ala Pro Tyr Met Ala Ala Asp
            115                 120                 125

Asp Trp Leu Gly Ser Tyr Arg Glu Phe Ala Val Met Glu Gln Val Leu
130                 135                 140

Arg Gly Ile Ser Arg Arg Leu Thr Gln Pro Glu Glu Leu Gly Tyr Ala
145                 150                 155                 160

Met Gln Glu Leu Arg Val Leu Tyr Glu Pro Leu Ser Glu Asp Phe Arg
                165                 170                 175

Leu Phe Tyr Pro Glu Leu Gln Ala Phe Ala Leu Gln Phe
            180                 185

<210> SEQ ID NO 77

<400> SEQUENCE: 77

000

<210> SEQ ID NO 78
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Residue at position 2 modified at side chain
      with phosphopantethiene-coumarin

<400> SEQUENCE: 78

Asp Ser Leu Glu Phe Ile Ala Ser Lys Leu Ala
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue at position 1 modified at N-terminal
      with fluorescein
<220> FEATURE:
<221> NAME/KEY: MISC_FEATURE
<222> LOCATION: (2)..(2)
<223> OTHER INFORMATION: Residue at position 2 modified at side chain
      with phosphopantetheine-coumarin

<400> SEQUENCE: 79

Asp Ser Leu Glu Phe Ile Ala Ser Lys Leu Ala
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue at position 1 modified at N-terminal
      with fluorescein
<220> FEATURE:
<221> NAME/KEY: MISC_FEATURE
<222> LOCATION: (2)..(2)
<223> OTHER INFORMATION: Residue at position 2 modified at side chain
      with phosphopantetheine-rhodamine

<400> SEQUENCE: 80

Asp Ser Leu Glu Phe Ile Ala Ser Lys Leu Ala
1               5                   10

<210> SEQ ID NO 81
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 81

```
Ala Ser Phe Val Glu Asp Leu Gly Ala Asp Ser Leu Asp Thr Val Glu
1               5                   10                  15

Leu Val Met Ala Leu
            20

<210> SEQ ID NO 82
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 82

Ala Ser Phe Val Glu Asp Leu Gly Ala Asp Ser Leu Asp Thr Val Glu
1               5                   10                  15

Leu Val Met Ala Leu
            20

<210> SEQ ID NO 83
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 83

Ala Ser Phe Val Asp Asp Leu Gly Ala Asp Ser Leu Asp Thr Val Glu
1               5                   10                  15

Leu Val Met Ala Leu
            20

<210> SEQ ID NO 84
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 84

Ser Asn Phe Thr Lys Asp Leu Gly Ala Asp Ser Leu Asp Leu Val Glu
1               5                   10                  15

Leu Ile Met Ala Leu
            20

<210> SEQ ID NO 85
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 85

Lys Ser Phe Val Glu Asp Leu Asp Ile Asp Ser Leu Ser Met Val Glu
1               5                   10                  15

Ile Ala Val Gln Thr
            20

<210> SEQ ID NO 86
<211> LENGTH: 21
<212> TYPE: PRT
<213> ORGANISM: Artificial Sequence
<220> FEATURE:
<223> OTHER INFORMATION: Synthetic polypeptide
```

```
<400> SEQUENCE: 86

Asp Ser Asn Phe Ala Asp Met Gly Ile Asp Ser Leu Ser Ser Met Val
1               5                   10                  15

Ile Gly Ser Arg Phe
            20

<210> SEQ ID NO 87
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 87

Thr Thr Leu Leu Ala Asp Leu Gly Val Asp Ser Leu Met Ser Leu Thr
1               5                   10                  15

Ile Leu Gly Asn Phe
            20

<210> SEQ ID NO 88
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 88

Ser Thr Ser Phe Asn Arg Tyr Gly Leu Asp Ser Ser Ala Ser Ile Ser
1               5                   10                  15

Leu Thr Ser Asp Phe
            20

<210> SEQ ID NO 89
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 89

Asp Leu Arg Phe Glu Asp Ile Gly Tyr Asp Ser Leu Ala Leu Met Glu
1               5                   10                  15

Thr Ala Ala Arg Leu
            20

<210> SEQ ID NO 90
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 90

Thr Asp Ser Leu Lys Asn Leu Gly Ile Asp Ser Val Asn Arg Ala Glu
1               5                   10                  15

Ile Ile Met Met Val
            20

<210> SEQ ID NO 91
<211> LENGTH: 21
<212> TYPE: PRT
<213> ORGANISM: Artificial Sequence
<220> FEATURE:
<223> OTHER INFORMATION: Synthetic polypeptide
```

<400> SEQUENCE: 91

Gln Glu Asn Leu Leu Phe Leu Gly Leu Asp Ser Ile Arg Ala Ile Gln
1               5                   10                  15

Leu Leu Glu Lys Trp
            20

<210> SEQ ID NO 92
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 92

Asp Asp Ser Phe Phe Asp Ile Gly Gly His Ser Leu Leu Ala Thr Arg
1               5                   10                  15

Leu Val Ala Arg Ile
            20

<210> SEQ ID NO 93
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 93

Thr Pro Leu Leu Glu Trp Gly Ile Leu Asn Ser Met Asn Ile Val Lys
1               5                   10                  15

Leu Met Val Tyr Ile
            20

<210> SEQ ID NO 94
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 94

Asn Asp Asp Phe Phe Asp Ser Gly Gly Thr Ser Ser Leu Ala Leu Ile
1               5                   10                  15

Arg Ser Leu Ser Lys
            20

<210> SEQ ID NO 95
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 95

Asp Arg Ser Phe Ile Glu Tyr Gly Leu Asp Ser Leu Gly Met Leu Glu
1               5                   10                  15

Met Arg Thr His Val
            20

<210> SEQ ID NO 96
<211> LENGTH: 21
<212> TYPE: PRT
<213> ORGANISM: Artificial Sequence
<220> FEATURE:

```
<223> OTHER INFORMATION: Synthetic polypeptide

<400> SEQUENCE: 96

Leu Leu Ala Glu Glu Gly Leu Ala Leu Asp Ser Val Asp Val Leu Asp
1               5                   10                  15

Ile Phe Val Gly Ile
            20

<210> SEQ ID NO 97
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 97

Asp Ser Leu Asp Thr Val Glu Leu Val
1               5

<210> SEQ ID NO 98
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 98

Asp Ser Leu Asp Thr Val Glu Leu Val Met Ala
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 99

Ala Asp Ser Leu Asp Thr Val Glu Leu Val
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 100

Gly Ala Asp Ser Leu Asp Thr Val Glu Leu Val
1               5                   10

<210> SEQ ID NO 101
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 101

Val Glu Asp Leu Gly Ala Asp Ser Leu Asp Thr Val Glu Leu Val
1               5                   10                  15

<210> SEQ ID NO 102
<211> LENGTH: 20
<212> TYPE: PRT
```

<213> ORGANISM: Artificial Sequence
<220> FEATURE:
<223> OTHER INFORMATION: Synthetic polypeptide

<400> SEQUENCE: 102

```
Asn Ser Ala Ser Phe Val Glu Asp Leu Gly Ala Asp Ser Leu Asp Thr
1               5                   10                  15

Val Glu Leu Val
            20
```

<210> SEQ ID NO 103
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 103

```
Asp Leu Gly Xaa Asp Ser Leu Asp Xaa Val Glu Leu
1               5                   10
```

<210> SEQ ID NO 104
<211> LENGTH: 224
<212> TYPE: PRT
<213> ORGANISM: Bacillus subtilis

<400> SEQUENCE: 104

```
Met Lys Ile Tyr Gly Ile Tyr Met Asp Arg Pro Leu Ser Gln Glu Glu
1               5                   10                  15

Asn Glu Arg Phe Met Thr Phe Ile Ser Pro Glu Lys Arg Glu Lys Cys
                20                  25                  30

Arg Arg Phe Tyr His Lys Glu Asp Ala His Arg Thr Leu Leu Gly Asp
            35                  40                  45

Val Leu Val Arg Ser Val Ile Ser Arg Gln Tyr Gln Leu Asp Lys Ser
        50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Gly Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205
```

```
Pro Asp Phe Pro Glu Asp Ile Thr Met Val Ser Tyr Glu Glu Leu Leu
    210                 215                 220
```

<210> SEQ ID NO 105
<211> LENGTH: 121
<212> TYPE: PRT
<213> ORGANISM: Bacillus subtilis

<400> SEQUENCE: 105

```
Met Ile Tyr Gly Ile Gly Leu Asp Ile Thr Glu Leu Lys Arg Ile Ala
1               5                   10                  15

Ser Met Ala Gly Arg Gln Lys Arg Phe Ala Glu Arg Ile Leu Thr Arg
            20                  25                  30

Ser Glu Leu Asp Gln Tyr Tyr Glu Leu Ser Glu Lys Arg Lys Ile Glu
        35                  40                  45

Phe Leu Ala Gly Arg Phe Ala Ala Lys Glu Ala Phe Ser Lys Ala Phe
    50                  55                  60

Gly Thr Gly Ile Gly Arg Gln Leu Ser Phe Gln Asp Ile Glu Ile Arg
65                  70                  75                  80

Lys Asp Gln Asn Gly Lys Pro Tyr Ile Ile Cys Thr Lys Leu Ser Gln
                85                  90                  95

Ala Ala Val His Val Ser Ile Thr His Thr Lys Glu Tyr Ala Ala Ala
            100                 105                 110

Gln Val Val Ile Glu Arg Leu Ser Ser
        115                 120
```

<210> SEQ ID NO 106
<211> LENGTH: 242
<212> TYPE: PRT
<213> ORGANISM: Pseudomonas aeruginosa

<400> SEQUENCE: 106

```
Met Arg Ala Met Asn Asp Arg Leu Pro Ser Phe Cys Thr Pro Leu Asp
1               5                   10                  15

Asp Arg Trp Pro Leu Pro Val Ala Leu Pro Gly Val Gln Leu Arg Ser
            20                  25                  30

Thr Arg Phe Asp Pro Ala Leu Leu Gln Pro Gly Asp Phe Ala Leu Ala
        35                  40                  45

Gly Ile Gln Pro Pro Ala Asn Ile Leu Arg Ala Val Ala Lys Arg Gln
    50                  55                  60

Ala Glu Phe Leu Ala Gly Arg Leu Cys Ala Arg Ala Ala Leu Phe Ala
65                  70                  75                  80

Leu Asp Gly Arg Ala Gln Thr Pro Ala Val Gly Glu Asp Arg Ala Pro
                85                  90                  95

Val Trp Pro Ala Ala Ile Ser Gly Ser Ile Thr His Gly Asp Arg Trp
            100                 105                 110

Ala Ala Ala Leu Val Ala Ala Arg Gly Asp Trp Arg Gly Leu Gly Leu
        115                 120                 125

Asp Val Glu Thr Leu Leu Glu Ala Glu Arg Ala Arg Tyr Leu His Gly
    130                 135                 140

Glu Ile Leu Thr Glu Gly Glu Leu Arg Phe Ala Asp Asp Leu Glu
145                 150                 155                 160

Arg Arg Thr Gly Leu Leu Val Thr Leu Ala Phe Ser Leu Lys Glu Ser
                165                 170                 175

Leu Phe Lys Ala Leu Tyr Pro Leu Val Gly Lys Arg Phe Tyr Phe Glu
            180                 185                 190
```

His Ala Glu Leu Leu Glu Trp Arg Ala Asp Gly Gln Ala Arg Leu Arg
            195                 200                 205

Leu Leu Thr Asp Leu Ser Pro Glu Trp Arg His Gly Ser Glu Leu Asp
    210                 215                 220

Ala Gln Phe Ala Val Leu Asp Gly Arg Leu Leu Ser Leu Val Ala Val
225                 230                 235                 240

Gly Ala

<210> SEQ ID NO 107
<211> LENGTH: 126
<212> TYPE: PRT
<213> ORGANISM: Escherichia coli

<400> SEQUENCE: 107

Met Ala Ile Leu Gly Leu Gly Thr Asp Ile Val Glu Ile Ala Arg Ile
1               5                   10                  15

Glu Ala Val Ile Ala Arg Ser Gly Glu Arg Leu Ala Arg Arg Val Leu
            20                  25                  30

Ser Asp Asn Glu Trp Glu Ile Trp Lys Thr His His Gln Pro Val Arg
        35                  40                  45

Phe Leu Ala Lys Arg Phe Ala Val Lys Glu Ala Ala Ala Lys Ala Phe
    50                  55                  60

Gly Thr Gly Ile Arg Asn Gly Leu Ala Phe Asn Gln Phe Glu Val Phe
65                  70                  75                  80

Asn Asp Glu Leu Gly Lys Pro Arg Leu Arg Leu Trp Gly Glu Ala Leu
                85                  90                  95

Lys Leu Ala Glu Lys Leu Gly Val Val Asn Met His Val Thr Leu Ala
            100                 105                 110

Asp Glu Arg His Tyr Ala Cys Ala Thr Val Ile Ile Glu Ser
        115                 120                 125

<210> SEQ ID NO 108
<211> LENGTH: 206
<212> TYPE: PRT
<213> ORGANISM: Escherichia coli

<400> SEQUENCE: 108

Met Lys Thr Thr His Thr Ser Leu Pro Phe Ala Gly His Thr Leu His
1               5                   10                  15

Phe Val Glu Phe Asp Pro Ala Ser Phe Arg Glu Gln Asp Leu Leu Trp
            20                  25                  30

Leu Pro His Tyr Ala Gln Leu Gln His Ala Gly Arg Lys Arg Lys Thr
        35                  40                  45

Glu His Leu Ala Gly Arg Ile Ala Ala Ile Tyr Ala Leu Arg Glu Tyr
    50                  55                  60

Gly Tyr Lys Cys Val Pro Ala Ile Gly Glu Leu Arg Gln Pro Val Trp
65                  70                  75                  80

Pro Ala Gly Val Tyr Gly Ser Ile Ser His Cys Gly Thr Thr Ala Leu
                85                  90                  95

Ala Val Val Ser Arg Gln Pro Ile Gly Ile Asp Ile Glu Glu Ile Phe
            100                 105                 110

Ser Ala Gln Thr Ala Arg Glu Leu Thr Asp Asn Ile Ile Thr Pro Ala
        115                 120                 125

Glu His Lys Arg Leu Ala Asp Cys Gly Leu Ala Phe Pro Leu Ala Leu
    130                 135                 140

| | | | | | | | | | | | | | | |
|---|---|---|---|---|---|---|---|---|---|---|---|---|---|---|
| Thr | Leu | Ala | Phe | Ser | Ala | Lys | Glu | Ser | Ala | Phe | Lys | Ala | Ser | Glu | Ile |
| 145 | | | | | 150 | | | | | 155 | | | | | 160 |
| Gln | Ala | Ala | Gln | Gly | Phe | Leu | Asp | Tyr | Gln | Ile | Ile | Ser | Trp | Asn | Lys |
| | | | | 165 | | | | | 170 | | | | | 175 | |
| Gln | Gln | Ile | Ile | Ile | Arg | Leu | Glu | Asp | Glu | Gln | Phe | Ala | Val | His | Trp |
| | | | | 180 | | | | | 185 | | | | | 190 | |
| Gln | Ile | Lys | Glu | Lys | Ile | Val | Ile | Thr | Leu | Cys | Gln | His | Asp | | |
| | | 195 | | | | | 200 | | | | | 205 | | | |